United States Patent
Overdijk et al.

(10) Patent No.: US 10,882,913 B2
(45) Date of Patent: *Jan. 5, 2021

(54) ANTI-DR5 ANTIBODIES AND METHODS OF USE THEREOF

(71) Applicant: GENMAB B.V., Utrecht (NL)

(72) Inventors: Marije Overdijk, Utrecht (NL); Kristin Strumane, Werkhoven (NL); Rik Rademaker, Copenhagen V (DK); Esther Breij, Utrecht (NL); Janine Schuurman, Diemen (NL); Paul Parren, Odijk (NL)

(73) Assignee: GENMAB B.V., Utrecht (NL)

(*) Notice: Subject to any disclaimer, the term of this patent is extended or adjusted under 35 U.S.C. 154(b) by 0 days.

This patent is subject to a terminal disclaimer.

(21) Appl. No.: 16/451,714

(22) Filed: Jun. 25, 2019

(65) Prior Publication Data

US 2019/0315877 A1   Oct. 17, 2019

Related U.S. Application Data

(63) Continuation of application No. 15/780,268, filed as application No. PCT/EP2016/079518 on Dec. 1, 2016.

(30) Foreign Application Priority Data

Dec. 1, 2015 (DK) .................... 2015 00771
Dec. 7, 2015 (DK) .................... 2015 00787
(Continued)

(51) Int. Cl.
*C07K 16/28* (2006.01)
*C07K 16/30* (2006.01)
(Continued)

(52) U.S. Cl.
CPC .......... *C07K 16/2878* (2013.01); *A61P 35/00* (2018.01); *C07K 16/30* (2013.01);
(Continued)

(58) Field of Classification Search
None
See application file for complete search history.

(56) References Cited

U.S. PATENT DOCUMENTS 6,444,640 B1   9/2002   Nagane et al.
6,461,823 B1   10/2002   Ni et al.
(Continued)

FOREIGN PATENT DOCUMENTS

CA         2878790 A1 *  1/2014
WO    2008/004760 A1     1/2008
(Continued)

OTHER PUBLICATIONS

Herbst et al., A first-in-human study of Conatumumab in adult patients with advanced solid tumors, Clin. Canc. Res. 16(23):5883-91. (Year: 2010).*

(Continued)

*Primary Examiner* — Claire Kaufman
(74) *Attorney, Agent, or Firm* — Nelson Mullins Riley & Scarborough LLP; Jane E. Remillard, Esq.; Christopher L. Frank

(57) ABSTRACT

The present invention relates to monospecific or bispecific antibody molecules that specifically bind the human DR5 antigen. The invention relates in particular to DR5-specific antibody molecules of the IgG1 isotype having a mutation in the Fc region that enhances clustering of IgG molecules after cell-surface antigen binding leading to the induction of DR5 signaling, apoptosis and cell death. The invention further relates to a combination of antibody molecules binding different epitopes on DR5. The invention also relates to (Continued)

pharmaceutical compositions containing these molecules and the treatment of cancer using these compositions.

23 Claims, 66 Drawing Sheets

Specification includes a Sequence Listing.

(30) Foreign Application Priority Data

| Dec. 7, 2015 | (DK) | 2015 00788 |
| Nov. 10, 2016 | (DK) | 2016 00701 |
| Nov. 10, 2016 | (DK) | 2016 00702 |

(51) Int. Cl.

| *C12N 15/10* | (2006.01) |
| *A61P 35/00* | (2006.01) |
| *C12N 15/62* | (2006.01) |
| *A61K 39/00* | (2006.01) |
| *C07K 16/46* | (2006.01) |
| *A61K 38/00* | (2006.01) |

(52) U.S. Cl.
CPC .............. *C12N 15/62* (2013.01); *A61K 38/00* (2013.01); *A61K 2039/505* (2013.01); *A61K 2039/507* (2013.01); *C07K 16/46* (2013.01); *C07K 2317/24* (2013.01); *C07K 2317/31* (2013.01); *C07K 2317/52* (2013.01); *C07K 2317/526* (2013.01); *C07K 2317/73* (2013.01); *C07K 2317/75* (2013.01)

(56) References Cited

U.S. PATENT DOCUMENTS

| 6,469,144 | B1 | 10/2002 | Ashkenazi | |
| 6,521,228 | B1 | 2/2003 | Wiley et al. | |
| 6,740,739 | B1 | 5/2004 | Ashkenazi et al. | |
| 6,872,568 | B1 | 3/2005 | Ni et al. | |
| 7,064,189 | B2 | 6/2006 | Salcedo et al. | |
| 7,704,502 | B2 | 4/2010 | Zhou et al. | |
| 7,736,637 | B2 | 6/2010 | Wiley et al. | |
| 7,740,847 | B2 * | 6/2010 | Allan | C07K 16/2896 424/133.1 |
| 9,127,070 | B2 * | 9/2015 | Ohtsuka | C07K 14/70578 |
| 2002/0155109 | A1 | 10/2002 | Lynch | |
| 2004/0147725 | A1 | 7/2004 | Chuntharapai et al. | |
| 2005/0233958 | A1 | 10/2005 | Ni et al. | |
| 2005/0244857 | A1 | 11/2005 | Ni et al. | |
| 2007/0026000 | A1 | 2/2007 | Ashkenazi et al. | |
| 2008/0248037 | A1 | 10/2008 | Li et al. | |
| 2009/0013117 | A1 | 1/2009 | Huang | |
| 2009/0022707 | A1 | 1/2009 | Kimberly et al. | |
| 2015/0175707 | A1 | 6/2015 | De Jong et al. | |
| 2015/0353636 | A1 | 12/2015 | Parren et al. | |
| 2019/0144554 | A1 | 5/2019 | Overdijk et al. | |
| 2019/0202926 | A1 | 7/2019 | Beurskens et al. | |
| 2019/0276549 | A1 | 9/2019 | De Jong et al. | |
| 2020/0181277 | A1 | 6/2020 | Beurskens et al. | |

FOREIGN PATENT DOCUMENTS

| WO | 2010/003766 | A2 | 1/2010 |
| WO | 2013/004842 | A2 | 1/2013 |
| WO | 2014/006217 | A1 | 1/2014 |
| WO | 2014/009358 | A1 | 1/2014 |
| WO | 2014/108198 | A1 | 7/2014 |
| WO | 2017/093447 | A1 | 6/2017 |
| WO | 2017/093448 | A1 | 6/2017 |

OTHER PUBLICATIONS

Chen et al., Enhancement and destruction of antibody function by somatic mutation:unequal occurrence is controlled by V gene combinatorial associations, EMBO J. 14(12):2784-2794. (Year: 1995).*
Lamminmaki et al., Crystal structure of a recombinant anti-estradiol Fab complex with 17Beta-estradiol, J. Biol. Chem. 276(39): 36687-94. (Year: 2001).*
MacCallum et al., Antibody-antigen interactions: contact analysis and binding site topography, J. Mol. Blol. 262:732-745. (Year: 1996).*
Sadarangani et al., TRAIL mediates apoptosis in cancerous but not normal primary cultured cells of the human reproductive tract., Apoptosis, 12(1):73-85, Jan. 2007.*
MacFarlane, M. Death receptors at the molecular level: therapeutic implications, in *Cell Death*, Melino and Vaux, Eds., John Wiley & Sons: Singapore, 2010., pp. 117-136, only pp. 117, 124-126 attached.*
Qiu et al., A novel anti-DR5 chimeric antibody and epirubicin synergistically suppress tumor growth, IUBMB Life, 64(9):757-765, Sep. 2012.*
Secchiero et al., Selection and characterization of a novel agonistic human recombinant anti-TRAIL-R2 minbody with anti-leukimeic activity, Int. J.Immunopathol. Pharmacol. 22(1):73-83, 2009.*
Yano et al., Distribution and function of EGFR in human tissue and the effect of EGFR tyrosine kinase inhibition, Anticancer Res. 23:3629-3650, 2003.*
Adams, C., et al, "Structural and functional analysis of the interaction between the agonistic monoclonal antibody Apomab and the proapoptotic receptor DR5," Cell Death & Differentiation, vol. 15 : 751-761(2008).
Ashkenazi, A. et al., "Safety and antitumor activity of recombinant soluble Apo2 ligand," J Clin Invest., vol. 104 (2):155-162 (1999).
Chinnaiyan, A.M., et al., "Combined effect of tumor necrosis factor-related apoptosis-inducing ligand and ionizing radiation in breast cancer therapy," PNAS, vol. 97(4):1754-1759 (2000).
De Jong, R. et al., "A Novel Platform for the Potentiation of Therapeutic Antibodies Based on Antigen-Dependent Formation of IgG Hexamers at the Cell Surface," PLOS Biology, vol. 14 (1): e1002344 (2016).
Derosier, L. et al., "Combination Treatment with TRA-8 Anti-Death Receptor 5 Antibody and CPT-11 Induces Tumor Regression in an Orthotopic Model of Pancreatic Cancer," Clin Cancer Res., vol. 13(18 Pt2) 5535s-5543s (2007).
Derosier, L. et al., "TRA-8 anti-DR5 monoclonal antibody and gemcitabine induce apoptosis and inhibit radiologically validated orthotopic pancreatic tumor growth," Mol Cancer Ther., vol. 6(12 Pt 1):3198-3207 (2007).
Gieffers, C. et al., "APG350 induces superior clustering of TRAIL receptors and shows therapeutic antitumor efficacy independent of cross-linking via Fcgamma receptors," Mol Cancer Ther., vol. 12(12): 2735-2747 (2013).
Hotte, S.J. et al., "A Phase 1 Study of Mapatumumab (Fully Human Monoclonal Antibody to TRAIL-R1) in Patients with Advanced Solid Malignancies," Clin Cancer Res., vol. 14(11):3450-3455 (2008).
Huet, H. et al., "Multivalent nanobodies targeting death receptor 5 elicit superior tumor cell killing through efficient caspase induction," MAbs, vol. 6(6):1560-1570 (2014).
Hymowitz, S. et al., "Triggering cell death: the crystal structure of Ap2L/TRAIL in a complex with death receptor 5," Mol Cell., vol. 4(4):563-71 (1999).
International Preliminary Report on Patentability, PCT/EP2013/064466, dated Jan. 13, 2015, 7 pages.
International Preliminary Report on Patentability, PCT/EP2016/079517, dated Jun. 5, 2018, 13 pages.
International Preliminary Report on Patentability, PCT/EP2016/079518, dated Jun. 5, 2018, 14 pages.
International Search Report and Written Opinion, PCT/EP2013/064466, dated Sep. 30, 2013, 10 pages.
International Search Report and Written Opinion, PCT/EP2016/079517, dated Mar. 31, 2017, 19 pages.

(56) References Cited

OTHER PUBLICATIONS

International Search Report and Written Opinion, PCT/EP2016/079518, dated Mar. 31, 2017, 21 pages.
Nagane, M. et al., "Predominant antitumor effects by fully human anti-TRAIL-receptor2 (DR5) monoclonal antibodies in human glioma cells in vitro and in vivo," Neuro-Oncology, vol. 12(7): 687-700 (2010).
Oliver, PG et al., "Treatment of human colon cancer xenografts with TRA-8 anti-death receptor 5 antibody alone or in combination with CPT-11," Clin Cancer Res., vol. 14(7):2180-2189 (2008).
Plummer, R. et al., "Phase 1 and pharmacokinetic study of lexatumumab in patients with advanced cancers," Clin Cancer Res., vol. 30 (13):6187-6194 (2007).
Reddy, A. et al., "Gene Expression Ratios Lead to Accurate and Translatable Predictors of DR5 Agonism across Multiple Tumor Lineages," PLoS One, vol. 10(9): e0138486 (2015).
Rowinsky, E., "Targeted Induction of Apoptosis in Cancer Management: The Emerging Role of Tumor Necrosis Factor-Related Apoptosis-Inducing Ligand Receptor Activating Agents," J Clin Oncol., vol. 23(36):9394-9407 (2005).
Trivedi, R., et al., "Trailing TRAIL Resistance: Novel Targets for TRAIL Sensitization in Cancer Cells," Front Oncol., vol. 5 (69):20 pages (2015).
Twomey, J. et al., "Spatial dynamics of TRAIL death receptors in cancer cells," Drug Resist Updat., vol. 19:13-21 (2015).
Valley, C. et al., "Tumor Necrosis Factor-related Apoptosis-inducing Ligand (TRAIL) Induces Death Receptor 5 Networks That Are Highly Organized," J Biol Chem., vol. 287(25):21265-21278 (2012).
Wakelee, H.A et al., "Phase I and pharmacokinetic study of lexatumumab (HGS-ETR2) given every 2 weeks in patients with advanced solid tumors," Annals of Oncology, vol. 21, Issue 2:376-381 (2010).
Wang, et al., "Characterization of a novel anti-DR5 monoclonal antibody WD1 with the potential to induce tumor cell apoptosis," Cellular & Molecular Immunology, vol. 5: 55-60 (2008).
Wiley, S.R., et al., "Identification and Characterization of a New Member of the TNF Family that Induces Apoptosis," Immunity, vol. 3:673-682 (1995).
Wolf, E. et al., "Monoclonal antibody homodimers: enhanced antitumor activity in nude mice," Cancer Research, vol. 53(11):2560-2565 (1993).
Ashkenazi, A. et al., "Directing cancer cells to self-destruct with pro-apoptotic receptor agonists," Nat Rev Drug Discov., vol. 7(12):1001-1012 (2008).
Beurskens, F. et al., "Functional aspects of antigen- and Fc-dependent IgG hexamer formation," Antibody Biology & Engineering Gordon Research Conference, Mar. 22, 2016 Galveston, TX, 15 pages.
Breij, E. et al., "Functional aspects and therapeutic application of antigen-dependent formation of IgG hexamers at the cell surface," IBC Antibody Engineering & Therapeutics 2015, Dec. 7, 2015 San Diego, 25 pages.
Buchsbaum DJ et al., "Antitumor Efficacy of TRA-8 Anti-DR5 Monoclonal Antibody Alone or in Combination with Chemotherapy and/or Radiation Therapy in a Human Breast Cancer Model1," Cancer Res., vol. 9:3731-3734 (2003).
Buchsbaum DJ et al., "TRAIL receptor-targeted therapy," Future Oncol., vol. 2(4):493-508 (2006).
Daniel PT et al., "Activation induces sensitivity toward APO-1 (CD95)-mediated apoptosis in human B cells," J Immunol., vol. 152 (12) 5624-5632 (1994).
De Jong, R. et al., Improving therapeutic activity of agonistic DR5 antibodies by inducing target binding-dependent hexamer formation, PEGS DR 5, 1 page (2016).
De Jong, R. et al., "Therapeutic antibody potentiation by antigen- and Pc-dependent IgG hexamer formation," MipTec International Life Science Exhibition Session Biotherapeutics—Current challenges in protein science, Sep. 21, 2016, Basel, Switzerland, 37 pages.

Fox N.L. et al. "Tumor necrosis factor-related apoptosis-inducing ligand (TRAIL) receptor-1 and receptor-2 agonists for cancer therapy," Exper Opin Biol Ther., vol. 5(10):1-18 (2010).
Friess, T. et al., "Induction of avidity-driven hyperclustering of DR5 by a new FAP-DR5 bispecific antibody (RG7386) leads to strong antitumor efficacy," Abstract 952:, AACR 106th Annual Meeting 2015; Apr. 18-22, 2015; Philadelphia, PA, 5 pages (2015).
Georgakis GV et al., "Activity of selective fully human agonistic antibodies to the TRAIL death receptors TRAIL-R1 and TRAIL-R2 in primary and cultured lymphoma cells: induction of apoptosis and enhancement of doxorubicin- and bortezomib-induced cell death," British Journal of Hematology , vol. 25(37):5145-54 (2006).
Gura, T. et al., "How TRAIL Kills Cancer Cells, But Not Normal Cells," Science, vol. 277 (5327) 7 pages (1997).
Herbst R.S. et al., "A phase I safety and pharmacokinetic (PK) study of recombinant Apo2L/TRAIL, an poptosis-inducing protein in patients with advanced cancer," Abstract No. 3013, J Clin Oncol., vol. 24, 5 pages (2006).
Hibbert, R ., "From biology to technology: the HexaBody® platform," BPI Europe 2016, 27 pages.
Holland, P. et al., "Death receptor agonist therapies for cancer, which is the right TRAIL?," Cytokine Growth Factor Rev., vol. 25(2):185-193 (2014).
Ichikawa K. et al., "Tumoricidal activity of a novel anti-human DR5 monoclonal antibody without hepatocyte cytotoxicity," Nat. Med., vol. 7(8):954-960 (2001).
Kaplan-Lefko, P. et al., "AMG 655, a fully human agonistic antibody against death receptor 5, enhances the anti-tumor activity of gemcitabine in MiaPaCa2/T2, a pancreatic cancer model," AACR Annual Meeting—Apr 12-16, 2008; San Diego, CA, Abstract 399, 4 pages (2008).
Li J. et al,, "Antitumor efficacy of LBY135, an anti-DR5 monoclonal antibody, alone or in combination with chemotherapy in human colon tumor cell lines and xenografts," AACR Annual Meeting—Apr 14-18, 2007; Los Angeles, CA,. Abstract 4874, 4 pages (2007).
Li, J. et al., "DART® molecules with enhanced DR5 agonistic activity for improved cancer cell Cytotoxicity," Abstract 2464, AACR 106th Annual Meeting 2015, Apr. 18-22, 2015 Philadelphia, PA, 4 pages (2015).
Lim, B. et al., "Targeting TRAIL in the treatment of cancer: new developments," Expert Opin Ther Targets, vol. 19 (9):1171-1185 (2015).
Liu, F. et al., "The tetravalent anti-DR5 antibody without cross-linking direct induces apoptosis of cancer cells," Biome Pharmacother., vol. 70:41-45 (2015).
Long JW. et al., "TRA-8 (TRAIL-R2 Antibody) Based Combination Chemotherapy Produces a Survival Benefit in a Pancreatic Cancer Orthotopic Model," Abstract 40, J Virg Res., vol. 37:167 (2007).
Marini P. et al., "Combined treatment of colorectal tumours with agonistic TRAIL receptor antibodies HGS-ETR1 and HGS-ETR2 and radiotherapy: enhanced effects in vitro and dose-dependent growth delay in vivo," Oncogene, vol. 25 (37):5145-5154 (2006).
Miilenic, D. et al., "Construction, Binding Properties, Metabolism, and Tumor Targeting of a Single-Chain Fv Derived from the Pancarcinoma Monoclonal Antibody CC49," Cancer Res., vol. 51:6363-6371 (1991).
Zhang, X. et al., "Mechanisms of resistance of normal cells to TRAIL induced apoptosis vary between different cell types," FEBS Letters, vol. 482: 193-199 (2000).
Overdijk, M. et al., "Improving therapeutic activity of agonistic DR5 antibodies by inducing target binding-dependent hexamer formation," Abstract No. 592 , AACR DR5, 1 page (2016).
Pan, G. et al., "An Antagonist Decoy Receptor and a Death Domain-Containing Receptor for TRAIL," Science, vol. 277 (5327):815-818 (1997).
Parren P. Targeting cell surface antigens with a novel therapeutic antibody concept, Peptalk, 14th CIMT Annual meeting: Mechanisms of efficacy in cancer immunotherapy, May 12, 2016—Mainz, Germany, 30 pages.
Parren, P. et al., "Functional aspects and therapeutic application of antigen- and Fc-dependent formation of IgG hexamers at the cell surface," Keystone symposium "Antibodies as Drugs" Whistler, Canada, Mar. 7, 2016, 33 pages.

(56) References Cited

OTHER PUBLICATIONS

Schuurman, J. et al., "Functional Aspects of Antigen- and Fc-Dependent IgG Hexamer Formation," PEGS EU, Nov. 3, 2016, Lisbon, Portugal, 30 pages.

Sessler, T. et al., "Structural determinants of DISC function: new insights into death receptor-mediated apoptosis signaling," Pharmacol Ther., vol. 140(2):186-199 (2013).

Sheridan, J., et al., "Control of TRAIL-Induced Apoptosis by a Family of Signaling and Decoy Receptors," Science, vol. 277 (5327): 818-821 (1997).

Spierings, D. et al., "Tissue Distribution of the Death Ligand TRAIL and Its Receptors," Journal of Histochemistry & Cytochemistry, vol. 52(6): 821-831 (2004).

Vermot-Desroches C. et al., "Characterization of monoclonal antibodies directed against trail or trail receptors," Cellular Immunology, vol. 236 (1-2): 86-91 (2005).

Walczak et al., "Tumoricidal activity of tumor necrosis factor-related apoptosis-inducing ligand in vivo," Nature Medicine., vol. 5:157-163 (1999).

Wall J. et al., "AMG 655, a monoclonal antibody agonist directed against Death Receptor 5, induces apoptosis in human colon carcinoma cell lines and its therapeutic potential is enhanced in combination with chemotherapeutic agentsm," AACR Annual Meeting—Apr 12-16, 2008; San Diego, CA, Abstract 1326, 4 pages (2008).

Wartha, K. et al., "A novel bispecific Fap-Dr5 antibody inducing potent and tumor-specific death receptor 5 (Dr5) activation by fibroblast activation protein (Fap)-dependent crosslinking," Abstract 4573, Proceedings of the 105th Annual Meeting of the American Association for Cancer Research; Apr. 5-9, 2014; San Diego, CA. Philadelphia (PA): , 5 pages (2014).

Wassenaar, T. et al., "The conformation of the extracellular binding domain of Death Receptor 5 in the presence and absence of the activating ligand TRAIL: a molecular dynamics study," Protein, vol. 70(2):333-343 (2008).

Amgen Inc., "A phase lb study to evaluate the safety and tolerability of AMG 655 in combination with bortezomib or vorinostat in subjects with relapsed or refractory lymphoma," Public Results Redacted CSR Synopsis, Abbrev. Clin. Study Report: 20060340: pp. 2-11 (2012).

U.S. Appl. No. 14/413,178, filed Mar. 17, 2015, Rob N. De Jong.
U.S. Appl. No. 14/760,135, filed Jul. 9, 2015, Paul Parren.
U.S. Appl. No. 16/345,044, filed Apr. 25, 2019, Rob De Jong.
U.S. Appl. No. 16/482,747, filed Aug. 1, 2019, Frank Beurskens.
U.S. Appl. No. 14/413,178, dated Jun. 8, 2020.
U.S. Appl. No. 14/413,178, dated Apr. 24, 2019.
U.S. Appl. No. 14/413,178, dated Sep. 28, 2017.
U.S. Appl. No. 14/413,178, dated Mar. 24, 2017.
U.S. Appl. No. 14/413,178, dated Oct. 11, 2016.
U.S. Appl. No. 14/760,135, dated Jul. 10, 2019.
U.S. Appl. No. 14/760,135, dated Sep. 13, 2018.
U.S. Appl. No. 14/760,135, dated Jan. 24, 2018.
U.S. Appl. No. 14/760,135, dated Oct. 5, 2017.
U.S. Appl. No. 15/780,285, dated Feb. 21, 2020.

* cited by examiner

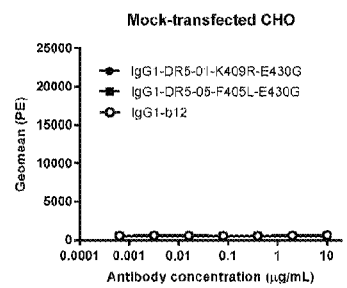
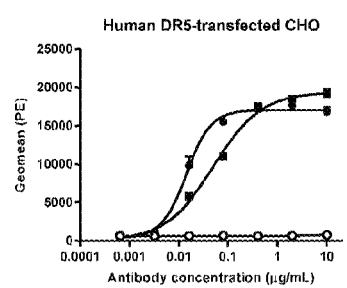
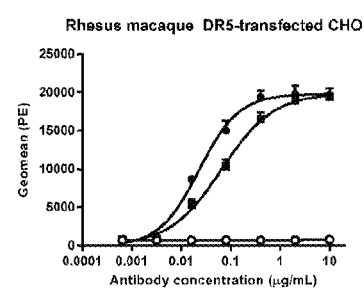
FIG. 4A        FIG. 4B        FIG. 4C

```
H.s.  --ITQQDLAPQQRAAPQQKRSSPSEGLCPPGHHISEDGRDCISCKYGQDY
          :  . :  :.   ::: : :   : ..::   .: :. : ::
M.m.  NP------AHNRPAGLQRPEESPSRGPCLAGQYLSEG--NCKPCREGIDY

H.s.  STHWNDLL-FCLRCTRCDSGEVELSPCTTTRNTVCQCEEGTFREEDSPEM
      ..: :   :  :. :: :   .: ,  :   : :::::.. ::: ..::::.
M.m.  TSHSNHSLDSCILCTVCKEDKVVETRCNITTNTVCRCKPGTFEDKDSPEI

H.s.  CRKCRTGCPRGMVKVGDCTPWSDIECVHK
      :. : . :  :   ..  :::   . .:: :
M.m.  CQSC-SNCTDGEEELTSCTPRENRKCVSK
```

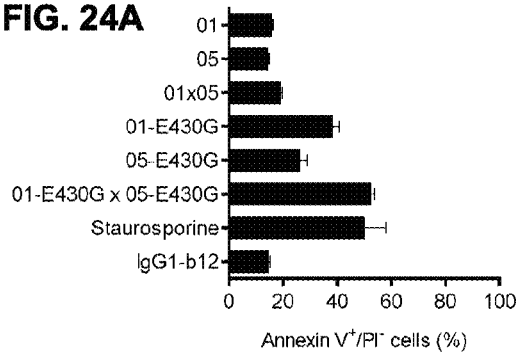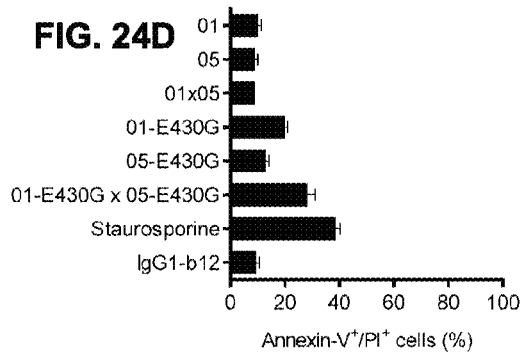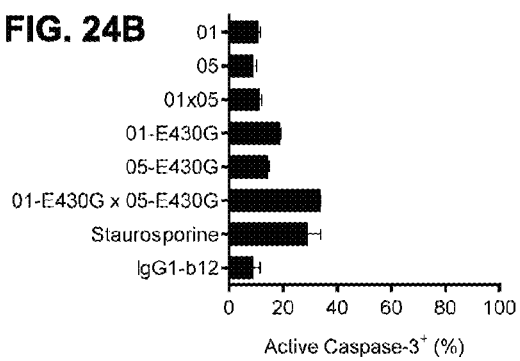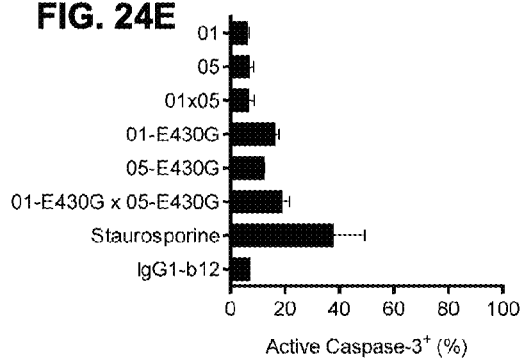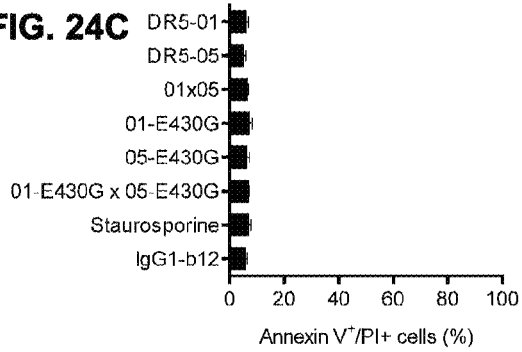

FIG. 46B
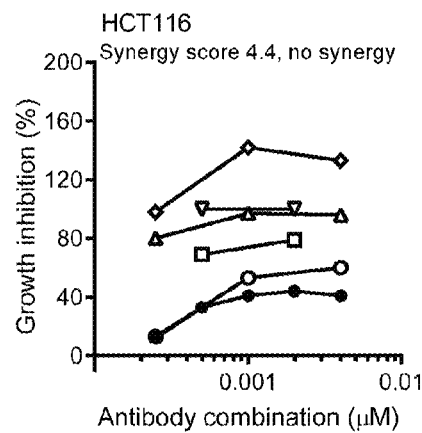
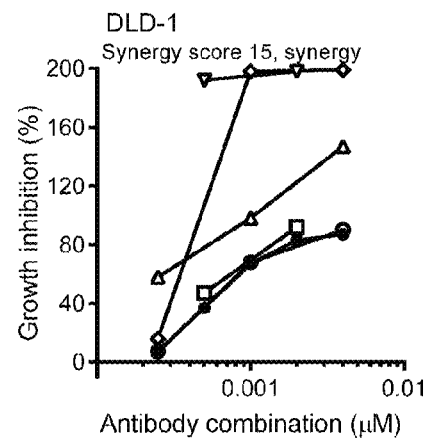
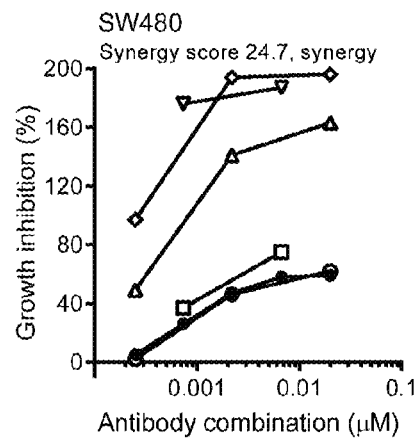
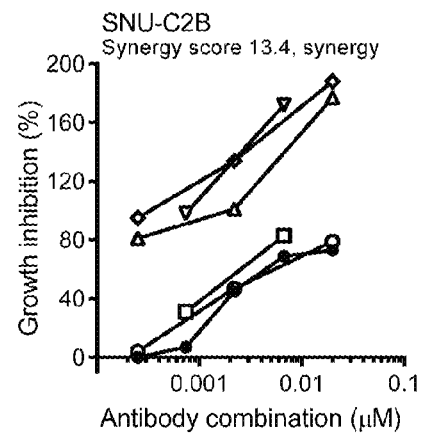
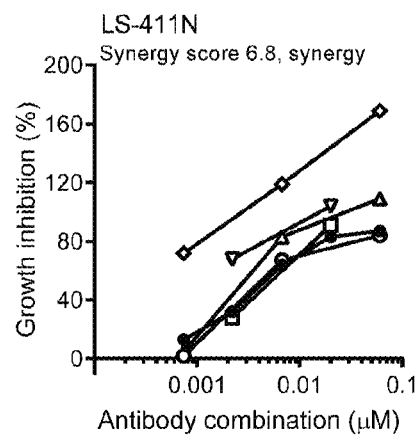

FIG. 46E
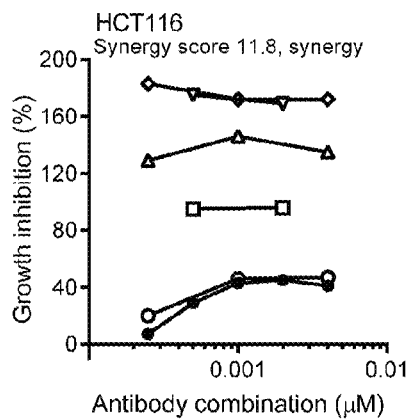
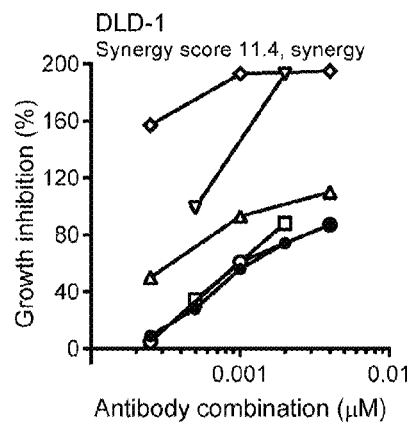
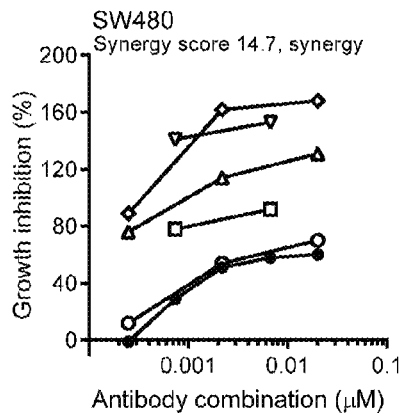
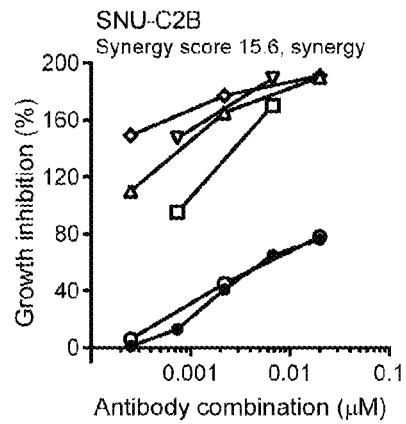
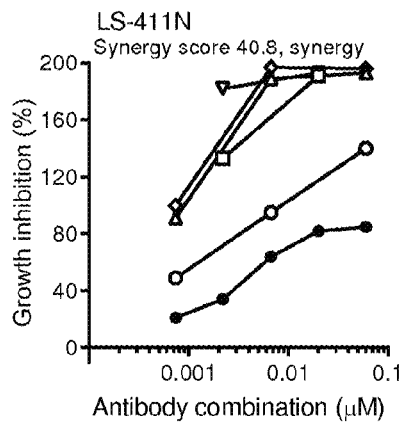

ANTI-DR5 ANTIBODIES AND METHODS OF USE THEREOF

CROSS-REFERENCE TO RELATED APPLICATIONS

This application is a Continuation of application Ser. No. 15/780,268, filed May 31, 2018, which is a 35 U.S.C. 371 national stage filing of International Application No. PCT/EP2016/079518, filed Dec. 1, 2016, which claims the benefit of Danish Patent Application Nos. PA 2015 00771, filed Dec. 1, 2015, PA 2015 00787, filed Dec. 7, 2015, PA 2015 00788, filed Dec. 7, 2015, PA 2016 00701, filed Nov. 10, 2016, and PA 2016 00702, filed Nov. 10, 2016. The contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Jun. 25, 2019, is named GMI_169AUSCN_SEQ.txt and is 144,175 bytes in size.

FIELD OF THE INVENTION

The present invention relates to monospecific or bispecific antibody molecules that specifically bind the human DR5 antigen. The invention relates in particular to DR5-specific antibody molecules of the IgG1 isotype having a mutation in the Fc region that enhances clustering of IgG molecules after cell surface antigen binding. The invention further relates to a combination of antibody molecules binding different epitopes on human DR5. The invention also relates to pharmaceutical compositions containing these molecules and the treatment of cancer and other diseases using these compositions.

BACKGROUND OF THE INVENTION

DR5, also known as death receptor 5, Tumor necrosis factor receptor superfamily member 10B, TNFRSF10B, TNF-related apoptosis-inducing ligand receptor 2, TRAIL receptor 2, TRAIL-R2 and CD262, is a cell surface receptor of the TNF receptor superfamily that binds tumor necrosis factor-related apoptosis-inducing ligand (TRAIL) and mediates apoptosis. DR5 is a single-pass type I membrane protein with three extracellular cysteine-rich domains (CRDs), a transmembrane domain (TM) and a cytoplasmic domain containing a death domain (DD). In the absence of ligand, DR5 exists in the cell membrane either as monomer or as pre-assembled complexes of two or three receptors through interactions of the first cysteine-rich domain, also known as pre-ligand assembly domain (PLAD) (Wassenaar et al., Proteins. 2008 Feb. 1; 70(2):333-43; Valley et al., J Biol Chem. 2012 Jun. 15; 287(25):21265-78; Sessler et al., Pharmacol Ther. 2013 November; 140(2):186-99). A Crystal structure of TRAIL in complex with the DR5 ectodomain showed that TRAIL binds to CRD2 and CRD3 in the extracellular domain of DR5 in a complex containing a trimeric receptor and a trimeric ligand (Hymowitz et al., Mol Cell. 1999 October; 4(4):563-71). The DR5 trimers can further cluster into higher-order receptor aggregates in lipid macrodomains, so-called lipid rafts (Sessler et al., Pharmacol Ther. 2013 November; 140(2):186-99). In the ligand-bound conformation, the cytoplasmic death domain-containing adaptor protein FADD associate with the intracellular DD surface of the oligomerized DR5 molecules and engage initiator caspases caspase-8 and caspase-10 to form the death-inducing signaling complex (DISC).

Based on the sensitivity of cancer cells to TRAIL-mediated apoptosis, numerous agents were developed to activate this pathway to induce apoptosis selectively in cancer cells. Human recombinant TRAIL (hrTRAIL), is being developed as dulanermin, and a series of conventional (monospecific, bivalent) anti-DR5 antibodies have been developed and tested in the clinic (reviewed in Ashkenazi et al., Nat Rev Drug Discov. 2008 December; 7(12):1001-12; Trivedi et al., Front Oncol. 2015 Apr. 2; 5:69): DR5 antibodies include lexatumumab (HGS-ETR2), HGS-TR2J, conatumumab (AMG655), tigatuzumab (CS-1008), drozitumab (Apomab) and LBY-135. Clinical studies with these compounds demonstrated that DR5 antibodies were generally well tolerated but failed to show convincing and significant clinical benefit. Efforts to enhance the efficacy of DR5 targeting antibodies mainly focus on (i) improving the sensitivity of cancer cells to DR5 agonists through combination treatment, (ii) developing biomarkers for better patient stratification, and (iii) the development of DR5-targeting agents that activate DR5 signaling and apoptosis-induction more effectively (reviewed in Lim et al., Expert Opin Ther Targets. 2015 May 25: 1-15; Twomey et al., Drug Resist Updat. 2015 March; 19:13-21; Reddy et al., PLoS One. 2015 Sep. 17; 10(9)). Different therapeutic formats for increasing DR5 activation have been described and include oligomerization of synthetic DR5 binding peptides, linear fusions of DR5-specific scaffolds, nanoparticle-based delivery systems of rhTRAIL or conatumumab and multivalent DR5 antibody-based formats (reviewed in Holland et al., Cytokine Growth Factor Rev. 2014 April; 25(2):185-93). APG880 and derivatives exist of two single chain TRAIL receptor binding (scTRAIL-RBD) molecules (TRAIL mimics) fused to the Fc part of a human IgG. Each scTRAIL-RBD has three receptor binding sites resulting in a hexavalent binding mode in the fusion protein (WO 2010/003766 A2). A prototype scTRAIL-RBD (APG350) has been described to induce FcγR-independent antitumor efficacy in vivo (Gieffers et al., Mol Cancer Ther, 2013. 12(12): p. 2735-47). A tetravalent anti-DR5 antibody fragment-derived construct, assembled by fusion of an anti-DR5 scFv fragment, human serum albumin residues and the tetramerization domain of human p53, has been shown to induce apoptosis more potently than the monovalent construct (Liu et al., Biomed Pharmacother. 2015 March; 70:41-5). Nanobody molecules are single domain antibody fragments (VHH) derived from camelid heavy chain-only antibodies, which, similarly to scFvs, can be linked to form multivalent molecules. Preclinical in vitro studies showed that TAS266, a tetravalent anti-DR5 Nanobody® molecule, was more potent than TRAIL or cross-linked DR5 antibody LBY-135, which was attributed to more rapid caspase activation kinetics (Huet et al., MAbs. 2014; 6(6):1560-70). TAS266 was also more potent in vivo than the parental murine mAb of LBY-135. MultYbody™ molecules (MultYmab technology) are based on the fusion of a homomultimerizing peptide to the Fc of one heavy chains in an IgG heterodimer (knob into hole), making MultYbody molecules intrinsically multivalent in solution. An anti-DR5 MultYbody was shown to induce potent killing in vitro. Dual-affinity re-targeting (DART) molecules are covalently-linked Fv-based diabodies. DR5 targeting tetravalent Fc DARTs comprising either tetravalency for a single (mono-epitopic DARTs) or two DR5 epitopes (bi-epitopic DARTs) were shown to be more potent than TRAIL and a conatumumab variant in inducing in cytotoxicity in vitro and in vivo (Li et al., AACR Annual Meeting Apr. 20, 2015, Poster abstract #2464). Alternatively, FcγR-independent avidity-driven DR5 hyperclustering can be mediated by a bispecific DR5×FAP antibody (RG7386) through simultaneous binding to DR5 on the cancer cell and to fibroblast activation protein (FAP) that is expressed on fibroblasts in the tumor microenvironment (Friess et al., AACR Annual Meeting Apr. 19, 2015, Presentation abstract #952; Wartha et al., Proceedings of the 105th Annual Meeting of the American Association for Cancer Research; 2014 Apr. 5-9; San Diego, Calif. Philadelphia (PA): AACR; Cancer Res 2014; 74(19 Suppl):Abstract nr 4573. doi:10.1158/1538-7445.AM2014-4573). Finally, specific combinations of two anti-DR5 antibodies recognizing different epitopes have shown enhanced agonistic efficacy in vitro and in vivo compared to combinations of two anti-DR5 antibodies recognizing overlapping or similar epitopes (WO2014/009358).

Above described approaches show enhanced efficacy compared to the conventional anti-DR5 antibodies in pre-clinical studies, however clinical data indicate that there is still a need for improving the DR5 agonists. Moreover, it is desirable for antibody-based formats to preserve a pharmacokinetic (PK) as well as other Fc-mediated effector functions of regular IgG, which usually is not the case with antibody fragment-based constructs. There is still a need for providing further DR5 agonists with improved properties.

Consequently, there is a need for providing improved anti-DR5 antibodies for the treatment of cancer, of infectious disease, autoimmune disease, cardiovascular anomalies and other diseases.

SUMMARY OF THE INVENTION

Surprisingly the inventors of the present invention have found that the introduction of a specific point mutation in the Fc region of an anti-DR5 antibody, which facilitates antibody clustering conditional on cell-surface antigen binding independent on secondary cross-linking, results in DR5 activation and significantly enhances the potency of the antibody in inducing apoptosis and cell death.

The objective of the present invention is to provide an improved anti-DR5 antibody for use in the treatment of cancer and other diseases. Such an improved antibody comprises a mutation in the Fc region. A further object of the present invention is to provide an improved composition for the treatment of cancer and other diseases comprising one or more anti-DR5 antibodies according the invention, e.g. wherein said antibodies bind to different epitopes on DR5. Such an improved composition as described herein comprises at least one anti-DR5 antibody according to the invention and more preferably the composition comprises two anti-DR5 antibodies binding to different regions on DR5, such as different non-competing epitopes on DR5.

The present invention provides an anti-DR5 antibody comprising an Fc region of a human immunoglobulin IgG and an antigen binding region binding to DR5, wherein the Fc region comprises a mutation at an amino acid position corresponding to position E430, E345 or S440 in human IgG1 according to EU numbering (Edelman et al., Proc Natl Acad Sci USA. 1969 May; 63(1):78-85; Kabat et al., Sequences of Proteins of Immunological Interest, Fifth Edition. 1991 NIH Publication No. 91-3242).

That is, the inventors of the present invention have in a first aspect of the invention found that anti-DR5 antibodies of the invention comprising a mutation in the Fc region increase apoptosis of DR5 positive cells such as tumor cells compared to anti-DR5 antibodies without a mutation at an amino acid position corresponding to position E430, E345 or S440 in human IgG1, EU numbering. That is, the anti-DR5 antibody of the present invention is suitable for the treatment of DR5 positive or expressing tumors.

In one embodiment of the present invention the anti-DR5 antibody comprises a mutation at an amino acid position corresponding to E430 in human IgG1 according to EU numbering, wherein the mutation is selected form the group consisting of: E430G, E430S, E430F and E430T.

In one embodiment of the present invention the anti-DR5 antibody comprises an Fc region of a human immunoglobulin IgG and an antigen binding region binding to DR5, wherein the Fc region comprises the mutation E430G (glutamic acid at position 430 into glycine) or E345K (glutamic acid at position 345 into lysine) in human IgG1 according to EU numbering.

In one embodiment of the present invention the anti-DR5 antibody comprises an Fc region of a human IgG1 and an antigen binding region binding to DR5, wherein the Fc region comprises a E430G mutation.

In one embodiment of the present invention the anti-DR5 antibody comprises a mutation at an amino acid position corresponding to E345 in human IgG1 according to EU numbering, wherein the mutation is selected form the group consisting of: E345K, E345Q, E345R and E345Y.

In one embodiment of the present invention the anti-DR5 antibody comprises an Fc region of a human IgG1 and an antigen binding region binding to DR5, wherein the Fc region comprises an E345K mutation.

In one embodiment of the present invention the anti-DR5 antibody comprises a mutation at an amino acid position corresponding to S440 in human IgG1 according to EU numbering, wherein the mutation is selected form the group consisting of: S440W and S440Y.

In one embodiment of the present invention the anti-DR5 antibody comprises an Fc region of a human IgG1 and an antigen binding region binding to DR5, wherein the Fc region comprises a S440Y mutation.

In one aspect the invention provides a composition comprising one or more antibodies binding to DR5. In one embodiment the composition comprises one or more antibodies binding to different epitopes on DR5. Hereby are embodiments are provided where the antibodies bind different epitopes or require different amino acids within the DR5 sequence (SEQ ID NO 46) for binding to DR5. In one embodiment the composition comprises anti-DR5 antibodies which do not compete for binding to DR5, that is in one embodiment the anti-DR5 antibodies bind to non-overlapping epitopes.

In another aspect the invention provides a bispecific antibody comprising one or more antigen binding regions binding to DR5.

In one embodiment of the present invention the bispecific antibody comprises an Fc region comprising a first and a second heavy chain, wherein said first and second heavy chain comprises a mutation at an amino acid position corresponding to E430, E345 or S440 in human IgG1, EU numbering.

In one embodiment of the present invention the bispecific antibody comprises an Fc region comprising a first and a second heavy chain, wherein said first heavy chain comprises a mutation corresponding to position F405 and E430 and wherein said second heavy chain comprises a mutation corresponding to position K409 and E430, wherein the amino acid position is corresponding to human IgG1 according to EU numbering.

In one embodiment of the present invention the bispecific antibody comprises an Fc region comprising a first heavy chain with a F405L mutation and a second heavy chain with a K409R mutation in human IgG1 according to EU numbering. In another embodiment of the invention the bispecific antibody comprises an Fc region comprising a first heavy chain with a K409R mutation and a second heavy chain with a F405L mutation in human IgG1 according to EU numbering.

In yet another aspect the invention provides a method of treating a disease comprising administering to an individual in need thereof an effective amount of an antibody or composition as described herein. In one embodiment of the invention the disease is cancer.

In another aspect of the invention the anti-DR5 antibody, bispecific antibody or composition according to the present invention is for use as a medicament. In one embodiment the anti-DR5 antibody, bispecific antibody or composition is for use in treatment of a disease. In one embodiment the disease is a cancer or a tumor.

In another aspect the invention provides a kit of parts comprising an antibody or composition according to any one of the preceding claims, wherein said antibody or composition is in one or more containers such as a vial.

In another aspect the invention provides for the use of an antibody or a composition as described herein for the manufacture of a medicament for treatment of a disease. In one embodiment the invention provides the use of an antibody or a composition as described herein for the manufacture of a medicament for treatment of cancer.

The anti-DR5 antibodies and compositions comprising anti-DR5 antibodies described herein are directed against or specific for human DR5. The anti-DR5 antibodies and compositions described herein cross-react with rhesus and cynomolgus monkey DR5. In particular, in one embodiment of the invention the anti-DR5 antibodies and compositions bind specifically to the extracellular domain of human DR5. In one particular embodiment of the invention the antibodies and compositions comprising anti-DR5 antibodies bind to human DR5 at non-overlapping epitopes. That is in one embodiment the composition comprises at least one anti-DR5 antibody according to the invention. In one embodiment the composition comprises a first anti-DR5 antibody and a second anti-DR5 antibody according to the invention. That is a first anti-DR5 antibody described herein does not block binding of a second anti-DR5 antibody described herein. In one particular embodiment a composition described herein comprise a first and a second anti-DR5 antibody binding to human DR5 and the first anti-DR5 antibody does not block binding of the second anti-DR5 antibody to human DR5.

The anti-DR5 antibodies and compositions comprising anti-DR5 antibodies of the present invention i.e. anti-DR5 antibodies comprising an amino acid mutation in the Fc region can generally be used to modulate the activity of DR5. In one embodiment the anti-DR5 antibody or composition may trigger, activate and/or increase or enhance the signaling that is mediated by DR5. That anti-DR5 antibodies comprising an amino acid mutation in the Fc region according to the invention may increase or enhance the signaling that is mediated by DR5 is to be understood as when the signaling is compared to the same anti-DR5 antibody without said mutation in the Fc region. In one embodiment the anti-DR5 antibody or composition will have an agonistic effect on DR5 and in particular trigger or increase the downstream effects of DR5. That anti-DR5 antibodies comprising an amino acid mutation in the Fc region according to the invention may have an agonistic effect on DR5 is to be understood as when the agonistic effect is compared to the DR5 ligand TRAIL or the same anti-DR5 antibody i.e. having the same CDR sequences but without said mutation in the Fc region according to the invention. That is anti-DR5 antibodies or compositions of the present invention in able to induce apoptosis or cell death in cells, tumor mass or tissues expressing DR5, such as cancer cells or a tumor.

In one embodiment of the invention the anti-DR5 antibody or composition described herein induce, trigger, increase or enhance apoptosis, cell death or growth arrest in cells or tissues expressing DR5, such as cancer cells, tumor cells or a tumor compared to the same anti-DR5 antibody or composition without said mutation in the Fc region. In one embodiment the anti-DR5 antibodies or compositions described herein are capable of binding to DR5 on a cell surface, and in particular binding to DR5 in such a way that the signaling mediated by DR5 is induced, triggered, increased or enhanced compared to the same anti-DR5 antibody or composition without said mutation in the Fc region. In one embodiment the antibodies or compositions described herein may be such that they are capable of binding to DR5 in such a way that apoptosis or cell death is induced in cancer or tumor cells, tumors or tissues expressing DR5.

In one embodiment the antibodies or compositions of the present invention induce, trigger, increase or enhance apoptosis or cell death in cancer cells or cancer tissues expressing DR5. The increased or enhanced apoptosis or cell death can be measured by an increase or enhanced level of phosphatidylserine exposure on cells exposed to or treated with one or more anti-DR5 antibodies of the invention. Alternatively, the increase or enhanced apoptosis or cell death can be measured by measuring activation of caspase 3 or caspase 7 in cells that have been exposed to or treated with one or more anti-DR5 antibodies of the invention. Alternatively, the increase or enhanced apoptosis or cell death can be measured by a loss of viability in cell cultures that have been exposed to or treated with one or more anti-DR5 antibodies of the invention, compared to untreated cell cultures. Induction of caspase-mediated apoptosis can be assessed by demonstrating inhibition of the loss of viability after exposure to DR5 antibody by a caspase-inhibitor, for example ZVAD.

were tested flowcytometric analysis on FACS for binding to COLO 205 cells. Binding is expressed as geometric mean of fluorescence intensity. Anti-gp120 antibody IgG1-b12 was used as negative control. Error bars indicate the standard deviation.

FIGS. 4A-4C show binding of anti-DR5 antibodies to human and rhesus monkey DR5. Human-mouse chimeric antibodies IgG1-DR5-01-K409R-E430G and IgG1-DR5-05-F405L-E430G were tested in flowcytometric analysis on FACS for binding to (FIG. 4A) mock-transfected CHO cells, (FIG. 4B) human DR5-transfected CHO cells and (FIG. 4C) Rhesus macaque DR5-transfected CHO cells. Binding is expressed as geometric mean of fluorescence intensity. Error bars indicate the standard deviation.

FIGS. 5A-5D show (FIG. 5A) Sequence alignment of part of the extracellular domains of human DR5 and mouse DR5 using EMBOSS Matcher (www.ebi.ac.uk/Tools/psa/emboss_matcher/); (.) similar amino acid; (:) identical amino acid. (FIG. 5B) Graphical representation of the domain-swapped DR5 extracellular domain (white: human DR5 sequences; black: mouse DR5 sequences). Amino acid number refer to the human sequence and domain swaps were made based on the alignment shown in panel A. (FIG. 5C) Binding of IgG1-hDR5-01-F405L and the isotype control antibody IgG1-b12 to a panel of human-mouse chimeric DR5 molecules, as assessed by flow cytometry. In each domain-swapped DR5 molecule, specific human amino acids have been replaced by the mouse sequence, as indicated on the x-axis. Error bars indicate the standard deviation of duplicate samples. (FIG. 5D) Binding of IgG1-hDR5-05-F405L to a panel of human-mouse chimeric DR5 molecules, as assessed by flow cytometry. In each domain-swapped DR5 molecule, specific human amino acids had been replaced by the mouse sequence, as indicated on the x-axis. IgG1-b12 was included an isotype control antibody. Error bars indicate the standard deviation of duplicate samples.

Figure 6A:
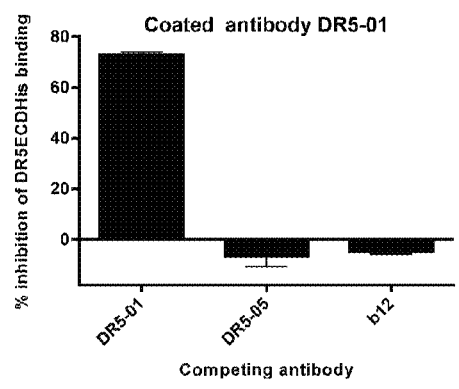
Figure 6B:
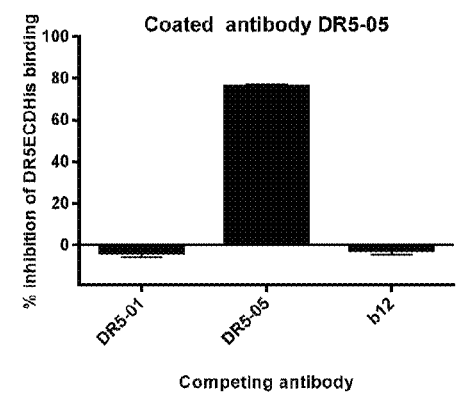

FIGS. 6A and 6B show crossblock ELISA with DR5-01 and DR5-05 antibodies. Graphs represent inhibition of binding of coated IgG1-hDR5-01-E430G (FIG. 6A) or IgG1-hDR5-05-E430G (FIG. 6B) to soluble DR5ECD-FcHisCtag in the presence of competing antibody IgG1-hDR5-01-E430G or IgG1-hDR5-05-E430G as measured by ELISA. Anti-gp120 antibody IgG1-b12 (b12) was used as negative control. DR5-01 is IgG1-hDR5-01-E430G; DR5-05 is IgG1-hDR5-05-E430G.

Figure 7A:
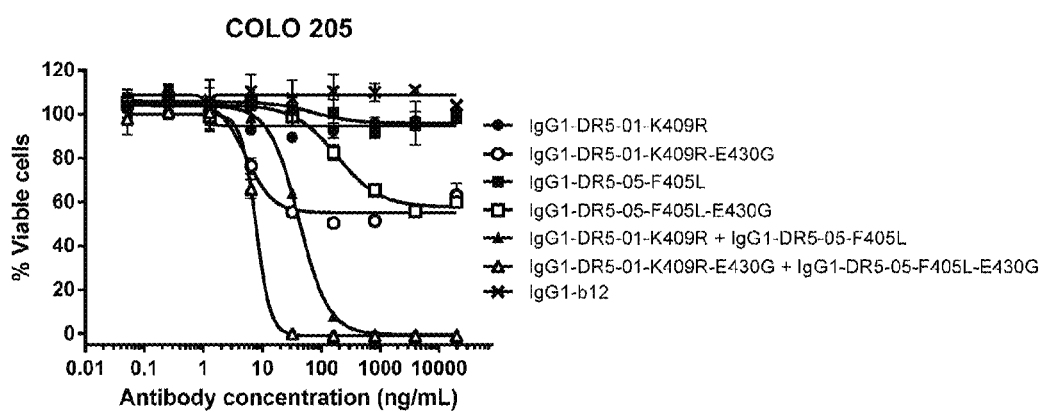
Figure 7B:
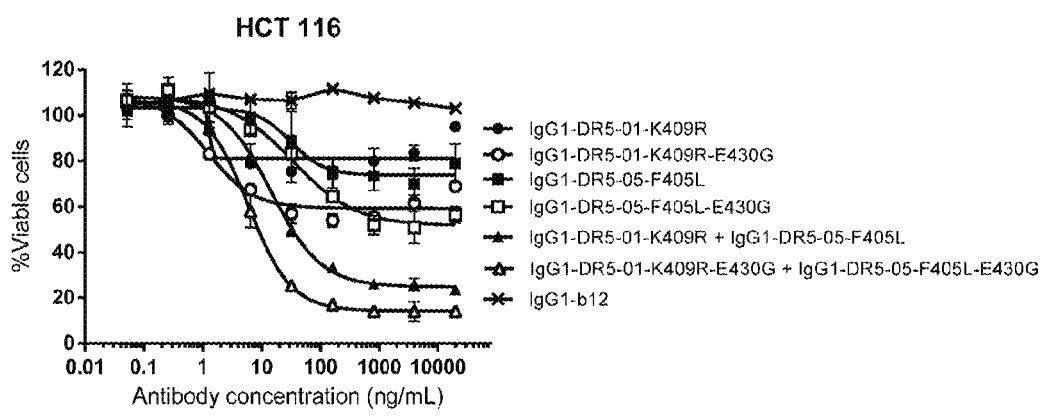

FIGS. 7A and 7B show a viability assay with variants of DR5-01 and DR5-05 antibodies. Introduction of the E430G hexamerization-enhancing mutation results in enhanced induction of killing of DR5-positive COLO 205 (FIG. 7A) and HCT 116 (FIG. 7B) colon cancer cells by the single human-mouse chimeric antibodies IgG1-DR5-01-K409R and IgG1-DR5-05-F405L used alone and by the combination thereof. Error bars indicate standard deviation.

Figure 8A:
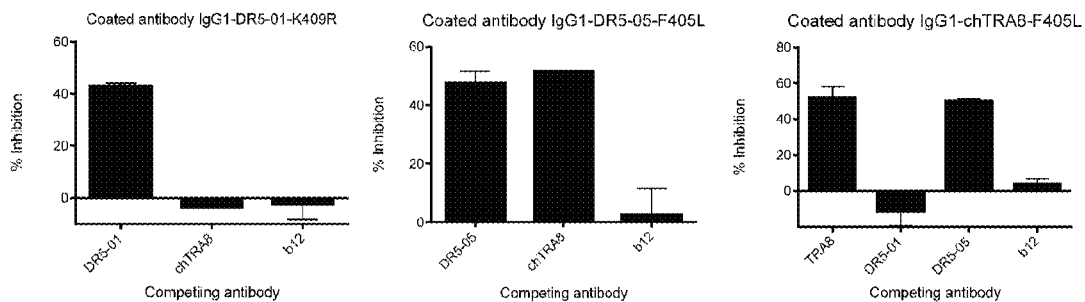
Figure 8B:
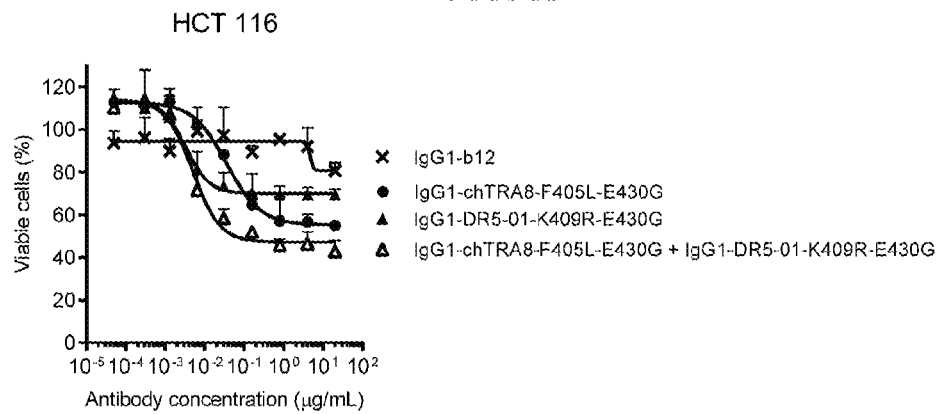
Figure 8C:
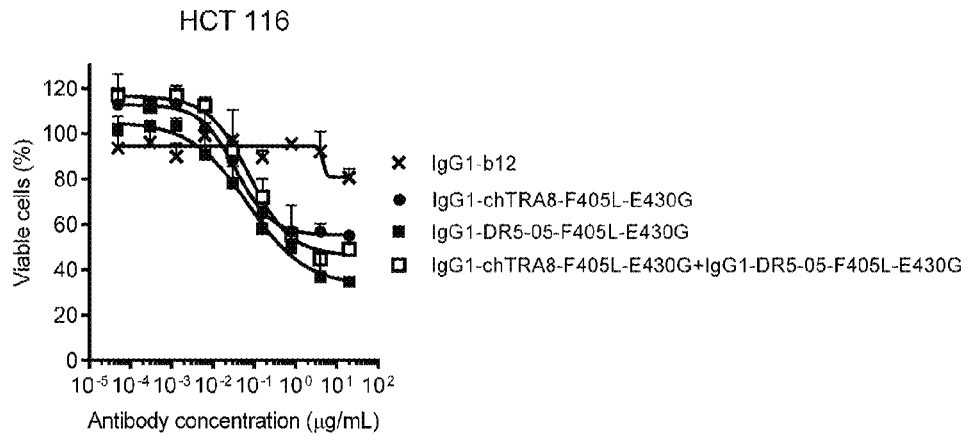

FIGS. 8A-8C show (FIG. 8A) crossblock ELISA between IgG1-chTRA8-F405L and IgG1-DR5-01-K409R or IgG1-DR5-05-F405L, respectively. Combining the two non-crossblocking anti-DR5 antibodies IgG1-chTRA8-F405L-E430G and IgG1-DR5-01-K409R-E430G (FIG. 8B) resulted in enhanced induction of killing of HCT 116 colon cancer cells (decreased EC50), whereas combining the two crossblocking antibodies IgG1-chTRA8-F405L-E430G and IgG1-DR5-05-F405L-E430G (FIG. 8C) did not, as determined in a 3-days viability assay. Error bars indicate standard deviation.

Figure 9A:
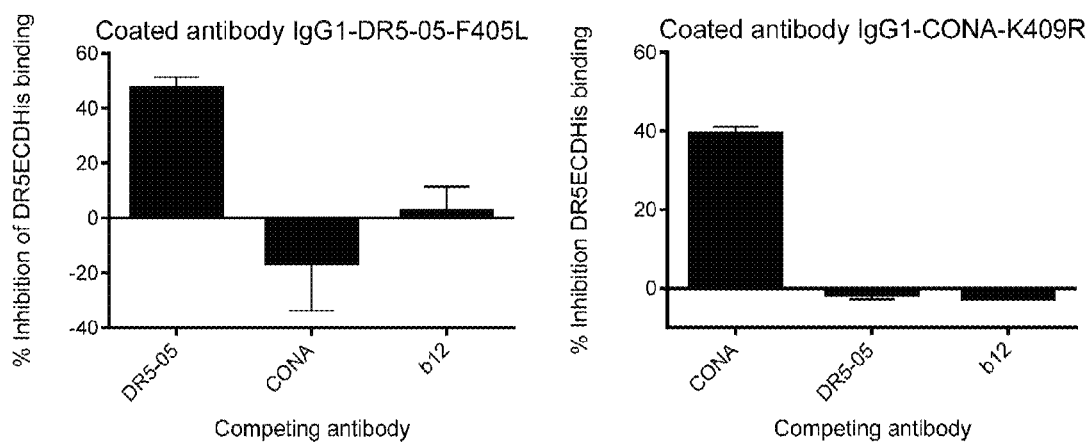
Figure 9B:
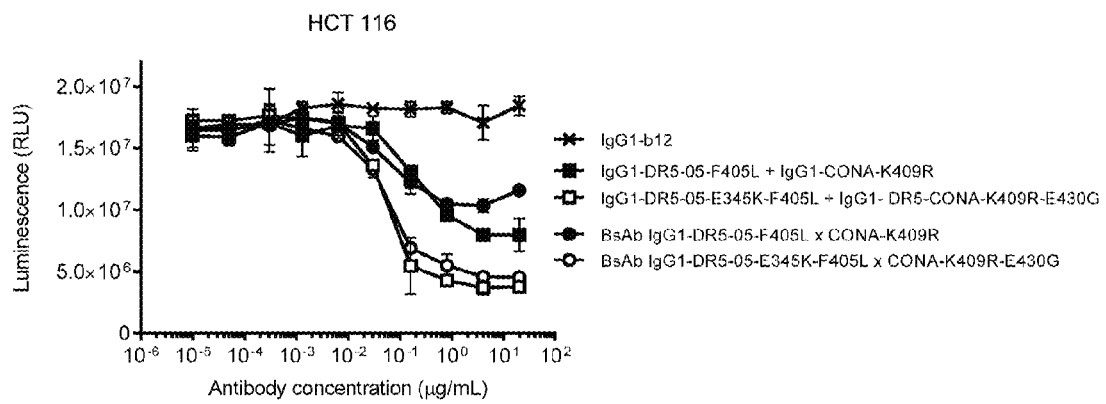

FIGS. 9A and 9B that introduction of a hexamerization-enhancing mutation results in enhanced induction of killing of HCT 116 colon cancer cells by the combination of non-crossblocking antibodies IgG1-DR5-05-F405L-E345K+IgG1-CONA-K409R-E430G and BsAb IgG1-DR5-05-F405L-E345K×CONA-K409R-E430G. (FIG. 9A) crossblock ELISA with IgG1-CONA-K409R and IgG1-DR5-05-F405L. (FIG. 9B) 3-days viability assay. Error bars indicate standard deviation. RLU: Relative Luminescence Units.

Figure 10:
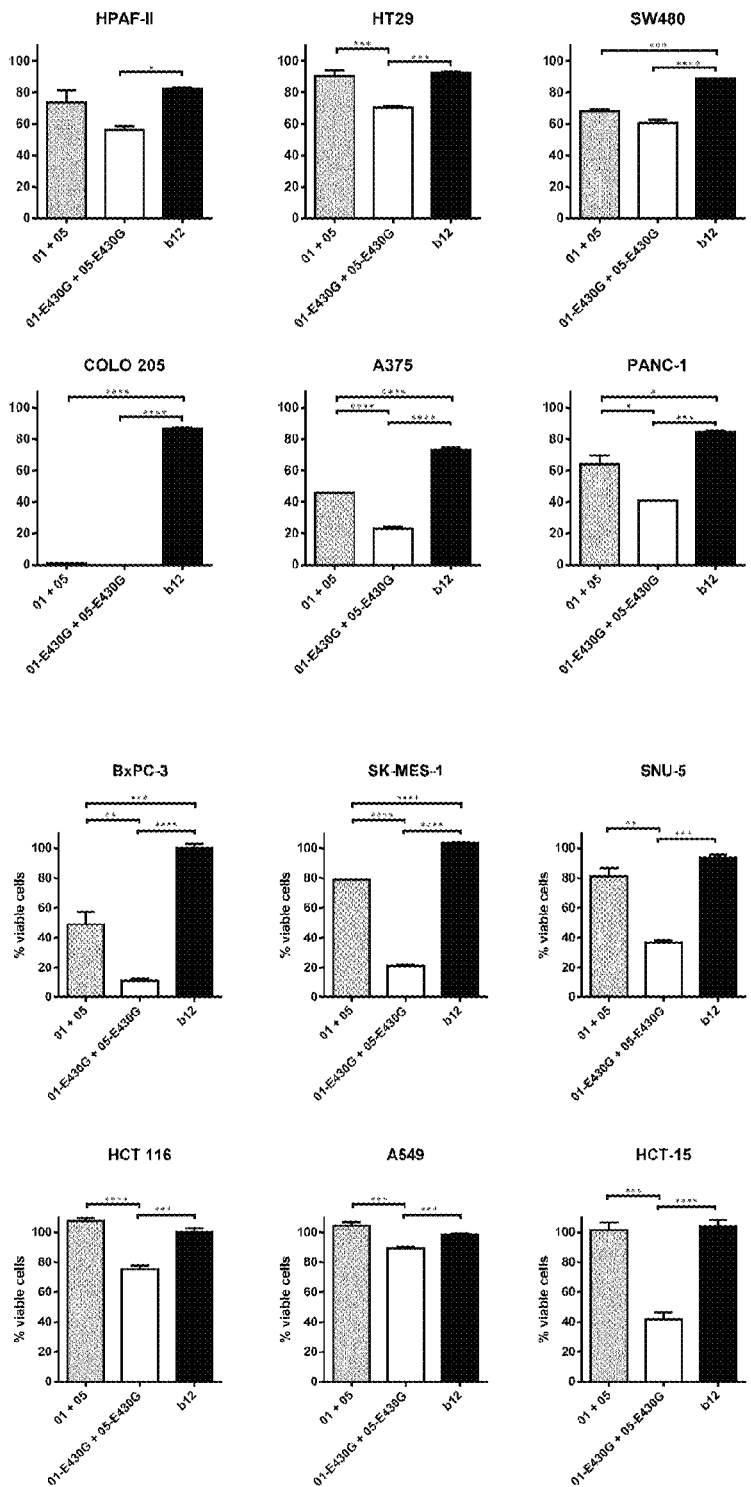

FIG. 10 shows that the combination of IgG1-DR5-01-K409R-E430G+IgG1-DR5-05-F405L-E430G reduces the viability of a large panel of different human cancer cell lines, as determined in a 3-days viability assay. Graphs show the mean+/−standard deviation from duplicate samples. * p<0.05,  p<0.01, * p<0.001, **** p<0.0001 (One-way ANOVA with Tukey's multiple comparisons test).

Figure 11:
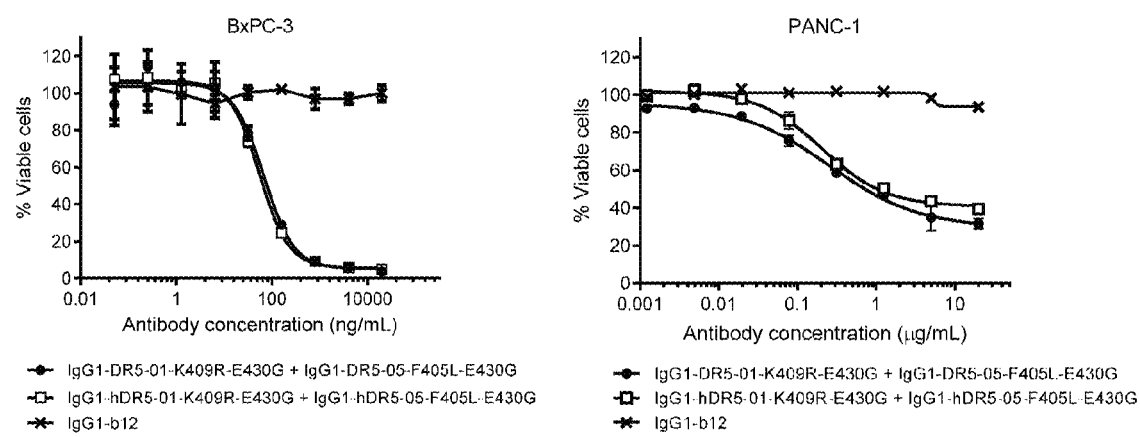

FIG. 11 shows the potency of the combination of humanized IgG1-hDR5-01-K409R-E430G+IgG1-hDR5-05-F405L-E430G antibodies and of the combination of chimeric IgG1-DR5-01-K409R-E430G+IgG1-DR5-05-F405L-E430G antibodies as measured in a viability assay on B×PC-3 and PANC-1 pancreatic cancer cell lines. Graphs represent mean values of duplicate (B×PC-3) or triplicate (PANC-1) samples+/−standard deviation.

Figure 12A:
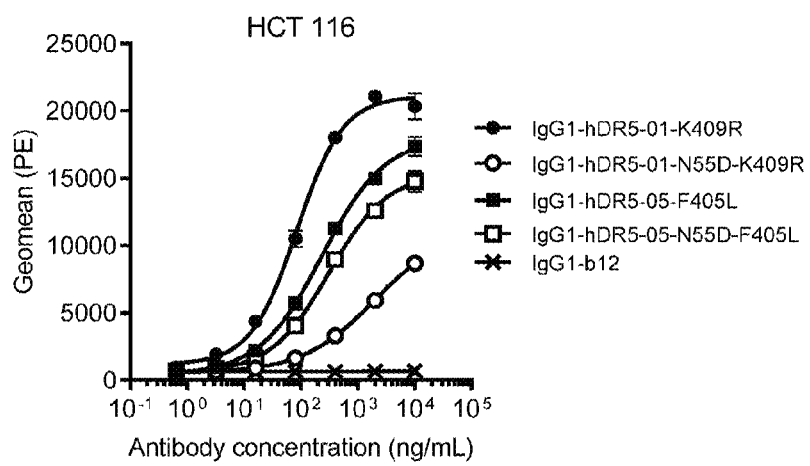
Figure 12B:
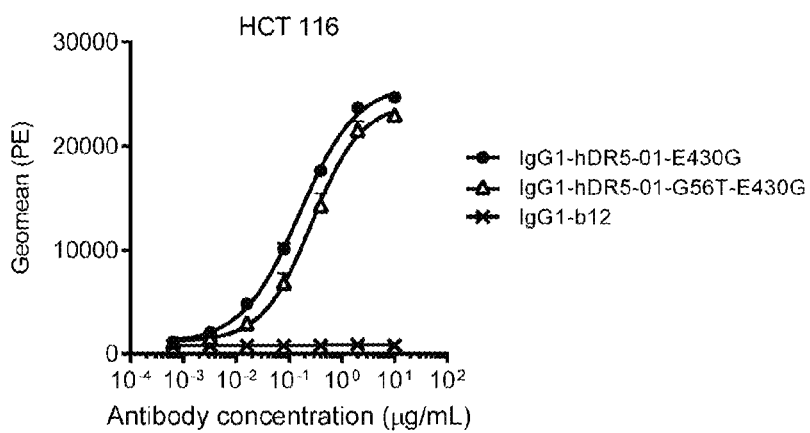
Figure 12C:
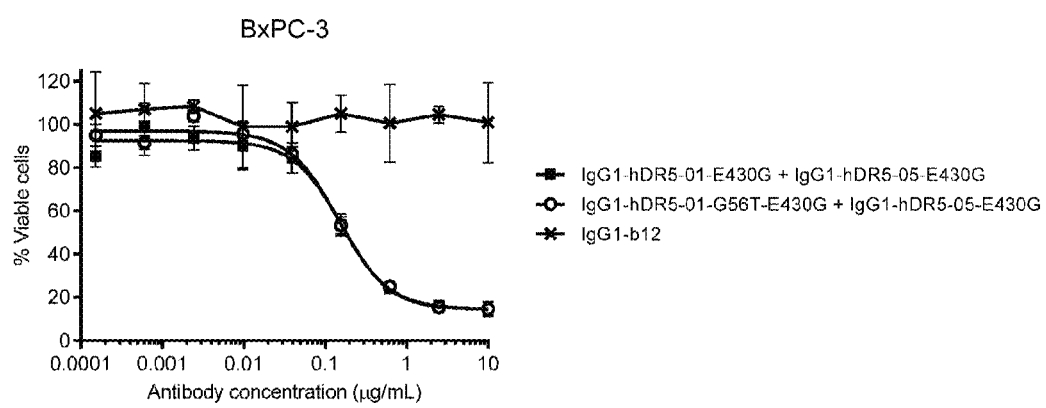

FIGS. 12A-12C show (FIG. 12A) Flowcytometric analysis using FACS analysis to study the effect of mimicking deamidation in humanized antibodies IgG1-hDR5-01-K409R and IgG1-hDR5-05-F405L on binding to HCT 116 human colon cancer cells. Introduction of the Asn deamidation-mimicking mutation N55D resulted in decreased binding of IgG1-hDR5-01-K409R, but had minimal effect on binding of IgG1-hDR5-05-F405L. (FIG. 12B) Flowcytometry analysis to study the effect of preventing deamidation in humanized antibody DR5-01 on binding to HCT 116 human colon cancer cells. Introduction of the amino acid substitution G56T in IgG1-hDR5-01-E430G had no effect on the binding of the antibody to HCT 116 cells. Binding is expressed as Geometric mean of fluorescence intensity. (FIG. 12C) Potency of the combination of humanized antibodies IgG1-hDR5-01-G56T-E430G+IgG1-hDR5-05-E430G as measured in a viability assay on B×PC-3 pancreatic cancer cells. Graphs represent mean values of duplicate samples+/−standard deviation.

Figure 13A:
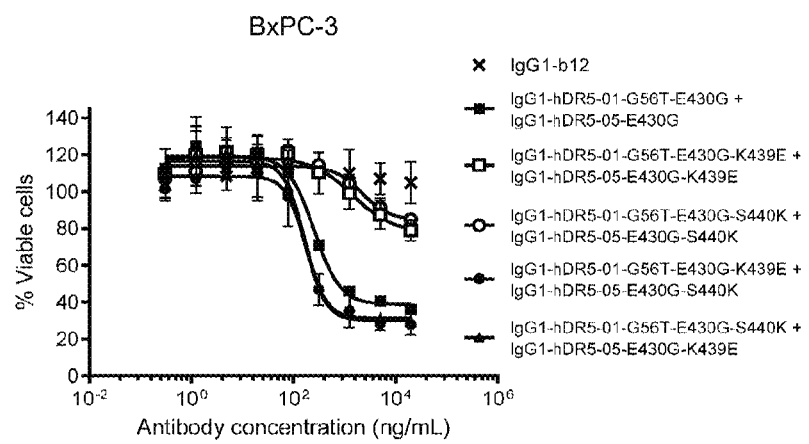
Figure 13B:
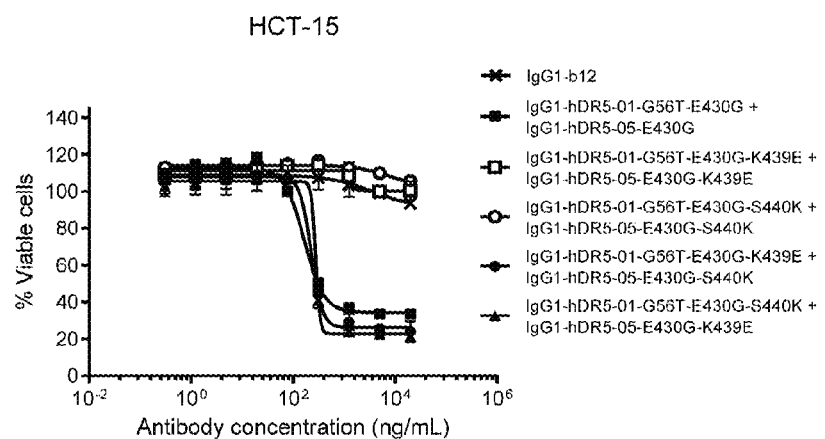

FIGS. 13A and 13B viability assay with repulsing and complementary variants of IgG1-hDR5-01-G56T-E430G and IgG1-hDR5-05-E430G. Introduction of the same repulsing mutation (K439E or S440K) in both antibodies results in diminished induction of killing of B×PC-3 pancreatic (FIG. 13A) and HCT-15 colon cancer cells (FIG. 13B). By combining the two mutations (K439E and S440K) in both antibodies, repulsion is neutralized and killing restored. Error bars indicate standard deviation.

Figure 14:
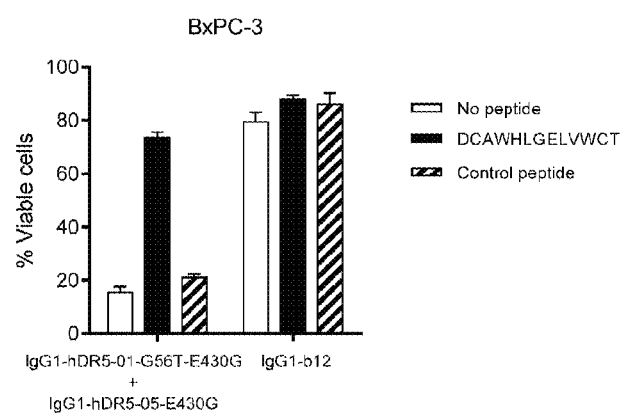

FIG. 14: Involvement of Fc interactions in the capacity of the antibody combination IgG1-hDR5-01-G56T-E430G+IgG1-hDR5-05-E430G with hexamerization-enhancing mutation to induce receptor clustering on the cell surface and induction of apoptosis. Induction of apoptosis is inhibited by the Fc-binding peptide DCAWHLGELVWCT as shown in a 3-days viability assay on B×PC-3 human cancer cells.

Figure 15:
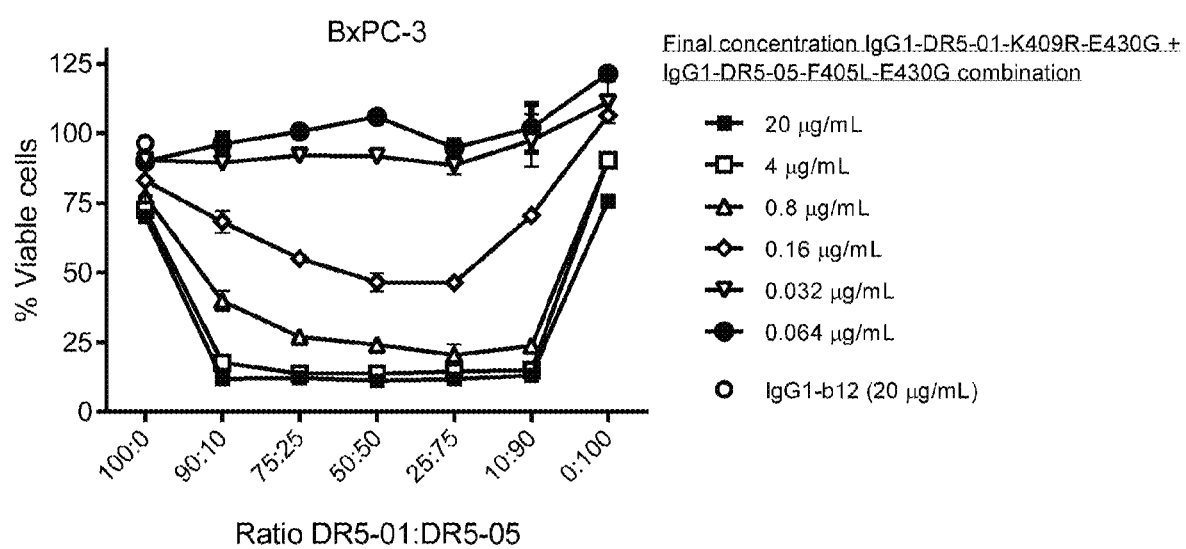

FIG. 15 shows the efficacy of different ratios of combinations of IgG1-DR5-01-K409R-E430G and IgG1-DR5-05-F405L-E430G (DR5-01:DR5-05) on adherent B×PC-3 human cancer cells as determined in a 3-days viability assay.

Figure 16A:
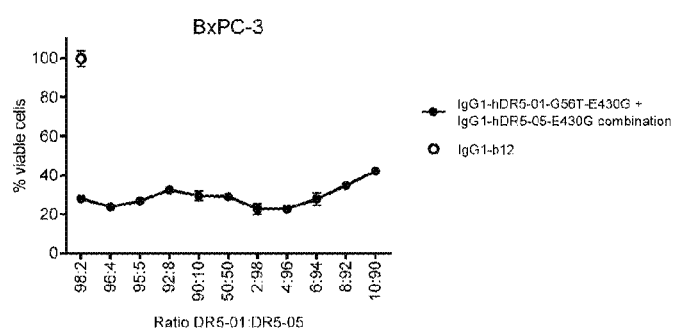
Figure 16B:
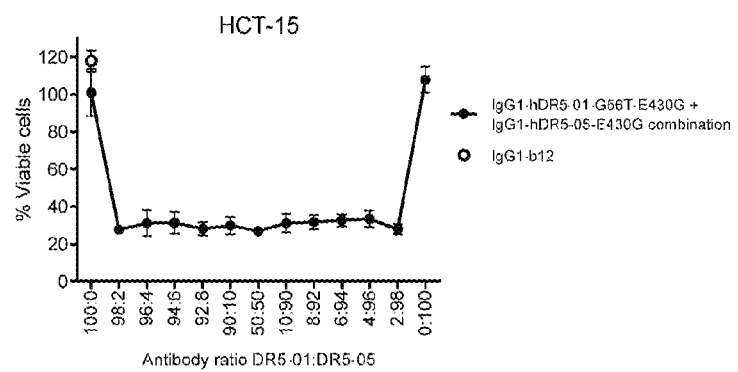

FIGS. 16A and 16B show efficacy of different ratios of IgG1-hDR5-01-G56T-E430G and IgG1-hDR5-05-E430G (DR5-01:DR5-05) on adherent B×PC-3 (FIG. 16A) and HCT-15 (FIG. 16B) human cancer cells as determined in a 3-days viability assay.

Figure 17A:
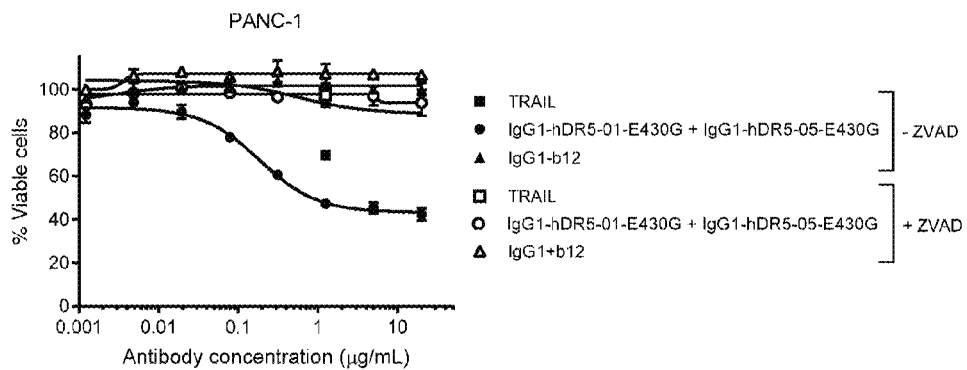
Figure 17B:
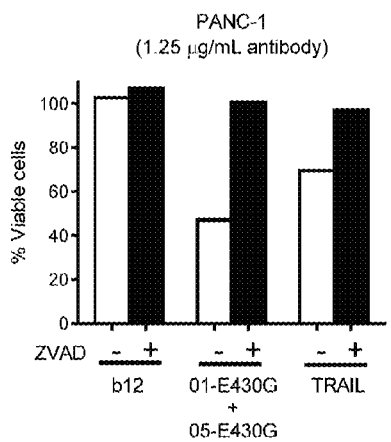
Figure 17C:
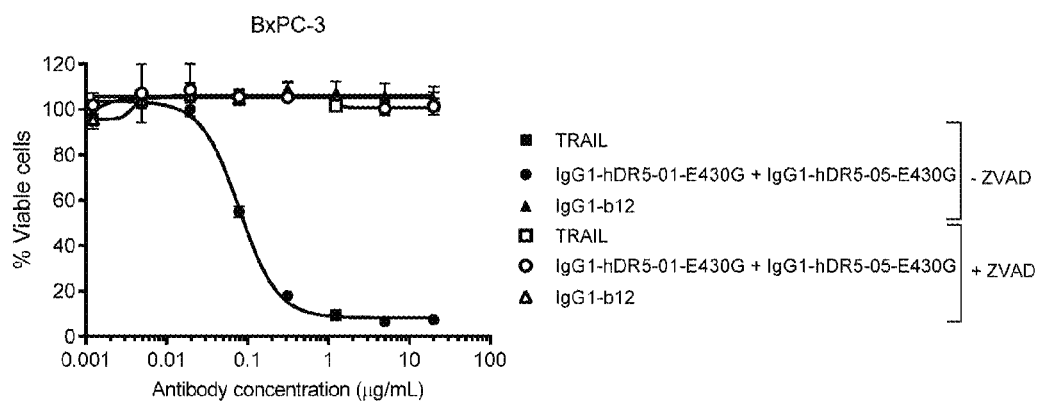

FIGS. 17A-17C show Caspase-dependent programmed cell death by the combination of humanized IgG1-hDR5-01-E430G+IgG1-hDR5-05-E430G antibodies as measured in a viability assay on PANC-1 (FIGS. 17A and 17B) and BxPC-3 (FIG. 17C) pancreatic cancer cells. 01-E430G is IgG1-hDR5-01-E430G; 05-E430G is IgG1-hDR5-05-E430G; ZVAD is pan-caspase inhibitor Z-Val-Ala-DL-Asp-fluoromethylketone (Z-VAD-FMK).

Figure 18A:
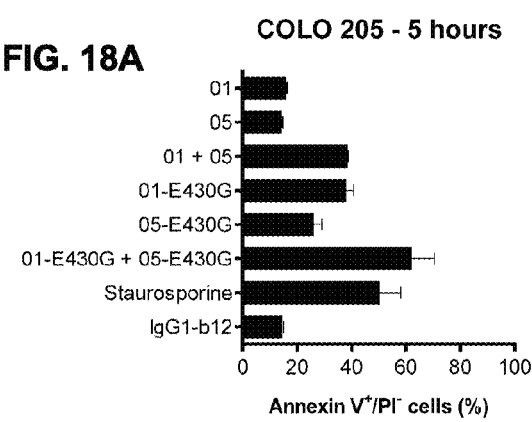
Figure 18D:
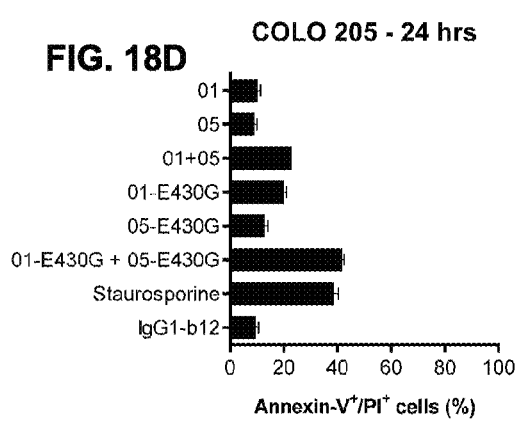
Figure 18B:
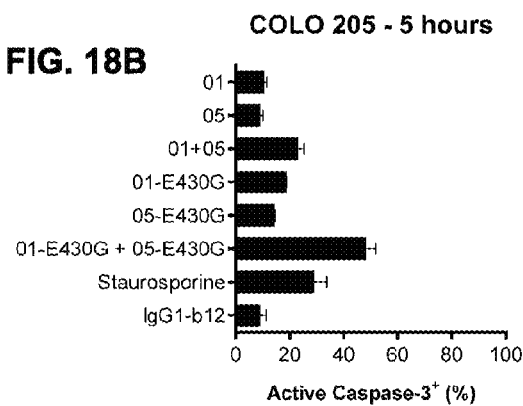
Figure 18E:
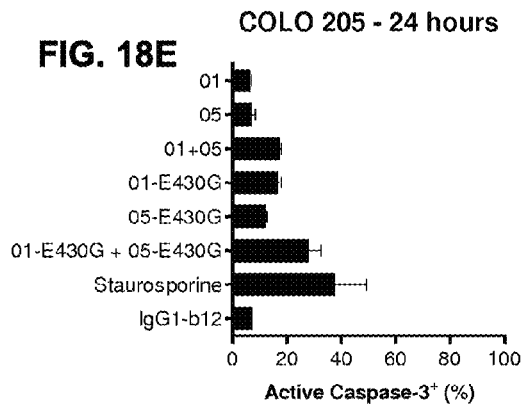
Figure 18C:
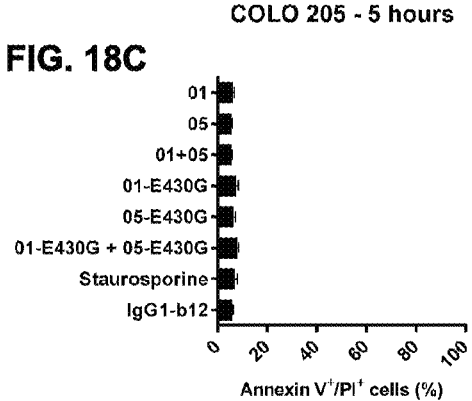

FIGS. 18A-18E show cell death induction upon binding of anti-DR5 antibody or anti-DR5 antibody combinations on COLO 205 colon cancer cells. COLO 205 cells were incubated with antibody sample for 5 hours (FIGS. 18A-18C) and 24 hours (FIGS. 18D-18E). Different stages of cell death induction were analyzed by Annexin V/PI double staining and Active caspase-3 staining. Panels C and D show Annexin V/PI double staining at 5 and 24 hours respectively. Error bars indicate the standard deviation of 2 duplicate samples. 01 is IgG1-DR5-01-K409R, 05 is IgG1-DR5-05-F405L, 01-E430G is IgG1-DR5-01-K409R-E430G, 05-E430G is IgG1-DR5-05-F405L-E430G.

Figure 19:
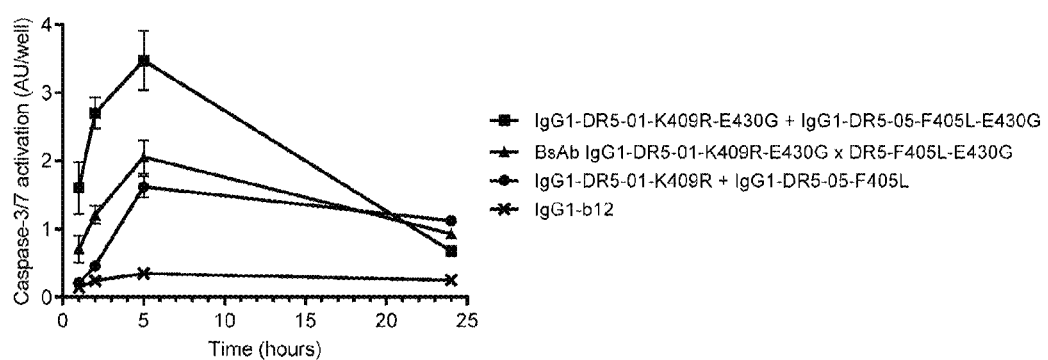

FIG. 19 shows the kinetics of Caspase-3/7 activation upon binding of DR5 antibodies on COLO 205 colon cancer cells. COLO 205 cells were incubated with antibody for 1, 2, 5 and 24 hours. Caspase-3/7 activation was analyzed in a homogenous luminescence assay. AU, arbitrary units. Error bars indicate the standard deviation of duplicate samples.

Figure 20:
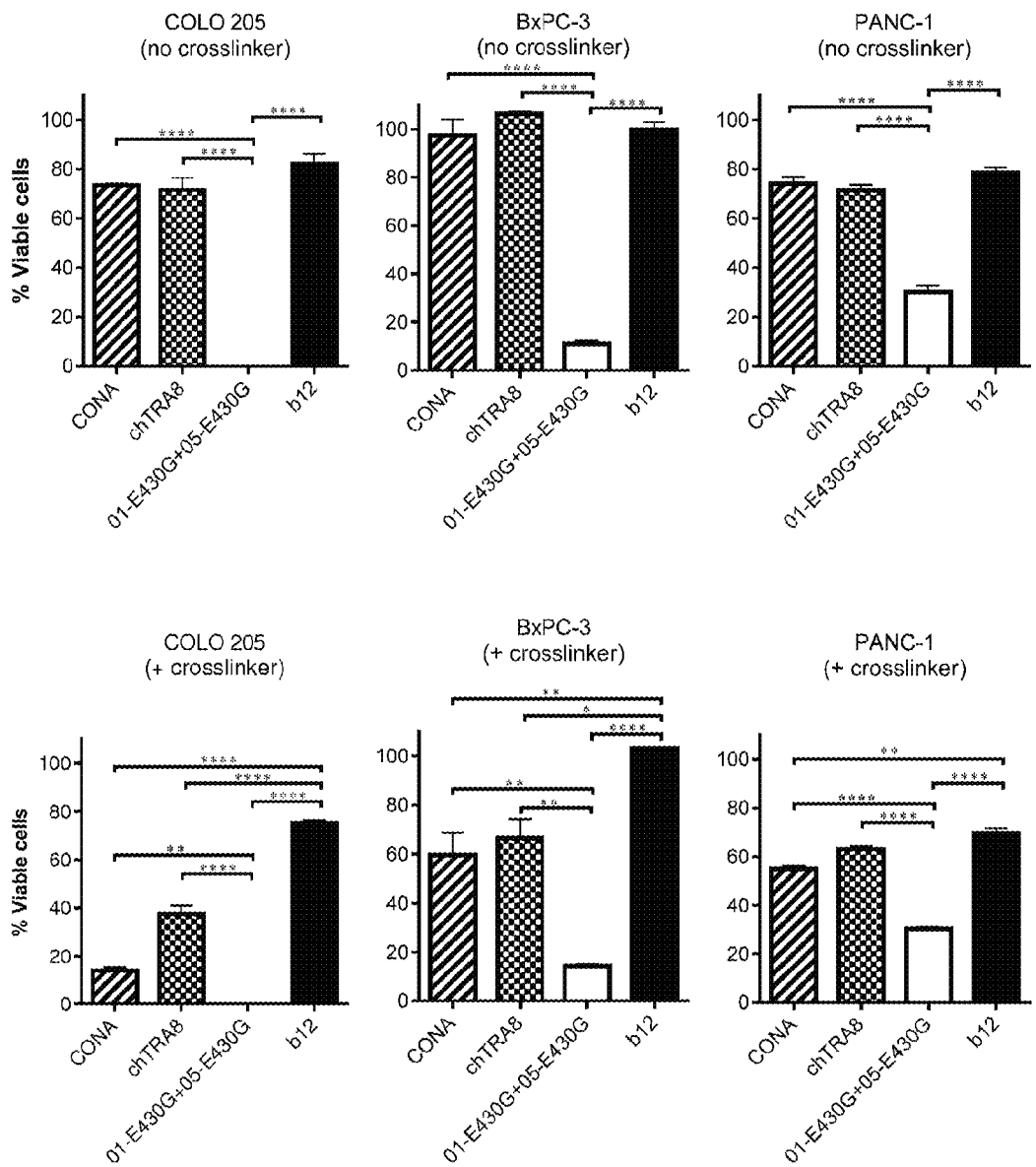

FIG. 20 shows efficacy of the combination of IgG1-DR5-01-K409R-E430G+IgG1-DR5-05-F405L-E430G in the presence or absence of Fc crosslinking by F(ab')$_2$ fragments of an anti-human IgG antibody and comparison to the anti-DR5 antibodies IgG1-DR5-CONA and IgG1-DR5-chTRA8-F405L in a 3-days viability assay on adherent COLO 205 colon cancer and BxPC-3 and PANC-1 pancreatic cancer cells. The non-target binding antibody IgG1-b12 was included as a negative control. Graphs show the mean+/−standard deviation from duplicate samples. * $p<0.05$, $p<0.01$, * $p<0.001$, **** $p<0.0001$ (One-way ANOVA with Bonferroni post-test for multiple comparisons).

Figure 21:
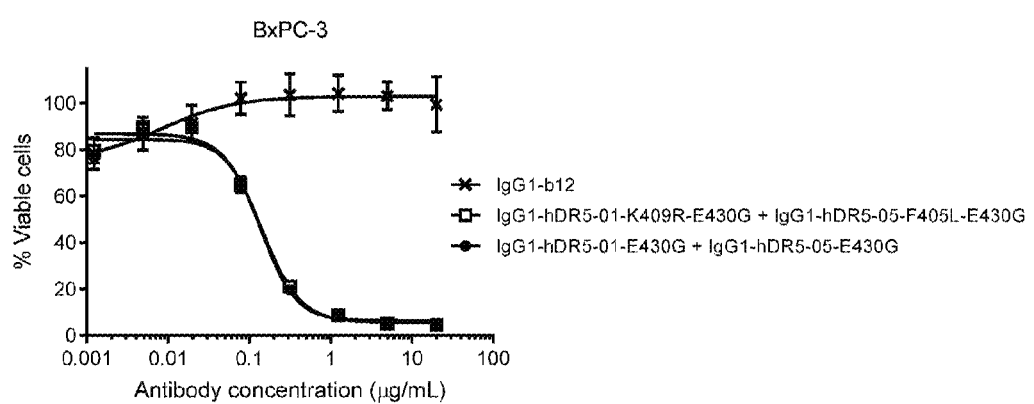

FIG. 21 shows the potency of the combination of humanized IgG1-hDR5-01-K409R-E430G+IgG1-hDR5-05-F405L-E430G antibodies and of the combination of humanized IgG1-DR5-01-E430G+IgG1-DR5-05-E430G antibodies as measured in a viability assay on BxPC-3 pancreatic cancer cells. Graphs represent mean values of duplicate samples+/−standard deviation.

Figure 22:
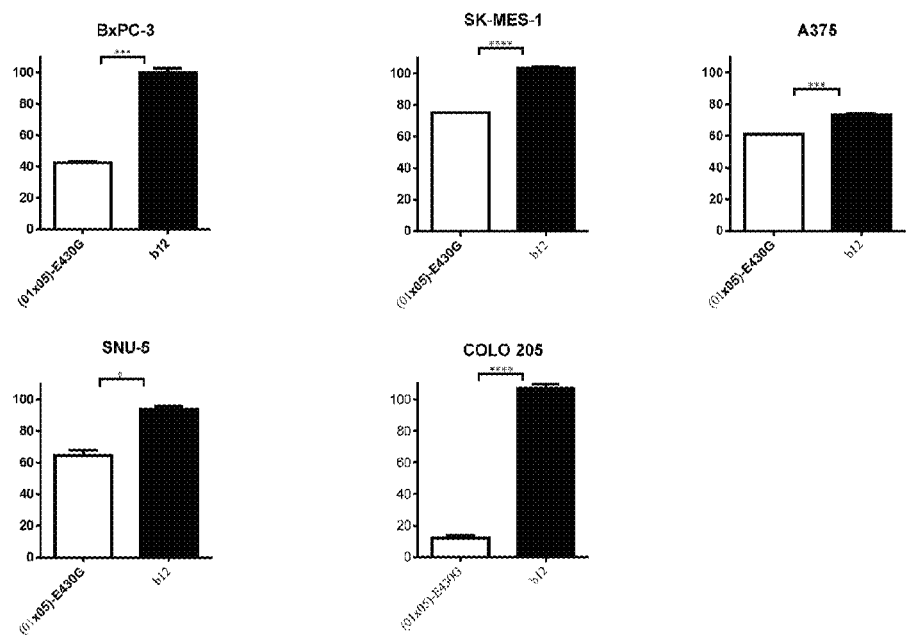

FIG. 22 shows the potency of the chimeric BsAb IgG1-DR5-01-K409R-E430GxDR5-05-F405L-E430G antibody on different human cancer cell lines determined in a 3-days viability assay on adherent cells from COLO 205 colon, BxPC-3 pancreatic, SNU-5 gastric, SK-MES-1 lung, and A375 skin cancer cell lines. Graphs show the mean+/−standard deviation from duplicate samples. * $p<0.05$, * $p<0.001$, ** $p<0.0001$ (One-way ANOVA with Bonferroni post-test for multiple comparisons). (01x05)-E430G is BsAb IgG1-DR5-01-K409R-E430GxDR5-05-F405L-E430G.

Figure 23:
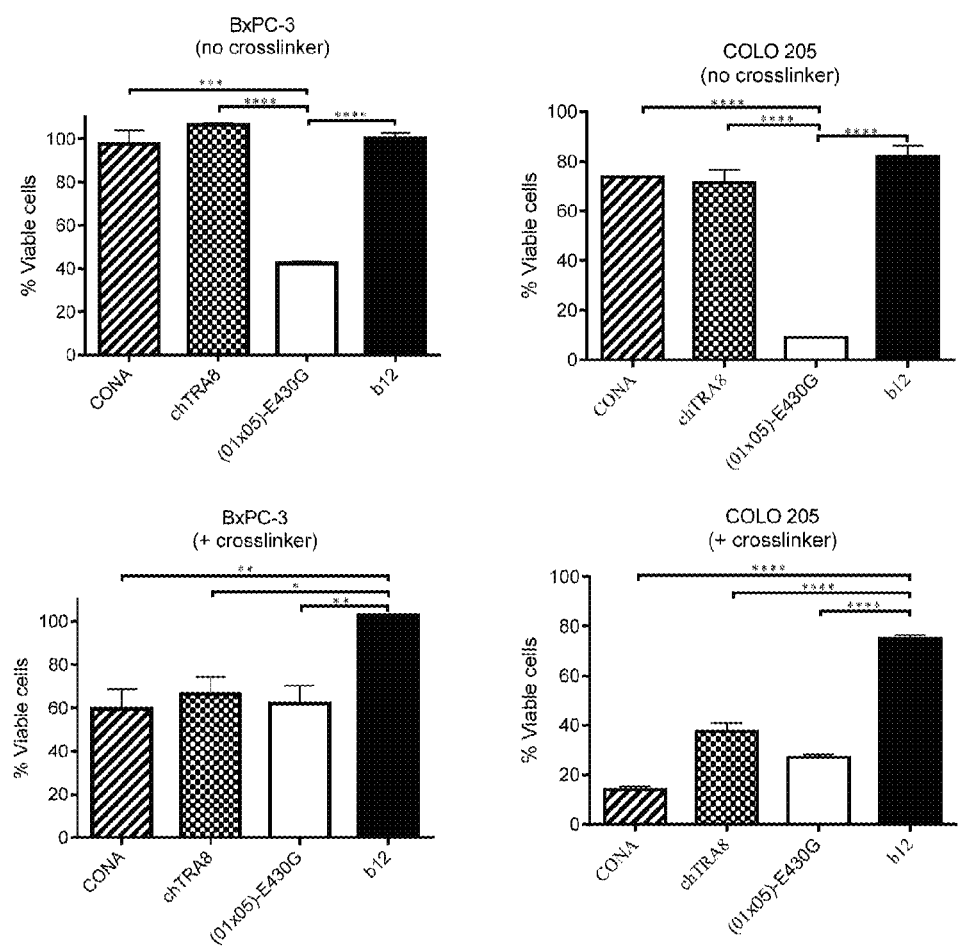

FIG. 23 shows the efficacy of chimeric BsAb IgG1-DR5-01-K409R-E430GxDR5-05-F405L-E430G in the presence or absence of Fc crosslinking by F(ab')$_2$ fragments of an anti-human IgG antibody in comparison with the anti-DR5 antibodies IgG1-DR5-CONA and IgG1-DR5-chTRA8-F405L in a 3-days viability assay on adherent BxPC-3 pancreatic and COLO 205 colon cancer cells. The non-target binding antibody IgG1-b12 was included as a negative control. Graphs show the mean+/−standard deviation from duplicate samples. * $p<0.05$, $p<0.01$, * $p<0.001$, **** $p<0.0001$ (One-way ANOVA with Bonferroni post-test for multiple comparisons). (01x05)-E430G is BsAb IgG1-DR5-01-K409R-E430GxIgG1-DR5-05-F405L-E430G FIGS. 24A-24E show cell death induction upon binding of bispecific DR5 antibodies on COLO 205 colon cancer cells. COLO 205 cells were incubated with 1 μg/mL antibody for 5 hours (FIGS. 24A-24C) and 24 hours (FIGS. 24D-24E). Different stages of cell death induction were analyzed by Annexin V/PI double staining and Active caspase-3 staining. Error bars indicate the standard deviation of 2 duplicate samples. 01 is IgG1-DR5-01-K409R, 05 is IgG1-DR5-05-F405L, 01-E430G is IgG1-DR5-01-K409R-E430G, 05-E430G is IgG1-DR5-05-F405L-E430G, 01x05 is BsAb IgG1-DR5-01-K409RxDR5-05-F405L, 01-E430Gx05-E430G is BsAb IgG1-DR5-01-K409R-E430GxDR5-05-F405L-E430G.

Figure 25A:
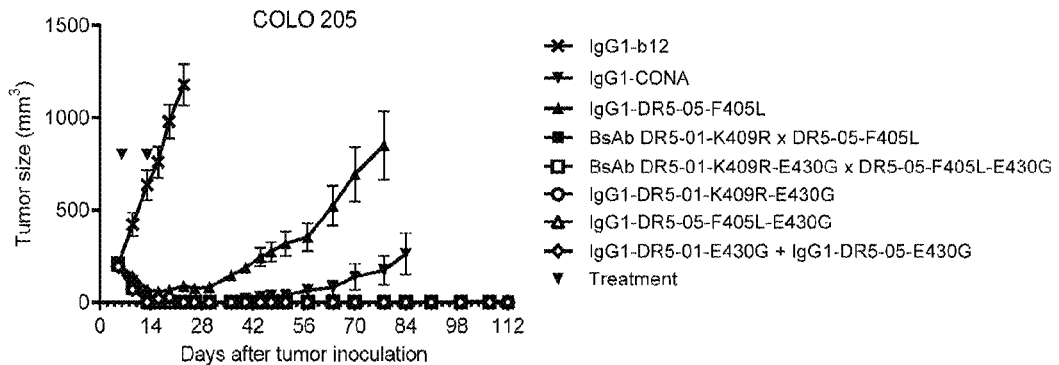
Figure 25B:
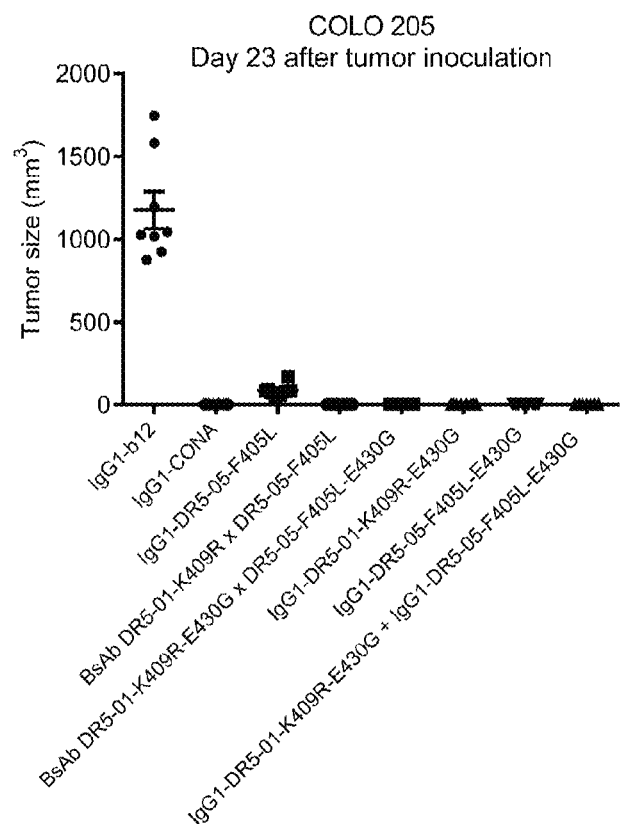
Figure 25C:
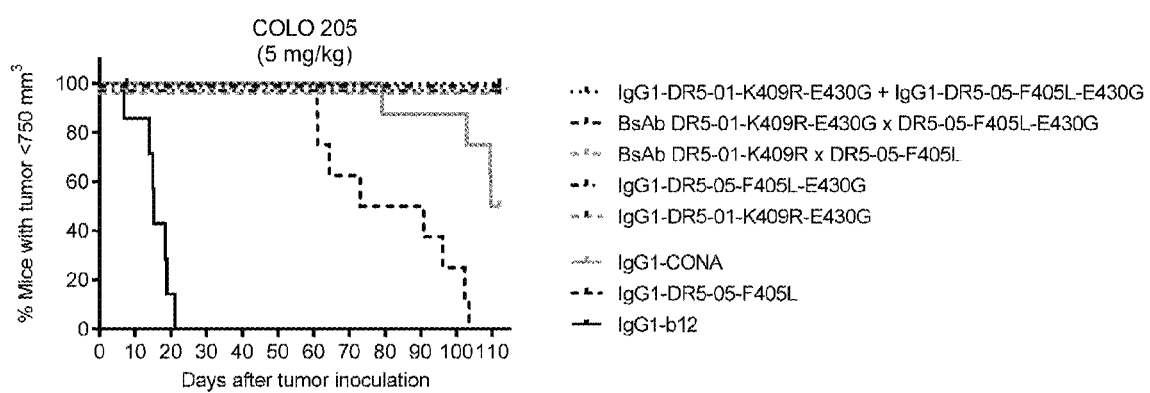

FIGS. 25A-25C show evaluation of the in vivo efficacy of the combination of the chimeric IgG1-DR5-01-K409R-E430G+IgG1-DR5-05-F405L-E430G antibodies in a subcutaneous xenograft model with COLO 205 human colon cancer cells. Tumor size (mean & SEM) in mice treated with the indicated antibodies (5 mg/kg) is shown in time (FIG. 25A) and at day 23 (FIG. 25B). In (FIG. 25C) the percentage of mice with tumor sizes smaller than 750 mm$^3$ is shown in a Kaplan-Meier plot.

Figure 26A:
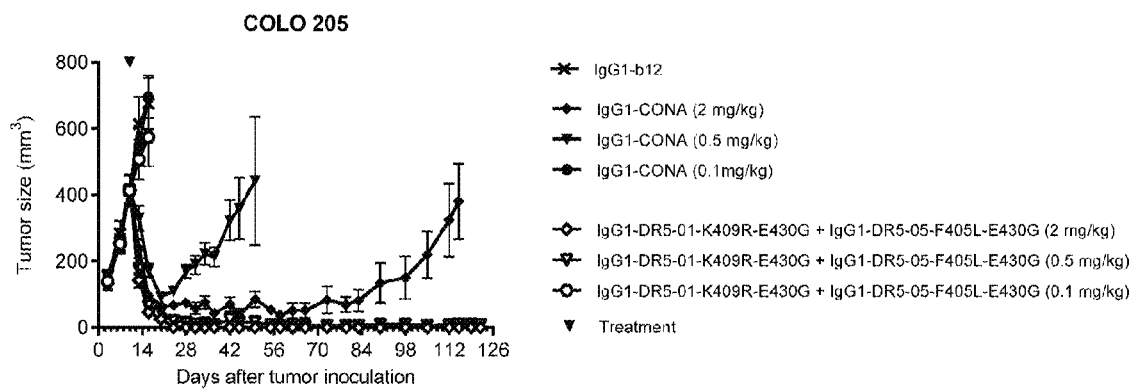
Figure 26B:
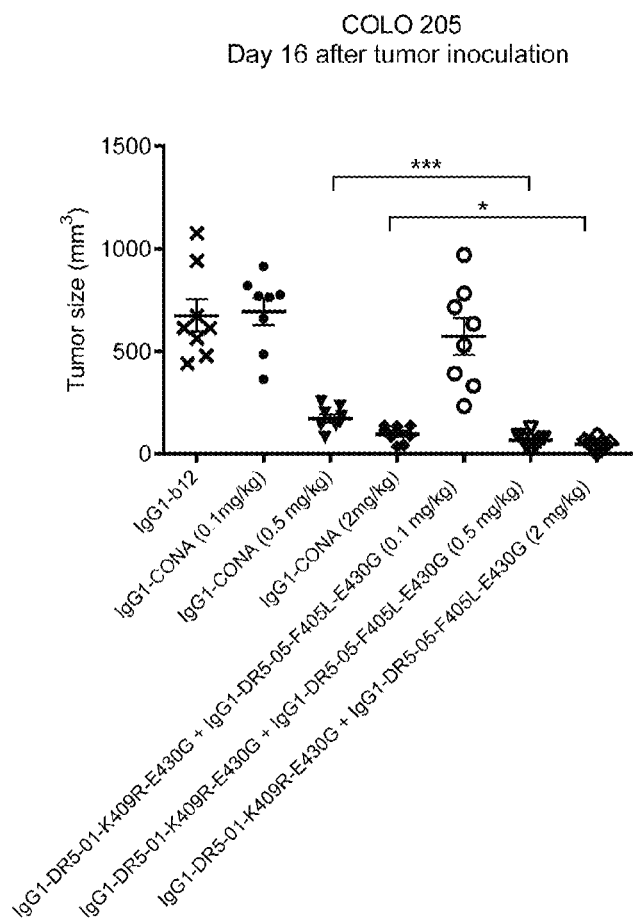
Figure 26C:
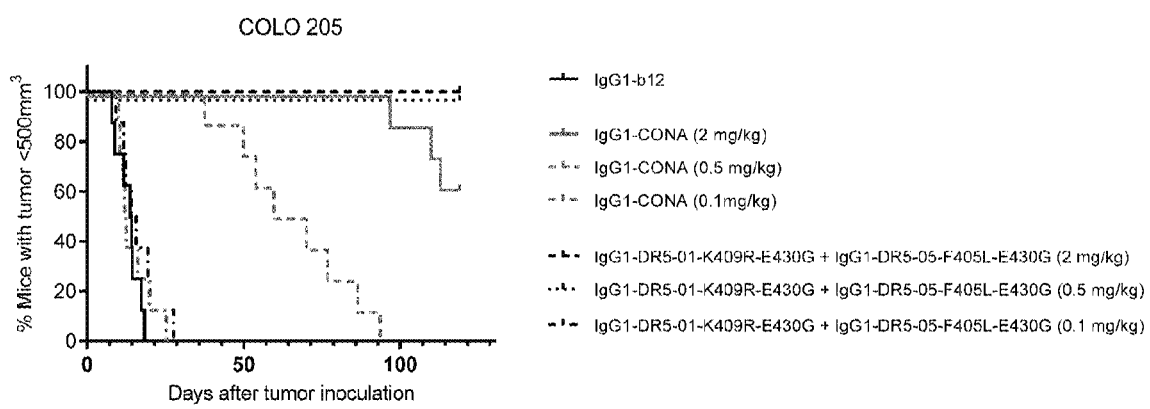

FIGS. 26A-26C show evaluation of the in vivo efficacy of different doses of the IgG1-DR5-01-K409R-E430G+IgG1-DR5-05-F405L-E430G antibody combination and comparison to IgG1-CONA in a subcutaneous COLO 205 colon cancer xenograft. Tumor size (mean & SEM) in mice treated with the indicated antibody dose is shown in time (FIG. 26A) and on day 16 (FIG. 26B). In (FIG. 26C) the percentage of mice with tumor sizes smaller than 500 mm$^3$ is shown in a Kaplan-Meier plot. * $p<0.05$, *** $p<0.001$.

Figure 27A:
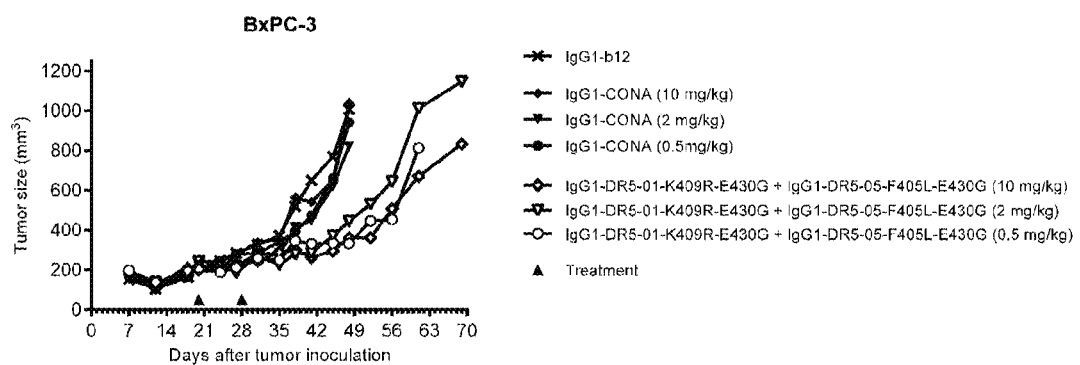
Figure 27B:
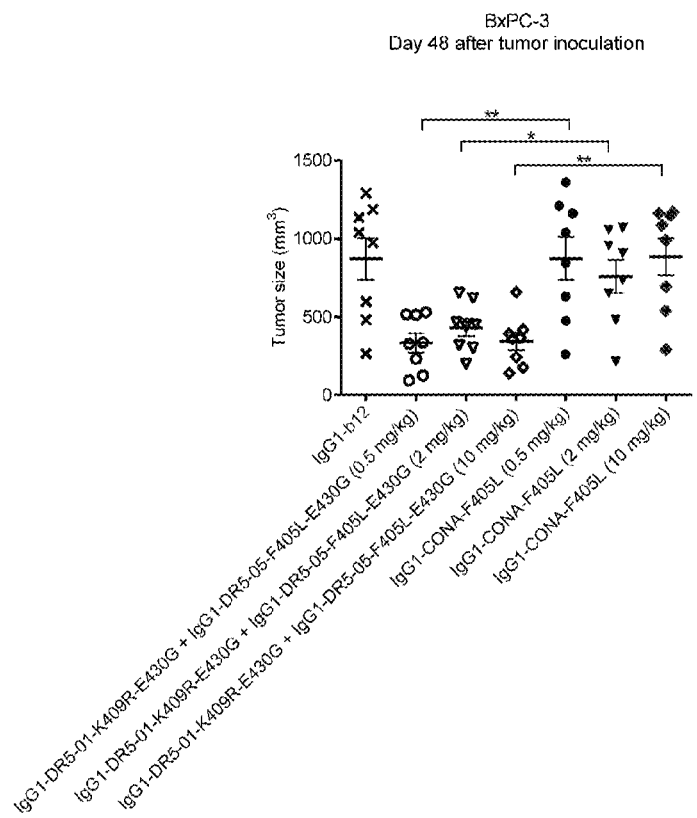
Figure 27C:
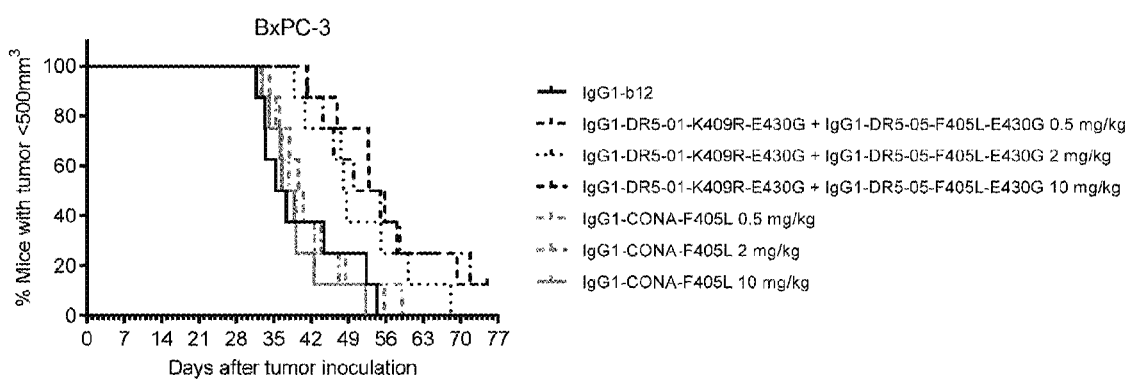

FIGS. 27A-27C show evaluation of the in vivo efficacy of different doses of the IgG1-DR5-01-K409R-E430G+IgG1-DR5-05-F405L-E430G antibody combination and comparison to IgG1-CONA-F405L in a subcutaneous xenograft model with BxPC-3 human pancreatic cancer cells. Tumor size in mice treated with the indicated antibodies is shown in time (FIG. 27A, median tumor size) and at day 48 after tumor inoculation (FIG. 27B, mean tumor size & SEM). * $p<0.05$, ** $p<0.01$ (Unpaired t-test). In (FIG. 27C) the percentage of mice with tumor sizes smaller than 500 mm$^3$ is shown in a Kaplan-Meier plot.

Figure 28A:
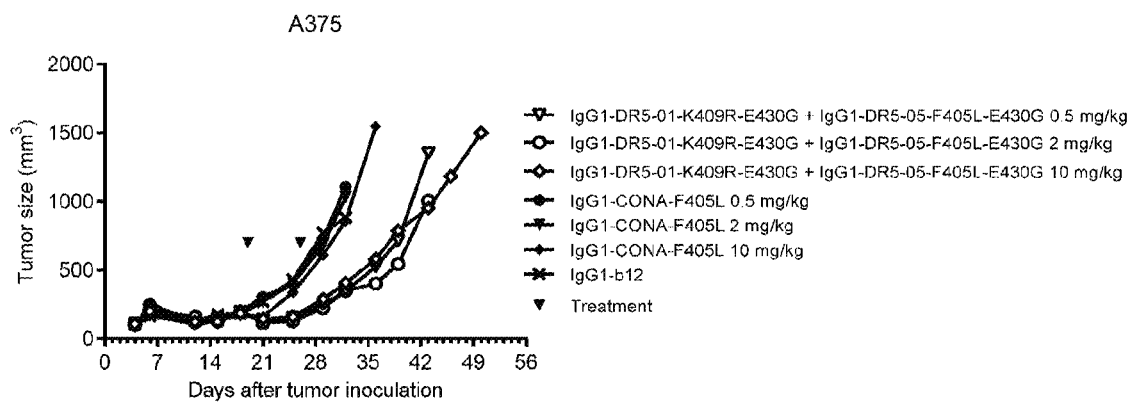
Figure 28B:
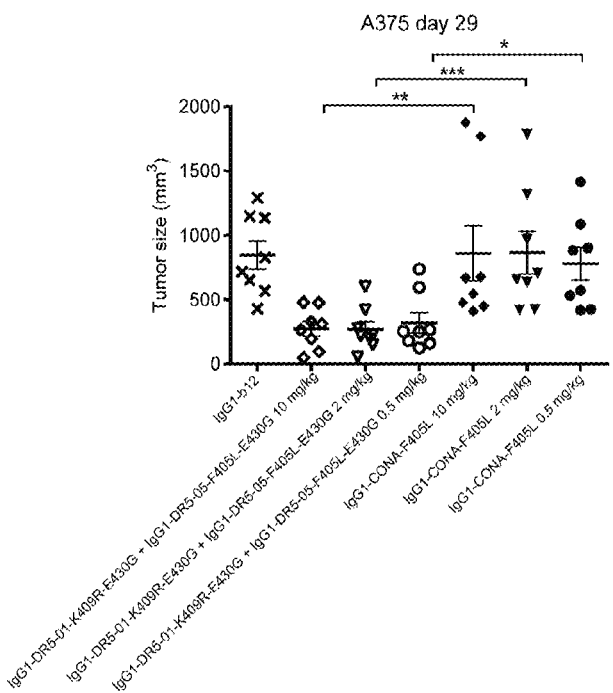

FIGS. 28A and 28B show evaluation of the in vivo efficacy of different doses of the IgG1-DR5-01-K409R-E430G+IgG1-DR5-05-F405L-E430G antibody combination and comparison to IgG1-CONA-F405L in a subcutaneous xenograft model with A375 human skin cancer cells. Tumor size in mice treated with the indicated antibodies is shown in time (FIG. 28A, median tumor size) and at day 29 after tumor inoculation (FIG. 28B, mean tumor size & SEM). * $p<0.05$,  $p<0.01$, * $p<0.001$ (Mann Whitney test).

Figure 29A:
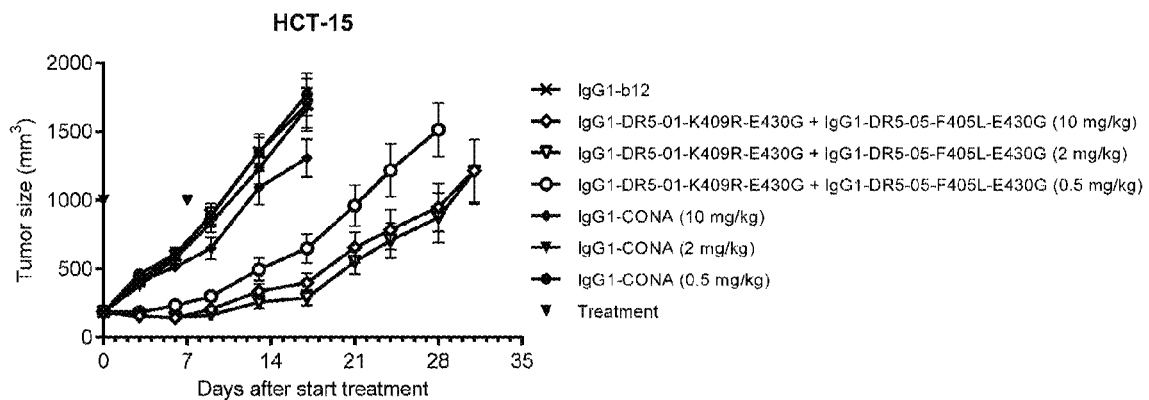
Figure 29B:
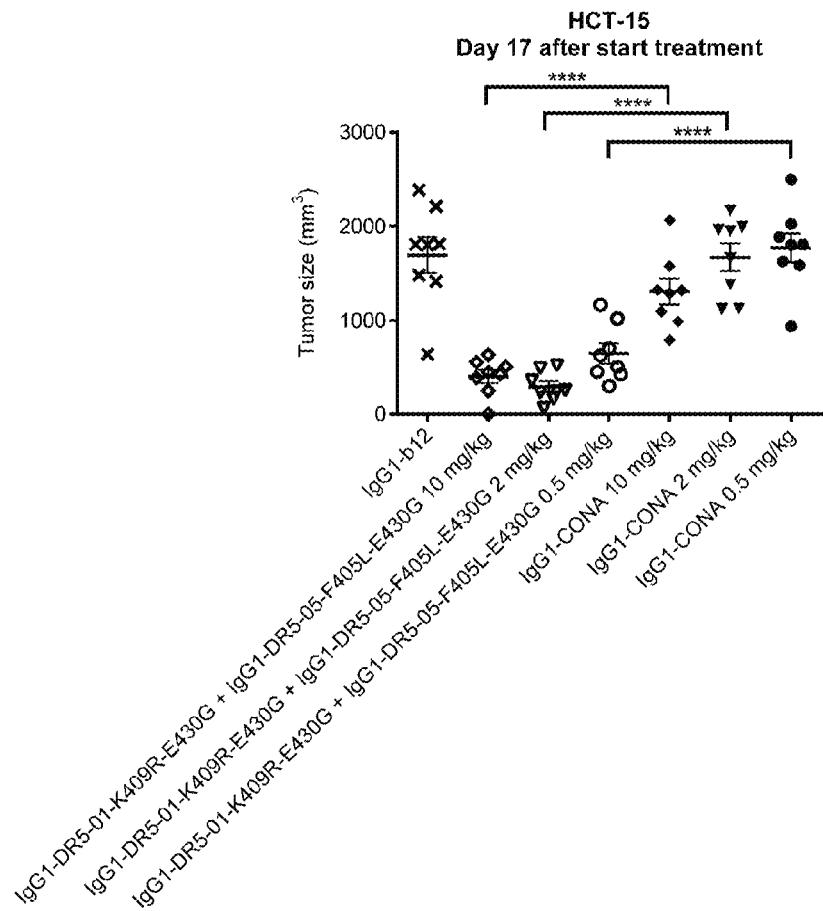
Figure 29C:
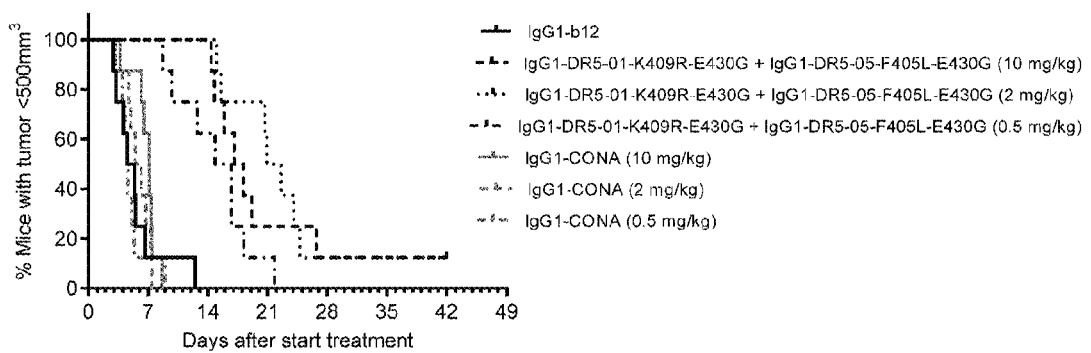

FIGS. 29A-29C show evaluation of the in vivo efficacy of different doses of the IgG1-DR5-01-K409R-E430G+IgG1-DR5-05-F405L-E430G antibody combination and comparison to IgG1-CONA in a subcutaneous xenograft model with HCT-15 human colon cancer cells. Tumor size (mean & SEM) in mice treated with the indicated antibodies is shown in time (FIG. 29A) and at day 17 after start treatment (FIG. 29B). **** $p<0.001$ (Unpaired t test). In (FIG. 29C) the percentage of mice with tumor sizes smaller than 500 mm$^3$ is shown in a Kaplan-Meier plot.

Figure 30A:
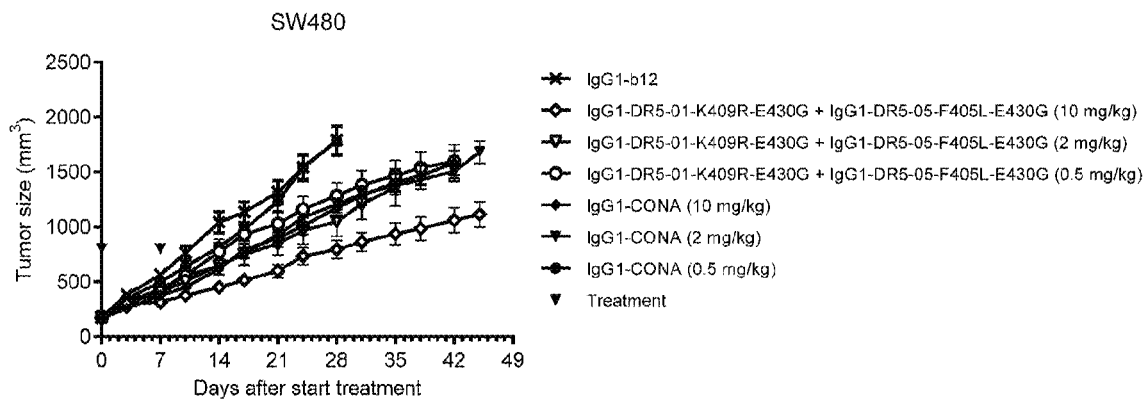
Figure 30B:
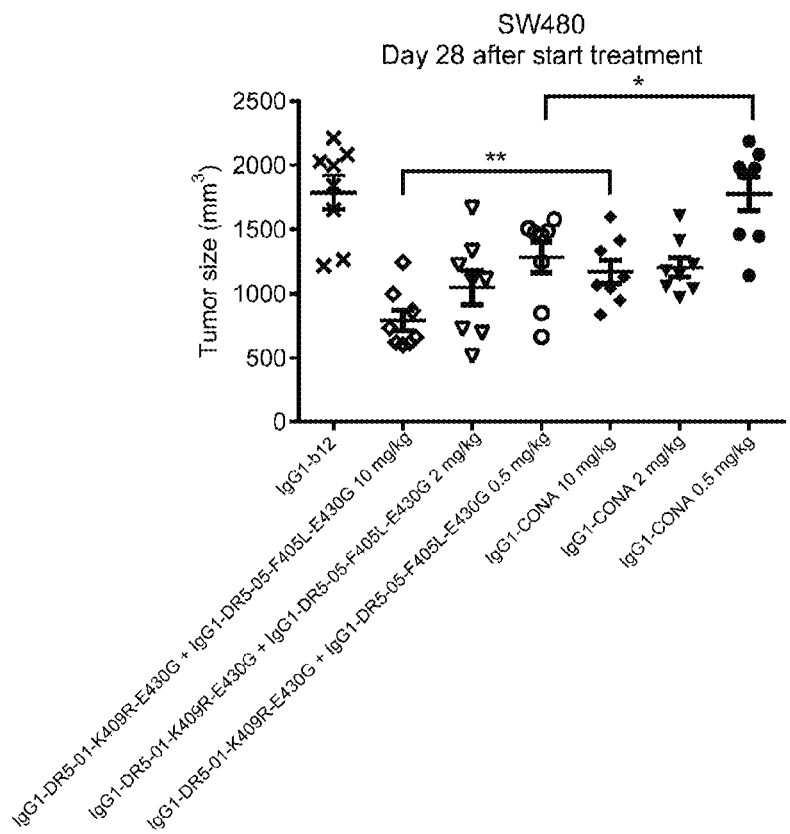
Figure 30C:
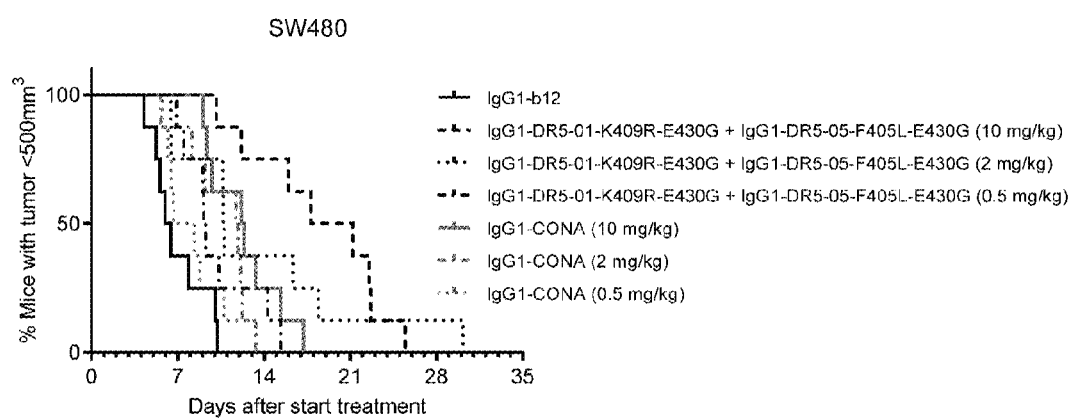

FIGS. 30A-30C show evaluation of the in vivo efficacy of different doses of the IgG1-DR5-01-K409R-E430G+IgG1-

DR5-05-F405L-E430G antibody combination and comparison to IgG1-CONA in a subcutaneous xenograft model with SW480 human colon cancer cells. Tumor size (mean & SEM) in mice treated with the indicated antibodies is shown in time (FIG. 30A) and at day 28 after start treatment (FIG. 30B). * $p<0.05$, ** $p<0.01$ (Unpaired t-test). In (FIG. 30C) the percentage of mice with tumor sizes smaller than 500 mm$^3$ is shown in a Kaplan-Meier plot.

Figure 31A:
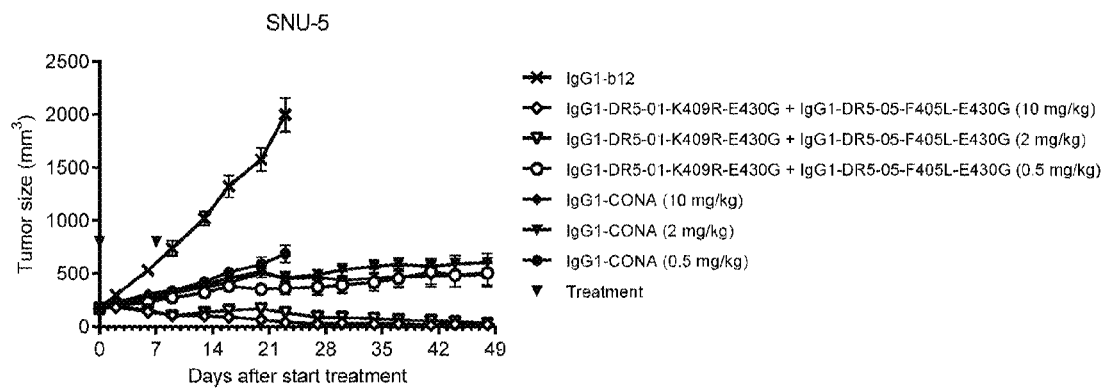
Figure 31B:
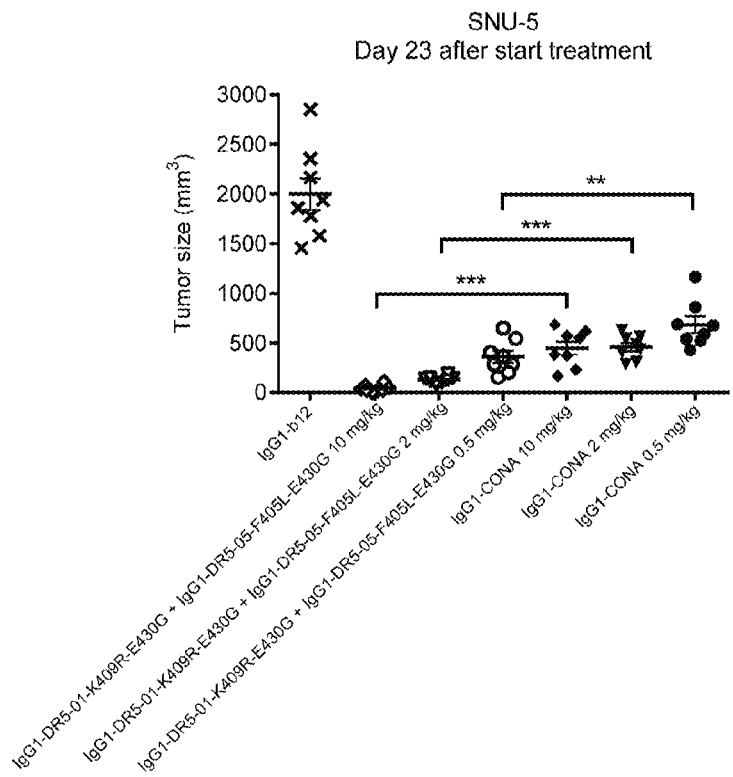
Figure 31C:
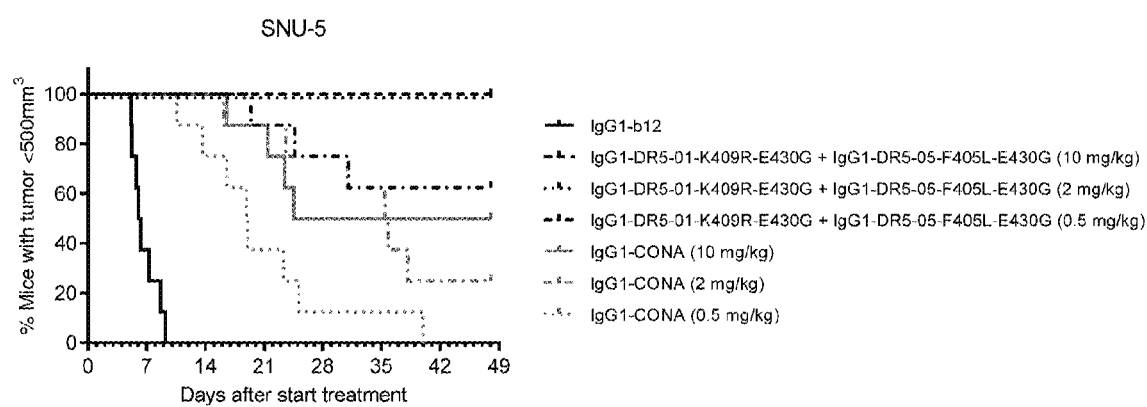

FIG. 31A-31C show evaluation of the in vivo efficacy of different doses of the IgG1-DR5-01-K409R-E430G+IgG1-DR5-05-F405L-E430G antibody combination and comparison to IgG1-CONA in a subcutaneous xenograft model with SNU-5 human gastric cancer cells. Tumor size (mean & SEM) in mice treated with the indicated antibodies is shown in time (FIG. 31A) and at day 23 after start treatment (FIG. 31B).  $p<0.01$, * $p<0.001$ (Mann Whitney test). In (FIG. 31C) the percentage of mice with tumor sizes smaller than 500 mm$^3$ is shown in a Kaplan-Meier plot.

Figure 32A:
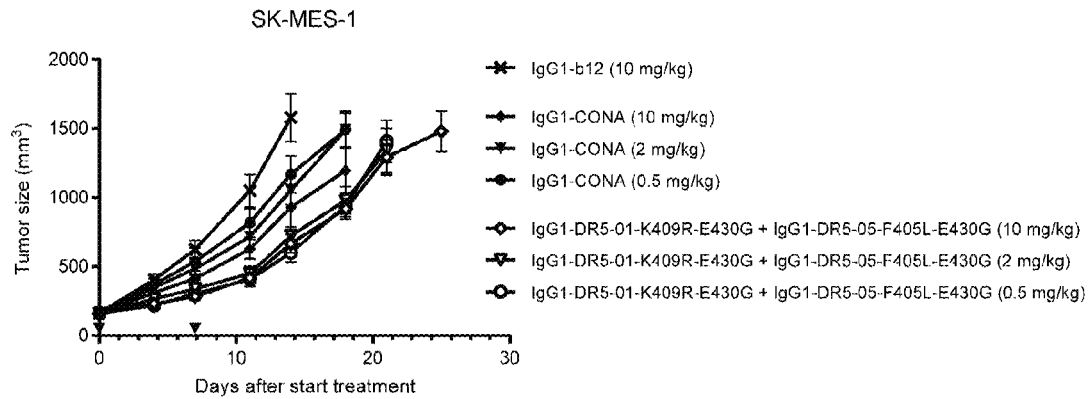
Figure 32B:
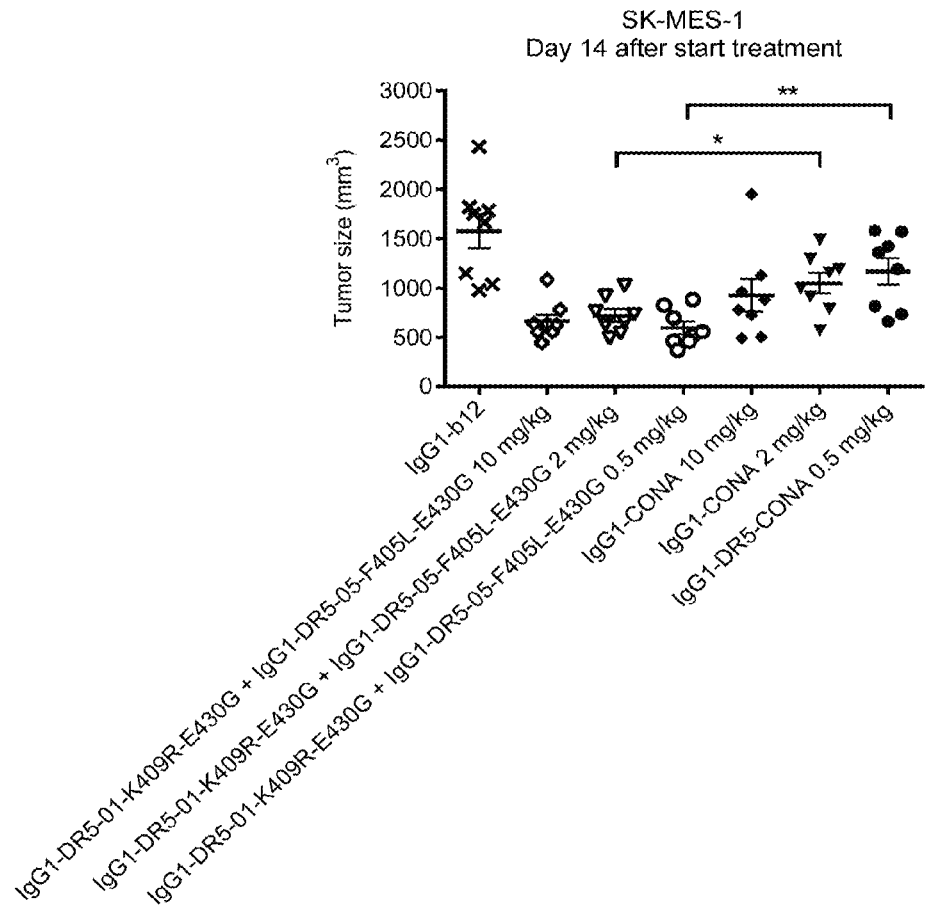
Figure 32C:
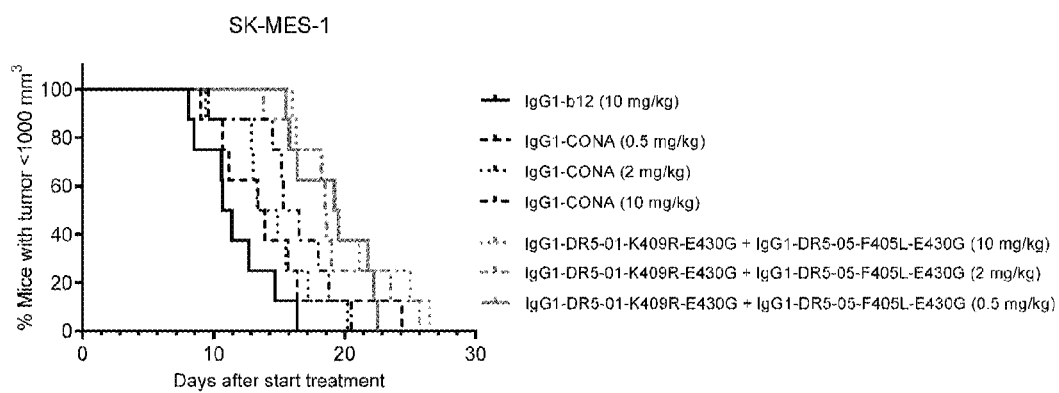

FIGS. 32A-32C show evaluation of the in vivo efficacy of different doses of the IgG1-DR5-01-K409R-E430G+IgG1-DR5-05-F405L-E430G antibody combination and comparison to IgG1-CONA in a subcutaneous xenograft model with SK-MES-1 human lung cancer cells. Tumor size (mean & SEM) in mice treated with the indicated antibodies is shown in time (FIG. 32A) and at day 14 after start treatment (FIG. 32B). In (FIG. 32C) the percentage of mice with tumor sizes smaller than 1.000 mm$^3$ is shown in a Kaplan-Meier plot.

Figure 33:
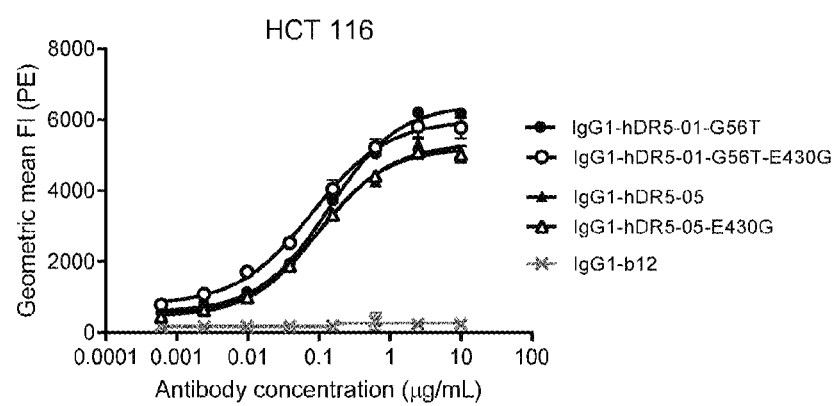

FIG. 33 shows binding to DR5-positive HCT 116 human colon cancer cells by anti-DR5 antibodies IgG1-hDR5-01-G56T and IgG1-hDR5-05 with and without the E430G mutation as measured by flow cytometry. Anti-gp120 antibody IgG1-b12 was used as a negative control. Binding is expressed as geometric mean fluorescence intensity (FI). Error bars indicate the standard deviation. A representative example of seven experiments is shown.

Figure 34:
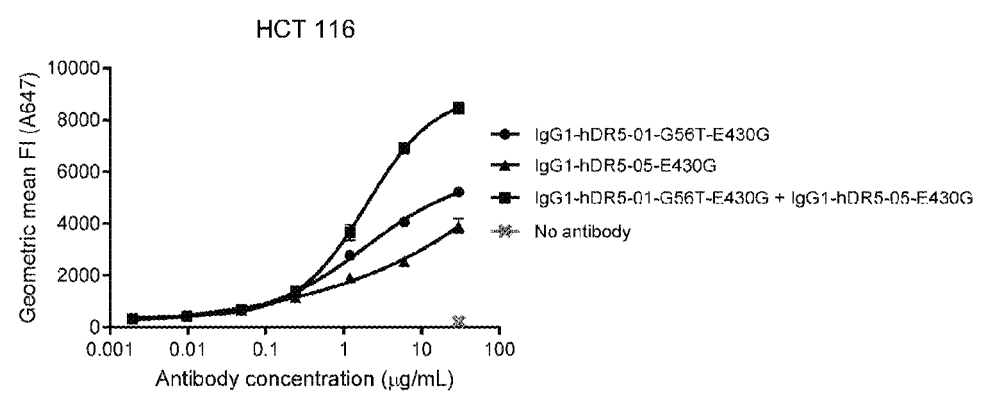

FIG. 34 shows binding to DR5-positive HCT 116 human colon cancer cells by anti-DR5 antibodies IgG1-hDR5-01-G56T-E430G and IgG1-hDR5-05-E430G as measured by flow cytometry with directly labeled antibodies. Binding is expressed as Geometric mean Alexa 647 fluorescence intensity (FI). Error bars indicate the standard deviation.

Figure 35A:
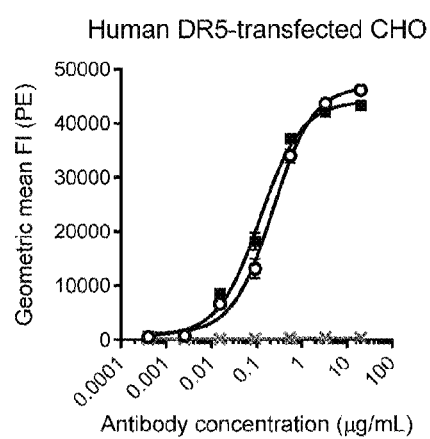
Figure 35B:
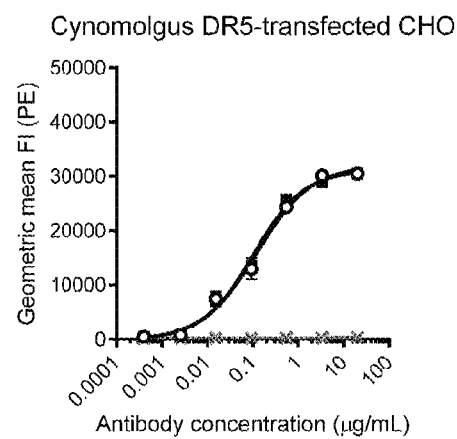

FIGS. 35A and 35B show binding of anti-DR5 antibodies to human and cynomolgus monkey DR5. Antibodies IgG1-hDR5-01-G56T-E430G and IgG1-hDR5-05-E430G were tested by flow cytometry for binding to (FIG. 35A) human DR5-transfected CHO cells and (FIG. 35B) cynomolgus DR5-transfected CHO cells. Binding is expressed as geometric mean of fluorescence intensity (FI). Error bars indicate the standard deviation.

Figure 36:
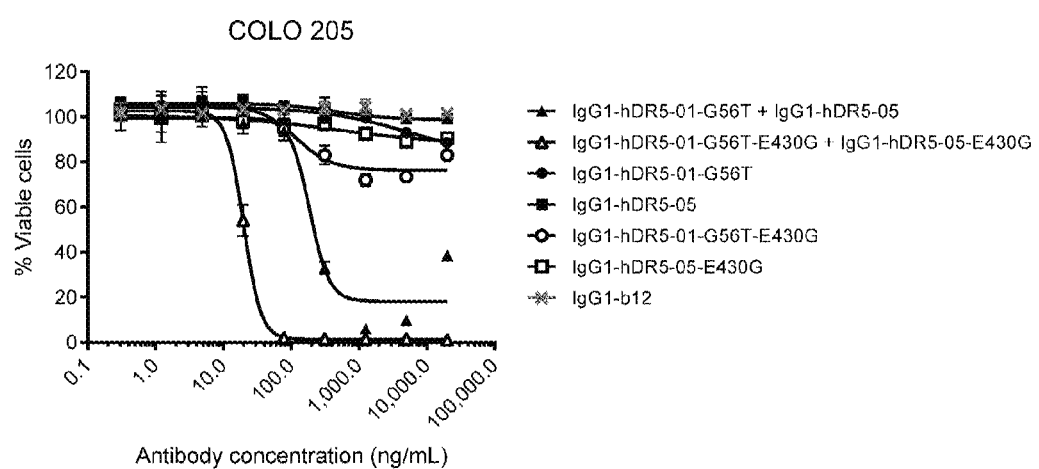

FIG. 36 shows a 3-days viability assay to show the effect of introducing the E430G mutation in the non-crossblocking antibodies IgG1-hDR5-01-G56T and IgG1-hDR5-05 on COLO 205 colon cancer cells. Error bars indicate standard deviation. A representative example of four experiments is shown.

Figure 37A:
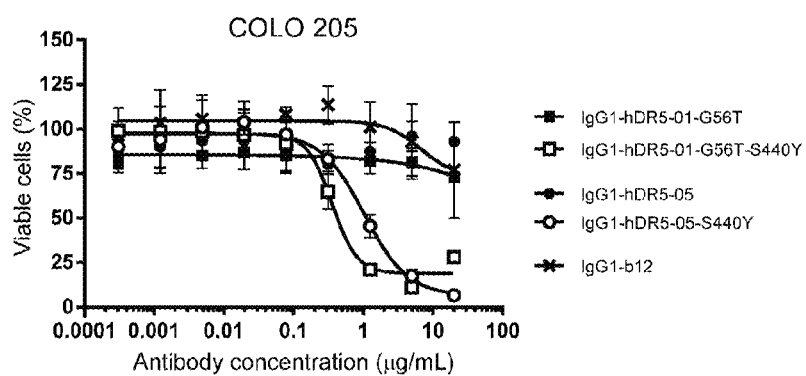
Figure 37B:
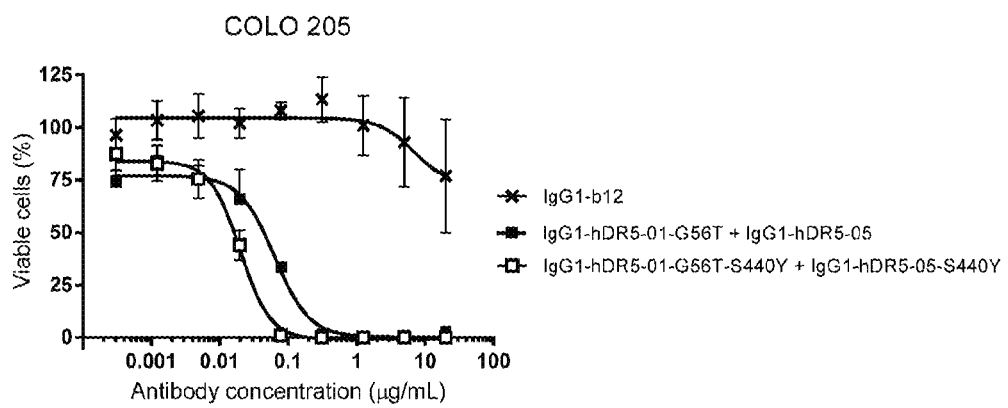

FIGS. 37A and 37B show a viability assay with DR5 antibodies on COLO 205 human colon cancer cells. Introduction of the hexamerization-enhancing mutation S440Y resulted in induction of killing by the single antibodies IgG1-hDR5-01-G56T and IgG1-hDR5-05 (FIG. 37A) and increased efficacy of the antibody combination IgG1-hDR5-01-G56T+IgG1-hDR5-05 (FIG. 37B). Error bars indicate standard deviation.

Figure 38A:
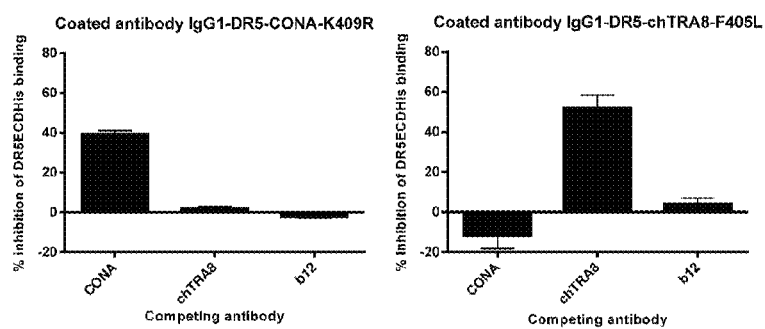
Figure 38B:
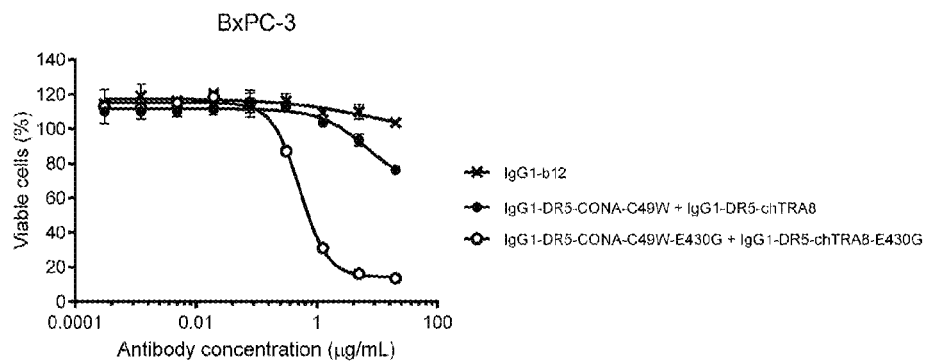

FIGS. 38A and 38B show the efficacy of non-crossblocking antibodies IgG1-DR5-CONA-E430G+IgG1-DR5-chTRA8-E430G to induce killing of BxPC-3 human pancreatic cancer cells. (FIG. 38A) Crossblock ELISA between IgG1-DR5-CONA-K409R (CONA) and IgG1-DR5-chTRA8-F405L (chTRA8). (FIG. 38B) Introduction of the E430G hexamerization-enhancing mutation resulted in enhanced induction of killing of BxPC-3 cells by the combination of IgG1-DR5-CONA-C49W-E430G+IgG1-DR5-chTRA8-E430G as determined in a 3-days viability assay. Error bars indicate standard deviation.

Figure 39:
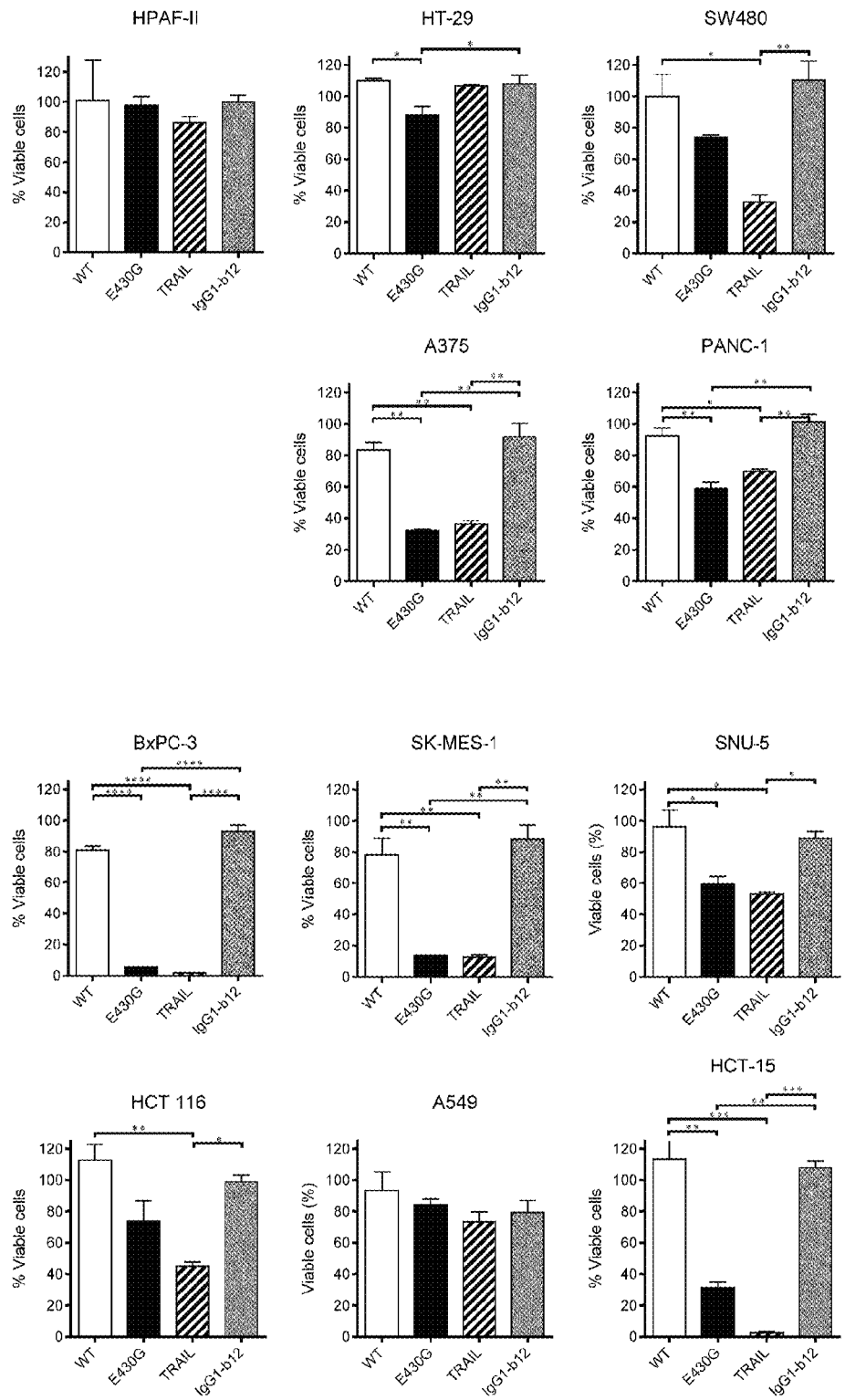

FIG. 39 shows 3-days viability assays with 133 nM human recombinant TRAIL or 133 nM of the antibody combinations IgG1-hDR5-01-G56T-E430G+IgG1-hDR5-05-E430G (E430G) and IgG1-hDR5-01-G56T+IgG1-hDR5-05 (WT) on different human cancer cell lines. Graphs show the mean+/−standard deviation from duplicate samples. * $p<0.05$,  $p<0.01$, * $p<0.001$, **** $p<0.0001$ (One-way ANOVA with Tukey's multiple comparisons test).

Figure 40A:
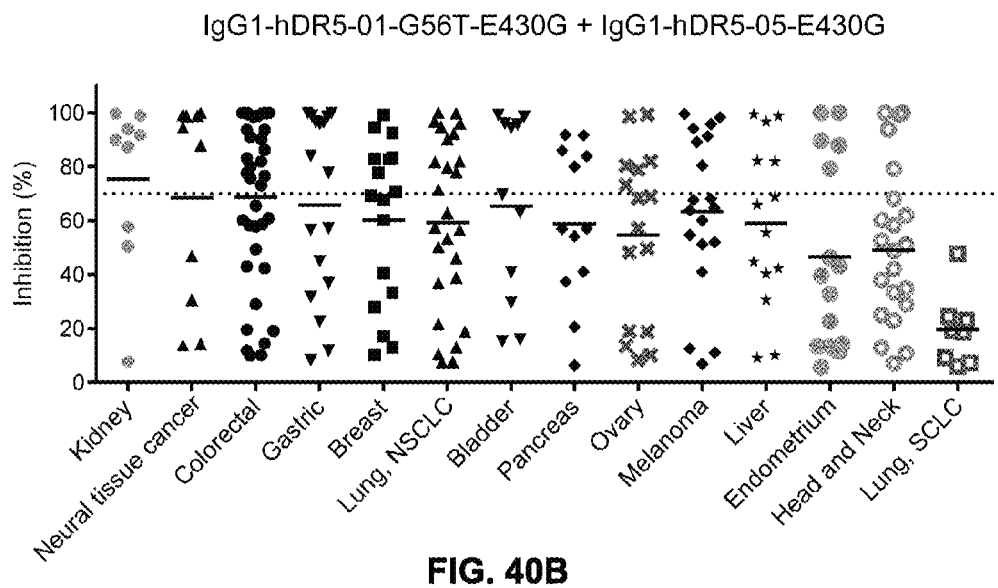
Figure 40B:
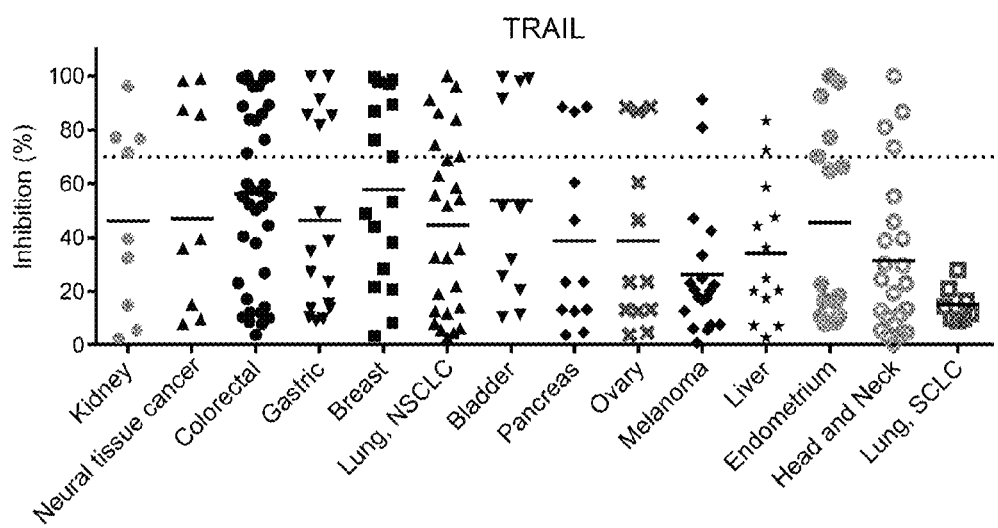

FIGS. 40A and 40B show the percentage inhibition by (FIG. 40A) antibody (IgG1-hDR5-01-G56T-E430G+IgG1-hDR5-05-E430G) and (FIG. 40B) TRAIL therapy as determined in a 3-days viability assay screening of a cell line panel at Horizon, UK. Each data point represents an individual cell line of the indicated human cancer indication. Dotted lines indicate the 70% maximum response threshold value that was set to categorize cell lines as responders 70% inhibition) and non-responders (<70% inhibition).

Figures 41A, 41B:
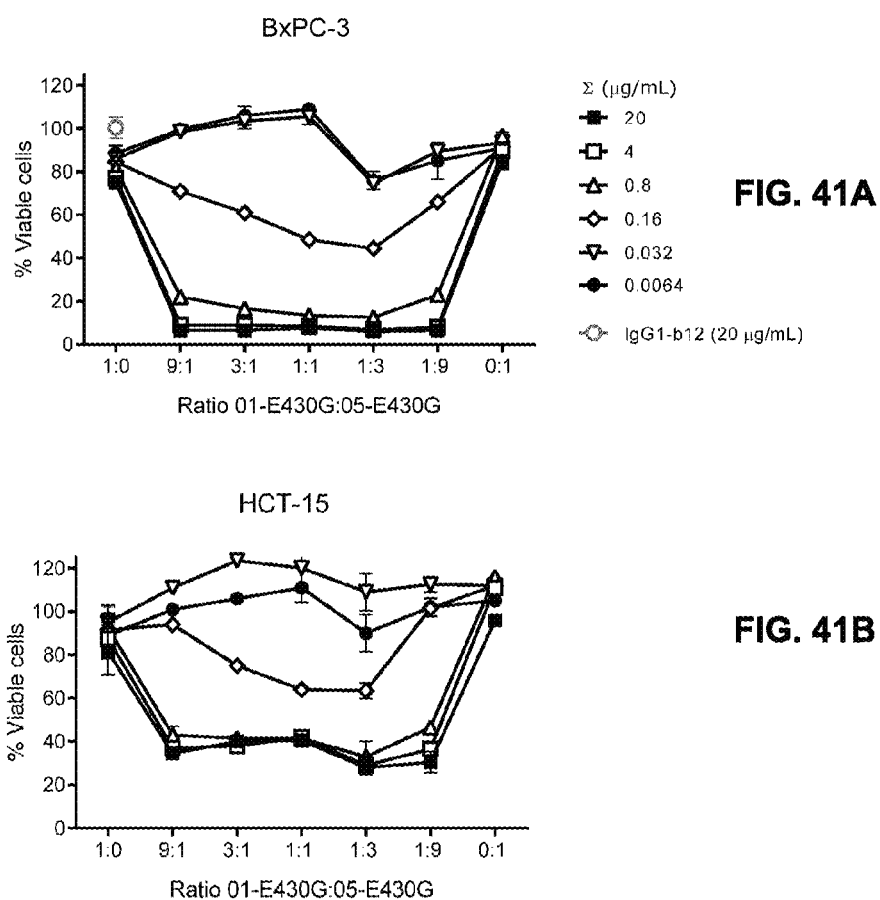

FIGS. 41A and 41B show the efficacy of different antibody ratios in the combination IgG1-hDR5-01-G56T-E430G+IgG1-hDR5-05-E430G (indicated as 01-E430G:05-E430G) on adherent human (FIG. 41A) BxPC-3 pancreatic and (FIG. 41B) HCT-15 colon cancer cells as determined in a 3-days viability assay. Representative examples of two and three experiments are shown for HCT-15 and BxPC-3, respectively.

Figure 42:
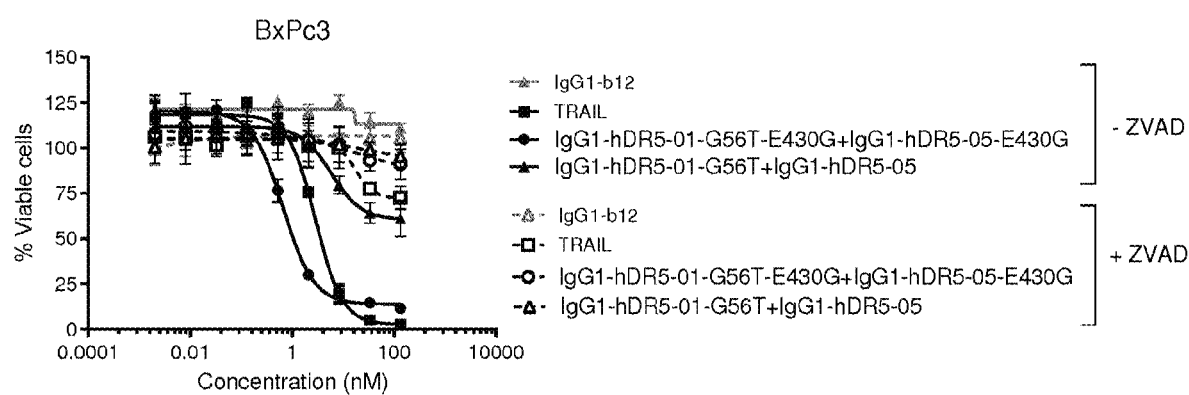

FIG. 42 shows Caspase-dependent programmed cell death by the combination of IgG1-hDR5-01-G56T-E430G+IgG1-hDR5-05-E430G antibodies, the parental WT combination without the E430G mutation and TRAIL as measured in a viability assay on BxPC-3 pancreatic cancer cells. ZVAD is pan-caspase inhibitor Z-Val-Ala-DL-Asp-fluoromethylketone (Z-VAD-FMK).

Figure 43:
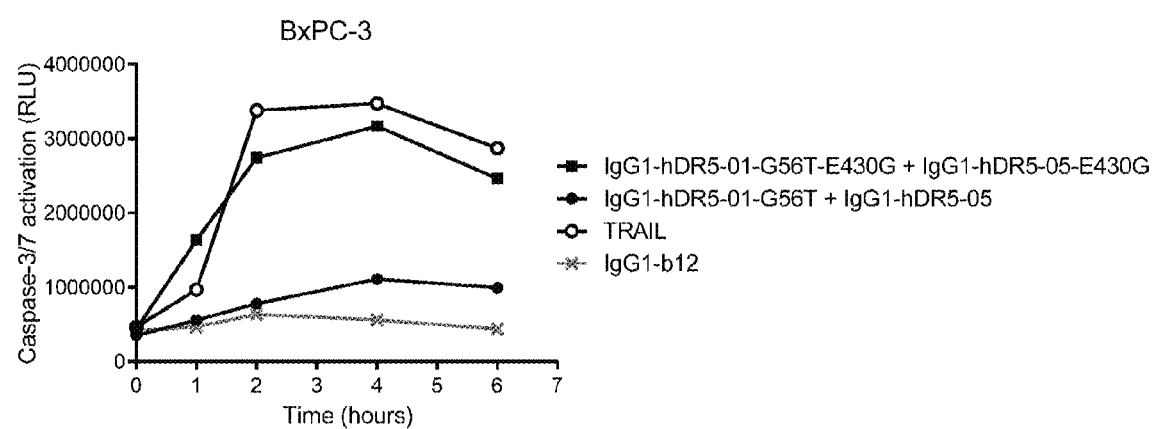

FIG. 43 shows the kinetics of Caspase-3/7 activation upon binding of the antibody combination IgG1-hDR5-01-G56T-E430G+IgG1-hDR5-05-E430G on BxPC-3 pancreatic cancer cells, compared to the parental WT combination without the E430G mutation and TRAIL. BxPC-3 cells were incubated with antibody for 1, 2, 4 and 6 hours. Caspase-3/7 activation was analyzed in a homogenous luminescence assay. RLU, relative luminescence units. A representative example of four experiments is shown.

Figure 44:
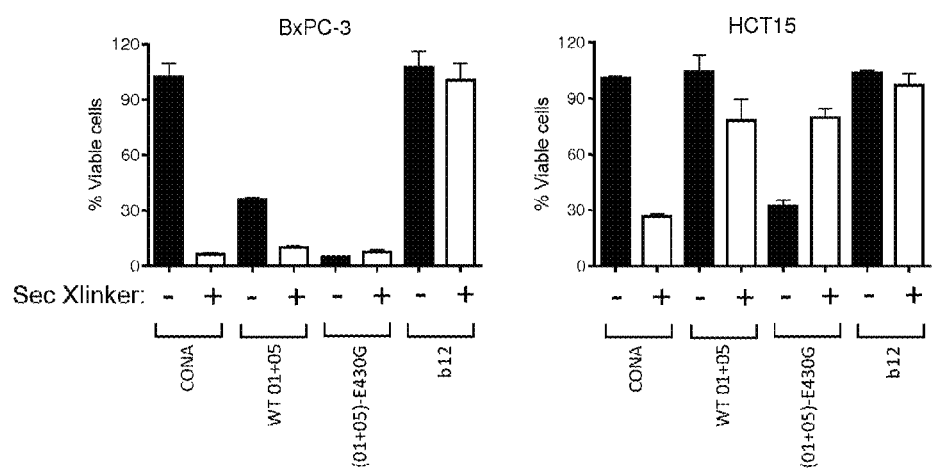

FIG. 44 shows efficacy of the combination of IgG1-hDR5-01-G56T-E430G+IgG1-hDR5-05-E430G in the presence or absence of Fc crosslinking by F(ab')$_2$ fragments of an anti-human IgG antibody and comparison to the anti-DR5 antibody IgG1-DR5-CONA and the combination of WT antibodies IgG1-hDR5-01-G56T+IgG1-hDR5-05 in a 3-days viability assay on adherent HCT-15 human colon cancer and BxPC-3 pancreatic cancer cells. The non-target binding antibody IgG1-b12 was included as a negative control. Graphs show the mean+/−standard deviation from duplicate samples. For both cell lines, a representative example of two experiments is shown.

Figure 45A:
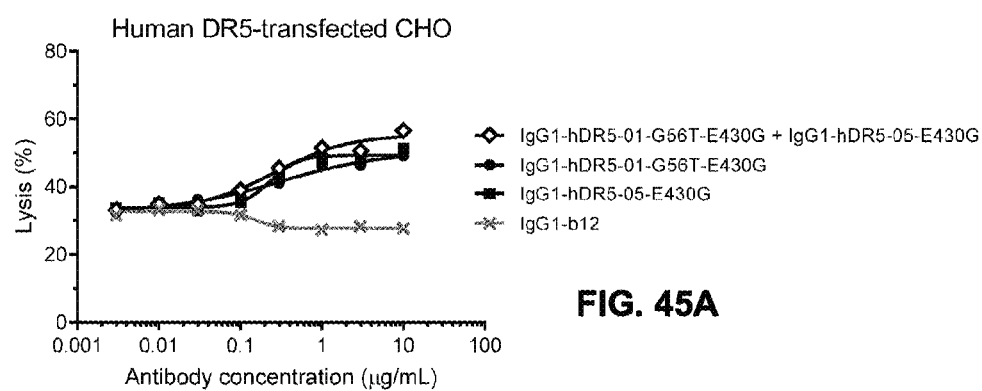
Figure 45B:
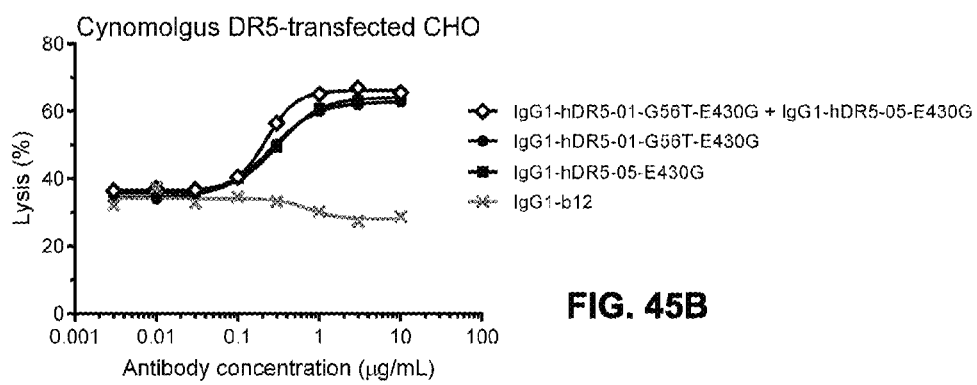
Figure 45C:
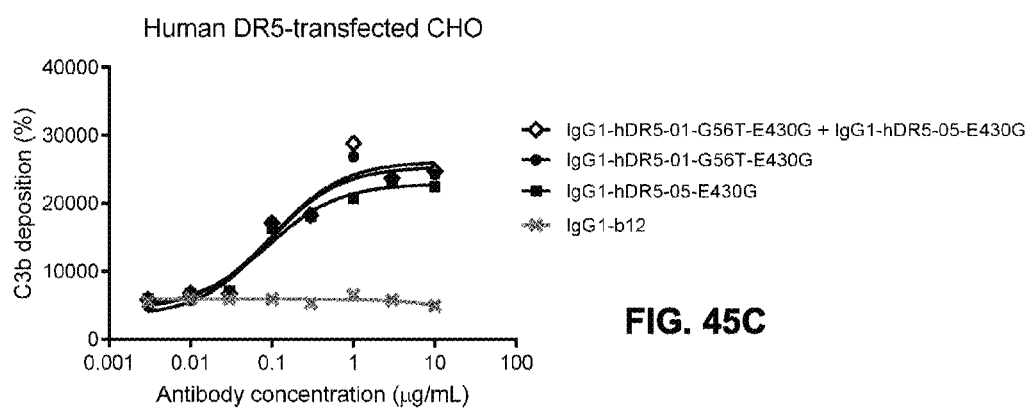
Figure 45D:
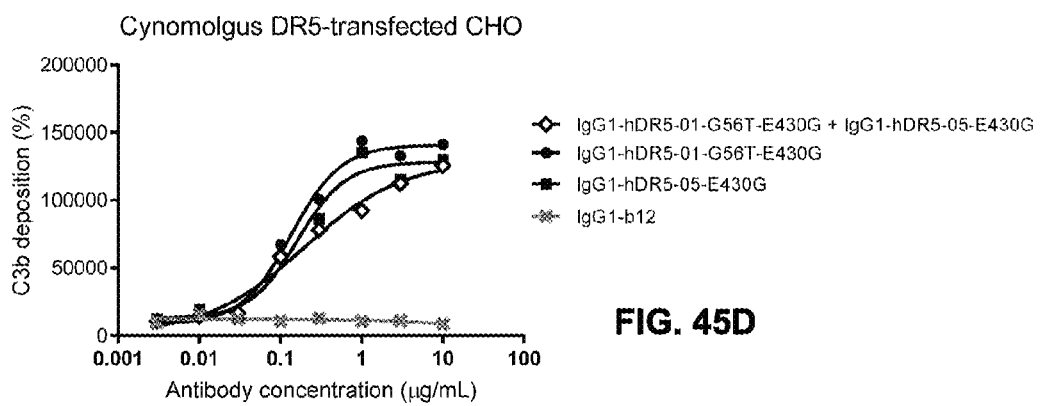

FIGS. 45A-45D show the analysis of IgG1-hDR5-01-G56T-E430G and IgG1-hDR5-05-E430G to induce complement activation upon target cell binding on CHO cells transfected with human (FIG. 45A, FIG. 45C) or cynomolgus DR5 (FIG. 45B, FIG. 45D). (FIGS. 45A and 45B) In vitro CDC assay with antibody concentration series in the presence of 20% pooled normal human serum. CDC efficacy is presented as the percentage lysis determined by the percentage propidium iodide (PI)-positive cells. (FIGS. 45C and 45D) Deposition of complement activation products upon antibody binding in the presence of C5-depleted serum is expressed as geometric mean of fluorescence intensity. The IgG1-b12 mAb against HIV gp120 was used in as a non-binding isotype control antibody.

FIGS. 46A-46E show the effect of combining the antibody combination IgG1-hDR5-01-G56T-E430G+IgG1-hDR5-05-E430G with different therapeutic agents as determined in a viability assay on five different colon cancer cell lines. Five examples are shown from a synergy screen of 100 compounds from different therapeutic classes.

Figure 47A:
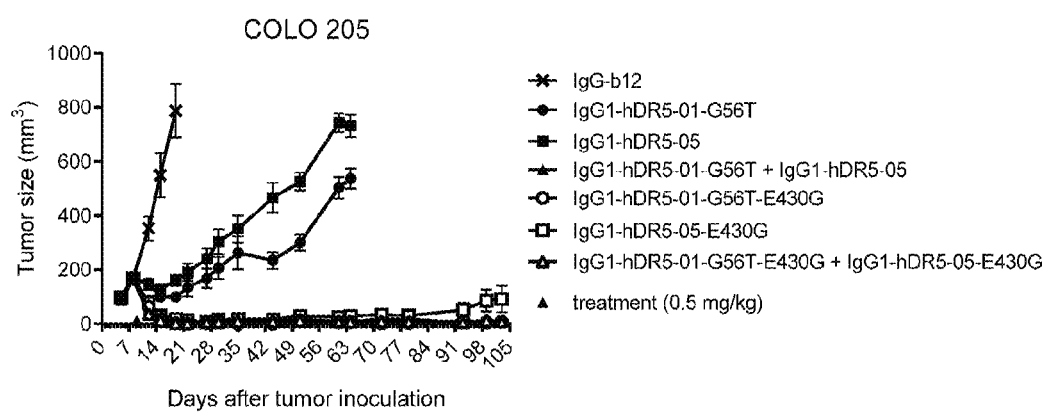
Figure 47B:
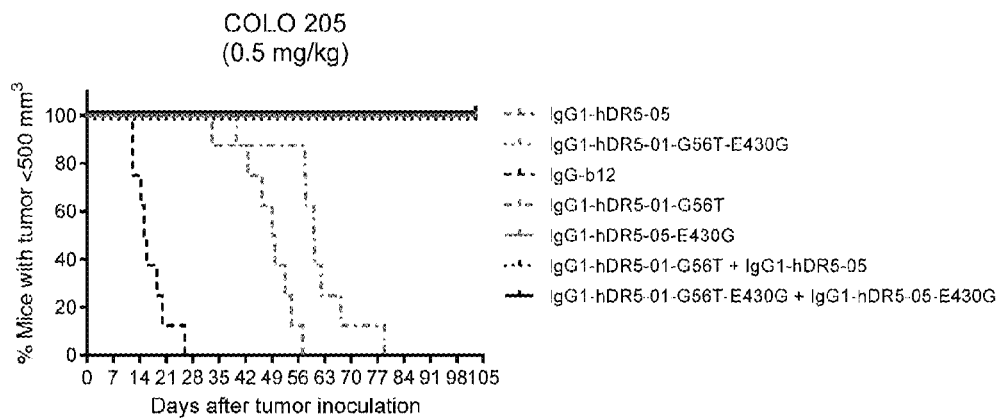

FIGS. 47A and 47B show evaluation of the in vivo efficacy of the antibodies IgG1-hDR5-01-G56T-E430G and IgG1-hDR5-05-E430G, both as single agents and as a combination in comparison to the parental antibodies without the E430G mutation in a subcutaneous xenograft model with COLO 205 human colon cancer cells. (FIG. 47A) Tumor size (mean & SEM) in mice treated with the indicated antibodies (0.5 mg/kg) as shown in time. (FIG. 47B) Kaplan-Meier plot of tumor progression, with a cutoff set at a tumor volume>500 mm$^3$.

Figure 48A:
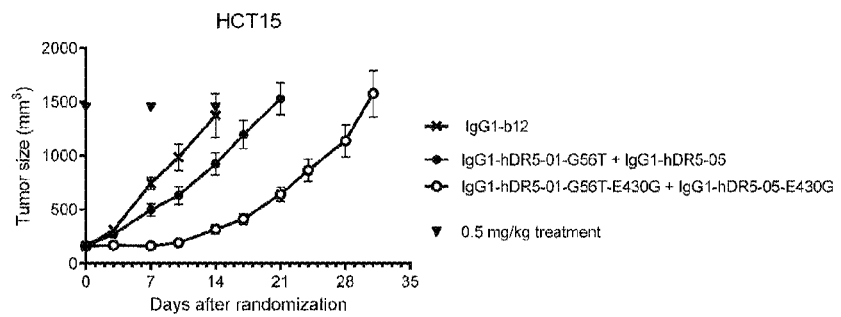
Figure 48B:
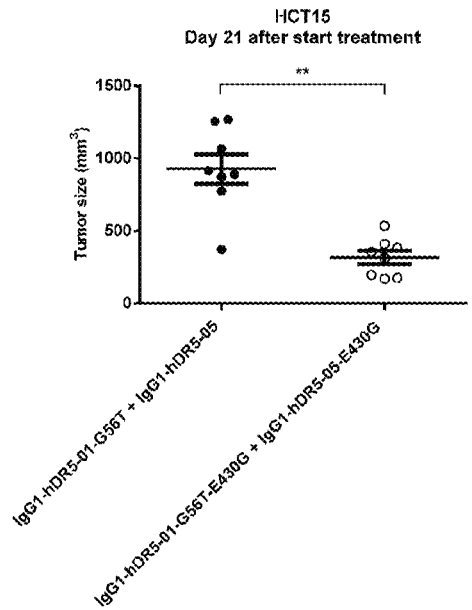
Figure 48C:
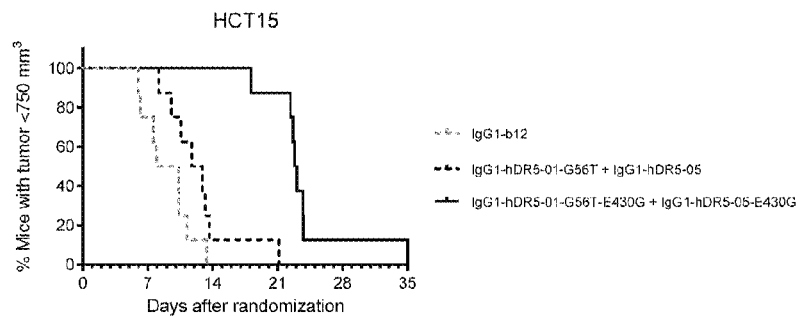

FIGS. 48A-48C shows the evaluation of the in vivo efficacy of the anti-DR5 antibody concentration IgG1-hDR5-01-G56T+IgG1-hDR5-05 with and without the hexamerization-enhancing mutation E430G in a subcutaneous xenograft model with HCT15 human colon cancer cells. Tumor size (mean & SEM) in mice treated with the 0.5 mg/kg antibodies is shown in time (FIG. 48A) and at day 21 after start treatment (FIG. 48B). **$P<0.0011$ (Mann Whitney test). In (FIG. 48C) the percentage of mice with tumor sizes smaller than 750 mm3 is shown in a Kaplan-Meier plot.

Figure 49A:
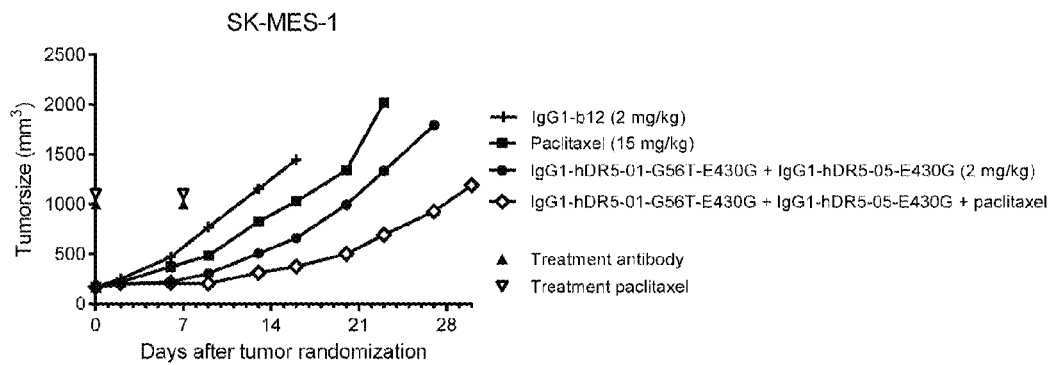
Figure 49B:
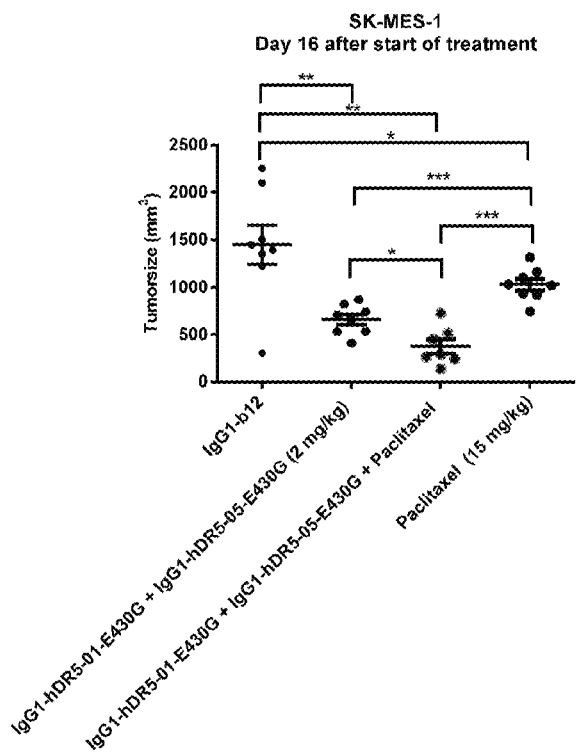
Figure 49C:
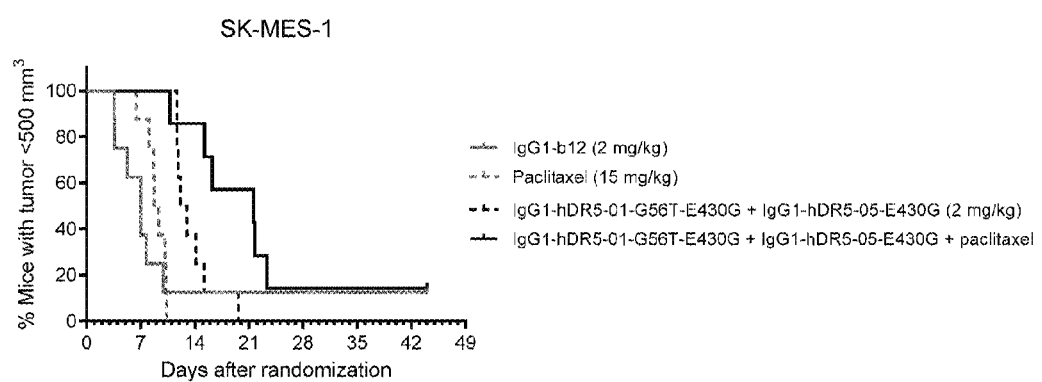

FIGS. 49A-49C show evaluation of the in vivo efficacy of the combination of IgG1-hDR5-01-G56T-E430G+IgG1-hDR5-05-430G antibodies in combination with 15 mg/kg paclitaxel in a subcutaneous xenograft model with SK-MES-1 human lung cancer cells. (FIG. 49A) Tumor size (mean & SEM) in mice treated with the indicated compounds is shown in time. (FIG. 49B) Tumor volume per treatment group at day 16. (FIG. 49C) The percentage of mice with tumor sizes smaller than 500 mm$^3$ is shown in a Kaplan-Meier plot.

Figure 50A:
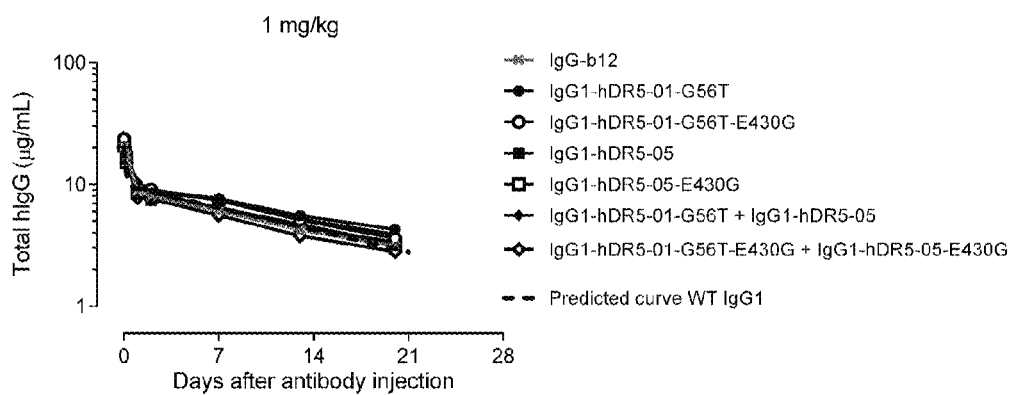
Figure 50B:
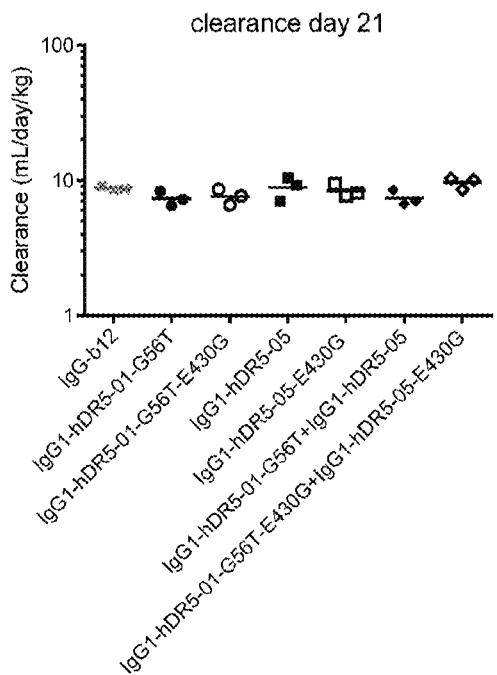

FIGS. 50A and 50B show the clearance rate in SCID mice of 1 mg/kg i.v. administered IgG1-hDR5-01-G56T-E430G, IgG1-hDR5-05-E430G or the combination of the two antibodies in comparison to the parental WT antibodies without the E430G mutation. (FIG. 50A) Total human IgG in serum samples was determined by ELISA and plotted in a concentration versus time curve. Each data point represents the mean+/−standard deviation of four serial diluted samples. (FIG. 50B) Clearance until day 21 after administration of the antibody was determined following the formula D*1.000/AUC with D, injected dose and AUC, area under the curve of the concentration-time curve.

Figure 51:
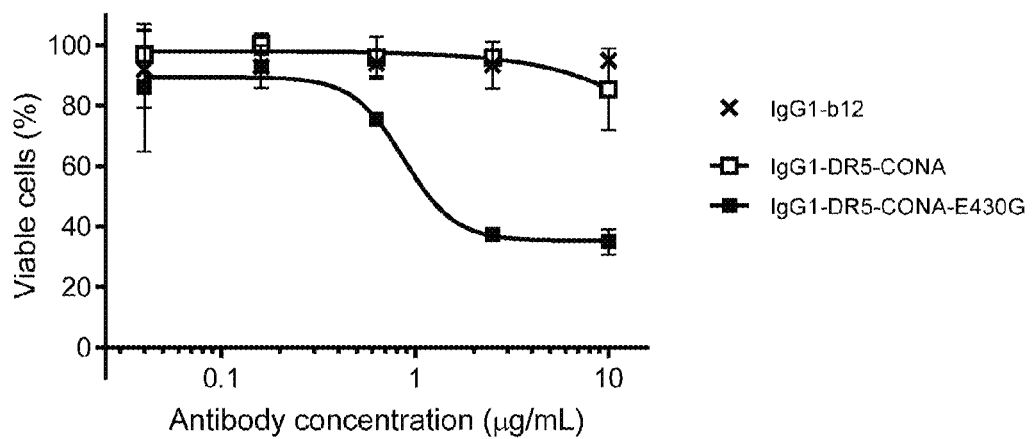

FIG. 51 shows a viability assays with DR5 antibodies IgG1-DR5-CONA and IgG1-DR5-CONA-E430G on attached COLO 205 human colon cancer cells. Introduction of the hexamerization-enhancing mutation E430G resulted in induction of killing. Data are presented as % viable cells calculated from the luminescence relative to samples incubated without antibody (no kill) and samples incubated with Staurosporine (maximal kill). Error bars indicate standard deviation.

DETAILED DESCRIPTION OF THE INVENTION

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose.

As described herein, surprisingly antibodies binding to DR5 and comprising a hexamerization enhancing mutation in the Fc region corresponding to position E430 or E345 of human IgG1 according to EU numbering, were found to be superior at inducing apoptosis in tumor cells expressing DR5 compared to antibodies binding DR5 without a mutation in one of the above mentioned positions. Furthermore, compositions comprising two anti-DR5 antibodies of the invention, which bind different epitopes on DR5, were found superior in in vitro and in vivo studies to compositions comprising the same anti-DR5 antibodies without the mutation. That is compositions with two antibodies of the present invention were superior at inducing apoptosis and/or inhibiting cell growth of tumor cells expressing DR5 compared to compositions comprising two DR5 antibodies without a mutation in the Fc region. By introducing specific mutations in the Fc region, hexamerization upon target binding on the cell surface can be enhanced, while the antibody molecules remain monomeric in solution WO2013/004842, WO2014/108198.

Definitions

The term "immunoglobulin" as used herein, refers to a class of structurally related glycoproteins consisting of two pairs of polypeptide chains, one pair of light (L) low molecular weight chains and one pair of heavy (H) chains, all four potentially inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as VH) and a heavy chain constant region. The heavy chain constant region of IgG antibodies typically is comprised of three domains, CH1, CH2, and CH3. The heavy chains are inter-connected via disulfide bonds in the so-called "hinge region". Each light chain typically is comprised of a light chain variable region (abbreviated herein as VL) and a light chain constant region. The light chain constant region typically is comprised of one domain, CL. The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901 917 (1987)). Unless otherwise stated or contradicted by context, reference to amino acid positions in the present invention is according to the EU-numbering (Edelman et al., Proc Natl Acad Sci USA. 1969 May; 63(1):78-85; Kabat et al., Sequences of Proteins of Immunological Interest, Fifth Edition. 1991 NIH Publication No. 91-3242).

The term "hinge region" as used herein is intended to refer to the hinge region of an immunoglobulin heavy chain.

Thus, for example the hinge region of a human IgG1 antibody corresponds to amino acids 216-230 according to the EU numbering.

The term "CH2 region" or "CH2 domain" as used herein is intended to refer the CH2 region of an immunoglobulin heavy chain. Thus, for example the CH2 region of a human IgG1 antibody corresponds to amino acids 231-340 according to the EU numbering. However, the CH2 region may also be any of the other isotypes or allotypes as described herein.

The term "CH3 region" or "CH3 domain" as used herein is intended to refer to the CH3 region of an immunoglobulin heavy chain. Thus, for example the CH3 region of a human IgG1 antibody corresponds to amino acids 341-447 according to the EU numbering. However, the CH3 region may also be any of the other isotypes or allotypes as described herein.

The term "fragment crystallizable region", "Fc region", "Fc fragment" or "Fc domain", which may be used interchangeably herein, refers to an antibody region comprising, arranged from amino-terminus to carboxy-terminus, at least a hinge region, a CH2 domain and a CH3 domain. An Fc region of an IgG1 antibody can, for example, be generated by digestion of an IgG1 antibody with papain. The Fc region of an antibody may mediate the binding of the immunoglobulin to host tissues or factors, including various cells of the immune system (such as effector cells) and components of the complement system such as C1q, the first component in the classical pathway of complement activation.

The term "Fab fragment" in the context of the present invention, refers to a fragment of an immunoglobulin molecule, which comprises the variable regions of the heavy chain and light chain as well as the constant region of the light chain and the CH1 region of the heavy chain of an immunoglobulin. The "CH1 region" refers e.g. to the region of a human IgG1 antibody corresponding to amino acids 118-215 according to the EU numbering. Thus, the Fab fragment comprises the binding region of an immunoglobulin.

The term "antibody" (Ab), as used herein refers to an immunoglobulin molecule, a fragment of an immunoglobulin molecule, or a derivative of either thereof. The antibody of the present invention comprises an Fc-region of an immunoglobulin and an antigen-binding region. The Fc region generally contains two CH2-CH3 regions and a connecting region, e.g. a hinge region. The variable regions of the heavy and light chains of the immunoglobulin molecule contain a binding domain that interacts with an antigen. The term "antibody" as used herein, also refers to, unless otherwise specified or contradicted by the context, polyclonal antibodies, oligoclonal antibodies, monoclonal antibodies (such as human monoclonal antibodies), antibody mixtures, recombinant polyclonal antibodies, chimeric antibodies, humanized antibodies and human antibodies. An antibody as generated can potentially possess any class or isotype.

The term "human antibody", as used herein, refers to antibodies having variable and constant regions derived from human germline immunoglobulin sequences. The human antibodies of the invention may include amino acid residues not encoded by human germline immunoglobulin sequences (e.g., mutations, insertions or deletions introduced by random or site-specific mutagenesis in vitro or by somatic mutation in vivo). However, the term "human antibody", as used herein, is not intended to include antibodies in which CDR sequences derived from the germline of another species, such as a mouse, have been grafted onto human framework sequences.

The term "chimeric antibody", as used herein, refers to an antibody in which both chain types i.e. heavy chain and light chain are chimeric as a result of antibody engineering. A chimeric chain is a chain that contains a foreign variable domain (originating from a non-human species, or synthetic or engineered from any species including human) linked to a constant region of human origin.

The term "humanized antibody, as used herein, refers to an antibody in which both chain types are humanized as a result of antibody engineering. A humanized chain is typically a chain in which the complementarity determining regions (CDR) of the variable domains are foreign (originating from a species other than human, or synthetic) whereas the remainder of the chain is of human origin. Humanization assessment is based on the resulting amino acid sequence, and not on the methodology per se, which allows protocols other than grafting to be used.

The term "isotype", as used herein, refers to the immunoglobulin class (for instance IgG1, IgG2, IgG3, IgG4, IgD, IgA1, IgA2, IgE, or IgM) that is encoded by heavy chain constant region genes. To produce a canonical antibody, each heavy chain isotype is to be combined with either a kappa (κ) or lambda (λ) light chain.

Figure 1:
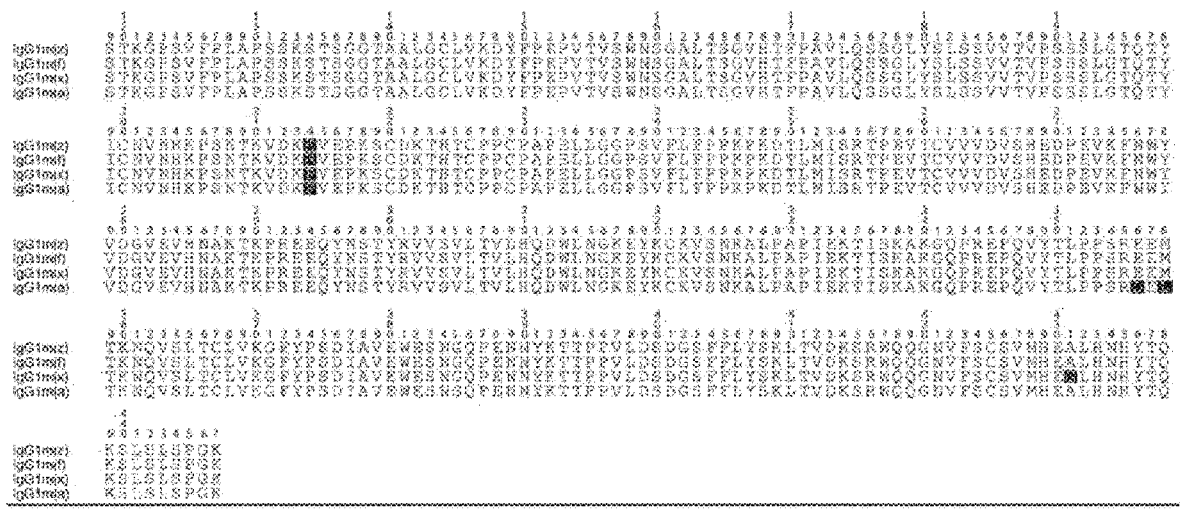
FIG. 1 shows an amino acid alignment of the four different human IgG1 Fc allotypes. The Fc sequence of the IgG1m(f), IgG1m(z), IgG1m(a), IgG1m(x) is specified in SEQ ID: 29, 30, 31 and 32 respectively.

The term "allotype", as used herein, refers to the amino acid variation within one isotype class in the same species. The predominant allotype of an antibody isotype varies between ethnicity individuals. The known allotype variations within the IgG1 isotype of the heavy chain result from 4 amino acid substitutions in the antibody frame as illustrated in FIG. 1. In one embodiment the antibody of the invention is of the IgG1m(f) allotype as defined in SEQ ID NO 29. In one embodiment of the invention the antibody is of the IgG1m(z) allotype as defined in SEQ ID NO 30, the IgG1m(a) allotype as defined in SEQ ID NO 31, the IgG1m (x) allotype as defined in SEQ ID NO 32, or any allotype combination, such as IgG1m(z,a), IgG1m(z,a,x), IgG1m(f,a) (de Iange Exp Clin Immunogenet. 1989; 6(1):7-17).

The terms "monoclonal antibody", "monoclonal Ab", "monoclonal antibody composition", "mAb", or the like, as used herein refer to a preparation of Ab molecules of single molecular composition. A monoclonal antibody composition displays a single binding specificity and affinity for a particular epitope. Accordingly, the term "human monoclonal antibody" refers to Abs displaying a single binding specificity which have variable and constant regions derived from human germline immunoglobulin sequences. The human mAbs may be generated by a hybridoma which includes a B cell obtained from a transgenic or transchromosomal non-human animal, such as a transgenic mouse, having a genome comprising a human heavy chain transgene repertoire and a human light chain transgene repertoire, rearranged to produce a functional human antibody and fused to an immortalized cell. Alternatively, the human mAbs may be generated recombinantly.

The term "antibody mimetics" as used herein, refers to compounds that, like antibodies, can specifically bind antigens, but that are not structurally related to antibodies. They are usually artificial peptides, proteins, nucleic acids or small molecules.

The term "bispecific antibody" refers to an antibody having specificities for at least two different, typically non-overlapping, epitopes. Such epitopes may be on the same or different targets Examples of different classes of bispecific antibodies comprising an Fc region include but are not limited to: asymmetric bispecific molecules e.g. IgG-like molecules with complementary CH3 domains and symmetric bispecific molecules e.g. recombinant IgG-like dual targeting molecules wherein each antigen-binding region of the molecule binds at least two different epitopes.

Examples of bispecific molecules include but are not limited to Triomab® (Trion Pharma/Fresenius Biotech, WO/2002/020039), Knobs-into-Holes (Genentech, WO9850431), CrossMAbs (Roche, WO 2009/080251, WO 2009/080252, WO 2009/080253), electrostatically-matched Fc-heterodimeric molecules (Amgen, EP1870459 and WO2009089004; Chugai, US201000155133; Oncomed, WO2010129304), LUZ-Y (Genentech), DIG-body, PIG-body and TIG-body (Pharmabcine), Strand Exchange Engineered Domain body (SEEDbody) (EMD Serono, WO2007110205), Bispecific IgG1 and IgG2 (Pfizer/Rinat, WO11143545), Azymetric scaffold (Zymeworks/Merck, WO2012058768), mAb-Fv (Xencor, WO2011028952), XmAb (Xencor), Bivalent bispecific antibodies (Roche, WO2009/080254), Bispecific IgG (Eli Lilly), DuoBody® molecules (Genmab A/S, WO 2011/131746), DuetMab (Medimmune, US2014/0348839), Biclonics (Merus, WO 2013/157953), NovImmune (κλBodies, WO 2012/023053), FcΔAdp (Regeneron, WO 2010/151792), (DT)-Ig (GSK/Domantis), Two-in-one Antibody or Dual Action Fabs (Genentech, Adimab), mAb2 (F-Star, WO2008003116), Zybodies™ (Zyngenia), CovX-body (CovX/Pfizer), FynomAbs (Covagen/Janssen Cilag), DutaMab (Dutalys/Roche), iMab (Medimmune), Dual Variable Domain (DVD)-Ig™ (Abbott, U.S. Pat. No. 7,612,18), dual domain double head antibodies (Unilever; Sanofi Aventis, WO20100226923), Ts2Ab (Medimmune/AZ), BsAb (Zymogenetics), HERCULES (Biogen Idec, US007951918), scFv-fusions (Genentech/Roche, Novartis, Immunomedics, Changzhou Adam Biotech Inc, CN 102250246), TvAb (Roche, WO2012025525, WO2012025530), ScFv/Fc Fusions, SCORPION (Emergent BioSolutions/Trubion, Zymogenetics/BMS), Interceptor (Emergent), Dual Affinity Retargeting Technology (Fc-DART™) (MacroGenics, WO2008/157379, WO2010/080538), BEAT (Glenmark), Di-Diabody (Imclone/Eli Lilly) and chemically crosslinked mAbs (Karmanos Cancer Center), and covalently fused mAbs (AIMM therapeutics).

The term "full-length antibody" when used herein, refers to an antibody (e.g., a parent or variant antibody) which contains all heavy and light chain constant and variable domains corresponding to those that are normally found in a wild-type antibody of that class or isotype.

The term "oligomer" as used herein, refers to a molecule that consists of more than one but a limited number of monomer units (e.g. antibodies) in contrast to a polymer that, at least in principle, consists of an unlimited number of monomers. Exemplary oligomers are dimers, trimers, tetramers, pentamers and hexamers. Greek prefixes are often used to designate the number of monomer units in the oligomer, for example a tetramer being composed of four units and a hexamer of six units. Likewise, the term "oligomerization", as used herein, is intended to refer to a process that converts molecules to a finite degree of polymerization. Herein, it is observed, that antibodies and/or other dimeric proteins comprising target-binding regions according to the invention can form oligomers, such as hexamers, via non-covalent association of Fc-regions after target binding, e.g., at a cell surface.

The term "antigen-binding region", "antigen binding region", "binding region" or antigen binding domain, as used herein, refers to a region of an antibody which is capable of binding to the antigen. This binding region is typically defined by the VH and VL domains of the antibody which may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). The antigen can be any molecule, such as a polypeptide, e.g. present on a cell, bacterium, or virion or in solution. The terms "antigen" and "target" may, unless contradicted by the context, be used interchangeably in the context of the present invention.

The term "target", as used herein, refers to a molecule to which the antigen binding region of the antibody binds. The target includes any antigen towards which the raised antibody is directed. The term "antigen" and "target" may in relation to an antibody be used interchangeably and constitute the same meaning and purpose with respect to any aspect or embodiment of the present invention.

The term "epitope" means a protein determinant capable of specific binding to an antibody. Epitopes usually consist of surface groupings of building blocks such as amino acids, sugar side chains or a combination thereof and usually have specific three-dimensional structural characteristics, as well as specific charge characteristics. Conformational and non-conformational epitopes are distinguished in that the binding to the former but not the latter is lost in the presence of denaturing solvents. The epitope may comprise amino acid residues directly involved in the binding and other amino acid residues, which are not directly involved in the binding, such as amino acid residues which are effectively blocked by the specifically antigen binding peptide (in other words, the amino acid residue is within the footprint of the specifically antigen binding peptide).

The term "binding" as used herein refers to the binding of an antibody to a predetermined antigen or target, typically with a binding affinity corresponding to a $K_D$ of about $10^{-6}$ M or less, e.g. $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the antibody as the analyte or visa versa, and binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antibody, so that when the $K_D$ of the antibody is very low (that is, the antibody is highly specific), then the degree with which the affinity for the antigen is lower than the affinity for a non-specific antigen may be at least 10,000 fold. The term "$K_D$" (M), as used herein, refers to the dissociation equilibrium constant of a particular antibody-antigen interaction, and is obtained by dividing $k_d$ by $k_a$.

The term "$k_d$" (sec$^{-1}$), as used herein, refers to the dissociation rate constant of a particular antibody-antigen interaction. Said value is also referred to as the $k_{off}$ value or off-rate.

The term "$k_a$" (M$^{-1}$×sec$^{-1}$), as used herein, refers to the association rate constant of a particular antibody-antigen interaction. Said value is also referred to as the $k_{on}$ value or on-rate.

The term "$K_A$" (M$^{-1}$), as used herein, refers to the association equilibrium constant of a particular antibody-antigen interaction and is obtained by dividing $k_a$ by $k_d$.

As used herein, the term "affinity" is the strength of binding of one molecule, e.g. an antibody, to another, e.g. a target or antigen, at a single site, such as the monovalent binding of an individual antigen binding site of an antibody to an antigen.

As used herein, the term "avidity" refers to the combined strength of multiple binding sites between two structures, such as between multiple antigen binding sites of antibodies simultaneously interacting with a target. When more than one binding interactions are present, the two structures will only dissociate when all binding sites dissociate, and thus, the dissociation rate will be slower than for the individual binding sites, and thereby providing a greater effective total binding strength (avidity) compared to the strength of binding of the individual binding sites (affinity).

The term "hexamerization enhancing mutation", as used herein, refers to a mutation of an amino acid position corresponding to E430, E345 or S440 in human IgG1 according to EU numbering. The hexamerization enhancing mutation strengthens Fc-Fc interactions between neighbouring IgG antibodies that are bound to a cell surface target, resulting in enhanced hexamer formation of the target-bound antibodies, while the antibody molecules remain monomeric in solution as described in WO2013/004842; WO2014/108198.

The term "repulsing mutation" or "self-repulsing mutation" or "hexamerization-inhibiting mutation", as used herein, refers to a mutation of an amino acid position of human IgG1 that can result in charge repulsion between amino acids at the Fc-Fc interface, resulting in weakening of the Fc-Fc interaction between two adjacent Fc region containing polypeptides, and thus inhibiting hexamerization. Examples of such a repulsing mutation in human IgG1 are K439E and S440K. The repulsion in the Fc-Fc interaction between two adjacent Fc region containing polypeptides at the position of a repulsing mutation can be neutralized by introduction of a second mutation (complementary mutation) in the amino acid position that interacts with the position harboring the first mutation. This second mutation can be present either in the same antibody or in a second antibody. The combination of the first and second mutation results in neutralization of the repulsion and restoration of the Fc-Fc interactions and thus hexamerization. Examples of such first and second mutations are K439E (repulsing mutation) and S440K (neutralizing the repulsion by K439E), and vice versa S440K (repulsing mutation) and K439E (neutralizing the repulsion by S440K).

The term "complementary mutation", as used herein, refers to a mutation of an amino acid position in a Fc region-containing polypeptide that relates to a first mutation in an adjacent Fc region containing polypeptide that preferably interacts with the Fc region-containing polypeptide containing the complementary mutation due to the combination of the two mutations in the two adjacent Fc region-containing polypeptides. The complementary mutation and the related first mutation can be present either in the same antibody (intramolecular) or in a second antibody (intermolecular). An example of intramolecular complementary mutations is the combination K409R and F405L that mediates preferential heterodimerization in a bispecific antibody according to WO 2011/131746. The combination of the K439E and S440K mutations that results in neutralization of repulsion and restoration of Fc-Fc interactions between two adjacent Fc region containing polypeptides and thus hexamerization is an example of complementary mutations that can be applied both inter- and intramolecularly.

The term "apoptosis", as used herein refers to the process of programmed cell death (PCD) that may occur in a cell. Biochemical events lead to characteristic cell changes (morphology) and death. These changes include blebbing, cell shrinkage, phosphatidylserine exposure, loss of mitochondrial function, nuclear fragmentation, chromatin condensation, caspase activation, and chromosomal DNA fragmentation. In a particular embodiment, apoptosis by one or more agonistic anti-DR5 antibodies can be determined using methods such as, e.g., caspase-3/7 activation assays described in examples 19, 20, 25 and 45 or phosphatidylserine exposure described in examples 19 and 25. Anti-DR5 antibody at a fixed concentration of e.g. 1 µg/mL may be added to adhered cells and incubated for 1 to 24 hours. Caspase-3/7 activation can be determined by using special kits for this purpose, such as the PE Active Caspase-3 Apoptosis Kit of BD Pharmingen (Cat nr 550914) (example 19 and 25) or the Caspase-Glo 3/7 assay of Promega (Cat nr G8091) (examples 20 and 45). Phosphatidylserine exposure and cell death can be determined by using special kits for this purpose, such as the FITC Annexin V Apoptosis Detection Kit I from BD Pharmingen (Cat nr 556547) (examples 19 and 25).

The term "programmed cell-death" or "PCD", as used herein refers to the death of a cell in any form mediated by an intracellular signaling, e.g. apoptosis, autophagy or necroptosis.

The term "Annexin V", as used herein, refers to a protein of the annexin group that binds phosphatidylserine (PS) on the cell surface.

The term "caspase activation", as used herein, refers to cleavage of inactive pro-forms of effector caspases by initiator caspases, leading to their conversion into effector caspases, which in turn cleave protein substrates within the cell to trigger apoptosis.

The term "caspase-dependent programmed cell death", as used herein refers to any form of programmed cell death mediated by caspases. In a particular embodiment, caspase-dependent programmed cell death by one or more agonistic anti-DR5 antibodies can be determined by comparing the viability of a cell culture in the presence and absence of pan-caspase inhibitor Z-Val-Ala-DL-Asp-fluoromethylketone (Z-VAD-FMK) as described in examples 18 and 44. Pan-caspase inhibitor Z-VAD-FMK (5 µM end concentration) may be added to adhered cells in 96-well flat bottom plates and incubated for one hour at 37° C. Next, antibody concentration dilution series (e.g. starting from e.g. 20,000 ng/mL to 0.05 ng/mL final concentration in 5-fold dilutions) may be added and incubated for 3 days at 37° C. Cell viability can be quantified using special kits for this purpose, such as the CellTiter-Glo luminescent cell viability assay of Promega (Cat nr G7571).

The term "cell viability", as used herein refers to the presence of metabolically active cells. In a particular embodiment, cell viability after incubation with one or more agonistic anti-DR5 antibodies can be determined by quantifying the ATP present in the cells as described in examples 8-18, 21-24, 38-44, 46 and 48. Antibody concentration dilution series (e.g. starting from e.g. 20,000 ng/mL to 0.05 ng/mL final concentration in 5-fold dilutions) may be added to cells in 96-well flat bottom plates, medium may be used as negative control and 5 µM staurosporine may be used as positive control for the induction of cell death. After 3 days incubation cell viability may be quantified using special kits for this purpose, such as the CellTiter-Glo luminescent cell viability assay of Promega (Cat nr G7571). The percentage viable cells can be calculated using the following formula:

% viable cells=[(luminescence antibody sample−luminescence staurosporine sample)/(luminescence no antibody sample−luminescence staurosporine sample)]*100.

The term "DR5", as used herein, refers to death receptor 5, also known as CD262 and TRAILR2, which is a single-pass type I membrane protein with three extracellular cysteine-rich domains (CRD's), a transmembrane domain (TM) and a cytoplasmic domain containing a death domain (DD). In humans, the DR5 protein is encoded by a nucleic acid sequence encoding the amino acid sequence shown in SEQ ID NO 46, (human DR5 protein: UniprotKB/Swissprot 014763).

The term "antibody binding DR5", "anti-DR5 antibody" DR5-binding antibody", "DR5-specific antibody", "DR5 antibody" which may be used interchangeably herein, refers to any antibody binding an epitope on the extracellular part of DR5."

The term "agonist" as used herein, refers to a molecule such as an anti-DR5 antibody that is able to trigger a response in a cell when bound to DR5, wherein the response may be programmed cell death. That the anti-DR5 antibody is agonistic is to be understood as that the antibody stimulates, activates or clusters DR5 as the result from anti-DR5 binding to DR5. That is an agonistic anti-DR5 antibody comprising an amino acid mutation in the Fc region according to the present invention bound to DR5 results in DR5 stimulation, clustering or activation of the same intracellular signaling pathways as TRAIL bound to DR5. In a particular embodiment, the agonistic activity of one or more antibodies can be determined by incubating target cells for 3 days with an antibody concentration dilution series (e.g. from 20,000 ng/mL to 0.05 ng/mL final concentration in 5-fold dilutions). The antibodies may be added directly when cells are seeded (described in examples 8, 9, 10, 39), or alternatively the cells are first allowed to adhere to 96-well flat-bottom plates before adding the antibody samples (described in examples 11, 12, 13, 14, 15, 16, 17, 18, 21, 22, 23, 24, 38, 40, 41, 42, 43, 44, 46, 48). The agonistic activity i.e. the agonistic effect can be quantified by measuring the amount of viable cells using special kits for this purpose, such as the CellTiter-Glo luminescent cell viability assay of Promega (Cat nr G7571).

The terms "DR5 positive" and "DR5 expressing" as used herein, refers to tissues or cell lines which show binding of a DR5-specific antibody which can be measured with e.g. flow cytometry or immunohistochemistry.

A "variant" or "antibody variant" of the present invention is an antibody molecule which comprises one or more mutations as compared to a "parent" antibody. Exemplary parent antibody formats include, without limitation, a wild-type antibody, a full-length antibody or Fc-containing antibody fragment, a bispecific antibody, a human antibody, humanized antibody, chimeric antibody or any combination thereof.

Exemplary mutations include amino acid deletions, insertions, and substitutions of amino acids in the parent amino acid sequence. Amino acid substitutions may exchange a native amino acid present in the wild-type protein for another naturally-occurring amino acid, or for a non-naturally-occurring amino acid derivative. The amino acid substitution may be conservative or non-conservative. In the context of the present invention, conservative substitutions may be defined by substitutions within the classes of amino acids reflected in one or more of the following three tables:

Amino Acid Residue Classes for Conservative Substitutions

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Alternative Conservative Amino Acid Residue Substitution Classes

| | | | |
|---|---|---|---|
| 1 | A | S | T |
| 2 | D | E | |
| 3 | N | Q | |
| 4 | R | K | |
| 5 | I | L | M |
| 6 | F | Y | W |

Alternative Physical and Functional Classifications of Amino Acid Residues

| | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, D, E, and R |

In the context of the present invention, a substitution in a variant is indicated as:

Original amino acid–position–substituted amino acid;

The three letter code, or one letter code, are used, including the codes Xaa and X to indicate amino acid residue. Accordingly, the notation "E345R" or "Glu345Arg" means, that the variant comprises a substitution of Glutamic acid with Arginine in the variant amino acid position corresponding to the amino acid in position 345 in the parent antibody. Where a position as such is not present in an antibody, but the variant comprises an insertion of an amino acid, for example: Position–substituted amino acid; the notation, e.g., "448E" is used. Such notation is particular relevant in connection with modification(s) in a series of homologous polypeptides or antibodies. Similarly when the identity of the substitution amino acid residues(s) is immaterial: Original amino acid–position; or "E345".

For a modification where the original amino acid(s) and/or substituted amino acid(s) may comprise more than one, but not all amino acid(s), the substitution of Glutamic acid for Arginine, Lysine or Tryptophan in position 345: "Glu345Arg,Lys,Trp" or "E345R,K,W" or "E345R/K/W" or "E345 to R, K or W" may be used interchangeably in the context of the invention. Furthermore, the term "a substitution" embraces a substitution into any one of the other nineteen natural amino acids, or into other amino acids, such as non-natural amino acids. For example, a substitution of amino acid E in position 345 includes each of the following substitutions: 345A, 345C, 345D, 345G, 345H, 345F, 345I, 345K, 345L, 345M, 345N, 345Q, 345R, 345S, 345T, 345V, 345W, and 345Y. This is, by the way, equivalent to the designation 345X, wherein the X designates any amino acid.

These substitutions can also be designated E345A, E345C, etc, or E345A,C,ect, or E345A/C/ect. The same applies to analogy to each and every position mentioned herein, to specifically include herein any one of such substitutions.

For the purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment).

For the purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment–Total Number of Gaps in Alignment).

The sequence of CDR variants may differ from the sequence of the CDR of the parent antibody sequences through mostly conservative, physical or functional amino acids substitutions at most 5 mutations or substitutions selected from conservative, physical or functional amino acids in total across the six CDR sequences of the antibody binding region, such as at most 4 mutations or substitutions selected from conservative, physical or functional amino acids, such as at most 3 mutations or substitutions selected from conservative, physical or functional amino acids, such as at most 2 mutations selected from conservative, physical or functional amino acids or substitutions, such as at most 1 mutation or substitution selected from a conservative, physical or functional amino acid, in total across the six CDR sequences of the antibody binding region. The conservative, physical or functional amino acids are selected from the 20 natural amino acids found i.e, Arg (R), His (H), Lys (K), Asp (D), Glu (E), Ser (S), Thr (T), Asn (N), Gln (Q), Cys (C), Gly (G), Pro (P), Ala (A), Ile (I), Leu (L), Met (M), Phe (F), Trp (W), Tyr (Y) and Val (V).

The sequence of CDR variants may differ from the sequence of the CDR of the parent antibody sequences through mostly conservative, physical or functional amino acids substitutions; for instance at least about 75%, about 80% or more, about 85% or more, about 90% or more, (e.g., about 75-95%, such as about 92%, 93% or 94%) of the substitutions in the variant are mutations or substitutions selected from conservative, physical or functional amino acids residue replacements.

The conservative, physical or functional amino acids are selected from the 20 natural amino acids found i.e, Arg (R), His (H), Lys (K), Asp (D), Glu (E), Ser (S), Thr (T), Asn (N), Gln (Q), Cys (C), Gly (G), Pro (P), Ala (A), Ile (I), Leu (L), Met (M), Phe (F), Trp (W), Tyr (Y) and Val (V).

An amino acid or segment in one sequence that "corresponds to" an amino acid or segment in another sequence is one that aligns with the other amino acid or segment using a standard sequence alignment program such as ALIGN, ClustalW or similar, typically at default settings. Hence a standard sequence alignment program can be used to identify which amino acid in an e.g. immunoglobulin sequence corresponds to a specific amino acid in e.g. human IgG1. Further a standard sequence alignment program can be used to identify sequence identity e.g. a sequence identity to SEQ ID NO:29 of at least 80%, or 85%, 90%, or at least 95%. For example, the sequence alignments shown in FIG. 1 can be used to identify any amino acid in the Fc region of one IgG1 allotype that corresponds to a particular amino acid in another allotype of an IgG1 Fc sequence.

The term "vector," as used herein, refers to a nucleic acid molecule capable of inducing transcription of a nucleic acid segment ligated into the vector. One type of vector is a "plasmid", which is in the form of a circular double stranded DNA loop. Another type of vector is a viral vector, wherein the nucleic acid segment may be ligated into the viral genome. Certain vectors are capable of autonomous replication in a host cell into which they are introduced (for instance bacterial vectors having a bacterial origin of replication and episomal mammalian vectors). Other vectors (such as non-episomal mammalian vectors) may be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present invention is intended to include such other forms of expression vectors, such as viral vectors (such as replication defective retroviruses, adenoviruses and adeno-associated viruses), which serve equivalent functions.

The term "recombinant host cell" (or simply "host cell"), as used herein, is intended to refer to a cell into which an expression vector has been introduced. It should be understood that such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO-S cells, HEK-293F cells, Expi293F cells, PER.C6, NSO cells, and lymphocytic cells, and prokaryotic cells such as E. coli and other eukaryotic hosts such as plant cells and fungi, as well as prokaryotic cells such as E. coli.

Specific Embodiments of the Invention

The present invention is based, at least in part, on the discovery that the ability of an anti-DR5 antibody to induce cell death in a target cell expressing DR5 can be greatly enhanced by introducing a specific mutation in the Fc region corresponding to amino acid positions E430, E345 or S440 in human IgG1 according to EU numbering. The invention is further based on the surprising finding that a combination of two antibodies binding to a first and a second epitope on DR5 and each comprising a mutation in the Fc region may form heterohexamers and show superior induction of cell death in a target cell compared to a combination of the two antibodies without the mutation in the Fc region.

In one aspect the present invention relates to an anti-DR5 antibody comprising an Fc region of a human immunoglobulin IgG and an antigen binding region binding to DR5, wherein the Fc region comprises a mutation at an amino acid position corresponding to position E430, E345 or S440 in human IgG1 according to EU numbering.

The positions corresponding to E430, E345 and S440 in human IgG1 according to EU numbering are located in the CH3 domain of the Fc region.

The anti-DR5 antibody according to the present invention comprises an Fc region comprising a first and a second heavy chain, wherein a mutation at a position according to the present invention corresponding to E430, E345 or S440 in human IgG1 according to EU numbering is present in both the first and the second heavy chain, or less preferred only be present in one of the heavy chains. In the context of the present invention the hexamerization enhancing mutation is an amino acid mutation at a position corresponding to E430, E345 or S440 in human IgG1 according to EU numbering. The hexamerixation enhancing mutation strengthens the Fc-Fc interactions between antibodies comprising the mutation when bound to the corresponding target on a cell surface.

By introducing specific mutations in the Fc region corresponding to at least one of the following positions E430, E345 and S440 in human IgG1 hexamerization upon target binding on the cell surface is enhanced, while the antibody molecules remain monomeric in solution (WO2013/004842; WO2014/108198).

In one embodiment of the present invention the Fc region of the anti-DR5 antibody comprises a mutation corresponding to E430G, E430S, E430F, E430T, E345K, E345Q, E345R, E345Y, S440Y or S440W in human IgG1, EU numbering. Thus the anti-DR5 antibody comprises a mutation selected from the group of: E430G, E430S, E430F, E430T, E345K, E345Q, E345R, E345Y, S440Y and S440W in human IgG1, EU numbering. Hereby are embodiments provided that allow for enhanced hexamerization of antibodies upon cell-surface antigen binding. The anti-DR5 antibody comprises an Fc region comprising a first heavy chain and a second heavy chain, wherein one of the above mentioned hexamerization enhancing mutations may be present in the first and/or the second heavy chain.

In a preferred embodiment of the present invention the Fc region comprises a mutation corresponding to E430G or E345K in human IgG1 EU numbering. Thus the Fc region comprises a mutation selected from E430G and E345K.

In one embodiment of the present invention the anti-DR5 antibody comprises a mutation at an amino acid position corresponding to E430 in human IgG1 according to EU numbering, wherein the mutation is selected form the group consisting of: E430G, E430S, E430F and E430T.

In one embodiment of the present invention the Fc region comprises a mutation corresponding to E430G. Thus in one embodiment of the present invention the Fc region comprises an E430G mutation.

In one embodiment of the present invention the anti-DR5 antibody comprises a mutation at an amino acid position corresponding to E345 in human IgG1 according to EU numbering, wherein the mutation is selected form the group consisting of: E345K, E345Q, E345R and E345Y.

In one embodiment of the present invention the Fc region comprises a mutation corresponding to E345K. Thus in one embodiment of the present invention the Fc region comprises an E345K mutation.

In one embodiment of the present invention the anti-DR5 antibody comprises a mutation at an amino acid position corresponding to S440 in human IgG1 according to EU numbering, wherein the mutation is selected form the group consisting of: S440W and S440Y.

In one embodiment of the present invention the Fc region comprises a mutation corresponding to S440Y. Thus in one embodiment of the present invention the Fc region comprises an S440Y mutation.

In one embodiment of the present invention the Fc region comprises a further hexamerization-inhibiting mutation such as K439E or S440K in human IgG1, EU numbering. The hexamerization-inhibiting mutation such as K439E or S440K prevents Fc-Fc interaction with antibodies comprising the same hexamerization inhibiting mutation, but by combining antibodies with a K439E mutation and antibodies with a S440K mutation the inhibiting effect is neutralized and Fc-Fc interactions is restored. In one embodiment of the present invention the antibody comprises a further mutation at an amino acid position corresponding to one of the following positions S440 or K439 in human IgG1, EU numbering. In one embodiment of the invention the Fc region comprises a further mutation in a position corresponding to S440 or K439, with the proviso that the further mutation is not in position S440 if the hexamerization enhancing mutation is in S440. Antibodies comprising a mutation in a position corresponding to E430, E345 or S440 according to the present invention and a further mutation at an amino acid position corresponding to K439 such as a K439E mutation do not form oligomers with antibodies comprising a further mutation at an amino acid position corresponding to K439 such as a K439E mutation. However, antibodies comprising hexamerization enhancing mutation in E430, E345 or S440 and a further mutation in K439 such a K439E do form oligomers with antibodies comprising a hexamerization enhancing mutation in E430 or E345 and a further mutation in S440 such as S440K. Antibodies comprising a mutation in a position corresponding to E430 or E345 according to the present invention and a further mutation at an amino acid position corresponding to S440 such as a S440K mutation do not form oligomers with antibodies comprising a further mutation at an amino acid position corresponding to S440 such as a S440K mutation. However, antibodies comprising hexamerization enhancing mutation in E430 or E345 and a further mutation in S440 such a S440K do form oligomers with antibodies comprising a hexamerization enhancing mutation in E430 or E345 and a further mutation in K439 such as K439. In one embodiment of the present invention the Fc region comprises a hexamerization enhancing mutation such as E430G and a hexamerization inhibiting mutation such as K439E. In one embodiment of the present invention the Fc region comprises a hexamerization enhancing mutation such as E345K and a hexamerization inhibiting mutation such as K439E. In another embodiment of the present invention the Fc region comprises a hexamerization enhancing mutation such as E430G and a hexamerization inhibiting mutation such as S440K. In one embodiment of the present invention the Fc region comprises a hexamerization enhancing mutation such as E345K and a hexamerization inhibiting mutation such as S440K. In one embodiment of the present invention the Fc region comprises a hexamerization enhancing mutation such as S440Y and a hexamerization inhibiting mutation such as K439E Hereby embodiments are provided that allow for exclusive hexamerization between combinations of antibodies comprising a K439E mutation and antibodies comprising a S440K mutation.

The human DR5 molecule (Uniprot O14763) is comprised of 440 amino acids including a signaling peptide at the first 1-55 positions, followed by the extracellular domain at positions 56-210, a transmembrane domain at positions 211-231 and a cytoplasmic domain at positions 232-440. The extracellular domain is comprised of a 155 amino acid sequence. The isoform short of DR5 (Uniprot O14763-2) is missing 185-213 from the extracellular domain.

In one embodiment of the invention the anti-DR5 antibody comprises an antigen binding region binding to an epitope within the extracellular domain of DR5.

In one embodiment of the invention the antibody comprises an antigen binding region binding to the same binding site as TRAIL or a binding site overlapping with the binding site of TRAIL. The TRAIL binding motif is located in CRD2 and CRD3 based on a Crystal structure of TRAIL in complex with the DR5 ectodomain (Hymowitz et al., Mol Cell. 1999 October; 4(4):563-71). That is, in one embodiment of the invention the antibody comprises an antigen binding region binding to the same binding region on DR5 as TRAIL. Thus in one embodiment the DR5 antibody binds to CRD2 and/or CRD3 on DR5. In one embodiment of the invention the antibody comprises an antigen binding region that blocks TRAIL binding to DR5. In one embodiment of the invention the antibody comprises an antigen binding region that competes with TRAIL binding to DR5. In one embodiment of the invention the antibody blocks TRAIL induced mediated killing such as TRAIL induced apoptosis.

In another embodiment of the invention the antibody comprises an antigen binding region binding to an epitope on DR5 that is different from the binding site of TRAIL. In one embodiment of the invention the antibody comprises an antigen binding region binding to a different binding region on DR5 than TRAIL. In one embodiment of the invention the antibody does not block TRAIL induced mediated killing such as TRAIL induced apoptosis.

In an embodiment of the invention the antibody comprises an antigen binding region that binds to an epitope on DR5 comprising or requiring one or more amino acid residues located within amino acid residues 116-138 and one or more amino acid residues located within amino acid residues 139-166 of SEQ ID NO 46. That is the antigen binding region binds to or requires for binding to DR5 one or more amino acids located within positions 116-138 and one or more amino acids located within positions 139-166. That the antigen binding region binds to one or more amino acids comprised in a sequence is to be understood as the antigen binding region is in contact with or directly interacts with one or more amino acids within the sequence. That the antigen binding region requires one or more amino acids within a sequence means that no contact or direct interaction between antigen binding region and one or more amino acids in the sequence is needed, but that one or more amino acids are required for keeping the three-dimensional structure of the epitope.

In another preferred embodiment of the present invention the antibody comprises an antigen binding region that binds to an epitope on DR5 comprising or requiring one or more amino acid residues located within amino acid residues 79-138 of SEQ ID NO 46.

In one embodiment of the invention the anti-DR5 antibody comprises an antigen binding region comprising a variable heavy chain (VH) region comprising CDR1, CDR2 and CDR3 domains and a variable light chain (VL) region comprising CDR1, CDR2 and CDR3 domains having the amino acid sequences of:

a) (VH) SEQ ID NOs: 1, 2, 3 and (VL) SEQ ID NOs: 5, FAS, 6;
    b) (VH) SEQ ID NOs: 1, 8, 3 and (VL) SEQ ID NOs: 5, FAS, 6;
    c) (VH) SEQ ID NOs 10, 2, 11 and (VL) SEQ ID NOs 13, RTS, 14;
    d) (VH) SEQ ID NOs 16, 17, 18 and VL) SEQ ID NOs 21, GAS, 22 or
    e) the (VH) CDR1, CDR2, CDR3 and (VL) CDR1, CDR2 and CDR3 as defined in any of a) to d) above having one to five mutations e.g. substitutions in total across said six CDR sequences.

That is in one embodiment up to five mutations such as substitutions in total are allowed across the six CDRs comprising the antigen binding region. In some embodiments of the invention up to five mutations e.g. substitutions such as one, two, three, four or five mutations e.g. substitutions, are made across the three CDRs of the VH region and no mutations are made across the CDRs of the VL region. In other embodiments no mutations e.g. substitutions are made across the CDRs of the VH region but up to five mutations e.g. substitutions, such as one, two, three, four or five are found across the CDRs of the VL region.

In one embodiment of the invention, the anti-DR5 antibody as defined in any of the embodiments disclosed herein comprises an antigen binding region comprising a variable heavy chain (VH) region comprising CDR1, CDR2 and CDR3 domains and a variable light chain (VL) region comprising CDR1, CDR2 and CDR3 domains, wherein said VH region and said VL region has at least 75%, 80%, 85% 90%, at least 95%, at least 97%, or at least 99% amino acid sequence identity to the amino acid sequence as set forth in the six CDR sequences selected from the group consisting of:

a) (VH) SEQ ID NOs: 1, 2, 3 and (VL) SEQ ID NOs: 5, FAS, 6;
    b) (VH) SEQ ID NOs: 1, 8, 3 and (VL) SEQ ID NOs: 5, FAS, 6;
    c) (VH) SEQ ID NOs: 10, 2, 11 and (VL) SEQ ID NOs: 13, RTS, 14; and
    d) (VH) SEQ ID NOs: 16, 17, 18 and (VL) SEQ ID NOs: 21, GAS, 22.

In one embodiment of the invention the anti-DR5 antibody comprises a variable heavy chain (VH) region comprising CDR1, CDR2 and CDR3 domains and a variable light chain (VL) region comprising CDR1, CDR2 and CDR3 domains having the CDR sequences selected from one of the groups consisting of:

a) (VH) SEQ ID NOs 1, 8, 3 and (VL) SEQ ID NOs 5, FAS, 6 or
    b) (VH) SEQ ID NOs 10, 2, 11 and (VL) SEQ ID NOs 13, RTS, 14 or
    c) the (VH) CDR1, CDR2 and CDR3 and (VL) CDR1, CDR2 and CDR3 as defined in any one of (a) or (b) above having one to five mutations in total across said six CDR sequences. That is in one embodiment up to five mutations such as substitutions in total are allowed across the six CDRs comprising the antigen binding region. In some embodiments of the invention up to five mutations e.g. substitutions such as one, two, three, four or five mutations e.g. substitutions, are made across the three CDRs of the VH region and no mutations are made across the CDRs of the VL region. In other embodiments no mutations e.g. substitutions are made across the CDRs of the VH region but up to five mutations e.g. substitutions, such as one, two, three, four or five are found across the CDRs of the VL region.

In one embodiment of the invention the anti-DR5 antibody comprises a variable heavy chain (VH) region comprising CDR1, CDR2 and CDR3 domains and a variable light chain (VL) region comprising CDR1, CDR2 and CDR3 domains having the CDR sequences selected from one of the groups consisting of:
  a) (VH) SEQ ID NOs 1, 2, 3 and (VL) SEQ ID NOs 5, FAS, 6 or
  b) (VH) SEQ ID NOs 10, 2, 11 and (VL) SEQ ID NOs 13, RTS, 14 or
  c) the (VH) CDR1, CDR2 and CDR3 and (VL) CDR1, CDR2 and CDR3 as defined in (a) or (b) above having up to five mutations in total across said six CDR sequences.

That is in one embodiment up to five mutations such as substitutions in total are allowed across the six CDRs comprising the antigen binding region. In some embodiments of the invention up to five mutations e.g. substitutions, such as one, two, three, four or five mutations e.g. substitutions are made across the three CDRs of the VH region and no mutations are made across the three CDRs or the VL region. In other embodiments no mutations e.g. substitutions are made across the three CDRs of the VH region but up to five mutations e.g. substitutions are made across the six CDRs of the VL region, wherein the mutations e.g. substitutions are conservative or concern amino acids with similar physical or functional properties and preferably do not modify binding affinity to DR5.

In one embodiment of the invention, the anti-DR5 antibody as defined in any of the embodiments disclosed herein comprises an antigen binding region comprising a variable heavy chain (VH) region and a variable light chain (VL) region, wherein said VH region and said VL region has at least 75%, 80%, 85% 90%, at least 95%, at least 97%, or at least 99% amino acid sequence identity to the amino acid sequence as set forth in the VH and VL sequences selected from the group consisting of:
  a) (VH) SEQ ID NO:4 and (VL) SEQ ID NO:7;
  b) (VH) SEQ ID NO:9 and (VL) SEQ ID NO:7;
  c) (VH) SEQ ID NO:12 and (VL) SEQ ID NO:15;
  d) (VH) SEQ ID NO:19 and (VL) SEQ ID NO:23; and
  e) (VH) SEQ ID NO:20 and (VL) SEQ ID NO:23.

In one embodiment of the invention the antibody comprises an antigen binding region comprising a variable heavy chain (VH) region and a variable light chain (VL) region having the amino acid sequences of:
  a) (VH) SEQ ID NO:4 and (VL) SEQ ID NO:7;
  b) (VH) SEQ ID NO:9 and (VL) SEQ ID NO:7;
  c) (VH) SEQ ID NO:12 and (VL) SEQ ID NO:15;
  d) (VH) SEQ ID NO:19 and (VL) SEQ ID NO:23;
  e) (VH) SEQ ID NO:20 and (VL) SEQ ID NO:23 or
  f) the (VH) and (VL) as defined in any one of a) to e) above having one to 10 mutations or substitutions in total across said (VH) and (VL) sequences. That is in one embodiment up to 10 mutations such as substitutions in total are allowed across the VH and VL regions defined by the VH and VL sequences. In some embodiments of the invention up to ten mutations e.g. substitutions, such as one, two, three, four, five, six, seven, eight, nine or ten mutations e.g. substitutions are made across the VH or VL sequences. In one embodiment of the invention up to10 mutations or substitutions are made in the VH sequence and no mutations are made in the VL sequence. In one embodiment of the invention no mutations are made in the VH sequence and up to ten mutations e.g. substitutions are made in the VL sequence. Hereby are embodiments provided that allow for up to 10 mutations such as substitutions across the VH and VL sequences, wherein the mutations such as substitutions are conservative or concern amino acids with similar physical or functional properties, thereby allowing mutations e.g. substitutions within the VH and VL sequence without modifying binding affinity or function of the anti-DR5 antibody.

In one embodiment of the present invention the antibody is a monoclonal antibody. In one embodiment of the present invention the antibody is of the IgG1, IgG2, IgG3, IgG4, IgA, IgE, IgD or IgM isotype.

In a preferred embodiment of the invention the antibody is an IgG1 antibody.

In one embodiment of the present invention the antibody is an IgG1m(f), IgG1m(z), IgG1m(a) or an IgG1m(x) allotype, or any allotype combination, such as IgG1m(z,a), IgG1m(z,a,x), IgG1m(f,a).

In one embodiment of the present invention the antibody comprises an Fc region comprising an amino acid sequence of the group consisting of:
  a) SEQ ID NO:29;
  b) SEQ ID NO:30;
  c) SEQ ID NO:31;
  d) SEQ ID NO:32 or
  e) an amino acid sequence defined in any one of a) to d) having one to five mutations e.g. substitutions in total across said sequence. That is in one embodiment up to five mutations e.g. substitutions in total are allowed across the Fc region. In some embodiments of the invention up to five mutations e.g. substitutions such as one, two, three, four or five mutations e.g. substitutions, are allowed across the Fc region.

In one embodiment of the invention, the anti-DR5 antibody as defined in any of the embodiments disclosed herein comprises a heavy chain (HC) and a light chain (LC), wherein the LC comprises the sequence of SEQ ID NO:39 and wherein the HC has at least 75%, 80%, 85%, 90%, at least 95%, at least 97%, or at least 99% amino acid sequence identity to the amino acid sequence as set forth in the HCs sequences selected from the group consisting of:
  a) (HC) SEQ ID NO:33;
  b) (HC) SEQ ID NO:34;
  c) (HC) SEQ ID NO:35;
  d) (HC) SEQ ID NO:36;
  e) (HC) SEQ ID NO:37; and
  f) (HC) SEQ ID NO:38.

In one embodiment of the invention, the anti-DR5 antibody as defined in any of the embodiments disclosed herein comprises a heavy chain (HC) and a light chain (LC), wherein the LC has at least 75%, 80%, 85%, 90%, at 95%, at least 97%, or at least 99% amino acid sequence identity set forth in SEQ ID NO:39 and wherein the HC has the amino acid sequence as set forth in the HCs sequences selected from the group consisting of:
  a) (HC) SEQ ID NO:33;
  b) (HC) SEQ ID NO:34;
  c) (HC) SEQ ID NO:35;
  d) (HC) SEQ ID NO:36;
  e) (HC) SEQ ID NO:37; and
  f) (HC) SEQ ID NO:38.

In one embodiment according to the invention, the antibody comprises a heavy chain (HC) and a light chain (LC), wherein the LC comprises the sequence of SEQ ID NO:39 and wherein the HC comprises of one of the sequences selected from the group consisting of:

a) (HC) SEQ ID NO:33;
b) (HC) SEQ ID NO:34;
c) (HC) SEQ ID NO:35;
d) (HC) SEQ ID NO:36;
e) (HC) SEQ ID NO:37; and
f) (HC) SEQ ID NO:38; or
g) the (HC) as defined in any one of a) to f) above having one to ten mutations in total across said (HC) sequence. That is in one embodiment up to 10 mutations such as substitutions in total are allowed across the heavy chain defined by the heavy chain sequence. In some embodiments of the invention up to ten mutations e.g. substitutions, such as one, two, three, four, five, six, seven, eight, nine or ten mutations e.g. substitutions are made across the heavy chain sequence. Hereby are embodiments provided that allow for up to 10 mutations such as substitutions across the heavy chain sequence, wherein the mutations such as substitutions are conservative or concern amino acids with similar physical or functional properties, thereby allowing mutations or substitutions within the heavy chain sequence without modifying binding affinity or function of the anti-DR5 antibody.

In one embodiment of the invention, the anti-DR5 antibody as defined in any of the embodiments disclosed herein comprises a heavy chain (HC) and a light chain (LC), wherein the LC comprises the sequence of SEQ ID NO:43 and wherein the HC has at least 75%, 80%, 85%, 90%, at least 95%, at least 97%, or at least 99% amino acid sequence identity to the amino acid sequence as set forth in the HCs sequences selected from the group consisting of:
a) (HC) SEQ ID NO:40;
b) (HC) SEQ ID NO:41; and
c) (HC) SEQ ID NO:42.

In one embodiment of the invention, the anti-DR5 antibody as defined in any of the embodiments disclosed herein comprises a heavy chain (HC) and a light chain (LC), wherein the LC has at least 75%, 80%, 85%, 90%, at 95%, at least 97%, or at least 99% amino acid sequence identity set forth in SEQ ID NO:43 and wherein the HC has the amino acid sequence as set forth in the HCs sequences selected from the group consisting of:
a) (HC) SEQ ID NO:40;
b) (HC) SEQ ID NO:41; and
c) (HC) SEQ ID NO:42.

In one embodiment according to the invention the antibody comprises a heavy chain (HC) and a light chain (LC), wherein the LC comprises the sequence of SEQ ID NO:43 and wherein the HC comprises of one of the sequences selected from the group consisting of:
a) (HC) SEQ ID NO:40;
b) (HC) SEQ ID NO:41;
c) (HC) SEQ ID NO:42; or
d) the (HC) as defined in any one of a) to c) above having one to ten mutations e.g. substitutions in total across said (HC) sequence.

That is in one embodiment up to 10 mutations such as substitutions in total are allowed across the heavy chain defined by the heavy chain sequence. In some embodiments of the invention up to ten mutations e.g. substitutions, such as one, two, three, four, five, six, seven, eight, nine or ten mutations e.g. substitutions are made across the heavy chain sequence. Hereby are embodiments provided that allow for up to 10 mutations such as substitutions across the heavy chain sequence, wherein the mutations such as substitutions are conservative or concern amino acids with similar physical or functional properties, thereby allowing mutations such as substitutions within the heavy chain sequence without modifying binding affinity or function of the anti-DR5 antibody.

In one embodiment the antibody is a human antibody, a chimeric antibody or a humanized antibody.

In one embodiment of the present invention the anti-DR5 antibody is agonistic. That the antibody is agonistic is to be understood as that the antibody clusters, stimulates or activates DR5. In one embodiment, an agonistic anti-DR5 antibody of the present invention bound to DR5 activates the same intracellular pathways as TRAIL bound to DR5. The agonistic activity of one or more antibodies can be determined by incubating target cells for 3 days with an antibody concentration dilution series (e.g. from 20,000 ng/mL to 0.05 ng/mL final concentration in 5-fold dilutions). The antibodies may be added directly when cells are seeded (described in examples 8, 9, 10, 39), or alternatively the cells are first allowed to adhere to 96-well flat-bottom plates before adding the antibody samples (described in examples 11, 12, 13, 14, 15, 16, 17, 18, 21, 22, 23, 24, 38, 40, 41, 42, 43, 44, 46, 48). The agonistic activity i.e. the agonistic effect can be quantified by measuring the amount of viable cells using special kits for this purpose, such as the CellTiter-Glo luminescent cell viability assay of Promega (Cat nr G7571).

In one embodiment of the present invention the anti-DR5 antibody has enhanced agonistic activity. That the anti-DR5 antibody has activity is to be understood as the antibody is able to cluster DR5 or activate at least the same intracellular pathways as TRAIL bound to DR5. That is anti-DR5 antibody with enhanced agonistic activity is able to induce increased level of apoptosis or programmed cell death in a cell or tissue expressing DR5 compared to TRAIL or a wild-type IgG1 antibody against DR5.

In one embodiment of the present invention the anti-DR5 antibody induces programmed cell death in a target cell. In one embodiment of the present invention the anti-DR5 antibody induces caspase-dependent cell death. Caspase-dependent cell death may be induced by activation of caspase-3 and/or caspase-7. In one embodiment of the invention the anti-DR5 antibody induces caspase-3 and/or caspase-7 dependent cell death. In one embodiment of the present invention the antibody induces apoptosis. Apoptosis by one or more agonistic anti-DR5 antibodies can be determined using methods such as, e.g., caspase-3/7 activation assays described in examples 19, 20, 25 and 45 or phosphatidylserine exposure described in examples 19 and 25. Anti-DR5 antibody at a fixed concentration of e.g. 1 µg/mL may be added to adhered cells and incubated for 1 to 24 hours. Caspase-3/7 activation can be determined by using special kits for this purpose, such as the PE Active Caspase-3 Apoptosis Kit of BD Pharmingen (Cat nr 550914) (example 19 and 25) or the Caspase-Glo 3/7 assay of Promega (Cat nr G8091) (examples 20 and 45). Phosphatidylserine exposure and cell death can be determined by using special kits for this purpose, such as the FITC Annexin V Apoptosis Detection Kit I from BD Pharmingen (Cat nr 556547) (examples 19 and 25).

In one embodiment of the present invention the anti-DR5 antibody induces phosphatidylserine (PS) exposure, which can be measured by Annexin-V binding. In one embodiment of the present invention anti-DR5 induces translocation of PS to the cell surface of the target cell. Therefore, Annexin-V binding correlates to programmed cell death and can be used to measure the anti-DR5 antibody's ability to induce cellular events leading to programmed cell death.

In a preferred embodiment of the present invention the anti-DR5 antibody induces apoptosis in a target cell expressing DR5, such as a tumor cell.

In one embodiment of the invention the anti-DR5 antibody reduces cell viability.

In one embodiment of the present invention the anti-DR5 antibody induces DR5 clustering. That the antibody can induce clustering and even enhance clustering leads to activation of at least the same intracellular signaling pathways as TRAIL bound to DR5.

In one embodiment the antibodies or compositions of the present invention induce, trigger, increase or enhance apoptosis or cell death in cancer cells or cancer tissues expressing DR5. The increased or enhanced apoptosis or cell death can be measured by an increase or enhanced level of phosphatidylserine exposure on cells exposed to or treated with one or more anti-DR5 antibodies of the invention. Alternatively, the increase or enhanced apoptosis or cell death can be measured by measuring activation of caspase 3 or caspase 7 in cells that have been exposed to or treated with one or more anti-DR5 antibodies of the invention. Alternatively, the increase or enhanced apoptosis or cell death can be measured by a loss of viability in cell cultures that have been exposed to or treated with one or more anti-DR5 antibodies of the invention, compared to untreated cell cultures. Induction of caspase-mediated apoptosis can be assessed by demonstrating inhibition of the loss of viability after exposure to DR5 antibody by a caspase-inhibitor, for example ZVAD.

In one embodiment of the present invention the anti-DR5 antibody engages into oligomerization such as hexamerization of antibodies on target cells expressing DR5. Oligomerization such as hexamerization is mediated through Fc-Fc interactions. One method for determining this is by inhibiting Fc-Fc interactions which indicate that antibodies oligomerizies e.g. hexamerizies. The Fc-Fc interactions can be inhibited by a peptide binding to the hydrophobic patch involved in Fc-Fc interactions such as DCAWHLGELVWCT as described in example 15.

Bispecific Antibodies

In another aspect, the present invention comprises a bispecific antibody comprising at least one antigen binding region as described herein.

In another aspect, the present invention comprises a bispecific antibody comprising one or more antigen binding regions as described herein.

In one embodiment of the invention the bispecific antibody comprises a first antigen binding region and a second antigen binding region as defined herein.

In one embodiment of the invention the bispecific antibody comprises a first and a second antigen binding region, wherein said first antigen binding region and said second antigen binding region bind different epitopes on human DR5.

In one embodiment of the invention the bispecific antibody comprises a first and a second antigen binding region, wherein said first antigen binding region binding to human DR5 does not block binding of said second antigen binding region binding to human DR5.

In one embodiment of the present invention the bispecific anti-DR5 antibody comprises a first and a second Fc region, wherein the first and/or second Fc region comprises a mutation of an amino acid position corresponding to E430, E345 or S440 in human IgG1, EU numbering according to the invention. In one embodiment of the present invention the bispecific anti-DR5 antibody comprises a first and a second Fc region, wherein the first and second Fc region comprises a mutation of an amino acid position corresponding to E430, E345 or S440 in human IgG1, EU numbering. In one embodiment of the present invention the bispecific anti-DR5 antibody comprises a first and a second Fc region, wherein the first Fc region comprises a mutation of an amino acid position corresponding to E430, E345 or S440 in human IgG1, EU numbering. In one embodiment of the present invention the bispecific anti-DR5 antibody comprises a first and a second Fc region, wherein the second Fc region comprises a mutation of an amino acid position corresponding to E430, E345 or
S440 in human IgG1, EU numbering.

In one embodiment of the invention the bispecific antibody comprises a first and a second antigen binding region, wherein said first antigen binding region comprises the following six CDR sequences,
  a) (VH) SEQ ID NOs: 1, 2, 3 and (VL) SEQ ID NOs: 5, FAS, 6 and said second antigen binding region comprises the following six CDR sequences
  b) (VH) SEQ ID NOs: 10, 2, 11 and (VL) SEQ ID NOs: 13, RTS, 14, or wherein the said first antigen binding region and said second antigen binding region comprises, c) the six CDR sequences defined in (a) or (b) above having one to five mutations or substitutions in total across said six CDR sequences respectively.
  That is the one or more mutations or substitutions across the six CDR sequences of the antigen binding region do not change the binding characteristics of said first or second antibody such as the agonistic properties, the DR5 epitope binding and/or the ability to induce apoptosis in a target cell expressing DR5. That is in one embodiment up to five mutations or substitutions in total are allowed across the six CDRs comprising the antigen binding region. In some embodiments of the invention up to five mutations or substitutions such as one, two, three, four or five mutations or substitutions, are made across the three CDRs of the VH region and no mutations are made across the CDRs of the VL region. In other embodiments no mutations or substitutions are made across the CDRs of the VH region but up to five mutations or substitutions, such as one, two, three, four or five are found across the CDRs of the VL region.

In one embodiment of the invention the bispecific antibody comprises a first and a second antigen binding region, wherein said first antigen binding region comprises the following six CDR sequences,
  a) said first antigen binding region comprises the following six CDR sequences (VH) SEQ ID NOs: 1, 2, 3 and (VL) SEQ ID NOs: 5, FAS, 6 and said second antigen binding region comprises the following six CDR sequences (VH) SEQ ID NOs: 10, 2, 11 and (VL) SEQ ID NOs: 13, RTS, 14, or wherein said first antigen binding region and said second antigen binding region comprises, b) the six CDR sequences defined in (a) comprising one to five mutations e.g substitutions in total across said six CDR sequences of each first and second antigen binding region respectively. That is the one or more mutations e.g. substitutions across the six CDR sequences of the antigen binding region do not change the binding characteristics of said first or second antibody such as the agonistic properties, the DR5 epitope binding and/or the ability to induce apoptosis in a target cell expressing DR5. That is in one embodiment up to five mutations e.g. substitutions in total are allowed across the six CDRs comprising the antigen binding region. In some embodiments of the invention up to five mutations e.g. substitutions such as one, two, three, four or five mutations or substitutions, are made across the three CDRs of the VH region and no mutations are made across the CDRs of the VL region. In other embodiments no mutations e.g. substitutions are made across the CDRs of the VH region but up to five mutations e.g. substitutions, such as one, two, three, four or five are found across the CDRs of the VL region.

In one embodiment of the invention the bispecific antibody comprises a first and a second antigen binding region, wherein said first antigen binding region comprises the following six CDR sequences,
- a) (VH) SEQ ID NOs: 1, 8, 3 and (VL) SEQ ID NOs: 5, FAS, 6 and said second antigen binding region comprises the following six CDR sequences
- b) (VH) SEQ ID NOs: 10, 2, 11 and (VL) SEQ ID NO:s 13, RTS, 14, or wherein the said first antigen binding region and said second antigen binding region comprises, c) the six CDR sequences defined in (a) or (b) above having one to five mutations or substitutions in total across said six CDR sequences respectively. That is the one or more mutations or substitutions across the six CDR sequences of the antigen binding region do not change the binding characteristics of said first or second antibody such as the agonistic properties, the DR5 epitope binding and/or the ability to induce apoptosis in a target cell expressing DR5. That is in one embodiment up to five mutations or substitutions in total are allowed across the six CDRs comprising the antigen binding region. In some embodiments of the invention up to five mutations or substitutions such as one, two, three, four or five mutations or substitutions, are made across the three CDRs of the VH region and no mutations are made across the CDRs of the VL region. In other embodiments no mutations or substitutions are made across the CDRs of the VH region but up to five mutations or substitutions, such as one, two, three, four or five are found across the CDRs of the VL region.

In one embodiment of the invention the bispecific antibody comprises a first and a second antigen binding region wherein a) said first antigen binding region comprises the following six CDR sequences (VH) SEQ ID NOs: 1, 8, 3 and (VL) SEQ ID NOs: 5, FAS, 6 and said second antigen binding region comprises the following six CDR sequences (VH) SEQ ID NOs: 10, 2, 11 and (VL) SEQ ID NO:s 13, RTS, 14, or wherein the said first antigen binding region and said second antigen binding region comprises b) the six CDR sequences defined in (a having one to five mutations or substitutions in total across said six CDR sequences of each antigen binding region respectively. That is the one or more mutations e.g. substitutions across the six CDR sequences of the antigen binding region do not change the binding characteristics of said first or second antibody such as the agonistic properties, the DR5 epitope binding and/or the ability to induce apoptosis in a target cell expressing DR5. That is in one embodiment up to five mutations e.g. substitutions in total are allowed across the six CDRs comprising the antigen binding region. In some embodiments of the invention up to five mutations e.g. substitutions such as one, two, three, four or five mutations e.g. substitutions, are made across the three CDRs of the VH region and no mutations are made across the CDRs of the VL region. In other embodiments no mutations or substitutions are made across the CDRs of the VH region but up to five mutations e.g. substitutions, such as one, two, three, four or five are found across the CDRs of the VL region.

In one embodiment of the invention the bispecific antibody comprises a first and a second antigen binding region, wherein said first antigen binding region comprises the following six CDR sequences,
- a) (VH) SEQ ID NOs: 16, 17, 18 and (VL) SEQ ID NOs: 21, GAS, 6 and said second antigen binding region comprises the following six CDR sequences
- b) (VH) SEQ ID NOs: 10, 2, 11 and (VL) SEQ ID NOs: 13, RTS, 14, or wherein the said first antigen binding region and said second antigen binding region comprises,
- c) the six CDR sequences defined in a) or (b) above having one to five mutations or substitutions in total across said six CDR sequences. That is the one or more mutations or substitutions across the six CDR sequences of the antigen binding region do not change the binding characteristics of said first or second antibody such as the agonistic properties, the DR5 epitope binding and/or the ability to induce apoptosis in a target cell expressing DR5. That is in one embodiment up to five mutations or substitutions in total are allowed across the six CDRs comprising the antigen binding region. In some embodiments of the invention up to five mutations or substitutions such as one, two, three, four or five mutations or substitutions, are made across the three CDRs of the VH region and no mutations are made across the CDRs of the VL region. In other embodiments no mutations or substitutions are made across the CDRs of the VH region but up to five mutations or substitutions, such as one, two, three, four or five are found across the CDRs of the VL region.

In one embodiment of the invention the bispecific antibody comprises a first and a second antigen binding region, wherein,
- a) said first antigen binding region comprises the following six CDR sequences (VH) SEQ ID NOs: 16, 17, 18 and (VL) SEQ ID NOs: 21, GAS, 6 and said second antigen binding region comprises the following six CDR sequences (VH) SEQ ID NOs: 10, 2, 11 and (VL) SEQ ID NOs: 13, RTS, 14, or
- b) said first antigen binding region and said second antigen binding region comprises the six CDR sequences defined in a) comprising one to five mutations e.g. substitutions in total across said six CDR sequences of each antigen binding region. That is the one or more mutations e.g. substitutions across the six CDR sequences of each antigen binding region do not change the binding characteristics of said first or second antibody such as the agonistic properties, the DR5 epitope binding and/or the ability to induce apoptosis in a target cell expressing DR5. That is in one embodiment up to five mutations e.g. substitutions in total are allowed across the six CDRs comprising the antigen binding region. In some embodiments of the invention up to five mutations e.g. substitutions such as one, two, three, four or five mutations e.g. substitutions, are made across the three CDRs of the VH region and no mutations are made across the CDRs of the VL region. In other embodiments no mutations e.g. substitutions are made across the CDRs of the VH region but up to five mutations e.g. substitutions, such as one, two, three, four or five are found across the CDRs of the VL region.

In one embodiment of the invention the bispecific antibody comprises a first and a second antigen binding region, wherein said first antigen binding region comprises the following sequences (a) (VH) CDR1 SEQ ID NO 1, CDR2

SEQ ID NO 8, CDR3 SEQ ID NO 3 and (VL) CDR1 SEQ ID NO 5, CDR2 FAS, CDR3 SEQ ID NO 6, or b) the (VH) CDR1, CDR2 and CDR3 and (VL) CDR1, CDR2 and CDR3 as defined in (a) above having one to five mutations in total across said six CDR sequences and wherein said second antigen binding region comprises the following sequences (c) (VH) CDR1 SEQ ID NO 10, CDR2 SEQ ID NO 2, CDR3 SEQ ID NO 11 and (VL) CDR1 SEQ ID NO 13, CDR2 RTS, CDR3 SEQ ID NO 14 or (d) the (VH) CDR1, CDR2 and CDR3 and (VL) CDR1, CDR2 and CDR3 as defined in (c) above having one to five mutations in total across said six CDR sequences.

In one embodiment of the invention the bispecific antibody comprises a first and a second antigen binding region, wherein (a) said first antigen binding region comprises the following sequences (VH) CDR1 SEQ ID NO 1, CDR2 SEQ ID NO 8, CDR3 SEQ ID NO 3 and (VL) CDR1 SEQ ID NO 5, CDR2 FAS, CDR3 SEQ ID NO 6 and said second antigen binding region comprises the following sequences (VH) CDR1 SEQ ID NO 10, CDR2 SEQ ID NO 2, CDR3 SEQ ID NO 11 and (VL) CDR1 SEQ ID NO 13, CDR2 RTS, CDR3 SEQ ID NO 14 or b) said first antigen binding region or said second antigen binding region comprises one to five mutations in total across said six CDR sequences of each antigen binding region.

In one embodiment of the invention the bispecific antibody comprises a first and a second antigen binding region, wherein said first antigen binding region comprises the following sequences (a) (VH) CDR1 SEQ ID NO 1, CDR2 SEQ ID NO 2, CDR3 SEQ ID NO 3 and (VL) CDR1 SEQ ID NO 5, CDR2 FAS, CDR3 SEQ ID NO 6, or (b) the (VH) CDR1, CDR2 and CDR3 and (VL) CDR1, CDR2 and CDR3 as defined in (a) above having one to five mutations in total across said six CDR sequences and wherein said second antigen binding region comprises the following sequences (c) (VH) CDR1 SEQ ID NO 10, CDR2 SEQ ID NO 2, CDR3 SEQ ID NO 11 and (VL) CDR1 SEQ ID NO 13, CDR2 RTS, CDR3 SEQ ID NO 14 or (d) the (VH) CDR1, CDR2 and CDR3 and (VL) CDR1, CDR2 and CDR3 as defined in (c) above having one to five mutations in total across said six CDR sequences.

In one embodiment of the invention the bispecific antibody comprises a first and a second antigen binding region, wherein (a) said first antigen binding region comprises the following sequences (VH) CDR1 SEQ ID NO 1, CDR2 SEQ ID NO 2, CDR3 SEQ ID NO 3 and (VL) CDR1 SEQ ID NO 5, CDR2 FAS, CDR3 SEQ ID NO 6 and said second antigen binding region comprises the following sequences (VH) CDR1 SEQ ID NO 10, CDR2 SEQ ID NO 2, CDR3 SEQ ID NO 11 and (VL) CDR1 SEQ ID NO 13, CDR2 RTS, CDR3 SEQ ID NO 14 or b) said first antigen binding region or said second antigen binding region comprises one to five mutations in total across said six CDR sequences of each antigen binding region.

In one embodiment of the invention the bispecific antibody comprises a first and a second antigen binding region, wherein said first antigen binding region comprises the following sequences (a) (VH) CDR1 SEQ ID NO 16, CDR2 SEQ ID NO 17, CDR3 SEQ ID NO 18 and (VL) CDR1 SEQ ID NO 21, CDR2 GAS, CDR3 SEQ ID NO 22,or (b) the (VH) CDR1, CDR2 and CDR3 and (VL) CDR1, CDR2 and CDR3 as defined in (a) above having one to five mutations in total across said six CDR sequences and wherein said second antigen binding region comprises the following sequences (c) (VH) CDR1 SEQ ID NO 10, CDR2 SEQ ID NO 2, CDR3 SEQ ID NO 11 and (VL) CDR1 SEQ ID NO 13, CDR2 RTS, CDR3 SEQ ID NO 14 or (d) the (VH) CDR1, CDR2 and CDR3 and (VL) CDR1, CDR2 and CDR3 as defined in (c) above having one to five mutations in total across said six CDR sequences.

In one embodiment of the invention the bispecific antibody comprises a first and a second antigen binding region, wherein (a) said first antigen binding region comprises the following sequences (VH) CDR1 SEQ ID NO 16, CDR2 SEQ ID NO 17, CDR3 SEQ ID NO 18 and (VL) CDR1 SEQ ID NO 21, CDR2 GAS, CDR3 SEQ ID NO 22 and said second antigen binding region comprises the following sequences (VH) CDR1 SEQ ID NO 10, CDR2 SEQ ID NO 2, CDR3 SEQ ID NO 11 and (VL) CDR1 SEQ ID NO 13, CDR2 RTS, CDR3 SEQ ID NO 14 or b) said first antigen binding region or said second antigen binding region comprises one to five mutations in total across said six CDR sequences of each antigen binding region.

If the antibody is a bispecific antibody that comprises an Fc region comprising a first and a second heavy chain, a mutation according to the present invention i.e. a mutation in a position corresponding to E430, E345 or S440 in IgG1, EU numbering, may in principle only be present in one of the heavy chains; i.e. in either the first or second heavy chain, although in a preferred embodiment according to the present invention, the mutation is present in both the first and second heavy chain of the bispecific antibody.

In a particular embodiment the antibody may be bispecific antibody such as the heterodimeric protein described in WO 11/131746, which is hereby incorporated herein by reference.

In one embodiment, the antibody is a bispecific antibody which comprises a first heavy chain comprising a first Fc region of an immunoglobulin and a first antigen-binding region, and a second heavy chain comprising a second Fc region of an immunoglobulin and a second antigen-binding region, wherein the first and second antigen-binding regions bind different epitopes on the same antigen or on different antigens. In a further embodiment said first heavy chain comprising a first Fc region comprises a further amino acid substitution at a position selected from those corresponding to K409, T366, L368, K370, D399, F405, and Y407 in the Fc region of a human IgG1 heavy chain; and wherein said second heavy chain comprising a second Fc region comprises a further amino acid substitution at a position selected from those corresponding to F405, T366, L368, K370, D399, Y407, and K409 in the Fc region of a human IgG1 heavy chain, and wherein said further amino acid substitution in the first heavy chain comprising a first Fcregion is different from the said further amino acid substitution in the second heavy chain comprising a second Fc region.

In a further embodiment said first heavy chain comprising a first Fc region comprises an amino acid substitution at a position corresponding to K409 in the Fc-region of a human IgG1 heavy chain; and said second heavy chain comprising a second Fc region comprises an amino acid substitution at a position corresponding to F405 in the Fc-region of a human IgG1 heavy chain.

In one embodiment of the invention the bispecific antibody comprises introducing a first and second Fc region comprising a mutation in at least one amino acid residue selected from those corresponding to E345, E430, S440, Q386, P247, I253, S254, Q311, D/E356, T359, E382, Y436, and K447 in the Fc-region of a human IgG1 heavy chain, with the proviso that the mutation in S440 is S440Y or S440W.

In a further embodiment the mutation in the first and second Fc region in at least one amino acid residue selected from those corresponding to E345, E430, S440, Q386, P247, I253, S254, Q311, D/E356, T359, E382, Y436, and K447 in the Fc-region of a human IgG1 heavy chain, with the proviso that the mutation in S440 is S440Y or S440W, may be in the same amino acid residue position or a different position. In a further embodiment it may be the same or a different mutation in the same amino acid residue position in the first and second Fc region.

In another embodiment the bispecific antibody comprises a first or second CH2-CH3 region comprising a mutation in at least one amino acid residue selected from those corresponding to E345, E430, S440, Q386, P247, I253, S254, Q311, D/E356, T359, E382, Y436, and K447 in the Fc-region of a human IgG1 heavy chain, with the proviso that the mutation in S440 is S440Y or S440W.

In one embodiment of the invention the bispecific antibody comprises a first and a second heavy chain, wherein said first heavy chain comprises a mutation corresponding to F405L in human IgG1 according to EU numbering and said second heavy chain comprises a mutation corresponding to K409R in human IgG1 according EU numbering.

In one embodiment of the invention the bispecific antibody is comprised in a pharmaceutical composition.

Anti-DR5 Antibody Compositions

The anti-DR5 antibodies such as monoclonal antibodies or bispecific antibodies according to any aspect or embodiment of the present invention may be comprised in a composition, such as a pharmaceutical composition, diagnostic composition or any other composition.

In one aspect the invention relates to a composition comprising at least one anti-DR5 antibody according to any one of the embodiments described herein. In one aspect the invention relates to a composition comprising one or more anti-DR5 antibodies according to any one the embodiments described herein. The composition may comprise one, two or more anti-DR5 antibodies according to the invention as described herein that are not identical, such as a combination of two different monoclonal anti-DR5 antibodies.

In one embodiment of the present invention the composition comprises a first anti-DR5 antibody and a second anti-DR5 antibody as described herein. That is in one embodiment of the present invention the composition comprises a first antibody as described herein and a second antibody as described herein, wherein the first and the second antibody are not identical.

In one embodiment of the present invention the composition comprises a first anti-DR5 antibody comprising a mutation in the position corresponding to E430 in human IgG1, EU numbering and a second anti-DR5 antibody comprising a mutation in the position corresponding to E430 in human IgG1, EU numbering, wherein the first and second antibody binds different epitopes on DR5.

In one embodiment of the present invention the composition comprises a first anti-DR5 antibody comprising a mutation in the position corresponding to E430 in human IgG1, EU numbering and a second anti-DR5 antibody comprising a mutation in the position corresponding to E430 in human IgG1, EU numbering, wherein the first antibody does not block binding of the second antibody to DR5.

In one embodiment of the present invention the composition comprises a first and a second anti-DR5 antibody comprising a mutation in a position corresponding to E430 in human IgG1, EU numbering, such a mutation may be selected from the group consisting of: E430G, E430S and E430T.

In one embodiment of the present invention the composition comprises a first anti-DR5 antibody comprising an E430G and a second anti-DR5 antibody comprising an E430G mutation, wherein the first and second antibody binds different epitopes on DR5.

In one embodiment of the present invention the composition comprises a first anti-DR5 antibody and a second anti-DR5 antibody, wherein the first anti-DR5 antibody comprises the following six CDR sequences,
  a) (VH) SEQ ID NOs: 1, 2, 3 and (VL) SEQ ID NOs: 5, FAS, 6 and said second anti-DR5 antibody comprises the following six CDR sequences,
  b) (VH) SEQ ID NOs: 10, 2, 11 and (VL) SEQ ID NOs: 13, RTS, 14, and wherein the said first anti-DR5 antibody and said second anti-DR5 antibody comprises a mutation in the position corresponding to E430.

In one embodiment of the present invention the composition comprises a first anti-DR5 antibody and a second anti-DR5 antibody, wherein said first anti-DR5 antibody comprises the following six CDR sequences (VH) SEQ ID NOs: 1, 2, 3 and (VL) SEQ ID NOs: 5, FAS, 6 and said second anti-DR5 antibody comprises the following six CDR sequences (VH) SEQ ID NOs: 10, 2, 11 and (VL) SEQ ID NOs: 13, RTS, 14, and wherein the said first anti-DR5 antibody and said second anti-DR5 antibody comprises a mutation in the position corresponding to E430 in human IgG1, EU numbering.

In one embodiment of the present invention the composition comprises a first anti-DR5 antibody and a second anti-DR5 antibody, wherein the first anti-DR5 antibody comprises the following six CDR sequences,
  a) (VH) SEQ ID NOs: 1, 2, 3 and (VL) SEQ ID NOs: 5, FAS, 6 and said second anti-DR5 antibody comprises the following six CDR sequences,
  b) (VH) SEQ ID NOs: 10, 2, 11 and (VL) SEQ ID NOs: 13, RTS, 14, and wherein the said first anti-DR5 antibody and said second anti-DR5 antibody comprises an E430G mutation in the Fc region.

In one embodiment of the present invention the composition comprises a first anti-DR5 antibody and a second anti-DR5 antibody, wherein said first anti-DR5 antibody comprises the following six CDR sequences (VH) SEQ ID NOs: 1, 2, 3 and (VL) SEQ ID NOs: 5, FAS, 6 and said second anti-DR5 antibody comprises the following six CDR sequences (VH) SEQ ID NOs: 10, 2, 11 and (VL) SEQ ID NOs: 13, RTS, 14, and wherein the said first anti-DR5 antibody and said first anti-DR5 antibody and said second anti-DR5 antibody comprises an E430G mutation in the Fc region.

In one embodiment of the present invention the composition comprises a first anti-DR5 antibody and a second anti-DR5 antibody, wherein the first anti-DR5 antibody comprises the following six CDR sequences,
  a) (VH) SEQ ID NOs: 1, 8, 3 and (VL) SEQ ID NOs: 5, FAS, 6 and said second anti-DR5 antibody comprises the following six CDR sequences,
  b) (VH) SEQ ID NOs: 10, 2, 11 and (VL) SEQ ID NOs: 13, RTS, 14, and wherein the said first anti-DR5 antibody and said second anti-DR5 antibody comprises a mutation in the position corresponding to E430.

In one embodiment of the present invention the composition comprises a first anti-DR5 antibody and a second anti-DR5 antibody, wherein said first anti-DR5 antibody comprises the following six CDR sequences (VH) SEQ ID NOs: 1, 8, 3 and (VL) SEQ ID NOs: 5, FAS, 6 and said second anti-DR5 antibody comprises the following six CDR sequences (VH) SEQ ID NOs: 10, 2, 11 and (VL) SEQ ID NOs: 13, RTS, 14, and wherein the said first anti-DR5 antibody and said first anti-DR5 antibody and said second anti-DR5 antibody comprises a mutation in the position corresponding to E430 in human IgG1, EU numbering.

In one embodiment of the present invention the composition comprises a first anti-DR5 antibody and a second anti-DR5 antibody, wherein the first anti-DR5 antibody comprises the following six CDR sequences,
  a) (VH) SEQ ID NOs: 1, 8, 3 and (VL) SEQ ID NOs: 5, FAS, 6 and said second anti-DR5 antibody comprises the following six CDR sequences,
  b) (VH) SEQ ID NOs: 10, 2, 11 and (VL) SEQ ID NOs: 13, RTS, 14, and wherein the said first anti-DR5 antibody and said second anti-DR5 antibody comprises an E430G mutation in the Fc region.

In one embodiment of the present invention the composition comprises a first anti-DR5 antibody and a second anti-DR5 antibody, wherein said first anti-DR5 antibody comprises the following six CDR sequences (VH) SEQ ID NOs: 1, 8, 3 and (VL) SEQ ID NOs: 5, FAS, 6 and said second anti-DR5 antibody comprises the following six CDR sequences (VH) SEQ ID NOs: 10, 2, 11 and (VL) SEQ ID NOs: 13, RTS, 14, and wherein the said first anti-DR5 antibody and said first anti-DR5 antibody and said second anti-DR5 antibody comprises an E430G mutation in the Fc region.

In one embodiment of the present invention the composition comprises a first anti-DR5 antibody comprising a mutation in the position corresponding to E345 in human IgG1, EU numbering and a second anti-DR5 antibody comprising a mutation in the position corresponding to E345 in human IgG1, EU numbering, wherein the first and second antibody binds different epitopes on DR5.

In one embodiment of the present invention the composition comprises a first anti-DR5 antibody comprising a mutation in the position corresponding to E345 in human IgG1, EU numbering and a second anti-DR5 antibody comprising a mutation in the position corresponding to E345 in human IgG1, EU numbering, wherein the first antibody does not block binding of the second antibody to DR5.

In one embodiment of the present invention the composition comprises a first and a second anti-DR5 antibody comprising a mutation in a position corresponding to E345, such a mutation may be selected from the group consisting of: E345K, E345Q, E345R and E345Y.

In one embodiment of the present invention the composition comprises a first anti-DR5 antibody comprising an E345K and a second anti-DR5 antibody comprising an E345K mutation, wherein the first and second antibody binds different epitopes on DR5.

In one embodiment of the present invention the composition comprises a first anti-DR5 antibody and second anti-DR5 antibody, wherein the first anti-DR5 antibody comprises the following six CDR sequences,
  a) (VH) SEQ ID NOs: 1, 2, 3 and (VL) SEQ ID NOs: 5, FAS, 6 and said second anti-DR5 antibody comprises the following six CDR sequences,
  b) (VH) SEQ ID NOs: 10, 2, 11 and (VL) SEQ ID NOs: 13, RTS, 14, and wherein the said first anti-DR5 antibody and said second anti-DR5 antibody comprises a mutation in the position corresponding to E345.

In one embodiment of the present invention the composition comprises a first anti-DR5 antibody and a second anti-DR5 antibody, wherein said first anti-DR5 antibody comprises the following six CDR sequences (VH) SEQ ID NOs: 1, 2, 3 and (VL) SEQ ID NOs: 5, FAS, 6 and said second anti-DR5 antibody comprises the following six CDR sequences (VH) SEQ ID NOs: 10, 2, 11 and (VL) SEQ ID NOs: 13, RTS, 14, and wherein the said first anti-DR5 antibody and said second anti-DR5 antibody comprises a mutation in the position corresponding to E345 in human IgG1, EU numbering.

In one embodiment of the present invention the composition comprises a first anti-DR5 antibody and a second anti-DR5 antibody, wherein the first anti-DR5 antibody comprises the following six CDR sequences,
  a) (VH) SEQ ID NOs: 1, 2, 3 and (VL) SEQ ID NOs: 5, FAS, 6 and said second anti-DR5 antibody comprises the following six CDR sequences,
  b) (VH) SEQ ID NOs: 10, 2, 11 and (VL) SEQ ID NOs: 13, RTS, 14, and wherein the said first anti-DR5 antibody and said second anti-DR5 antibody comprises an E345K mutation in the Fc region.

In one embodiment of the present invention the composition comprises a first anti-DR5 antibody and a second anti-DR5 antibody, wherein said first anti-DR5 antibody comprises the following six CDR sequences (VH) SEQ ID NOs: 1, 2, 3 and (VL) SEQ ID NOs: 5, FAS, 6 and said second anti-DR5 antibody comprises the following six CDR sequences (VH) SEQ ID NOs: 10, 2, 11 and (VL) SEQ ID NOs: 13, RTS, 14, and wherein the said first anti-DR5 antibody and said second anti-DR5 antibody comprises an E345K mutation in the Fc region.

In one embodiment of the present invention the composition comprises a first anti-DR5 antibody and a second anti-DR5 antibody, wherein the first anti-DR5 antibody comprises the following six CDR sequences,
  a) (VH) SEQ ID NOs: 1, 8, 3 and (VL) SEQ ID NOs: 5, FAS, 6 and said second anti-DR5 antibody comprises the following six CDR sequences,
  b) (VH) SEQ ID NOs: 10, 2, 11 and (VL) SEQ ID NOs: 13, RTS, 14, and wherein the said first anti-DR5 antibody and said second anti-DR5 antibody comprises a mutation in the position corresponding to E345.

In one embodiment of the present invention the composition comprises a first anti-DR5 antibody and a second anti-DR5 antibody, wherein said first anti-DR5 antibody comprises the following six CDR sequences (VH) SEQ ID NOs: 1, 8, 3 and (VL) SEQ ID NOs: 5, FAS, 6 and said second anti-DR5 antibody comprises the following six CDR sequences (VH) SEQ ID NOs: 10, 2, 11 and (VL) SEQ ID NOs: 13, RTS, 14, and wherein the said first anti-DR5 antibody and said second anti-DR5 antibody comprises a mutation in the position corresponding to E345 in human IgG1, EU numbering.

In one embodiment of the present invention the composition comprises a first anti-DR5 antibody and a second anti-DR5 antibody, wherein the first anti-DR5 antibody comprises the following six CDR sequences,
  a) (VH) SEQ ID NOs: 1, 8, 3 and (VL) SEQ ID NOs: 5, FAS, 6 and said second anti-DR5 antibody comprises the following six CDR sequences,
  b) (VH) SEQ ID NOs: 10, 2, 11 and (VL) SEQ ID NOs: 13, RTS, 14, and wherein the said first anti-DR5 antibody and said second anti-DR5 antibody comprises an E345K mutation in the Fc region.

In one embodiment of the present invention the composition comprises a first anti-DR5 antibody and a second anti-DR5 antibody, wherein said first anti-DR5 antibody comprises the following six CDR sequences (VH) SEQ ID NOs: 1, 8, 3 and (VL) SEQ ID NOs: 5, FAS, 6 and said second anti-DR5 antibody comprises the following six CDR sequences (VH) SEQ ID NOs: 10, 2, 11 and (VL) SEQ ID NOs: 13, RTS, 14, and wherein the said first anti-DR5 antibody and said second anti-DR5 antibody comprises an E345K mutation in the Fc region.

In one embodiment of the present invention the composition comprises a first anti-DR5 antibody comprising a mutation in the position corresponding to S440 in human IgG1, EU numbering and a second anti-DR5 antibody comprising a mutation in the position corresponding to S440 in human IgG1, EU numbering, wherein the first and second antibody binds different epitopes on DR5.

In one embodiment of the present invention the composition comprises a first anti-DR5 antibody comprising a mutation in the position corresponding to S440 in human IgG1, EU numbering and a second anti-DR5 antibody comprising a mutation in the position corresponding to S440 in human IgG1, EU numbering, wherein the first antibody does not block binding of the second antibody to DR5.

In one embodiment of the present invention the composition comprises a first anti-DR5 antibody comprising an S440Y and a second anti-DR5 antibody comprising an S440Y mutation, wherein the first and second antibody binds different epitopes on DR5. In one embodiment of the present invention the composition comprises a first and a second anti-DR5 antibody comprising a mutation in a position corresponding to S440 in human IgG1, EU numbering, such a mutation may be selected from the group consisting of: S440W and S440Y.

In one embodiment of the present invention the composition comprises a first anti-DR5 antibody and a second anti-DR5 antibody, wherein the first anti-DR5 antibody comprises the following six CDR sequences,
 a) (VH) SEQ ID NOs: 1, 2, 3 and (VL) SEQ ID NOs: 5, FAS, 6 and said second anti-DR5 antibody comprises the following six CDR sequences,
 b) (VH) SEQ ID NOs: 10, 2, 11 and (VL) SEQ ID NOs: 13, RTS, 14, and wherein the said first anti-DR5 antibody and said second anti-DR5 antibody comprises a mutation in the position corresponding to S440.

In one embodiment of the present invention the composition comprises a first anti-DR5 antibody and a second anti-DR5 antibody, wherein said first anti-DR5 antibody comprises the following six CDR sequences (VH) SEQ ID NOs: 1, 2, 3 and (VL) SEQ ID NOs: 5, FAS, 6 and said second anti-DR5 antibody comprises the following six CDR sequences (VH) SEQ ID NOs: 10, 2, 11 and (VL) SEQ ID NOs: 13, RTS, 14, and wherein the said first anti-DR5 antibody and said second anti-DR5 antibody comprises a mutation in the position corresponding to S440 in human IgG1, EU numbering.

In one embodiment of the present invention the composition comprises a first anti-DR5 antibody and second anti-DR5 antibody, wherein the first anti-DR5 antibody comprises the following six CDR sequences,
 a) (VH) SEQ ID NOs: 1, 2, 3 and (VL) SEQ ID NOs: 5, FAS, 6 and said second anti-DR5 antibody comprises the following six CDR sequences,
 b) (VH) SEQ ID NOs: 10, 2, 11 and (VL) SEQ ID NOs: 13, RTS, 14, and wherein the said first anti-DR5 antibody and said second anti-DR5 antibody comprises an S440Y mutation in the Fc region.

In one embodiment of the present invention the composition comprises a first anti-DR5 antibody and a second anti-DR5 antibody, wherein said first anti-DR5 antibody comprises the following six CDR sequences (VH) SEQ ID NOs: 1, 2, 3 and (VL) SEQ ID NOs: 5, FAS, 6 and said second anti-DR5 antibody comprises the following six CDR sequences (VH) SEQ ID NOs: 10, 2, 11 and (VL) SEQ ID NOs: 13, RTS, 14, and wherein the said first anti-DR5 antibody and said second anti-DR5 antibody comprises an S440Y mutation in the Fc region.

In one embodiment of the present invention the composition comprises a first anti-DR5 antibody and a second anti-DR5 antibody, wherein the first anti-DR5 antibody comprises the following six CDR sequences,
 a) (VH) SEQ ID NOs: 1, 8, 3 and (VL) SEQ ID NOs: 5, FAS, 6 and said second anti-DR5 antibody comprises the following six CDR sequences,
 b) (VH) SEQ ID NOs: 10, 2, 11 and (VL) SEQ ID NOs: 13, RTS, 14, and wherein the said first anti-DR5 antibody and said second anti-DR5 antibody comprises a mutation in the position corresponding to S440.

In one embodiment of the present invention the composition comprises a first anti-DR5 antibody and a second anti-DR5 antibody, wherein said first anti-DR5 antibody comprises the following six CDR sequences (VH) SEQ ID NOs: 1, 8, 3 and (VL) SEQ ID NOs: 5, FAS, 6 and said second anti-DR5 antibody comprises the following six CDR sequences (VH) SEQ ID NOs: 10, 2, 11 and (VL) SEQ ID NOs: 13, RTS, 14, and wherein the said first anti-DR5 antibody and said second anti-DR5 antibody comprises a mutation in the position corresponding to S440 in human IgG1, EU numbering.

In one embodiment of the present invention the composition comprises a first anti-DR5 antibody and a second anti-DR5 antibody, wherein the first anti-DR5 antibody comprises the following six CDR sequences,
 a) (VH) SEQ ID NOs: 1, 8, 3 and (VL) SEQ ID NOs: 5, FAS, 6 and said second anti-DR5 antibody comprises the following six CDR sequences,
 b) (VH) SEQ ID NOs: 10, 2, 11 and (VL) SEQ ID NOs: 13, RTS, 14, and wherein the said first anti-DR5 antibody and said second anti-DR5 antibody comprises an S440Y mutation in the Fc region.

In one embodiment of the present invention the composition comprises a first anti-DR5 antibody and a second anti-DR5 antibody, wherein said first anti-DR5 antibody comprises the following six CDR sequences (VH) SEQ ID NOs: 1, 8, 3 and (VL) SEQ ID NOs: 5, FAS, 6 and said second anti-DR5 antibody comprises the following six CDR sequences (VH) SEQ ID NOs: 10, 2, 11 and (VL) SEQ ID NOs: 13, RTS, 14, and wherein the said first anti-DR5 antibody and said second anti-DR5 antibody comprises an S440Y mutation in the Fc region.

In one embodiment of the present invention the composition comprises a first anti-DR5 antibody and a second anti-DR5 antibody wherein the first and the second antibody comprises a further hexamerization-inhibiting mutation corresponding to K439E or S440K in human IgG1 EU numbering. In one embodiment of the present invention the composition comprises a first and a second anti-DR5 antibody, wherein the first and second anti-DR5 antibody comprises a hexamerization enhancing mutation in an amino acid position corresponding to E430, E345 or S440 in human IgG1, EU numbering and wherein the first antibody comprises a further mutation in an amino acid position corresponding to K439 or and wherein the second antibody comprises a further mutation in an amino acid position corresponding to S440, with the proviso that the hexamerization enhancing mutation is not in S440 when the further mutation is in S440. That is in one embodiment of the present invention the composition comprises a first and a second anti-DR5 antibody, wherein the first anti-DR5 antibody comprises a hexamerization enhancing mutation such as E430G and K439E, and wherein the second anti-DR5 antibody comprises a hexamerization enhancing mutation such as E430G and S440K. That is in one embodiment of the present invention the composition comprises a first and a second anti-DR5 antibody, wherein the first anti-DR5 antibody comprises a hexamerization enhancing mutation such as E345K and K439E, and wherein the second anti-DR5 antibody comprises a hexamerization enhancing mutation such as E345K and S440K. Hereby are embodiments provided that allow compositions wherein hexamerization exclusively occur between combinations of antibodies comprising a K439E mutation and antibodies comprising a S440K mutation.

In one embodiment of the present invention the composition comprises a first anti-DR5 antibody and a second anti-DR5 antibody binding different epitopes on human DR5. In one embodiment of the present invention the composition comprises a first anti-DR5 antibody comprising an antigen binding region that binds to an epitope on DR5 comprising or requiring one or more amino acid residues located within amino acid residues 116-138 and one or more amino acid residues located within amino acid residues 139-166 of SEQ ID NO 46 and a second anti-DR5 antibody comprising an antigen binding region that binds to an epitope on DR5 comprising or requiring one or more amino acid residues located within amino acid residues 79-138 of SEQ ID NO 46.

In one embodiment of the present invention the composition comprises said first anti-DR5 antibody binding to DR5, which does not block binding of said second anti-DR5 antibody to DR5. That is in one embodiment of the invention the composition comprises a first anti-DR5 antibody binding to DR5 and a second anti-DR5 antibody binding to DR5, wherein the first and the second anti-DR5 antibody does not compete for binding to DR5. Thus it is to be understood in the context of the present invention that a first anti-DR5 antibody that does not block binding of a second anti-DR5 antibody may be the same as a first anti-DR5 antibody that does not compete with a second anti-DR5 antibody.

In one embodiment of the invention, the composition comprises a first and a second anti-DR5 antibody, wherein said first antibody comprises a VH region and a VL region comprising six CDR sequences, wherein the six CDR sequences in total have at least 75%, 80%, 85%, 90%, 95%, 97%, or at least 99% amino acid sequence identity to the CDR sequences as set forth in the following: a) (VH) SEQ ID NOs: 1, 2, 3 and (VL) SEQ ID NOs: 5, FAS, 6; and said second antibody comprises a VH region and a VL region comprising six CDR sequences, wherein the six CDR sequences in total have at least 75%, 80%, 85%, 90%, 95%, 97%, or at least 99% amino acid sequence identity to the CDR sequences as set forth in the following; b) (VH) SEQ ID NOs: 10, 2, 11 and (VL) SEQ ID NOs: 13, RTS, 14.

In one embodiment thereof the sequence identity of the six CDR sequences in total of said first antibody and said second antibody is at least 85%, 90%, 95%, 97%, or 99%.

In one embodiment of the present invention the composition comprises a first and a second anti-DR5 antibody, wherein said first antibody comprises the following six CDR sequences,
  a) (VH) SEQ ID NOs: 1, 2, 3 and (VL) SEQ ID NOs: 5, FAS, 6 and said second antibody comprises the following six CDR sequences,
  b) (VH) SEQ ID NOs: 10, 2, 11 and (VL) SEQ ID NOs: 13, RTS, 14, or wherein the said first antibody and said second antibody comprises,
  c) the six CDR sequences defined in (a) or (b) above having one to five mutations or substitutions in total across said six CDR sequences respectively. That is the one or more mutations or substitutions across the six CDR sequences of the antigen binding region do not change the binding characteristics of said first or second antibody such as the agonistic properties, the DR5 epitope binding and/or the ability to induce apoptosis in a target cell expressing DR5. That is in one embodiment up to five mutations or substitutions in total are allowed across the six CDRs comprising the antigen binding region. In some embodiments of the invention up to five mutations or substitutions such as one, two, three, four or five mutations or substitutions, are made across the three CDRs of the VH region and no mutations are made across the CDRs of the VL region. In other embodiments no mutations or substitutions are made across the CDRs of the VH region but up to five mutations or substitutions, such as one, two, three, four or five are found across the CDRs of the VL region.

In one embodiment of the present invention the composition comprises a first and a second anti-DR5 antibody, wherein
  a) said first antibody comprises the following six CDR sequences (VH) SEQ ID NOs: 1, 2, 3 and (VL) SEQ ID NOs: 5, FAS, 6 and said second antibody comprises the following six CDR sequences (VH) SEQ ID NOs: 10, 2, 11 and (VL) SEQ ID NOs: 13, RTS, 14, or wherein
  b) the said first antibody and said second antibody comprises the six CDR sequences of each antibody defined in (a) or comprising one to five mutations e.g. substitutions in total across said six CDR sequences respectively. That is the one or more mutations e.g. substitutions across the six CDR sequences of the antigen binding region do not change the binding characteristics of said first or second antibody such as the agonistic properties, the DR5 epitope binding and/or the ability to induce apoptosis in a target cell expressing DR5. That is in one embodiment up to five mutations e.g. substitutions in total are allowed across the six CDRs comprising the antigen binding region. In some embodiments of the invention up to five mutations e.g. substitutions such as one, two, three, four or five mutations or substitutions, are made across the three CDRs of the VH region and no mutations are made across the CDRs of the VL region. In other embodiments no mutations e.g. substitutions are made across the CDRs of the VH region but up to five mutations e.g. substitutions, such as one, two, three, four or five are found across the CDRs of the VL region.

In one embodiment of the invention, the composition comprises a first and a second anti-DR5 antibody, wherein said first antibody comprises a VH region and a VL region comprising six CDR sequences, wherein the six CDR sequences in total have at least 75%, 80%, 85%, 90%, 95%, 97%, or at least 99% amino acid sequence identity to the CDR sequences as set forth in the following: a) (VH) SEQ ID NOs: 1, 8, 3 and (VL) SEQ ID NOs: 5, FAS; and said second antibody comprises a VH region and a VL region comprising six CDR sequences, wherein the six CDR sequences in total have at least 75%, 80%, 85%, 90%, 95%, 97%, or at least 99% amino acid sequence identity to the CDR sequences as set forth in the following; b) (VH) SEQ ID NOs: 10, 2, 11 and (VL) SEQ ID NOs: 13, RTS, 14. In one embodiment thereof the sequence identity of the six CDR sequences in total of said first antibody and said second antibody is at least 85%, 90%, 95%, 97%, or 99%.

In one embodiment of the present invention the composition comprises a first and a second anti-DR5 antibody, wherein said first antibody comprises the following six CDR sequences, a) (VH) SEQ ID NOs: 1, 8, 3 and (VL) SEQ ID NOs: 5, FAS, 6 and said second antibody comprises the following six CDR sequences b) (VH) SEQ ID NOs: 10, 2, 11 and (VL) SEQ ID NOs: 13, RTS, 14, or wherein the said first antibody and said second antibody comprises, c) the six CDR sequences defined in (a) or (b) above having one to five mutations or substitutions in total across said six CDR sequences respectively.

That is the one or more mutations or substitutions across the six CDR sequences of the antigen binding region do not change the binding characteristics of said first or second antibody such as the agonistic properties, the DR5 epitope binding and/or the ability to induce apoptosis in a target cell expressing DR5. That is in one embodiment up to five mutations or substitutions in total are allowed across the six CDRs comprising the antigen binding region. In some embodiments of the invention up to five mutations or substitutions such as one, two, three, four or five mutations or substitutions, are made across the three CDRs of the VH region and no mutations are made across the CDRs of the VL region. In other embodiments no mutations or substitutions are made across the CDRs of the VH region but up to five mutations or substitutions, such as one, two, three, four or five are found across the CDRs of the VL region.

In one embodiment of the present invention the composition comprises a first and a second anti-DR5 antibody, wherein a) said first antibody comprises the following six CDR sequences (VH) SEQ ID NOs: 1, 8, 3 and (VL) SEQ ID NOs: 5, FAS, 6 and said second antibody comprises the following six CDR sequences (VH) SEQ ID NOs: 10, 2, 11 and (VL) SEQ ID NOs: 13, RTS, 14, or wherein b) the said first antibody and said second antibody comprises the six CDR sequences of each antibody defined in (a) or comprising one to five mutations e.g. substitutions in total across said six CDR sequences respectively. That is the one or more mutations e.g. substitutions across the six CDR sequences of the antigen binding region do not change the binding characteristics of said first or second antibody such as the agonistic properties, the DR5 epitope binding and/or the ability to induce apoptosis in a target cell expressing DR5. That is in one embodiment up to five mutations e.g. substitutions in total are allowed across the six CDRs comprising the antigen binding region. In some embodiments of the invention up to five mutations e.g. substitutions such as one, two, three, four or five mutations or substitutions, are made across the three CDRs of the VH region and no mutations are made across the CDRs of the VL region. In other embodiments no mutations e.g. substitutions are made across the CDRs of the VH region but up to five mutations e.g. substitutions, such as one, two, three, four or five are found across the CDRs of the VL region.

In one embodiment of the invention, the composition comprises a first and a second anti-DR5 antibody, wherein said first antibody comprises a VH region and a VL region comprising six CDR sequences, wherein the six CDR sequences in total have at least 75%, 80%, 85%, 90%, 95%, 97%, or at least 99% amino acid sequence identity to the CDR sequences as set forth in the following: a) (VH) SEQ ID NOs: 16, 17, 18 and (VL) SEQ ID NOs: 21, GAS, 6; and said second antibody comprises a VH region and a VL region comprising six CDR sequences, wherein the six CDR sequences in total have at least 75%, 80%, 85%, 90%, 95%, 97%, or at least 99% amino acid sequence identity to the CDR sequences as set forth in the following; b) (VH) SEQ ID NOs: 10, 2, 11 and (VL) SEQ ID NOs: 13, RTS, 14. In one embodiment thereof the sequence identity of the six CDR sequences in total of said first antibody and said second antibody is at least 85%, 90%, 95%, 97%, or 99%.

In one embodiment of the present invention the composition comprises a first and a second anti-DR5 antibody, wherein said first antibody comprises the following six CDR sequences, a) (VH) SEQ ID NOs: 16, 17, 18 and (VL) SEQ ID NOs: 21, GAS, 6 and said second antibody comprises the following six CDR sequences b) (VH) SEQ ID NOs: 10, 2, 11 and (VL) SEQ ID NOs: 13, RTS, 14, or wherein the said first antibody and said second antibody comprises, c) the six CDR sequences defined in (a) or (b) above having one to five mutations or substitutions in total across said six CDR sequences. That is the one or more mutations or substitutions across the six CDR sequences of the antigen binding region do not change the binding characteristics of said first or second antibody such as the agonistic properties, the DR5 epitope binding and/or the ability to induce apoptosis in a target cell expressing DR5. That is in one embodiment up to five mutations or substitutions in total are allowed across the six CDRs comprising the antigen binding region. In some embodiments of the invention up to five mutations or substitutions such as one, two, three, four or five mutations or substitutions, are made across the three CDRs of the VH region and no mutations are made across the CDRs of the VL region. In other embodiments no mutations or substitutions are made across the CDRs of the VH region but up to five mutations or substitutions, such as one, two, three, four or five are found across the CDRs of the VL region.

In one embodiment of the present invention the composition comprises a first and a second anti-DR5 antibody, wherein a) said first antibody comprises the following six CDR sequences (VH) SEQ ID NOs: 16, 17, 18 and (VL) SEQ ID NOs: 21, GAS, 6 and said second antibody comprises the following six CDR sequences (VH) SEQ ID NOs: 10, 2, 11 and (VL) SEQ ID NOs: 13, RTS, 14, or wherein b) the said first antibody and said second antibody comprises the six CDR sequences of each antibody defined in (a) or comprising one to five mutations e.g. substitutions in total across said six CDR sequences respectively. That is the one or more mutations e.g. substitutions across the six CDR sequences of the antigen binding region do not change the binding characteristics of said first or second antibody such as the agonistic properties, the DR5 epitope binding and/or the ability to induce apoptosis in a target cell expressing DR5. That is in one embodiment up to five mutations e.g. substitutions in total are allowed across the six CDRs comprising the antigen binding region. In some embodiments of the invention up to five mutations e.g. substitutions such as one, two, three, four or five mutations or substitutions, are made across the three CDRs of the VH region and no mutations are made across the CDRs of the VL region. In other embodiments no mutations e.g. substitutions are made across the CDRs of the VH region but up to five mutations e.g. substitutions, such as one, two, three, four or five are found across the CDRs of the VL region.

In one embodiment of the present invention the composition comprises a first and a second anti-DR5 antibody as defined in any of the above embodiments wherein said first and second antibody further comprises a mutation in the Fc region corresponding to position K439 or S440 in human IgG1, EU numbering. In one embodiment of the invention the composition comprises a first antibody comprising a mutation corresponding to K439 such as K439E and a second antibody comprising a mutation corresponding to S440 such as S440K. In one embodiment of the invention the composition comprises a first antibody comprising a mutation corresponding to S440 such as S440K and a second antibody comprising a mutation corresponding to K439 such as K439E. Hereby embodiment are provided wherein the composition comprises a first antibody comprising at least two mutations such as E430G and K439E and a second antibody comprising at least two mutations such as E430G and S440K. In another embodiment of the present invention the composition comprises a first antibody comprising at least two mutations such as E345K and K439E and a second antibody comprising at least two mutation such as E345K and S440K. Hereby are embodiments provided that allow for hexamerization of antibodies with different specificities.

In one embodiment of the present invention the composition comprises a first and a second anti-DR5 antibody, wherein said first antibody comprises the following sequences (a) (VH) CDR1 SEQ ID NO 1, CDR2 SEQ ID NO 8, CDR3 SEQ ID NO 3 and (VL) CDR1 SEQ ID NO 5, CDR2 FAS, CDR3 SEQ ID NO 6 and said second antibody comprises the following sequences (b) (VH) CDR1 SEQ ID NO 10, CDR2 SEQ ID NO 2, CDR3 SEQ ID NO 11 and (VL) CDR1 SEQ ID NO 13, CDR2 RTS, CDR3 SEQ ID NO 14 or (c) the (VH) CDR1, CDR2 and CDR3 and (VL) CDR1, CDR2 and CDR3 as defined in (a) or (b) above having one to five mutations or substitutions in total across said six CDR sequences. That is the one or more mutations or substitutions across the six CDR sequences of the antigen binding region do not change the binding characteristics of said first or second antibody such as the agonistic properties, the DR5 epitope binding and/or the ability to induce apoptosis in a target cell expressing DR5.

In one embodiment of the present invention the composition comprises a first and a second anti-DR5 antibody, wherein said first and second antibody comprises the following CDR sequences (a) said first antibody comprises the following CDR sequences (VH) CDR1 SEQ ID NO 1, CDR2 SEQ ID NO 8, CDR3 SEQ ID NO 3 and (VL) CDR1 SEQ ID NO 5, CDR2 FAS, CDR3 SEQ ID NO 6 and said second antibody comprises the following CDR sequences (VH) CDR1 SEQ ID NO 10, CDR2 SEQ ID NO 2, CDR3 SEQ ID NO 11 and (VL) CDR1 SEQ ID NO 13, CDR2 RTS, CDR3 SEQ ID NO 14 or (b) the CDR sequences described in (a) for each antibody comprising one to five mutations e.g. substitutions in total across said CDR sequences for each antibody. That is the one or more mutations e.g. substitutions across the six CDR sequences of the antigen binding region do not change the binding characteristics of said first or second antibody such as the agonistic properties, the DR5 epitope binding and/or the ability to induce apoptosis in a target cell expressing DR5.

In one embodiment of the present invention the composition comprises a first and a second anti-DR5 antibody, wherein said first antibody comprises the following sequences (a) (VH) CDR1 SEQ ID NOs 1, CDR2 2, CDR3 3 and (VL) CDR1 SEQ ID NOs 5, CDR2 FAS, CDR3 6 and said second antibody comprises the following sequences (b) (VH) CDR1 SEQ ID NOs 10, CDR2 2, CDR3 11 and (VL) SEQ ID NOs CDR1 13, CDR2 RTS, CDR3 14 or (c) the (VH) CDR1, CDR2 and CDR3 and (VL) CDR1, CDR2 and CDR3 as defined in (a) or (b) above having one to five mutations or substitutions in total across said six CDR sequences. That is the one or more mutations or substitutions across the six CDR sequences of the antigen binding region do not change the binding characteristics of said first or second antibody such as the agonistic properties, the DR5 epitope binding and/or the ability to induce apoptosis in a target cell expressing DR5.

In one embodiment of the present invention the composition comprises a first and a second anti-DR5 antibody, wherein said first and second antibody comprises the following CDR sequences (a) said first antibody comprises the following CDR sequences (VH) CDR1 SEQ ID NO 1, CDR2 SEQ ID NO 2, CDR3 SEQ ID NO 3 and (VL) CDR1 SEQ ID NO 5, CDR2 FAS, CDR3 SEQ ID NO 6 and said second antibody comprises the following CDR sequences (VH) CDR1 SEQ ID NO 10, CDR2 SEQ ID NO 2, CDR3 SEQ ID NO 11 and (VL) CDR1 SEQ ID NO 13, CDR2 RTS, CDR3 SEQ ID NO 14 or (b) the CDR sequences described in (a) for each antibody comprising one to five mutations e.g. substitutions in total across said CDR sequences for each antibody. That is the one or more mutations e.g. substitutions across the six CDR sequences of the antigen binding region do not change the binding characteristics of said first or second antibody such as the agonistic properties, the DR5 epitope binding and/or the ability to induce apoptosis in a target cell expressing DR5.

In one embodiment of the present invention the composition comprises a first and a second anti-DR5 antibody, wherein said first antibody comprises the following sequences (a) (VH) CDR1 SEQ ID NO 16, CDR2 SEQ ID NO 17, CDR3 SEQ ID NO 18 and (VL) CDR1 SEQ ID NO 21, CDR2 GAS, CDR3 SEQ ID NO 22 and said second antibody comprises the following sequences (b) (VH) CDR1 SEQ ID NO 10, CDR2 SEQ ID NO 2, CDR3 SEQ ID NO 11 and (VL) CDR1 SEQ ID NO 13, CDR2 RTS, CDR3 SEQ ID NO 14 or (c) the (VH) CDR1, CDR2 and CDR3 and (VL) CDR1, CDR2 and CDR3 as defined in (a) or (b) above having one to five mutations or substitutions in total across said six CDR sequences. That is the one or more mutations or substitutions across the six CDR sequences of the antigen binding region do not change the binding characteristics of said first or second antibody such as the agonistic properties, the DR5 epitope binding and/or the ability to induce apoptosis in a target cell expressing DR5.

In one embodiment of the present invention the composition comprises a first and a second anti-DR5 antibody, wherein said first and second antibody comprises the following CDR sequences (a) said first antibody comprises the following CDR sequences (VH) CDR1 SEQ ID NO 16, CDR2 SEQ ID NO 17, CDR3 SEQ ID NO 18 and (VL) CDR1 SEQ ID NO 21, CDR2 GAS, CDR3 SEQ ID NO 22 and said second antibody comprises the following CDR sequences (VH) CDR1 SEQ ID NO 10, CDR2 SEQ ID NO 2, CDR3 SEQ ID NO 11 and (VL) CDR1 SEQ ID NO 13, CDR2 RTS, CDR3 SEQ ID NO 14 or (b) the CDR sequences described in (a) for each antibody comprising one to five mutations e.g. substitutions in total across said CDR sequences for each antibody. That is the one or more mutations e.g. substitutions across the six CDR sequences of the antigen binding region do not change the binding characteristics of said first or second antibody such as the agonistic properties, the DR5 epitope binding and/or the ability to induce apoptosis in a target cell expressing DR5.

In one embodiment of the invention the composition comprises a first and a second anti-DR5 antibody, wherein said first antibody and said second antibody are present in the composition at a 1:49 to 49:1 molar ratio, such as 1:1 molar ratio, a 1:2 molar ratio, a 1:3 molar ratio, a 1:4 molar ratio, a 1:5 molar ratio, a 1:6 molar ratio, a 1:7 molar ratio, a 1:8 molar ratio, a 1:9 molar ratio, a 1:10 molar ratio, a 1:15 molar ratio, a 1:20 molar ratio, a 1:25 molar ratio, a 1:30 molar ratio, a 1:35 molar ratio, a 1:40 molar ratio, a 1:45 molar ratio a 1:50 molar ratio, a 50:1 molar ratio, a 45:1 molar ratio, a 40:1 molar ratio, a 35:1 molar ratio, a 30:1 molar ratio a 25:1 molar ratio, a 20:1 molar ratio, a 15:1 molar ratio, a 10:1 molar ratio, a 9:1 molar ratio, a 8:1 molar ratio, a 7:1 molar ratio, a 6:1 molar ratio, a 5:1 molar ratio, a 4:1 molar ratio, a 3:1 molar ratio, a 2:1 molar ratio.

In one embodiment of the invention the composition comprises a first and a second anti-DR5 antibody, wherein said first antibody and said second antibody are present in the composition at a 1:9 to 9:1 molar ratio.

In one embodiment of the invention the composition comprises a first and a second anti-DR5 antibody, wherein said first antibody and said second antibody are present in the composition at approximately a 1:1 molar ratio.

In one embodiment of the invention the composition comprises a first and a second anti-DR5 antibody, wherein said first antibody and said second antibody are present in the composition at a 1:1 molar ratio.

In a preferred embodiment of the invention the composition comprises a first and a second anti-DR5 antibody, wherein said first antibody and second antibody and/or any additional antibodies are present in the composition at an equimolar ratio.

In one embodiment of the invention the composition is a pharmaceutical composition.

Pharmaceutical compositions of the present invention may comprise antibodies such as monoclonal antibodies or bispecific antibodies according to any aspect or embodiment of the present invention.

The pharmaceutical compositions may be formulated with pharmaceutically acceptable carriers or diluents as well as any other known adjuvants and excipients in accordance with conventional techniques such as those disclosed in (Rowe et al., Handbook of Pharmaceutical Excipients, 2012 June, ISBN 9780857110275)

The pharmaceutically acceptable carriers or diluents as well as any other known adjuvants and excipients should be suitable for the antibody or bispecific antibody of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.) upon antigen binding).

A pharmaceutical composition of the present invention may also include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition.

The actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering a compound of the present invention in vivo and in vitro are well known in the art and may be selected by those of ordinary skill in the art.

In one embodiment, the pharmaceutical composition of the present invention is administered parenterally.

The terms "parenteral administration" and "administered parenterally" as used herein refers to modes of administration other than enteral and topical administration, usually by injection, and include epidermal, intravenous, intramuscular, intra-arterial, intrathecal, intracapsular, intra-orbital, intracardiac, intradermal, intraperitoneal, intratendinous, transtracheal, subcutaneous, subcuticular, intra-articular, subcapsular, subarachnoid, intraspinal, intracranial, intrathoracic, epidural and intrasternal injection and infusion. In one embodiment, the pharmaceutical composition of the present invention is administered by intravenous or subcutaneous injection or infusion.

In one embodiment of the present invention the pharmaceutical composition comprises one or more antibodies according to the invention such as monoclonal antibodies or bispecific antibodies together with a pharmaceutical carrier.

Pharmaceutically acceptable carriers include any and all suitable solvents, dispersion media, coatings, antibacterial and antifungal agents, isotonicity agents, antioxidants and absorption-delaying agents, and the like that are physiologically compatible with a compound of the present invention.

Examples of suitable aqueous and non-aqueous carriers which may be employed in the pharmaceutical compositions of the present invention include water, saline, phosphate-buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metalchelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and micro-encapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, poly-ortho-esters, and polylactic acid alone or with a wax, or other materials well known in the art. Methods for the preparation of such formulations are generally known to those skilled in the art. In one embodiment, the compounds of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. Other active or therapeutic compounds may also be incorporated into the compositions.

Pharmaceutical compositions for injection or infusion must typically be sterile and stable under the conditions of manufacture and storage. The composition may be formulated as a solution, micro-emulsion, liposome, or other ordered structure suitable to high drug concentration. The carrier may be an aqueous or a non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum-drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum-drying and freeze-drying (lyophilization) that yield a powder of the active ingredient plus any additional desired ingredient from a previously sterile-filtered solution thereof.

The pharmaceutical composition of the present invention may contain one or more monoclonal antibodies or one or more bispecific antibodies of the present invention, a combination of an antibody or a bispecific antibody according to the invention with another therapeutic compound, or a combination of compounds of the present invention.

Therapeutic Applications

The antibodies such as monoclonal antibodies, bispecific antibodies or compositions according to any aspect or embodiment of the present invention may be used as a medicament, i.e. for therapeutic applications.

In one embodiment of the present invention the composition comprises one or more antibodies according to the invention such as monoclonal antibodies or bispecific antibodies for use as a medicament.

In another aspect, the present invention provides methods for treating or preventing a disorder involving cells expressing DR5 in a subject, which method comprises administration of a therapeutically effective amount of an anti-DR5 antibody, bispecific antibody or a composition comprising one or more antibodies of the present invention to a subject in need thereof. The method typically involves administering to a subject in need thereof an anti-DR5 antibody, a bispecific antibody or composition according to the present invention in an amount effective to treat or prevent the disorder.

The anti-DR5 antibodies of the present invention can be used in the treatment or prevention of disorders involving cells expressing DR5. For example, the antibodies may be administered to human subjects, e.g., in vivo, to treat or prevent disorders involving DR5-expressing cells. As used herein, the term "subject" is typically a human to whom the anti-DR5 antibody or bispecific antibody is administered. Subjects may for instance include human patients having disorders that may be corrected or ameliorated by modulating DR5 function or by killing of the DR5-expressing cell, directly or indirectly.

In one aspect, the present invention relates to an anti-DR5 antibody, bispecific antibody or composition as defined in any aspect or embodiment herein, for use in treatment or to ameliorate symptoms of a disease or disorder involving cells expressing DR5. In one embodiment of the present invention the composition comprising an anti-DR5 antibody or bispecific antibody according to any aspect or embodiment as disclosed herein, for use in treatment of infectious disease, autoimmune disease or cardiovascular anomalies.

In one aspect, the present invention relates to an anti-DR5 antibody, bispecific antibody or composition as defined in any aspect or embodiment herein, for use in treatment or to ameliorate symptoms of cancer and/or tumors.

In one embodiment of the present invention the composition comprising an anti-DR5 antibody or bispecific antibody according to any aspect or embodiment of the invention is for use in treatment of cancer and/or tumors.

The term "cancer" refers to or describes the physiological condition in mammals such as humans that is typically characterized by unregulated growth. Most cancers belong to one of two larger groups of cancers i.e., solid tumors and hematological tumors.

In a particular aspect, an anti-DR5 antibody, bispecific antibody or composition is administered prophylactically in order to reduce the risk of developing cancer, delay the onset of an event in cancer progression or reduce the risk of recurrence when a cancer is in remission and/or a primary tumor has been surgically removed. In the latter case, the anti-DR5 antibody, bispecific antibody or composition could, for example, be administered in association with (i.e., before, during, or after) the surgery. Prophylactic administration may also be useful in patients where it is difficult to locate a tumor that is believed to be present due to other biological factors.

In one embodiment the composition comprising one or more anti-DR5 antibodies or bispecific antibodies of the present invention is for use in treatment of solid tumors and/or hematological tumors In one embodiment the composition comprising one or more anti-DR5 antibodies or bispecific antibodies of the present invention is for use in treatment of solid tumors such as, colorectal cancer, including colorectal carcinoma and colorectal adenocarcinoma, bladder cancer, osteosarcoma, chondrosarcoma, breast cancer, including triple-negative breast cancer, cancers of the central nervous system, including glioblastoma, astrocytoma, neuroblastoma, neural fibrosarcoma, neuroendocrine tumors, cervical cancer, endometrium cancer, gastric cancer, including gastric adenocarcinoma, head and neck cancer, kidney cancer, liver cancer, including hepatocellular carcinoma, lung cancer, including non-small cell lung cancer (NSCLC) and small cell lung cancer (SCLC), ovarian cancer, pancreatic cancer, including pancreatic ductal carcinoma and pancreatic adenocarcinoma, sarcoma or skin cancer, including malignant melanoma and non-melanoma skin cancers.

In one embodiment of the invention the composition comprising one or more anti-DR5 antibodies or bispecific antibodies is for use in treatment of hematological tumors such as, leukemia, including chronic lymphocytic leukemia and myeloid leukemia, including acute myeloid leukemia and chronic myeloid leukemia, lymphoma, including Non-Hodgkin lymphoma or multiple myeloma, including Hodgkin Lymphoma, and including myelodysplastic syndromes.

In a particular embodiment of the present invention the composition comprising one or more anti-DR5 antibodies or bispecific antibodies is for use in treatment of a cancer selected from the following group of cancers; bladder cancer, bone cancer, colorectal cancer, sarcoma, endometrium cancer, fibroblast cancer, gastric cancer, head and neck cancer, kidney cancer, leukemia, liver cancer, lung cancer, lymphoma, muscle cancer, neural tissue cancer, ovary cancer, pancreas cancer and skin cancer.

In one embodiment of the invention the composition comprising one or more anti-DR5 antibodies or bispecific antibodies is for use in inhibiting growth of DR5 positive or DR5 expressing tumors or cancers.

In the present invention DR5 positive tumors or cancers are to be understood as tumor cells and/or cancer cells expressing DR5 on the cell surface. Such DR5 expression may be detected by immunohistochemistry, flow cytometry, imaging or other suitable diagnostic method.

In one embodiment of the invention the composition comprising one or more anti-DR5 antibodies or bispecific antibodies is for use in inhibiting growth of DR5 expressing tumors or cancers. Tumors and cancer tissues that show heterogeneous expression of DR5 are also considered as DR5 positive tumors and cancers.

Tumors and/or cancers may express DR5 on some tumor and/or cancer cells and/or tissues showing DR5 expression, some tumor and/or cancers may show over-expression or aberrant expression of DR5, whereas other tumors and/or cancers show heterogeneous expression of DR5. Such tumors and/or cancers may all be suitable targets for treatment with anti-DR5 antibodies, bispecific antibodies and compositions comprising such antibodies according to the present invention.

In one embodiment of the invention the composition comprising one or more anti-DR5 antibodies or bispecific antibodies is for use in induction of apoptosis in DR5 expressing tumors.

Another aspect of the present invention comprises a method of treating an individual having a cancer comprising administering to said individual an effective amount of an anti-DR5 antibody, bispecific antibody or composition according to the invention.

In one embodiment of the invention the method of treating an individual having a cancer comprising administering to said individual an effective amount of an anti-DR5 antibody, bispecific antibody or composition according to the invention, further comprises administering an additional therapeutic agent to the said individual.

In one embodiment of the invention the additional therapeutic agent is a single agent or a combination of agents comprising an agent or regimen selected from the group chemotherapeutics (including but not limited to paclitaxel, temozolomide, cisplatin, carboplatin, oxaliplatin, irinotecan, doxorubicin, gemcitabine, 5-fluorouracil, pemetrexed), kinase inhibitors (including but not limited to sorafenib, sunitinib or everolimus), apoptosis-modulating agents (including but not limited to recombinant human TRAIL or birinapant), RAS inhibitors, proteasome inhibitors (including but not limited to bortezomib), histon deacetylase inhibitors (including but not limited to vorinostat), nutraceuticals, cytokines (including but not limited to IFN-γ), antibodies or antibody mimetics (including but not limited to anti-TF, anti-AXL, anti-EGFR, anti-IGF-1R, anti-VEGF, anti-CD20, anti-CD38, anti-HER2, anti-PD-1, anti-PD-L1, anti-CTLA4, anti-CD40, anti-CD137, anti-GITR, anti-VISTA (or other immunomodulatory targets) antibodies and antibody mimetics), and antibody-drug conjugates such as brentuximab vedotin, trastuzumab emtansine, HuMax-TF-ADC or HuMax-AXL-ADC.

In a further aspect, the invention comprises a kit of parts comprising an anti-DR5 antibody, bispecific antibody or composition according to the, wherein said antibody, bispecific antibody or composition is in one or more containers such as one or more vials.

In one embodiment of the invention the kit of parts comprising an anti-DR5 antibody, bispecific antibody or composition according to the invention is for simultaneous, separate or sequential use in therapy.

In a further embodiment the present invention is for use of an anti-DR5 antibody, bispecific antibody or a composition according to the invention for the manufacture of a medicament for treatment of cancer.

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

In another aspect of the present invention, the invention comprises a nucleic acid construct encoding an antibody according to amino acid sequences set forth in table 1. That is in one embodiment, the present invention comprises, a nucleic acid construct encoding an antibody corresponding to the amino acid sequences set forth in SEQ ID Nos: 1 to 23 or 29 to 43. In one embodiment of the present invention, the nucleic acid construct encodes an antibody according to any embodiments disclosed herein.

In a further aspect, the present invention relates to a nucleic acid encoding an antibody according to the present invention, wherein the Fc region comprises a mutation of an amino acids position corresponding to E430, E345 or S440 in a human IgG1, EU numbering. It is further contemplated that the nucleic acid encoding an antibody according to the invention comprises the amino acid substitutions in the specific amino acid positions herein described. Thus, in one embodiment, the nucleic acid encodes an antibody having the sequence according to SEQ ID NO: 33, 34, 35, 36, 37, 38, 39, 40, 41, 42 or 43.

In another aspect, the invention relates to nucleic acids encoding a sequence of a human, humanized or chimeric anti-DR5 antibody for use in the invention, to expression vectors encoding the sequences of such an antibody, to host cells comprising such expression vectors, to hybridomas which produce such antibodies, and to methods of producing such an antibody by culturing such host cells or hybridomas under appropriate conditions whereby the antibody is produced and, optionally, retrieved. Humanized anti-DR5 antibodies may also be denoted as "huDR5".

In one embodiment, the invention provides an expression vector comprising a nucleotide sequence encoding one or more of the amino acid sequence according to SEQ ID Nos: 33 to 43

In one embodiment, the invention provides an expression vector comprising a nucleotide sequence encoding one or more amino acid sequences selected from the group consisting of SEQ ID NOs: 33, 34, 35, 36, 37, 38, 39, 40, 41, 42 and 43., or any combination thereof. In another embodiment, the expression vector comprises a nucleotide sequence encoding any one or more of the VH CDR3 amino acid sequences selected from SEQ ID NOs: 3 and 11. In another embodiment, the expression vector comprises a nucleotide sequence encoding a VH amino acid sequence selected from SEQ ID NOs: 4, 9 and 12. In another embodiment, the expression vector comprises a nucleotide sequence encoding a VL amino acid sequence selected from SEQ ID NOs: 7, and 15. In another embodiment, the expression vector comprises a nucleotide sequence encoding the constant region of a human antibody light chain, of a human antibody heavy chain, or both. In another embodiment, the expression vector comprising a nucleotide sequence encoding the constant region of a human antibody heavy chain of selected from the group consisting of: SEQ ID NOs:58, 59, 60, 61, 62, 63, 64, 65, 66, 67 and 68.

In a particular embodiment, the expression vector comprises a nucleotide sequence encoding a variant of one or more of the above amino acid sequences, said variant having at most 25 amino acid modifications, such as at most 20, such as at most 15, 14, 13, 12, or 11 amino acid modifications, such as 10, 9, 8, 7, 6, 5, 4, 3, 2, or 1 amino acid modifications, such as deletions or insertions, preferably substitutions, such as conservative substitutions, or at least 80% identity to any of said sequences, such as at least 85% identity or 90% identity or 95% identity, such as 96% identity or 97% identity or 98% identity or 99% identity to any of the afore-mentioned amino acid sequences.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, a humanized CD3 antibody-encoding nucleic acid is comprised in a naked DNA or RNA vector, including, for example, a linear expression element (as described in for instance Sykes and Johnston, Nat Biotech 17, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793-800 (2001)), or as a precipitated nucleic acid vector construct, such as a $CaPO_4$-precipitated construct (as described in for instance WO 00/46147, Benvenisty and Reshef, PNAS USA 83 9551-55 (1986), Wigler et al., Cell 14 725 (1978), and Coraro and Pearson, Somatic Cell Genetics 7, 603 (1981)). Such nucleic acid vectors and the usage thereof are well known in the art (see for instance U.S. Pat. Nos. 5,589,466 and 5,973,972). In one embodiment, the vector is suitable for expression of the humanized anti-DR5 antibody, in a bacterial cell. Examples of such vectors include expression vectors such as BlueScript (Stratagene), pIN vectors (Van Heeke & Schuster, J Biol Chem 264, 5503-5509 (1989)), pET vectors (Novagen, Madison, Wis.) and the like.

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516-544 (1987)).

A nucleic acid and/or vector may also comprise a nucleic acid sequence encoding a secretion/localization sequence, which can target a polypeptide, such as a nascent polypeptide chain, to the periplasmic space or into cell culture media. Such sequences are known in the art, and include secretion leader or signal peptides, organelle-targeting sequences (e.g., nuclear localization sequences, ER retention signals, mitochondrial transit sequences, chloroplast transit sequences), membrane localization/anchor sequences (e.g., stop transfer sequences, GPI anchor sequences), and the like.

In an expression vector of the invention, anti-DR5 antibody-encoding nucleic acids and the first and the second polypeptides nucleic acids may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE (the skilled artisan will recognize that such terms are actually descriptors of a degree of gene expression under certain conditions).

In one embodiment, the anti-DR5 antibody-encoding expression is positioned in and/or delivered to the host cell or host animal via a viral vector.

Such expression vectors may be used for recombinant production of anti-DR5 antibodies. In one aspect, the anti-DR5 antibodies of any aspect or embodiment described herein are provided by use of recombinant eukaryotic or prokaryotic host cell which produces the antibody. Accordingly, the invention provides a recombinant eukaryotic or prokaryotic host cell, such as a transfectoma, which produces an anti-DR5 antibody as defined herein. Examples of host cells include yeast, bacterial and mammalian cells, such as CHO or HEK-293 cells. For example, in one embodiment, the host cell comprises a nucleic acid stably integrated into the cellular genome that comprises a sequence coding for expression of a anti-DR5 antibody described herein. In one embodiment, the host cell comprises a nucleic acid stably integrated into the cellular genome that comprise a sequence coding for expression of a first or a second polypeptide described herein. In another embodiment, the host cell comprises a non-integrated nucleic acid, such as a plasmid, cosmid, phagemid, or linear expression element, which comprises a sequence coding for expression of a anti-DR5 antibody, a first or a second polypeptide described herein.

The term "recombinant host cell" (or simply "host cell"), as used herein, is intended to refer to a cell into which an expression vector has been introduced. It should be understood that such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, HEK-293 cells, PER.C6, NSO cells, and lymphocytic cells, and prokaryotic cells such as E. coli and other eukaryotic hosts such as plant cells and fungi.

The term "transfectoma", as used herein, includes recombinant eukaryotic host cells expressing the antibody or a target antigen, such as CHO cells, PER.C6, NSO cells, HEK-293 cells, plant cells, or fungi, including yeast cells.

In a further aspect, the invention relates to a method for producing an antibody of the invention, said method comprising the steps of
a) culturing a hybridoma or a host cell of the invention as described herein above, and
b) retrieving and/or purifying the antibody of the invention from the culture media.

In a further aspect, the nucleotide sequence encoding a sequence of an antibody further encodes a second moiety, such as a therapeutic polypeptide. Exemplary therapeutic antibodies are described elsewhere herein. In one embodiment, the invention relates to a method for producing an antibody fusion protein, said method comprising the steps of
a) culturing a host cell comprising an expression vector comprising such a nucleotide sequence, and
b) retrieving and/or purifying the antibody fusion protein from the culture media.

In one aspect of the present invention, the invention comprises an expression vector comprising on or more nucleic acid constructs encoding an antibody according to any embodiment disclosed herein.

In a further aspect of the invention, the invention comprises a host cell comprising an expression vector.

In one embodiment of the invention the host cell is a recombinant host cell, such as a recombinant prokaryotic cell, recombinant eukaryotic cell or recombinant microbial host cell.

SEQUENCE TABLE 1

| SEQ ID NO: | Name | Sequence | Clone |
| --- | --- | --- | --- |
| SEQ ID NO: 1 | VH hDR5-01 CDR1 | GFNIKDTF | hDR5-01 |
| SEQ ID NO: 2 | VH hDR5-01 CDR2 | IDPANGNT | |
| SEQ ID NO: 3 | VH hDR5-01 CDR3 | VRGLYTYYFDY | |
| SEQ ID NO: 4 | VH hDR5-01 | EVQLQQSGAEVVKPGA SVKLSCKAS<u>GFNIKDTF</u>I HWVKQAPGQGLEWIG R<u>IDPANGNT</u>KYDPKFQ GKATITTDTSSNTAYME LSSLRSEDTAVYYC<u>VRGL YTYYFDY</u>WGQGTLVTV SS | |
| SEQ ID NO: 5 | VL hDR5-01 CDR1 | QSISNN | |
| | VL hDR5-01 CDR2 | FAS | |
| SEQ ID NO: 6 | VL hDR5-01 CDR3 | QQGNSWPYT | |
| SEQ ID NO: 7 | VL hDR5-01 | EIVMTQSPATLSVSPGE RATLSCRAS<u>QSISNN</u>LH WYQQKPGQAPRLLIK<u>F AS</u>QSITGIPARFSGSGSG TEFTLTISSLQSEDFAVY YC<u>QQGNSWPYT</u>FGQG TKLEIK | |

SEQUENCE TABLE 1-continued

| SEQ ID NO: | Name | Sequence | Clone |
| --- | --- | --- | --- |
| SEQ ID NO: 1 | VH hDR5-01-G56T CDR1 | GFNIKDTF | hDR5-01-G56T |
| SEQ ID NO: 8 | VH hDR5-01-G56T CDR2 | IDPANTNT | |
| SEQ ID NO: 3 | VH hDR5-01-G56T CDR3 | VRGLYTYYFDY | |
| SEQ ID NO: 9 | VH hDR5-01-G56T | EVQLQQSGAEVVKPGA SVKLSCKAS<u>GFNIKDTF</u>I HWVKQAPGQGLEWIG <u>RIDPANTNT</u>KYDPKFQG KATITTDTSSNTAYMEL SSLRSEDTAVYYC<u>VRGL YTYYFDY</u>WGQGTLVTV SS | |
| SEQ ID NO: 5 | VL hDR5-01-G56T CDR1 | QSISNN | |
| | VL hDR5-01-G56T CDR2 | FAS | |
| SEQ ID NO: 6 | VL hDR5-01-G56T CDR3 | QQGNSWPYT | |
| SEQ ID NO: 7 | VL hDR5-01-G56T | EIVMTQSPATLSVSPGE RATLSCRAS<u>QSISNN</u>LH WYQQKPGQAPRLLIK<u>F ASQ</u>SITGIPARFSGSGSG TEFTLTISSLQSEDFAVY YC<u>QQGNSWPYT</u>FGQG TKLEIK | |
| SEQ ID NO: 10 | VH hDR5-05 CDR1 | GFNIKDTH | hDR5-05 |
| SEQ ID NO: 2 | VH hDR5-05 CDR2 | IDPANGNT | |
| SEQ ID NO: 11 | VH hDR5-05 CDR3 | ARWGTNVYFAY | |
| SEQ ID NO: 12 | VH hDR5-05 | QVQLVQSGAEVKKPGA SVKVSCKAS<u>GFNIKDTH</u> MHWVRQAPGQRLEWI G<u>RIDPANGNT</u>EYDQKF QGRVTITVDTSASTAYM ELSSLRSEDTAVYYC<u>AR WGTNVYFAY</u>WGQGTL VTVSS | |
| SEQ ID NO: 13 | VL hDR5-05 CDR1 | SSVSY | |
| | VL hDR5-05 CDR2 | RTS | |
| SEQ ID NO: 14 | VL hDR5-05 CDR3 | QQYHSYPPT | |
| SEQ ID NO: 15 | VL hDR5-05 | DIQLTQSPSSLSASVGD RVTITCSAS<u>SSVSY</u>MYW YQQKPGKAPKPWIY<u>RT SN</u>LASGVPSRFSGSGSG TDFTLTISSLQPEDFATY YC<u>QQYHSYPPT</u>FGGGT KVEIK | |
| SEQ ID NO: 16 | VH CONA-CDR1 | GGSISSGDYF | Conatumumab IgG1-DR5-CONA |
| SEQ ID NO: 17 | VH CONA-CDR2 | IHNSGTT | |
| SEQ ID NO: 18 | VH CONA-CDR3 | ARDRGGDYYYGMDV | |
| SEQ ID NO: 19 | VH CONA | QVQLQESGPGLVKPSQ TLSLTCTVS<u>GGSISSGDY F</u>WSWIRQLPGKGLECIG <u>HIHNSGTT</u>YYNPSLKSR VTISVDTSKKQFSLRLSS VTAADTAVYYC<u>ARDRG</u> | |

SEQUENCE TABLE 1-continued

| SEQ ID NO: | Name | Sequence | Clone |
|---|---|---|---|
| | | GDYYYGMDVWGQGTT<br>VTVSS | |
| SEQ ID NO: 20 | VH CONA-C49W | QVQLQESGPGLVKPSQ<br>TLSLTCTVSGGSISSGDY<br>FWSWIRQLPGKGLEWI<br>GHIHNSGTTYYNPSLKS<br>RVTISVDTSKKQFSLRLS<br>SVTAADTAVYYCARDR<br>GGDYYYGMDVWGQG<br>TTVTVSS | |
| SEQ ID NO: 21 | VL CONA-CDR1 | QGISRSY | |
| | VL CONA-CDR2 | GAS | |
| SEQ ID NO: 22 | VL CONA-CDR3 | QQFGSSPWT | |
| SEQ ID NO: 23 | VL CONA | EIVLTQSPGTLSLSPGER<br>ATLSCRASQGISRSYLA<br>WYQQKPGQAPSLLIYG<br>ASSRATGIPDRFSGSGS<br>GTDFTLTISRLEPEDFAV<br>YYCQQFGSSPWTFGQG<br>TKVEIK | |
| SEQ ID NO: 24 | Human DR5 | MEQRGQNAPAASGA<br>RKRHGPGPREARGA<br>RPGPRVPKTLVLVVA<br>AVLLLVSAESALITQ<br>QDLAPQQRAAPQQK<br>RSSPSEGLCPPGHHI<br>SEDGRDCISCKYGQ<br>DYSTHWNDLLFCLR<br>CTRCDSGEVELSPCT<br>TTRNTVCQCEEGTFR<br>EEDSPEMCRKCRTG<br>CPRGMVKVGDCTPW<br>SDIECVHKESGTKH<br>SGEVPAVEETVTSSP<br>GTPASPCSLSGIIIGV<br>TVAAVVLIVAVFVCK<br>SLLWKKVLPYLKGIC<br>SGGGGDPERVDRSS<br>QRPGAEDNVLNEIVS<br>ILQPTQVPEQEMEVQ<br>EPAEPTGVNMLSPGE<br>SEHLLEPAEAERSQR<br>RRLLVPANEGDPTET<br>LRQCFDDFADLVPFD<br>SWEPLMRKLGLMDN<br>EIKVAKAEAAGHRDT<br>LYTMLIKWVNKTGR<br>DASVHTLLDALETLG<br>ERLAKKIEDHLLSSG<br>KFMYLEGNADSAMS | |
| SEQ ID NO: 25 | Rhesus monkey DR5 | MGQLRQSAPAASGA<br>RKGRGPGPREARGA<br>RPGLRVLKTLVLVVA<br>AARVLVSADCAPITR<br>QSLDPQRRAAPQQK<br>RSSPTEGLCPPGHHI<br>SEDSRDCISCKYGQ<br>DYSTHWNDFLFCLR<br>CTKCDSGEVEVNSC<br>TTTRNTVCQCEEGTF<br>REEDSPEICRKCRTG<br>CPRGMVKVKDCTPW<br>SDIECVHKESGTKHT<br>GEVPAVEKTVTTSPG<br>TPASPCSLSGIIIGVI<br>VFVVIVVVAVIVWKT<br>SLWKKVLPYLKGVC<br>SGDGGDPERVDSSP<br>QRPGAEDNALNEIVS<br>IVQPSQVPEQEMEV<br>QEPAEQTDVNTLSP | |

SEQUENCE TABLE 1-continued

| SEQ ID NO: | Name | Sequence | Clone |
|---|---|---|---|
|  |  | GESEHLLEPAKAEGP<br>QRRGQLVPVNENDP<br>TETLRQCFDDFAAIV<br>PFDAWEPLVRQLGLT<br>NNEIKVAKAEAASSR<br>DTLYVMLIKWVNKT<br>GRAASVNTLLDALET<br>LEERLAKQKIQDRLL<br>SSGKFMYLEDNADS<br>ATS |  |
| SEQ ID NO: 26 | Murine DR5 | MEPPGPSTPTASAAA<br>RADHYTPGLRPLPKR<br>RLLYSFALLLAVLQAV<br>FVPVTANPAHNRPAG<br>LQRPEESPSRGPCLA<br>GQYLSEGNCKPCRE<br>GIDYTSHSNHSLDS<br>CILCTVCKEDKVVET<br>RCNITTNTVCRCKPG<br>TFEDKDSPEICQSCS<br>NCTDGEEELTSCTPR<br>ENRKCVSKTAWAS<br>WHKLGLWIGLLVPV<br>VLLIGALLVWKTGA<br>WRQWLLCIKRGCER<br>DPESANSVHSSLLD<br>RQTSSTTNDSNHNT<br>EPGKTQKTGKKLLVP<br>VNGNDSADDLKFIFE<br>YCSDIVPFDSWNRL<br>MRQLGLTDNQIQMV<br>KAETLVTREALYQML<br>LKWRHQTGRSASIN<br>HLLDALEAVEERDAM<br>EKIEDYAVKSGRFTY<br>QNAAAQPETGPGGS<br>QCV |  |
| SEQ ID NO: 27 | DR5ECD-FcHistag | MEQRGQNAPAASGAR<br>KRHGPGPREARGARPG<br>LRVPKTLVLVVAAVLLLV<br>SAESALITQQDLAPQQR<br>VAPQQKRSSPSEGLCPP<br>GHHISEDGRDCISCKYG<br>QDYSTHWNDLLFCLRC<br>TRCDSGEVELSPCTTTR<br>NTVCQCEEGTFREEDSP<br>EMCRKCRTGCPRGMV<br>KVGDCTPWSDIECVHK<br>ESGTKHSGEAPAVEETV<br>TSSPGTPASPCSPKSCD<br>KTHTCPPCPAPEAEGAP<br>SVFLFPPKPKDTLMISRT<br>PEVTCVVVDVSHEDPE<br>VKFNWYVDGVEVHNA<br>KTKPREEQYNSTYRVVS<br>VLTVLHQDWLNGKEYK<br>CKVSNKALPAPIEKTISK<br>AKGQPREPQVYTLPPSR<br>EEMTKNQVSLTCLVKGF<br>YPSDIAVEWESNGQPE<br>NNYKTAPPVLDSDGSFF<br>LYSKLTVDKSRWQQGN<br>VFSCSVMHEALHNHYT<br>QKSLSLSPGKHHHHHH<br>HHEPEA |  |
| SEQ ID NO: 28 | DR5ECDdelHis | MEQRGQNAPAASGA<br>RKRHGPGPREARGA<br>RPGPRVPKTLVLVVA<br>AVLLLVSAESALITQ<br>QDLAPQQRAAPQQK<br>RSSPSEGLCPPGHHI<br>SEDGRDCISCKYGQ<br>DYSTHWNDLLFCLR<br>CTRCDSGEVELSPCT<br>TTRNTVCQCEEGTFR |  |

SEQUENCE TABLE 1-continued

| SEQ ID NO: | Name | Sequence | Clone |
|---|---|---|---|
| | | EEDSPEMCRKCRTG CPRGMVKVGDCTPW SDIECVHKESGHHH HHHHH | |
| SEQ ID NO: 29 | Fc IgG1m(f) | STKGPSVFPLAPSSKSTS GGTAALGCLVKDYFPEP VTVSWNSGALTSGVHT FPAVLQSSGLYSLSSVVT VPSSSLGTQTYICNVNH KPSNTKVDKRVEPKSCD KTHTCPPCPAPELLGGP SVFLFPPKPKDTLMISRT PEVTCVVVDVSHEDPE VKFNWYVDGVEVHNA KTKPREEQYNSTYRVVS VLTVLHQDWLNGKEYK CKVSNKALPAPIEKTISK AKGQPREPQVYTLPPSR EEMTKNQVSLTCLVKGF YPSDIAVEWESNGQPE NNYKTTPPVLDSDGSFF LYSKLTVDKSRWQQGN VFSCSVMHEALHNHYT QKSLSLSPGK | |
| SEQ ID NO: 30 | Fc IgG1m(z) | STKGPSVFPLAPSSK STSGGTAALGCLVK DYFPEPVTVSWNSG ALTSGVHTFPAVLQS SGLYSLSSVVTVPSS SLGTQTYICNVNHKP SNTKVDKKVEPKSC DKTHTCPPCPAPELL GGPSVFLFPPKPKDT LMISRTPEVTCVVVD VSHEDPEVKFNWYV DGVEVHNAKTKPRE EQYNSTYRVVSVLTV LHQDWLNGKEYKCK VSNKALPAPIEKTISK AKGQPREPQVYTLPP SREEMTKNQVSLTCL VKGFYPSDIAVEWES NGQPENNYKTTPPVL DSDGSFFLYSKLTVD KSRWQQGNVFSCS VMHEALHNHYTQKS LSLSPGK | |
| SEQ ID NO: 31 | Fc IgG1m(a) | STKGPSVFPLAPSSK STSGGTAALGCLVK DYFPEPVTVSWNSG ALTSGVHTFPAVLQS SGLYSLSSVVTVPSS SLGTQTYICNVNHKP SNTKVDKPVEPKSC DKTHTCPPCPAPELL GGPSVFLFPPKPKDT LMISRTPEVTCVVVD VSHEDPEVKFNWYV DGVEVHNAKTKPRE EQYNSTYRVVSVLTV LHQDWLNGKEYKCK VSNKALPAPIEKTISK AKGQPREPQVYTLPP SRDELTKNQVSLTCL VKGFYPSDIAVEWES NGQPENNYKTTPPVL DSDGSFFLYSKLTVD KSRWQQGNVFSCS VMHEALHNHYTQKS LSLSPGK | |
| SEQ ID NO: 32 | Fc IgG1m(x) | STKGPSVFPLAPSSK STSGGTAALGCLVK DYFPEPVTVSWNSG ALTSGVHTFPAVLQS | |

SEQUENCE TABLE 1-continued

| SEQ ID NO: | Name | Sequence | Clone |
|---|---|---|---|
|  |  | SGLYSLSSVVTVPSS SLGTQTYICNVNHKP SNTKVDKPVEPKSC DKTHTCPPCPAPELL GGPSVFLFPPKPKDT LMISRTPEVTCVVVD VSHEDPEVKFNWYV DGVEVHNAKTKPRE EQYNSTYRVVSVLTV LHQDWLNGKEYKCK VSNKALPAPIEKTISK AKGQPREPQVYTLPP SREEMTKNQVSLTCL VKGFYPSDIAVEWES NGQPENNYKTTPPVL DSDGSFFLYSKLTVD KSRWQQGNVFSCS VMHEGLHNHYTQKS LSLSPGK |  |
| SEQ ID NO: 33 | HC-hDR5-01 | EVQLQQSGAEVVKPGA SVKLSCKAS<u>GFNIKDTFI</u> HWVKQAPGQGLEWIG <u>RIDPANGNT</u>KYDPKFQ GKATITTDTSSNTAYME LSSLRSEDTAVYYC<u>VRGL YTYYFDY</u>WGQGTLVTV SSASTKGPSVFPLAPSSK STSGGTAALGCLVKDYF PEPVTVSWNSGALTSG VHTFPAVLQSSGLYSLSS VVTVPSSSLGTQTYICN VNHKPSNTKVDKRVEP KSCDKTHTCPPCPAPEL LGGPSVFLFPPKPKDTL MISRTPEVTCVVVDVSH EDPEVKFNWYVDGVEV HNAKTKPREEQYNSTYR VVSVLTVLHQDWLNGK EYKCKVSNKALPAPIEKT ISKAKGQPREPQVYTLP PSREEMTKNQVSLTCLV KGFYPSDIAVEWESNG QPENNYKTTPPVLDSD GSFFLYSKLTVDKSRWQ QGNVFSCSVMHEALHN HYTQKSLSLSPGK |  |
| SEQ ID NO: 34 | HC-hDR5-01-E345K | EVQLQQSGAEVVKPGA SVKLSCKAS<u>GFNIKDTFI</u> HWVKQAPGQGLEWIG <u>RIDPANGNT</u>KYDPKFQ GKATITTDTSSNTAYME LSSLRSEDTAVYYC<u>VRGL YTYYFDY</u>WGQGTLVTV SSASTKGPSVFPLAPSSK STSGGTAALGCLVKDYF PEPVTVSWNSGALTSG VHTFPAVLQSSGLYSLSS VVTVPSSSLGTQTYICN VNHKPSNTKVDKRVEP KSCDKTHTCPPCPAPEL LGGPSVFLFPPKPKDTL MISRTPEVTCVVVDVSH EDPEVKFNWYVDGVEV HNAKTKPREEQYNSTYR VVSVLTVLHQDWLNGK EYKCKVSNKALPAPIEKT ISKAKGQPRKPQVYTLP PSREEMTKNQVSLTCLV KGFYPSDIAVEWESNG QPENNYKTTPPVLDSD GSFFLYSKLTVDKSRWQ QGNVFSCSVMHEALHN HYTQKSLSLSPGK |  |
| SEQ ID NO: 35 | HC-hDR5-01-E430G | EVQLQQSGAEVVKPGA SVKLSCKAS<u>GFNIKDTFI</u> |  |

SEQUENCE TABLE 1-continued

| SEQ ID NO: | Name | Sequence | Clone |
|---|---|---|---|
| | | HWVKQAPGQGLEWIG RIDPANGNTKYDPKFQ GKATITTDTSSNTAYME LSSLRSEDTAVYYCVRGL YTYYFDYWGQGTLVTV SSASTKGPSVFPLAPSSK STSGGTAALGCLVKDYF PEPVTVSWNSGALTSG VHTFPAVLQSSGLYSLSS VVTVPSSSLGTQTYICN VNHKPSNTKVDKRVEP KSCDKTHTCPPCPAPEL LGGPSVFLFPPKPKDTL MISRTPEVTCVVVDVSH EDPEVKFNWYVDGVEV HNAKTKPREEQYNSTYR VVSVLTVLHQDWLNGK EYKCKVSNKALPAPIEKT ISKAKGQPREPQVYTLP PSREEMTKNQVSLTCLV KGFYPSDIAVEWESNG QPENNYKTTPPVLDSD GSFFLYSKLTVDKSRWQ QGNVFSCSVMHGALH NHYTQKSLSLSPGK | |
| SEQ ID NO: 36 | HC-hDR5-01-G56T | EVQLQQSGAEVVKPGA SVKLSCKASGFNIKDTFI HWVKQAPGQGLEWIG RIDPANTNTKYDPKFQG KATITTDTSSNTAYMEL SSLRSEDTAVYYCVRGL YTYYFDYWGQGTLVTV SSASTKGPSVFPLAPSSK STSGGTAALGCLVKDYF PEPVTVSWNSGALTSG VHTFPAVLQSSGLYSLSS VVTVPSSSLGTQTYICN VNHKPSNTKVDKRVEP KSCDKTHTCPPCPAPEL LGGPSVFLFPPKPKDTL MISRTPEVTCVVVDVSH EDPEVKFNWYVDGVEV HNAKTKPREEQYNSTYR VVSVLTVLHQDWLNGK EYKCKVSNKALPAPIEKT ISKAKGQPREPQVYTLP PSREEMTKNQVSLTCLV KGFYPSDIAVEWESNG QPENNYKTTPPVLDSD GSFFLYSKLTVDKSRWQ QGNVFSCSVMHEALHN HYTQKSLSLSPGK | |
| SEQ ID NO: 37 | HC-hDR5-01-G56T-E345K | EVQLQQSGAEVVKPGA SVKLSCKASGFNIKDTFI HWVKQAPGQGLEWIG RIDPANTNTKYDPKFQG KATITTDTSSNTAYMEL SSLRSEDTAVYYCVRGL YTYYFDYWGQGTLVTV SSASTKGPSVFPLAPSSK STSGGTAALGCLVKDYF PEPVTVSWNSGALTSG VHTFPAVLQSSGLYSLSS VVTVPSSSLGTQTYICN VNHKPSNTKVDKRVEP KSCDKTHTCPPCPAPEL LGGPSVFLFPPKPKDTL MISRTPEVTCVVVDVSH EDPEVKFNWYVDGVEV HNAKTKPREEQYNSTYR VVSVLTVLHQDWLNGK EYKCKVSNKALPAPIEKT ISKAKGQPRKPQVYTLP PSREEMTKNQVSLTCLV KGFYPSDIAVEWESNG QPENNYKTTPPVLDSD | |

SEQUENCE TABLE 1-continued

| SEQ ID NO: | Name | Sequence | Clone |
|---|---|---|---|
| | | GSFFLYSKLTVDKSRWQ<br>QGNVFSCSVMHEALHN<br>HYTQKSLSLSPGK | |
| SEQ ID NO: 38 | HC-hDR5-01-G56T-E430G | EVQLQQSGAEVVKPGA<br>SVKLSCKAS<u>GFNIKDTFI</u><br>HWVKQAPGQGLEWIG<br><u>R</u>IDPAN<u>T</u>NTKYDPKFQG<br>KATITTDTSSNTAYMEL<br>SSLRSEDTAVYYC<u>VRGL</u><br><u>YTYYFDY</u>WGQGTLVTV<br>SSASTKGPSVFPLAPSSK<br>STSGGTAALGCLVKDYF<br>PEPVTVSWNSGALTSG<br>VHTFPAVLQSSGLYSLSS<br>VVTVPSSSLGTQTYICN<br>VNHKPSNTKVDKRVEP<br>KSCDKTHTCPPCPAPEL<br>LGGPSVFLFPPKPKDTL<br>MISRTPEVTCVVVDVSH<br>EDPEVKFNWYVDGVEV<br>HNAKTKPREEQYNSTYR<br>VVSVLTVLHQDWLNGK<br>EYKCKVSNKALPAPIEKT<br>ISKAKGQPREPQVYTLP<br>PSREEMTKNQVSLTCLV<br>KGFYPSDIAVEWESNG<br>QPENNYKTTPPVLDSD<br>GSFFLYSKLTVDKSRWQ<br>QGNVFSCSVMH<u>G</u>ALH<br>NHYTQKSLSLSPGK | |
| SEQ ID NO: 39 | LC-hDR5-01 | EIVMTQSPATLSVSPGE<br>RATLSCRAS<u>QSISNN</u>LH<br>WYQQKPGQAPRLLIK<u>F</u><br><u>AS</u>QSITGIPARFSGSGSG<br>TEFTLTISSLQSEDFAVY<br>YC<u>QQGNSWPYT</u>FGQG<br>TKLEIKRTVAAPSVFIFPP<br>SDEQLKSGTASVVCLLN<br>NFYPREAKVQWKVDN<br>ALQSGNSQESVTEQDS<br>KDSTYSLSSTLTLSKADY<br>EKHKVYACEVTHQGLSS<br>PVTKSFNRGEC | |
| SEQ ID NO: 40 | HC-hDR5-05 | QVQLVQSGAEVKKPGA<br>SVKVSCKAS<u>GFNIKDTH</u><br>MHWVRQAPGQRLEWI<br>G<u>RIDPANGNTE</u>YDQKF<br>QGRVTITVDTSASTAYM<br>ELSSLRSEDTAVYYC<u>AR</u><br><u>WGTNVYFAY</u>WGQGTL<br>VTVSSASTKGPSVFPLA<br>PSSKSTSGGTAALGCLV<br>KDYFPEPVTVSWNSGA<br>LTSGVHTFPAVLQSSGL<br>YSLSSVVTVPSSSLGTQT<br>YICNVNHKPSNTKVDKR<br>VEPKSCDKTHTCPPCPA<br>PELLGGPSVFLFPPKPKD<br>TLMISRTPEVTCVVVDV<br>SHEDPEVKFNWYVDGV<br>EVHNAKTKPREEQYNST<br>YRVVSVLTVLHQDWLN<br>GKEYKCKVSNKALPAPI<br>EKTISKAKGQPREPQVY<br>TLPPSREEMTKNQVSLT<br>CLVKGFYPSDIAVEWES<br>NGQPENNYKTTPPVLD<br>SDGSFFLYSKLTVDKSR<br>WQQGNVFSCSVMHEA<br>LHNHYTQKSLSLSPGK | |
| SEQ ID NO: 41 | HC-hDR5-05-E345K | QVQLVQSGAEVKKPGA<br>SVKVSCKAS<u>GFNIKDTH</u><br>MHWVRQAPGQRLEWI<br>G<u>RIDPANGNTE</u>YDQKF | |

SEQUENCE TABLE 1-continued

| SEQ ID NO: | Name | Sequence | Clone |
|---|---|---|---|
| | | QGRVTITVDTSASTAYM ELSSLRSEDTAVYYCAR WGTNVYFAYWGQGTL VTVSSASTKGPSVFPLA PSSKSTSGGTAALGCLV KDYFPEPVTVSWNSGA LTSGVHTFPAVLQSSGL YSLSSVVTVPSSSLGTQT YICNVNHKPSNTKVDKR VEPKSCDKTHTCPPCPA PELLGGPSVFLFPPKPKD TLMISRTPEVTCVVVDV SHEDPEVKFNWYVDGV EVHNAKTKPREEQYNST YRVVSVLTVLHQDWLN GKEYKCKVSNKALPAPI EKTISKAKGQPRKPQVY TLPPSREEMTKNQVSLT CLVKGFYPSDIAVEWES NGQPENNYKTTPPVLD SDGSFFLYSKLTVDKSR WQQGNVFSCSVMHEA LHNHYTQKSLSLSPGK | |
| SEQ ID NO: 42 | HC-hDR5-05-E430G | QVQLVQSGAEVKKPGA SVKVSCKASGFNIKDTH MHWVRQAPGQRLEWI GRIDPANGNTEYDQKF QGRVTITVDTSASTAYM ELSSLRSEDTAVYYCAR WGTNVYFAYWGQGTL VTVSSASTKGPSVFPLA PSSKSTSGGTAALGCLV KDYFPEPVTVSWNSGA LTSGVHTFPAVLQSSGL YSLSSVVTVPSSSLGTQT YICNVNHKPSNTKVDKR VEPKSCDKTHTCPPCPA PELLGGPSVFLFPPKPKD TLMISRTPEVTCVVVDV SHEDPEVKFNWYVDGV EVHNAKTKPREEQYNST YRVVSVLTVLHQDWLN GKEYKCKVSNKALPAPI EKTISKAKGQPREPQVY TLPPSREEMTKNQVSLT CLVKGFYPSDIAVEWES NGQPENNYKTTPPVLD SDGSFFLYSKLTVDKSR WQQGNVFSCSVMHG ALHNHYTQKSLSLSPGK | |
| SEQ ID NO: 43 | LC-hDR5-05 | DIQLTQSPSSLSASVGD RVTITCSASSSVSYMYW YQQKPGKAPKPWIYRT SNLASGVPSRFGSGSG TDFTLTISSLQPEDFATY YCQQYHSYPPTFGGGT KVEIKRTVAAPSVFIFPP SDEQLKSGTASVVCLLN NFYPREAKVQWKVDN ALQSGNSQESVTEQDS KDSTYSLSSTLTLSKADY EKHKVYACEVTHQGLSS PVTKSFNRGEC | |
| SEQ ID NO: 44 | Human DR5, K415N | MEQRGQNAPAASGAR KRHGPGPREARGARPG PRVPKTLVLVVAAVLLL VSAESALITQQDLAPQQ RAAPQQKRSSPSEGLCP PGHHISEDGRDCISCKY GQDYSTHWNDLLFCLR CTRCDSGEVELSPCTTT RNTVCQCEEGTFREEDS PEMCRKCRTGCPRGM VKVGDCTPWSDIECVH KESGTKHSGEVPAVEET | Human DR5, with K415N mutation |

SEQUENCE TABLE 1-continued

| SEQ ID NO: | Name | Sequence | Clone |
|---|---|---|---|
| | | VTSSPGTPASPCSLSGIII GVTVAAVVLIVAVFVCK SLLWKKVLPYLKGICSG GGGDPERVDRSSQRPG AEDNVLNEIVSILQPTQ VPEQEMEVQEPAEPTG VNMLSPGESEHLLEPAE AERSQRRLLVPANEG DPTETLRQCFDDFADLV PFDSWEPLMRKLGLMD NEIKVAKAEAAGHRDTL YTMLIKWVNKTGRDAS VHTLLDALETLGERLAN QKIEDHLLSSGKFMYLE GNADSAMS | |
| SEQ ID NO: 45 | Human DR5 (natural variant) (Accession: AAB70578) | MEQRGQNAPAASGA RKRHGPGPREARGA RPGLRVPKTLVLVVA AVLLLVSAESALITQ QDLAPQQRVAPQQK RSSPSEGLCPPGHHI SEDGRDCISCKYGQ DYSTHWNDLLFCLR CTRCDSGEVELSPCT TTRNTVCQCEEGTFR EEDSPEMCRKCRTG CPRGMVKVGDCTPW SDIECVHKESGTKH SGEAPAVEETVTSSP GTPASPCSLSGIIIGV TVAAVVLIVAVFVCK SLLWKKVLPYLKGIC SGGGGDPERVDRSS QRPGAEDNVLNEIVS ILQPTQVPEQEMEVQ EPAEPTGVNMLSPGE SEHLLEPAEAERSQR RRLLVPANEGDPTET LRQCFDDFADLVPFD SWEPLMRKLGLMDN EIKVAKAEAAGHRDT LYTMLIKWVNKTGR DASVHTLLDALETLG ERLAKQKIEDHLLSS GKFMYLEGNADSAM S | |
| SEQ ID NO: 46 | Human DR5 (Uniprot O14763) | MEQRGQNAPAASGA RKRHGPGPREARGA RPGPRVPKTLVLVVA AVLLLVSAESALITQ QDLAPQQRAAPQQK RSSPSEGLCPPGHHI SEDGRDCISCKYGQ DYSTHWNDLLFCLR CTRCDSGEVELSPCT TTRNTVCQCEEGTFR EEDSPEMCRKCRTG CPRGMVKVGDCTPW SDIECVHKESGTKH SGEVPAVEETVTSSP GTPASPCSLSGIIIGV TVAAVVLIVAVFVCK SLLWKKVLPYLKGIC SGGGGDPERVDRSS QRPGAEDNVLNEIVS ILQPTQVPEQEMEVQ EPAEPTGVNMLSPGE SEHLLEPAEAERSQR RRLLVPANEGDPTET LRQCFDDFADLVPFD SWEPLMRKLGLMDN EIKVAKAEAAGHRDT LYTMLIKWVNKTGR DASVHTLLDALETLG | |

SEQUENCE TABLE 1-continued

| SEQ ID NO: | Name | Sequence | Clone |
|---|---|---|---|
| | | ERLAKQKIEDHLLSS GKFMYLEGNADSAM S | |
| SEQ ID NO: 47 | Human DR5del-K386N | MEQRGQNAPAASGA RKRHGPGPREARGA RPGPRVPKTLVLVVA AVLLLVSAESALITQ QDLAPQQRAAPQQK RSSPSEGLCPPGHHI SEDGRDCISCKYGQ DYSTHWNDLLFCLR CTRCDSGEVELSPCT TTRNTVCQCEEGTFR EEDSPEMCRKCRTG CPRGMVKVGDCTPW SDIECVHKESGIIIGV TVAAVVLIVAVFVCK SLLWKKVLPYLKGIC SGGGGDPERVDRSS QRPGAEDNVLNEIVS ILQPTQVPEQEMEVQ EPAEPTGVNMLSPGE SEHLLEPAEAERSQR RRLLVPANEGDPTET LRQCFDDFADLVPFD SWEPLMRKLGLMDN EIKVAKAEAAGHRDT LYTMLIKWVNKTGR DASVHTLLDALETLG ERLANQKIEDHLLSS GKFMYLEGNADSAM S | |
| SEQ ID NO: 48 | Cynomolgus DR5 (NCBI XP_005562887.1) | MGQLRQSAPAASGA RKGRGPGPREARGA RPGLRVLKTLVLVVA AARVLLSVSADCAPI TRQSLDPQRRAAPQ QKRSSPTEGLCPPG HHISEDSRECISCKY GQDYSTHWNDFLFC LRCTKCDSGEVEVN SCTTTRNTVCQCEE GTFREEDSPEICRKC RTGCPRGMVKVKDC TPWSDIECVHKESG TKHTGEVPAVEKTVT TSPGTPASPCSLSGII IGVIVLVVIVVVAVIV WKTSLWKKVLPYLK GVCSGGGGDPERVD SSSHSPQRPGAEDN ALNEIVSIVQPSQVP EQEMEVQEPAEQTD VNTLSPGESEHLLEP AKAEGPQRRGQLVP VNENDPTETLRQCFD DFAAIVPFDAWEPLV RQLGLTNNEIKVAKA EAASSRDTLYVMLIK WVNKTGRAASVNTL LDALETLEERLAKQK IQDRLLSSGKFMYLE DNADSATS | |
| SEQ ID NO: 49 | Cynomolgus DR5-K420N | MGQLRQSAPAASGA RKGRGPGPREARGA RPGLRVLKTLVLVVA AARVLLSVSADCAPI TRQSLDPQRRAAPQ QKRSSPTEGLCPPG HHISEDSRECISCKY GQDYSTHWNDFLFC LRCTKCDSGEVEVN SCTTTRNTVCQCEE GTFREEDSPEICRKC RTGCPRGMVKVKDC | |

SEQUENCE TABLE 1-continued

| SEQ ID NO: | Name | Sequence | Clone |
|---|---|---|---|
| | | TPWSDIECVHKESG<br>TKHTGEVPAVEKTVT<br>TSPGTPASPCSLSGII<br>IGVIVLVVIVVVAVIV<br>WKTSLWKKVLPYLK<br>GVCSGGGGDPERVD<br>SSSHSPQRPGAEDN<br>ALNEIVSIVQPSQVP<br>EQEMEVQEPAEQTD<br>VNTLSPGESEHLLEP<br>AKAEGPQRRGQLVP<br>VNENDPTETLRQCFD<br>DFAAIVPFDAWEPLV<br>RQLGLTNNEIKVAKA<br>EAASSRDTLYVMLIK<br>WVNKTGRAASVNTL<br>LDALETLEERLANQK<br>IQDRLLSSGKFMYLE<br>DNADSATS | |
| SEQ ID NO: 50 | Cyno DR5Mfdel-K420N | MGQLRQSAPAASGA<br>RKGRGPGPREARGA<br>RPGLRVLKTLVLVVA<br>AARVLLSVSADCAPI<br>TRQSLDPQRRAAPQ<br>QKRSSPTEGLCPPG<br>HHISEDSRECISCKY<br>GQDYSTHWNDFLFC<br>LRCTKCDSGEVEVN<br>SCTTTRNTVCQCEE<br>GTFREEDSPEICRKC<br>RTGCPRGMVKVKDC<br>TPWSDIECVHKESGI<br>IGVIVLVVIVVVAVI<br>VWKTSLWKKVLPYL<br>KGVCSGGGGDPERV<br>DSSSHSPQRPGAED<br>NALNEIVSIVQPSQV<br>PEQEMEVQEPAEQT<br>DVNTLSPGESEHLLE<br>PAKAEGPQRRGQLV<br>PVNENDPTETLRQCF<br>DDFAAIVPFDAWEPL<br>VRQLGLTNNEIKVAK<br>AEAASSRDTLYVMLI<br>KWVNKTGRAASVNT<br>LLDALETLEERLANQ<br>KIQDRLLSSGKFMYL<br>EDNADSATS | |
| SEQ ID NO: 51 | VH chTRA8 CDR1 | GFTFSSYV | |
| SEQ ID NO: 52 | VH chTRA8 CDR2 | ISSGGSYT | |
| SEQ ID NO: 53 | VH chTRA8 CDR3 | ARRGDSMITTDY | |
| SEQ ID NO: 54 | VL chTRA8 CDR1 | QDVGTA | |
| | VL chTRA8 CDR2 | WAS | |
| SEQ ID NO: 55 | VL chTRA8 CDR3 | QQYSSYRT | |
| SEQ ID NO: 56 | HC-chTRA8 | EVMLVESGGGLVKP<br>GGSLKLSCAASGFT<br>FSSYVMSWVRQTPE<br>KRLEWVATISSGGS<br>YTYYPDSVKGRFTIS<br>RDNAKNTLYLQMSS<br>LRSEDTAMYYCARR<br>GDSMITTDYWGQG<br>TTLTVSSASTKGPSV<br>FPLAPSSKSTSGGTA<br>ALGCLVKDYFPEPVT<br>VSWNSGALTSGVHT<br>FPAVLQSSGLYSLSS<br>VVTVPSSSLGTQTYI<br>CNVNHKPSNTKVDK<br>RVEPKSCDKTHTCPP | |

SEQUENCE TABLE 1-continued

| SEQ ID NO: | Name | Sequence | Clone |
|---|---|---|---|
| | | CPAPELLGGPSVFLF PPKPKDTLMISRTPE VTCVVVDVSHEDPE VKFNWYVDGVEVHN AKTKPREEQYNSTYR VVSVLTVLHQDWLN GKEYKCKVSNKALPA PIEKTISKAKGQPRE PQVYTLPPSREEMTK NQVSLTCLVKGFYPS DIAVEWESNGQPEN NYKTTPPVLDSDGSF FLYSKLTVDKSRWQ QGNVFSCSVMHEAL HNHYTQKSLSLSPG K | |
| SEQ ID NO: 57 | LC-chTRA8 | DIVMTQSHKFMSTS VGDRVSITCKASQD VGTAVAWYQQKPG QSPKLLIYWASTRH TGVPDRFTGSGSGT DFTLTISNVQSEDLA DYFCQQYSSYRTFG GGTKLEIKRTVAAPS VFIFPPSDEQLKSGT ASVVCLLNNFYPREA KVQWKVDNALQSG NSQESVTEQDSKDS TYSLSSTLTLSKADY EKHKVYACEVTHQG LSSPVTKSFNRGEC | |
| SEQ ID NO: 58 | Fc IgG1m(f)-E430G | STKGPSVFPLAPSSK STSGGTAALGCLVK DYFPEPVTVSWNSG ALTSGVHTFPAVLQS SGLYSLSSVVTVPSS SLGTQTYICNVNHKP SNTKVDKRVEPKSC DKTHTCPPCPAPELL GGPSVFLFPPKPKDT LMISRTPEVTCVVVD VSHEDPEVKFNWYV DGVEVHNAKTKPRE EQYNSTYRVVSVLTV LHQDWLNGKEYKCK VSNKALPAPIEKTISK AKGQPREPQVYTLPP SREEMTKNQVSLTCL VKGFYPSDIAVEWES NGQPENNYKTTPPVL DSDGSFFLYSKLTVD KSRWQQGNVFSCS VMHGALHNHYTQKS LSLSPGK | |
| SEQ ID NO: 59 | Fc IgG1m(f)-E345K | STKGPSVFPLAPSSK STSGGTAALGCLVK DYFPEPVTVSWNSG ALTSGVHTFPAVLQS SGLYSLSSVVTVPSS SLGTQTYICNVNHKP SNTKVDKRVEPKSC DKTHTCPPCPAPELL GGPSVFLFPPKPKDT LMISRTPEVTCVVVD VSHEDPEVKFNWYV DGVEVHNAKTKPRE EQYNSTYRVVSVLTV LHQDWLNGKEYKCK VSNKALPAPIEKTISK AKGQPRKPQVYTLPP SREEMTKNQVSLTCL VKGFYPSDIAVEWES NGQPENNYKTTPPVL DSDGSFFLYSKLTVD KSRWQQGNVFSCS | |

SEQUENCE TABLE 1-continued

| SEQ ID NO: | Name | Sequence | Clone |
|---|---|---|---|
| | | VMHEALHNHYTQKS LSLSPGK | |
| SEQ ID NO: 60 | Fc IgG1m(f)-S440Y | STKGPSVFPLAPSSK STSGGTAALGCLVK DYFPEPVTVSWNSG ALTSGVHTFPAVLQS SGLYSLSSVVTVPSS SLGTQTYICNVNHKP SNTKVDKRVEPKSC DKTHTCPPCPAPELL GGPSVFLFPPKPKDT LMISRTPEVTCVVVD VSHEDPEVKFNWYV DGVEVHNAKTKPRE EQYNSTYRVVSVLTV LHQDWLNGKEYKCK VSNKALPAPIEKTISK AKGQPREPQVYTLPP SREEMTKNQVSLTCL VKGFYPSDIAVEWES NGQPENNYKTTPPVL DSDGSFFLYSKLTVD KSRWQQGNVFSCS VMHEALHNHYTQKY LSLSPGK | |
| SEQ ID NO: 61 | Fc IgG1m(f)-E430G-K439E | STKGPSVFPLAPSSK STSGGTAALGCLVK DYFPEPVTVSWNSG ALTSGVHTFPAVLQS SGLYSLSSVVTVPSS SLGTQTYICNVNHKP SNTKVDKRVEPKSC DKTHTCPPCPAPELL GGPSVFLFPPKPKDT LMISRTPEVTCVVVD VSHEDPEVKFNWYV DGVEVHNAKTKPRE EQYNSTYRVVSVLTV LHQDWLNGKEYKCK VSNKALPAPIEKTISK AKGQPREPQVYTLPP SREEMTKNQVSLTCL VKGFYPSDIAVEWES NGQPENNYKTTPPVL DSDGSFFLYSKLTVD KSRWQQGNVFSCS VMHGALHNHYTQES LSLSPGK | |
| SEQ ID NO: 62 | Fc IgG1m(f)-E430G-S440K | STKGPSVFPLAPSSK STSGGTAALGCLVK DYFPEPVTVSWNSG ALTSGVHTFPAVLQS SGLYSLSSVVTVPSS SLGTQTYICNVNHKP SNTKVDKRVEPKSC DKTHTCPPCPAPELL GGPSVFLFPPKPKDT LMISRTPEVTCVVVD VSHEDPEVKFNWYV DGVEVHNAKTKPRE EQYNSTYRVVSVLTV LHQDWLNGKEYKCK VSNKALPAPIEKTISK AKGQPREPQVYTLPP SREEMTKNQVSLTCL VKGFYPSDIAVEWES NGQPENNYKTTPPVL DSDGSFFLYSKLTVD KSRWQQGNVFSCS VMHGALHNHYTQKK LSLSPGK | |
| SEQ ID NO: 63 | Fc IgG1m(f)-K409R | STKGPSVFPLAPSSK STSGGTAALGCLVK DYFPEPVTVSWNSG | |

SEQUENCE TABLE 1-continued

| SEQ ID NO: | Name | Sequence | Clone |
|---|---|---|---|
| | | ALTSGVHTFPAVLQS<br>SGLYSLSSVVTVPSS<br>SLGTQTYICNVNHKP<br>SNTKVDKRVEPKSC<br>DKTHTCPPCPAPELL<br>GGPSVFLFPPKPKDT<br>LMISRTPEVTCVVVD<br>VSHEDPEVKFNWYV<br>DGVEVHNAKTKPRE<br>EQYNSTYRVVSVLTV<br>LHQDWLNGKEYKCK<br>VSNKALPAPIEKTISK<br>AKGQPREPQVYTLPP<br>SREEMTKNQVSLTCL<br>VKGFYPSDIAVEWES<br>NGQPENNYKTTPPVL<br>DSDGSFFLYSRLTVD<br>KSRWQQGNVFSCS<br>VMHEALHNHYTQKS<br>LSLSPGK | |
| SEQ ID NO: 64 | Fc IgG1m(f)-K409R-E345K | STKGPSVFPLAPSSK<br>STSGGTAALGCLVK<br>DYFPEPVTVSWNSG<br>ALTSGVHTFPAVLQS<br>SGLYSLSSVVTVPSS<br>SLGTQTYICNVNHKP<br>SNTKVDKRVEPKSC<br>DKTHTCPPCPAPELL<br>GGPSVFLFPPKPKDT<br>LMISRTPEVTCVVVD<br>VSHEDPEVKFNWYV<br>DGVEVHNAKTKPRE<br>EQYNSTYRVVSVLTV<br>LHQDWLNGKEYKCK<br>VSNKALPAPIEKTISK<br>AKGQPRKPQVYTLPP<br>SREEMTKNQVSLTCL<br>VKGFYPSDIAVEWES<br>NGQPENNYKTTPPVL<br>DSDGSFFLYSRLTVD<br>KSRWQQGNVFSCS<br>VMHEALHNHYTQKS<br>LSLSPGK | |
| SEQ ID NO: 65 | Fc IgG1m(f)-K409R-E430G | STKGPSVFPLAPSSK<br>STSGGTAALGCLVK<br>DYFPEPVTVSWNSG<br>ALTSGVHTFPAVLQS<br>SGLYSLSSVVTVPSS<br>SLGTQTYICNVNHKP<br>SNTKVDKRVEPKSC<br>DKTHTCPPCPAPELL<br>GGPSVFLFPPKPKDT<br>LMISRTPEVTCVVVD<br>VSHEDPEVKFNWYV<br>DGVEVHNAKTKPRE<br>EQYNSTYRVVSVLTV<br>LHQDWLNGKEYKCK<br>VSNKALPAPIEKTISK<br>AKGQPREPQVYTLPP<br>SREEMTKNQVSLTCL<br>VKGFYPSDIAVEWES<br>NGQPENNYKTTPPVL<br>DSDGSFFLYSRLTVD<br>KSRWQQGNVFSCS<br>VMHGALHNHYTQKS<br>LSLSPGK | |
| SEQ ID NO: 66 | Fc IgG1m(f)-F405L | STKGPSVFPLAPSSK<br>STSGGTAALGCLVK<br>DYFPEPVTVSWNSG<br>ALTSGVHTFPAVLQS<br>SGLYSLSSVVTVPSS<br>SLGTQTYICNVNHKP<br>SNTKVDKRVEPKSC<br>DKTHTCPPCPAPELL<br>GGPSVFLFPPKPKDT | |

SEQUENCE TABLE 1-continued

| SEQ ID NO: | Name | Sequence | Clone |
|---|---|---|---|
| | | LMISRTPEVTCVVVD VSHEDPEVKFNWYV DGVEVHNAKTKPRE EQYNSTYRVVSVLTV LHQDWLNGKEYKCK VSNKALPAPIEKTISK AKGQPREPQVYTLPP SREEMTKNQVSLTCL VKGFYPSDIAVEWES NGQPENNYKTTPPVL DSDGSFLLYSKLTVD KSRWQQGNVFSCS VMHEALHNHYTQKS LSLSPGK | |
| SEQ ID NO: 67 | Fc IgG1m(f)-F405L-E345K | STKGPSVFPLAPSSK STSGGTAALGCLVK DYFPEPVTVSWNSG ALTSGVHTFPAVLQS SGLYSLSSVVTVPSS SLGTQTYICNVNHKP SNTKVDKRVEPKSC DKTHTCPPCPAPELL GGPSVFLFPPKPKDT LMISRTPEVTCVVVD VSHEDPEVKFNWYV DGVEVHNAKTKPRE EQYNSTYRVVSVLTV LHQDWLNGKEYKCK VSNKALPAPIEKTISK AKGQPRKPQVYTLPP SREEMTKNQVSLTCL VKGFYPSDIAVEWES NGQPENNYKTTPPVL DSDGSFLLYSKLTVD KSRWQQGNVFSCS VMHEALHNHYTQKS LSLSPGK | |
| SEQ ID NO: 68 | Fc IgG1m(f)-F405L-E430G | STKGPSVFPLAPSSK STSGGTAALGCLVK DYFPEPVTVSWNSG ALTSGVHTFPAVLQS SGLYSLSSVVTVPSS SLGTQTYICNVNHKP SNTKVDKRVEPKSC DKTHTCPPCPAPELL GGPSVFLFPPKPKDT LMISRTPEVTCVVVD VSHEDPEVKFNWYV DGVEVHNAKTKPRE EQYNSTYRVVSVLTV LHQDWLNGKEYKCK VSNKALPAPIEKTISK AKGQPREPQVYTLPP SREEMTKNQVSLTCL VKGFYPSDIAVEWES NGQPENNYKTTPPVL DSDGSFLLYSKLTVD KSRWQQGNVFSCS VMHGALHNHYTQKS LSLSPGK | |

EXAMPLES

Example 1: Antibody and Antigen Constructs

Expression Constructs for DR5

Codon-optimized constructs for expression of full-length DR5 proteins of human (SEQ ID NO 46), rhesus monkey (SEQ ID NO 25) and mouse (SEQ ID NO 26) were generated based on available sequences: human (*Homo sapiens*) DR5 (Genbank accession no. NP_003833, UniprotKB/Swiss-Prot 014763-1), Rhesus monkey (*Macaca mulatta*) DR5 (Genbank accession no. EHH28346), murine (*Mus musculus*) DR5 (UniprotKB/Swiss-Prot Q9QZM4). For mapping of the binding regions of the DR5 antibodies (as described in Example 6) the following chimeric human/mouse DR5 constructs were made; human DR5 in which, respectively, the following parts were replaced by the corresponding mouse DR5 sequence (numbers refer to human sequence), construct A aa 56-68, construct B aa 56-78, construct C aa 69-78, construct D aa 79-115, construct E 79-138, construct F aa 97-138, construct G aa 139-166, construct H aa 139-182, construct I aa 167-182, construct J 167-210, construct K aa 183-210. The loss-of-function mutation K415N was introduced in the human DR5 death domain (SEQ ID NO 44). In addition, codon-optimized construct for the extracellular domain (ECD) of human DR5 with a C-terminal His tag were generated: DR5ECD-FcHistag (SEQ ID NO 27) and DR5ECDdelHis (SEQ ID NO 28). All constructs contained suitable restriction sites for cloning and an optimal Kozak (GCCGCCACC) sequence. The constructs were cloned in the mammalian expression vector pcDNA3.3 (Invitrogen).

Expression Constructs for Antibodies

For antibody expression the VH and VL sequences, as earlier described, of the chimeric human/mouse DR5 antibodies DR5-01 and DR5-05 (based on EP2684896A1) and their humanized variants hDR5-01 and hDR5-05 (based on WO2014/009358) were cloned in expression vectors (pcDNA3.3) containing the relevant constant HC and LC regions. Desired mutations were introduced either by gene synthesis or site directed mutagenesis.

In some of the Examples, reference antibodies against DR5 were used that have been previously described. IgG1-CONA (based on U.S. Pat. No. 7,521,048 B2 and WO2010/138725) and IgG1-chTRA8 (based on EP1506285B1 and U.S. Pat. No. 7,244,429B2) were cloned in the relevant antibody expression vectors as supra.

In some of the examples the human IgG1 antibody IgG1-b12, a gp120-specific antibody was used as a negative control (Barbas et al., J Mol Biol. 1993 Apr. 5; 230(3):812-23).

Transient Expression

Antibodies were expressed as IgG1,K. Plasmid DNA mixtures encoding both heavy and light chains of antibodies were transiently transfected in Expi293F cells (Life technologies, USA) using 293fectin (Life technologies) essentially as described by Vink et al. (Vink et al., Methods, 65 (1), 5-10 2014).

Membrane proteins were expressed in Freestyle CHO-S cells (Life technologies), using the freestyle Max reagent, as described by the manufacturer.

Purification and Analysis of Proteins

Antibodies were purified by immobilized protein G chromatography. His-tagged recombinant protein was purified by immobilized metal affinity chromatography. Protein batches were analyzed by a number of bioanalytical assays including SDS-PAGE, size exclusion chromatography and measurement of endotoxin levels.

Generation of Bispecific Antibodies

Bispecific IgG1 antibodies were generated by Fab-arm-exchange under controlled reducing conditions. The basis for this method is the use of complementary CH3 domains, which promote the formation of heterodimers under specific assay conditions as described in WO2011/131746. The F405L and K409R (EU numbering) mutations were introduced in anti-DR5 IgG1 antibodies to create antibody pairs with complementary CH3 domains. The F405L mutation was introduced in IgG1-DR5-05 and IgG1-DR5-05-E430G; the K409R mutation was introduced in IgG1-DR5-01 and IgG1-DR5-01-E430G. To generate bispecific antibodies, the two parental complementary antibodies, each antibody at a final concentration of 0.5 mg/mL, were incubated with 75 mM 2-mercaptoethylamine-HCl (2-MEA) in a total volume of 100 µL TE at 31° C. for 5 hours. The reduction reaction was stopped by removing the reducing agent 2-MEA using spin columns (Microcon centrifugal filters, 30 k, Millipore) according to the manufacturer's protocol. In this way the bispecific antibodies IgG1-DR5-01-K409R×IgG1-DR5-05-F405L (BsAb DR5-01-K409R×DR5-05-F405L) and IgG1-DR5-01-K409R-E430G×IgG1-DR5-05-F405L-E430G (BsAb DR5-01-K409R-E430G×DR5-05-F405L-E430G) were generated.

The K409R mutation and/or the F405L mutation have no effect on the antibody's binding to the corresponding antigen. That is the K409R mutation and/or the F405L mutation have no effect of the anti-DR5 antibody's binding to DR5.

Example 2: DR5 Expression Levels on Different Human Cancer Cell Lines

DR5 density per cell was quantified for different human cancer cell lines by indirect immunofluorescence using QIFIKIT (DAKO, Cat nr K0078) with mouse monoclonal antibody B-K29 (Diaclone, Cat nr 854.860.000). Cells were harvested by trypsinization and passed through a cell strainer. Cells were pelleted by centrifugation for 5 minutes at 1,200 rpm, washed with PBS and resuspended at a concentration of $2\times10^6$ cells/mL. The next steps were performed at 4° C. 50 µL of the single cell suspensions (100,000 cells per well) were seeded in polystyrene 96-well round-bottom plates (Greiner Bio-One, Cat nr 650101). Cells were pelleted by centrifugation for 3 minutes at 300×g and resuspended in 50 µL antibody sample or mouse IgG1 isotype control sample (BD/Pharmingen, Cat nr 555746) at 10 µg/mL saturating concentrations. After an incubation of 30 minutes at 4° C., cells were pelleted and resuspended in 150 µL FACS buffer (PBS+0.1% (w/v) bovine serum albumin (BSA)+0.02% (w/v) sodium azide). Set-up and calibration beads were added to the plate according to the manufacturer's instructions. Cells and beads in parallel were washed two more times with 150 µL FACS buffer and resuspended in 50 µL FITC-conjugated goat-anti-mouse IgG (1/50; DAKO, Cat nr F0479). Secondary antibody was incubated for 30 minutes at 4° C. protected from light. Cells and beads were washed twice with 150 µL FACS buffer and resuspended in 150 µL FACS buffer. Immunofluorescence was measured on a FACS Canto II (BD Biosciences) by recording 10,000 events within the population of viable cells. The Geometric mean of fluorescence intensity of the calibration beads was used to calculate the calibration curve that was forced to go through zero intensity and zero concentration using GraphPad Prism software (GraphPad Software, San Diego, Calif., USA). For each cell line, the antibody binding capacity (ABC), an estimate for the number of DR5 molecules expressed on the plasma membrane, was calculated using the Geometric mean fluorescence intensity of the DR5-antibody-stained cells, based on the equation of the calibration curve (interpolation of unknowns from the standard curve, using GraphPad Software). Generally, DR5 cell surface expression was low to moderate on the cell lines assessed here. Based on these data, cell lines were categorized according to low DR5 expression (ABC<10,000) and moderate DR5 expression (ABC>10, 000). HCT-15 (ATCC, CCL-225), HT-29 (ATCC, HTB-38) and SW480 (ATCC, CCL-228) colon cancer, BxPC-3 (ATCC, CRL-1687), HPAF-II (ATCC, CRL-1997) and PANC-1 (ATCC, CRL-1469) pancreatic cancer, and A549 (ATCC, CCL-185) and SK-MES-1 (ATCC, HTB-58) lung cancer cell lines were found to have low DR5 expression (QIFIKIT ABC range 3,081-8,411). COLO 205 (ATCC CCL-222™) and HCT 116 (ATCC CCL-247) colon cancer, A375 (ATCC, CRL-1619) skin cancer and SNU-5 (ATCC, CRL-5973) gastric cancer cell lines were found to have moderate DR5 expression (QIFIKIT ABC range 10,777-21, 262).

Example 3: Binding of Humanized DR5-01 and DR5-05 Antibodies to HCT 116 Cells The humanized antibodies hDR5-01 and hDR5-05 are described in patent application WO2014/009358. Binding of purified IgG1-hDR5-01-K409R and IgG1-hDR5-05-F405L to DR5-positive HCT 116 human colon cancer cells was analyzed and compared to binding of the chimeric antibodies IgG1-DR5-01-K409R and IgG1-DR5-05-F405L by FACS analysis. To prepare single cell suspensions, adherent HCT 116 cells were washed twice with PBS (B.Braun; Cat nr 3623140) before incubating with Trypsin 1×/EDTA 0.05% for 2 minutes at 37° C. 10 mL medium [McCoy's 5A medium with L-Glutamine and HEPES (Lonza; Cat nr BE12-168F)+10% Donor Bovine Serum with Iron (Life Technologies; Cat nr 10371-029)+100 Units Penicillin/100 Units Streptomycin (Lonza Cat nr DE17-603E)] was added before pelleting the cells by centrifugation for 5 minutes at 1200 rpm. Cells were resuspended in 10 mL medium, pelleted again by centrifugation for 5 minutes at 1200 rpm, and resuspended in FACS buffer at a concentration of $1.0 \times 10^6$ cells/mL. The next steps were performed at 4° C. 100 µL cell suspension samples (100,000 cells per well) were seeded in polystyrene 96-well round-bottom plates (Greiner Bio-One; Cat nr 650101) and pelleted by centrifugation at 300×g for 3 minutes at 4° C. Cells were resuspended in 100 µL samples of a serial dilution antibody preparation series (range 0 to 10 µg/mL in 5-fold dilutions) and incubated for 30 minutes at 4° C. Cells were pelleted by centrifugation at 300×g for 3 minutes at 4° C. and washed twice with 150 µL FACS buffer. Cells were incubated with 50 µL secondary antibody R-phycoerythrin (R-PE)-conjugated goat-anti-human IgG F(ab')$_2$ (Jackson ImmunoResearch; Cat nr 109-116-098; 1/100) for 30 minutes at 4° C., protected from light. Cells were washed twice with 150 µL FACS buffer, resuspended in 150 µL FACS buffer, and antibody binding was analyzed on a FACS Canto II (BD Biosciences) by recording 10,000 events. Binding curves were analyzed using non-linear regression analysis (sigmoidal dose-response with variable slope) using GraphPad Prism software.

Figure 2:
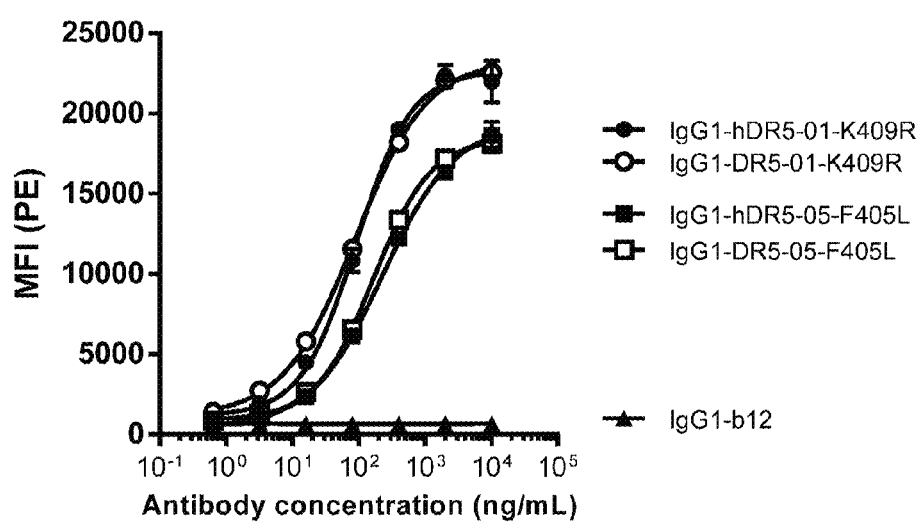
FIG. 2 shows binding of humanized (hDR5) and chimeric (DR5) anti-DR5 antibodies to DR5-positive HCT 116 human colon cancer cells as measured by flow cytometry on FACS. Anti-gp120 antibody IgG1-b12 was used as a negative control. Binding is expressed as MFI (mean fluorescence intensity). Error bars indicate the standard deviation.

As can be seen from FIG. 2 shows that the humanized antibodies IgG1-hDR5-01-K409R and IgG1-hDR5-05-F405L showed similar binding curves as their corresponding chimeric antibody IgG1-DR5-01-K409R or IgG1-DR5-05-F405L, respectively. Humanization had no effect on the binding of the DR5 antibodies.

Example 4: Introduction of a Hexamerization-Enhancing Mutation Does Not Affect Binding of Chimeric DR5-01 and DR5-05 Antibodies and Bispecific Antibody DR5-01×DR5-05 to DR5-Positive Human Colon Cancer Cells Binding of purified antibody variants of IgG1-DR5-01-K409R, IgG1-DR5-05-F405L and bispecific antibody IgG1-DR5-01-K409R×IgG1-DR5-05-F405L (BsAb DR5-01-K409R×DR5-05-F405L) with and without a hexamerization-enhancing mutation (E430G or E345K) to human colon cancer cells COLO 205 was analyzed by FACS analysis. Cells were harvested by pooling the culture supernatant containing non-adherent cells and trypsinized adherent COLO 205 cells. Cells were centrifuged for 5 minutes at 1,200 rpm and resuspended in 10 mL culture medium [RPMI 1640 with 25 mM Hepes and L-Glutamine (Lonza Cat nr BE12-115F)+10% Donor Bovine Serum with Iron (Life Technologies Cat nr 10371-029)+50 Units Penicillin/50 Units Streptomycin (Lonza Cat nr DE17-603E)]. Cells were counted, centrifuged again and resuspended in FACS buffer at a concentration of $0.3 \times 10^6$ cells/mL. The next steps were performed at 4° C. 100 µL cell suspension samples (30,000 cells per well) were seeded in polystyrene 96-well round-bottom plates and pelleted by centrifugation at 300×g for 3 minutes at 4° C. Cells were resuspended in 50 µL samples of a serial dilution antibody preparation series (range 0 to 10 µg/mL final concentrations in 5-fold dilutions) and incubated for 30 minutes at 4° C. Plates were centrifuged at 300×g for 3 minutes at 4° C. and cells were washed twice with 150 µL FACS buffer. Cells were incubated with 50 µL secondary antibody R-PE-conjugated goat-anti-human IgG F(ab')$_2$ (Jackson ImmunoResearch; Cat nr 109-116-098; 1/100) for 30 minutes at 4° C. protected from light. Cells were washed twice with 150 µL FACS buffer, resuspended in 100 µL FACS buffer, and antibody binding was analyzed on a FACS Canto II (BD Biosciences) by recording 5,000 events. Binding curves were analyzed using non-linear regression analysis (sigmoidal dose-response with variable slope) using GraphPad Prism software.

Figure 3A:
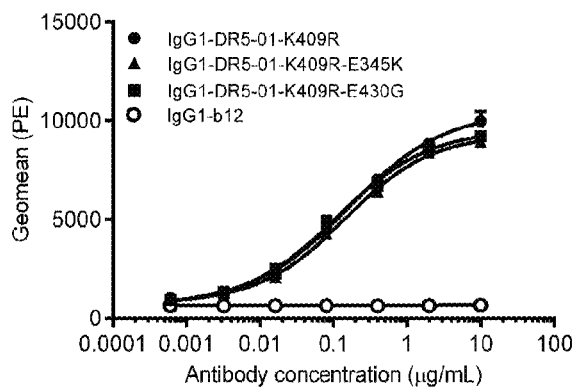
FIGS. 3A-3C show binding of anti-DR5 antibodies with and without hexamerization-enhancing mutations E430G or E345K to DR5-positive COLO 205 cells. Variants of the human-mouse chimeric antibodies IgG1-DR5-01-K409R (FIG. 3A), IgG1-DR5-05-F405L (FIG. 3B) and bispecific antibody IgG1-DR5-01-K409R×IgG1-DR5-05-F405L (BsAb IgG1-DR5-01-K409R×DR5-05-F405L) (FIG. 3C)
Figure 3B:
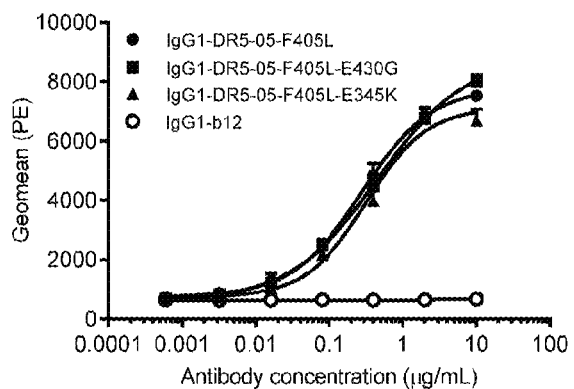
Figure 3C:
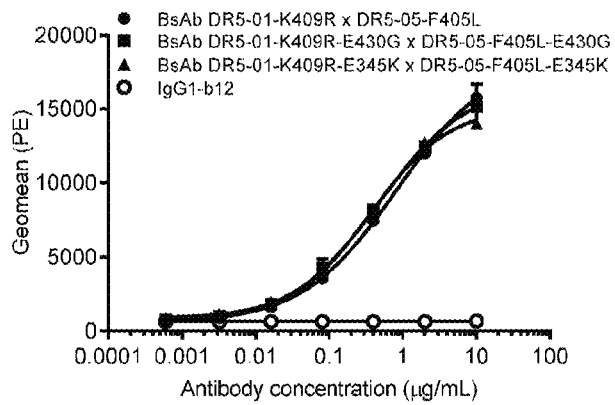

FIG. 3A shows that the antibodies IgG1-DR5-01-K409R-E430G and IgG1-DR5-01-K409R-E345K showed similar dose-dependent binding to human colon cancer cells COLO 205 as IgG1-DR5-01-K409R. FIG. 3B shows that the antibodies IgG1-DR5-05-F405L-E430G and IgG1-DR5-05-F405L-E345K showed similar dose-dependent binding to COLO 205 cells as IgG1-DR5-05-F405L. FIG. 3C shows that BsAb DR5-01-K409R-E430G×DR5-05-F405L-E430G and BsAb DR5-01-K409R-E345K×DR5-05-F405L-E345K showed similar dose-dependent binding to COLO 205 cells as BsAb DR5-01-K409R×DR5-05-F405L. These data indicate that introduction of the hexamerization-enhancing mutations E430G or E345K did not affect binding of antibodies IgG1-DR5-01-K409R, IgG1-DR5-05-F405L and BsAb DR5-01-K409R×DR5-05-F405L on DR5-positive COLO 205 cells.

Example 5: Binding of Chimeric DR5-01 and DR5-05 Antibodies to Rhesus Macaque DR5

Binding of purified IgG1-DR5-01-K409R-E430G and IgG1-DR5-05-F405L-E430G to CHO cells expressing Rhesus macaque DR5 or human DR5 (described in Example 1) was analyzed by FACS analysis. One day before FACS analysis, CHO cells were transiently transfected with a vector encoding Rhesus macaque DR5, human DR5 or a non-coding vector (mock). To prepare single cell suspensions, cells were washed with PBS and resuspended in FACS buffer at a concentration of $1.0 \times 10^6$ cells/mL. The next steps were performed at 4° C. 75 µL cell suspension samples (75,000 cells per well) were seeded in polystyrene 96-well round-bottom plates and pelleted by centrifugation at 300×g for 3 minutes at 4° C. Cells were resuspended in 50 µL samples of a serial dilution antibody preparation series (range 10 to 0 µg/mL in 5-fold dilutions) and incubated for 30 minutes at 4° C. Plates were centrifuged at 300×g for 3 minutes at 4° C. and cells were washed twice with 150 µL FACS buffer. Cells were incubated with 50 µL secondary antibody R-PE-conjugated goat-anti-human IgG F(ab')$_2$ (Jackson ImmunoResearch; Cat nr 109-116-098; 1/100) for 30 minutes at 4° C. protected from light. Cells were washed twice with 150 µL FACS buffer, resuspended in 100 µL FACS buffer, and antibody binding was analyzed on a FACS Canto II (BD Biosciences) by recording 100,000 events. Binding curves were analyzed using non-linear regression analysis (sigmoidal dose-response with variable slope) using GraphPad Prism software. FIG. 4 shows that the antibodies IgG1-DR5-01-K409R-E430G and IgG1-DR5-05-F405L-E430G showed dose-dependent binding to Rhesus macaque DR5 expressed on CHO cells. Binding to CHO cells transfected with human DR5 and mock-transfected CHO cell was tested as positive and negative control, respectively. For both IgG1-DR5-01-K409R-E430G and IgG1-DR5-05-F405L-E430G, $EC_{50}$ values for binding to human DR5 and Rhesus macaque DR5 were in the same range ([0.014-0.023 μg/mL] and [0.051-0.066 μg/mL], respectively), indicating that IgG1-DR5-01-K409R-E430G and IgG1-DR5-05-F405L-E430G show comparable binding to human and Rhesus macaque DR5.

Figures 5A, 5B:
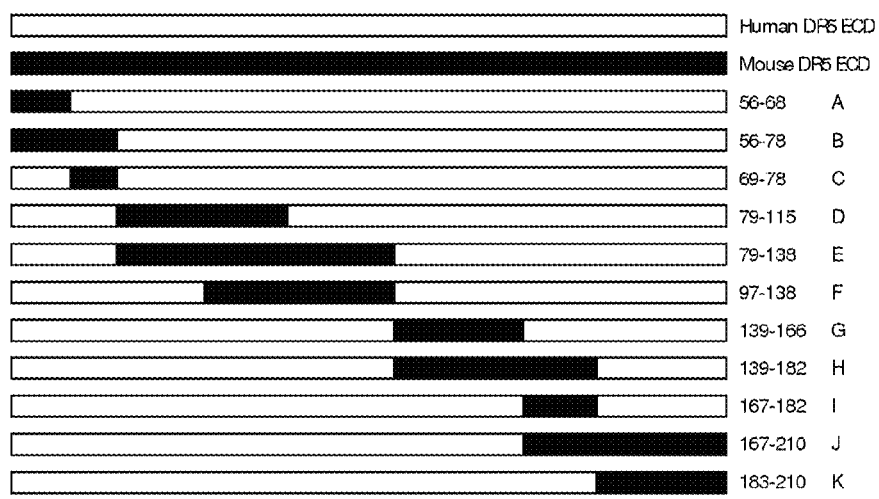
Figure 5C:
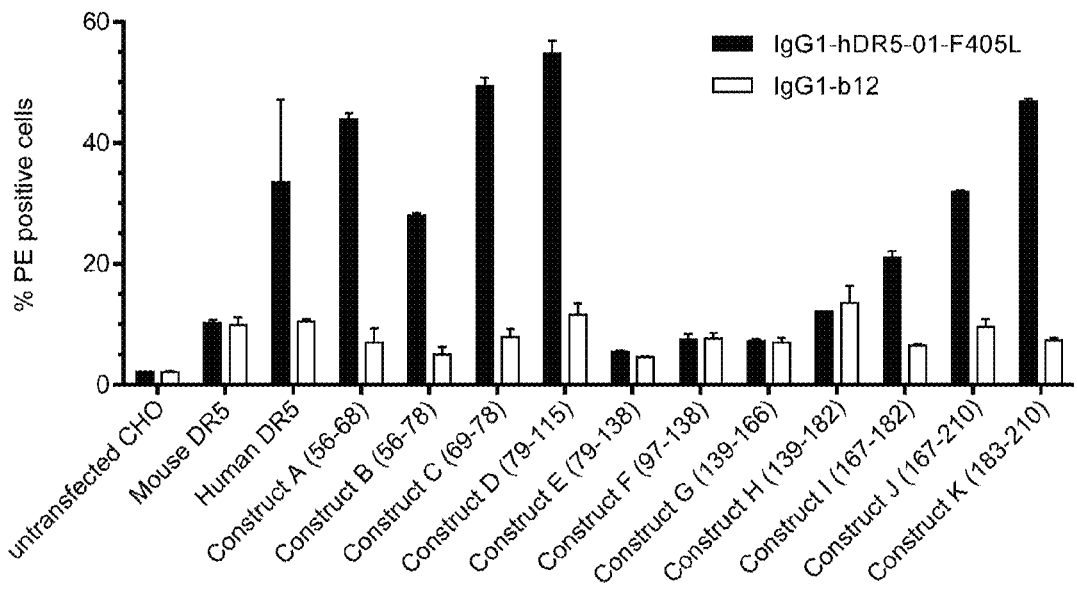
Figure 5D:
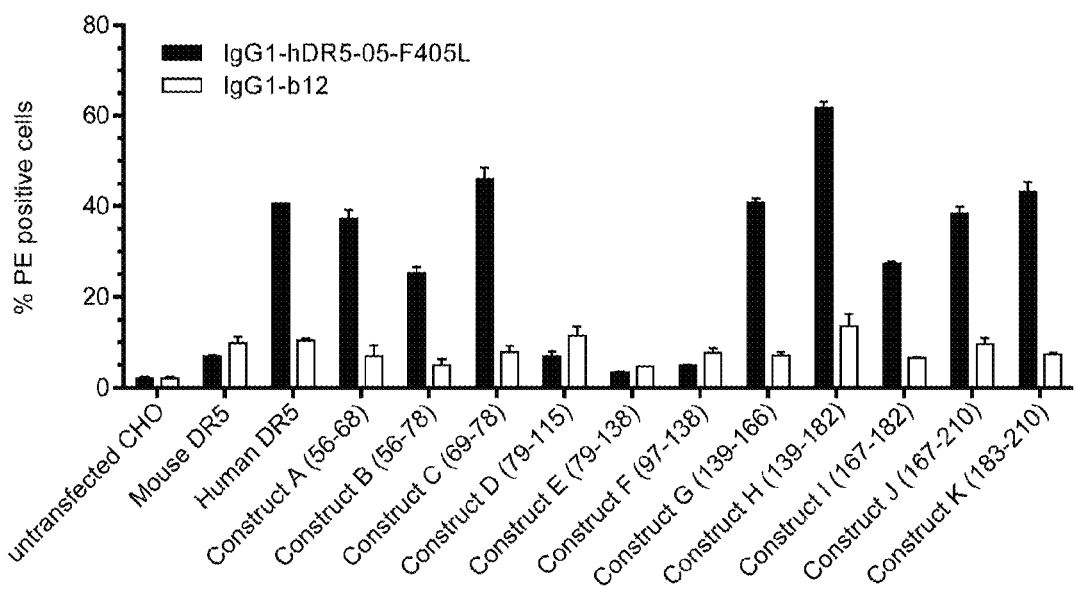

Example 6: Mapping of Binding Regions of DR5-01 and DR5-05 Antibodies on Human DR5 Using Domain-Swapped DR5 Molecules The amino acid sequences of the extracellular domains of human and murine DR5 show limited homology (FIG. 5A) and the humanized antibodies IgG1-hDR5-01-F405L and IgG1-hDR5-05-F405L do not bind murine DR5 (FIG. 5C, D). With the aim to identify amino acid stretches in the human DR5 extracellular domain that are involved in antibody binding, we developed eleven human-mouse chimeric DR5 molecules, in which specific human DR5 domains had been replaced by the mouse analogues (domain-swapped DR5 molecules described in Example 1) as visualized in FIG. 5B. The domain-swapped DR5 variants were transiently expressed on CHO cells. Loss of binding of the DR5 antibodies to domain-swapped DR5 molecules indicates that the swapped domain of human DR5 contains one or more amino acids that are crucial for binding. Vice versa, retention of binding of the DR5 antibodies to domain-swapped DR5 molecules indicates that the swapped domain of human DR5 does not contain amino acids that are crucial for binding. For the binding assay, $3 \times 10^6$ transfected cells were washed and resuspended in 3 mL FACS buffer. 100 μL cell suspension was added per well (100.000 cells per well) of 96-well round bottom plates (Greiner Bio-one; Cat nr 650101). The next steps were performed at 4° C. Cells were pelleted, resuspended in 50 μL DR5 antibody sample (10 μg/mL final concentration) and incubated for 30 minutes at 4° C. The cells were washed twice and incubated in 50 μL secondary antibody R-PE-conjugated goat-anti-human IgG F(ab')$_2$ (Jackson ImmunoResearch; Cat nr 109-116-098; 1/100) for 30 minutes at 4° C. protected from light. Cells were washed twice, resuspended in 120 μL FACS buffer, and analyzed on a FACS Canto II (BD Biosciences). The percentage of viable PE-positive cells was plotted using GraphPad Prism software. Surface expression was confirmed for each domain-swapped DR5 molecule using a panel of DR5 antibodies directed against different epitopes (not shown). The non-target binding antibody IgG1-b12 against gp120 was included as a negative control for binding. FIG. 5C shows that IgG1-hDR5-01-F405L showed loss of binding to constructs E (79-138), F (97-138), G (139-166) and H (139-182), whereas binding to constructs A-D (covering human DR5 sequence 56-115) and I-K (covering human DR5 sequence 167-210) was retained. Together, these data indicate that the amino acid regions 116-138 and 139-166 each contain one or more amino acids required for binding of IgG1-hDR5-01-F405L to human DR5. FIG. 5D shows that IgG1-hDR5-05-F405L showed loss of binding to constructs D (79-115), E (79-138) and F (97-138), whereas binding to constructs A-C (covering human DR5 sequence 56-78) and G-K (covering human DR5 sequence 139-210) was retained. Together, these data indicate that the amino acid region 79-138 contains one or more amino acids required for binding of IgG1-hDR5-05-F405L to human DR5.

Example 7: Crossblock ELISA with DR5-01 and DR5-05 Antibodies

The competition between humanized DR5-01 and DR5-05 antibodies for binding to the extracellular domain of DR5 was measured by sandwich binding assays in a sandwich enzyme-linked immunosorbent assay (ELISA) as described in this example and by Bio-Layer interferometry (BLI) using a ForteBio Octet® HTX system (data not shown). For the ELISA, 96-well flat bottom ELISA plates (Greiner bio-one; Cat nr 655092) were coated overnight at 4° C. with 2 μg/mL DR5 antibody (IgG1-hDR5-01-E430G or IgG1-hDR5-05-E430G) in 100 μL PBS. The wells were blocked by adding 200 μL PBSA [PBS/1% Bovine Serum Albumin (BSA; Roche Cat #10735086001)] and incubated for 1 hour at room temperature. The wells were washed three times with PBST [PBS/0.05% Tween-20 (Sigma-Aldrich; Cat nr 63158)]. Next, DR5ECD-FcHistag (SEQ ID 27) (0.2 μg/mL final concentration) and competing antibody (1 μg/mL final concentration) were added in a total volume of 100 μL PBSTA (PBST/0.2% BSA) and incubated for 1 hour at room temperature while shaking. After washing three times with PBST, wells were incubated on an ELISA shaker with 100 μL biotinylated anti-His tag antibody (R&D Systems; Cat nr BAM050; 1:2.000) in PBSTA for one hour at room temperature. After washing three times with PBST, wells were incubated with streptavidin-labelled Poly-HRP (Sanquin; Cat nr M2032; 1:10.000) in PBSTA for 20 minutes at room temperature on an ELISA shaker. After washing three times with PBST, the reaction was visualized through an incubation with 100 μL 2,2'-azino-bis (3-ethylbenzothiazoline-6-sulfonic acid [ABTS (Roche; Cat nr 11112597001)] for 30 minutes at RT protected from light. The substrate reaction was stopped by adding an equal volume of 2% oxalic acid. Fluorescence at 405 nm was measured on an ELISA reader (BioTek ELx808 Absorbance Microplate Reader). FIG. 6 shows binding competition expressed as percentage inhibition of DR5ECD-FcHisCtag binding to coated antibody in presence of competing antibody, relative to binding of DR5ECD-FcHisCtag in absence of competing antibody (% inhibition=100−[(binding in presence of competing antibody/binding in absence of competing antibody)]*100). Binding of DR5ECD-FcHistag to coated IgG1-hDR5-01-E430G was not inhibited in the presence of soluble IgG1-hDR5-05-E430G. Vice versa, binding of DR5ECD-FcHistag to coated IgG1-hDR5-05-E430G was also not inhibited in the presence of soluble IgG1-hDR5-01-E430G. These data indicate that IgG1-hDR5-01-E430G and IgG1-hDR5-05-E430G did not compete with each other for binding of DR5ECD-FcHisCtag, suggesting that they recognize distinct epitopes in the extracellular domain of human DR5. These data were confirmed by BLI using a classical sandwich assay, in which IgG1-hDR5-01-F405L or IgG1-hDR5-05-F405L (20 μg/ml in 10 mM Sodium Acetate pH 6.0, ForteBio Cat nr 18-1070) were immobilized on Amine-Reactive Second Generation biosensors (ForteBio Cat nr 18-5092). Subsequently, biosensors were incubated with DR5ECDdelHis (SEQ ID 28) (100 nM in Sample Diluent, ForteBio cat nr 18-1048) and binding of competing antibody (5 μg/mL in Sample Diluent) was analyzed (data not shown).

Example 8: Introduction of a Hexamerization-Enhancing Mutation Improves the Efficacy of Cell Death Induction by DR5-01 and DR5-05 Antibodies and of the Combination Thereof A viability assay was performed to study the effect the hexamerization-enhancing mutation E430G in IgG1-DR5-01-K409R and IgG1-DR5-05-F405L on the capacity of the antibodies to kill human colon cancer cells COLO 205 and HCT 116. The antibodies were tested as single agent and as combinations of DR5-01 and DR5-05 antibodies. COLO 205 cells were harvested by pooling the culture supernatant containing non-adherent cells and trypsinized adherent cells. HCT 116 cells were harvested by trypsinization. Cells were passed through a cell strainer, pelleted by centrifugation for 5 minutes at 1,200 rpm and resuspended in culture medium at a concentration of $0.5 \times 10^5$ cells/mL. 100 µL of the single cell suspension (5,000 cells per well) was seeded in polystyrene 96-well flat-bottom plates (Greiner Bio-One, Cat nr 655182). 50 µL of a serial dilution antibody preparation series (range 0.05 to 20,000 ng/mL final concentrations in 5-fold dilutions) was added and incubated for 3 days at 37° C. In samples that were treated with a combination of two antibodies, the total antibody concentration in the assay was the same as in the samples that were treated with single antibodies. As a positive control, cells were incubated with 5 µM staurosporine (Sigma Aldrich, Cat nr S6942). The viability of the cultured cells was determined in a CellTiter-Glo luminescent cell viability assay (Promega, Cat nr G7571) that quantifies the ATP present, which is an indicator of metabolically active cells. From the kit, 20 µL luciferin solution reagent was added per well and mixed by shaking the plate for 2 minutes at 500 rpm. Next, plates were incubated for 1.5 hours at 37° C. 100 µL supernatant was transferred to a white OptiPlate-96 (Perkin Elmer, Cat nr 6005299) and luminescence was measured on an EnVision Multilabel Reader (PerkinElmer). Data were analyzed and plotted using non-linear regression (sigmoidal dose-response with variable slope) using GraphPad Prism software. FIG. 7 shows the percentage viable cells, as calculated using the following formula: % viable cells=[(luminescence antibody sample−luminescence staurosporine sample)/(luminescence no antibody sample−luminescence staurosporine sample)]*100.

FIG. 7 shows that introduction of the E430G mutation enhanced the potency of the chimeric antibodies IgG1-DR5-01-K409R and IgG1-DR5-05-F405L in both COLO 205 (A) and HCT 116 (B) cells. The combination of IgG1-DR5-01-K409R-E430G and IgG1-DR5-05-F405L-E430G was more potent than either antibody alone and more potent than the combination of the antibodies without the E430G mutation. The combination of IgG1-DR5-01-K409R and IgG1-DR5-05-F405L was more potent than either antibody alone. These data show that introduction of the hexamerization-enhancing mutation E430G resulted in enhanced induction of cell killing upon binding of the chimeric DR5 antibodies 01 and 05, both as single antibodies and in combination, with the combination being the most potent.

Example 9: Combining Two Non-Crossblocking DR5 Antibodies with Hexamerization-Enhancing Mutations Results in Enhanced Target Cell Killing In Example 8 it is shown that combining the two non-crossblocking anti-DR5 antibodies IgG1-DR5-01-K409R-E430G and IgG1-DR5-05-F405L-E430G with hexamerization enhancing mutations resulted in enhanced killing on cancer cell lines compared to the efficacy of the single antibodies. Here, we compare the efficacy of two non-crossblocking versus two crossblocking anti-DR5 antibodies. A viability assay was performed to study the capacity of the combination of antibodies IgG1-chTRA8-F405L-E430G with either non-crossblocking antibody IgG1-DR5-01-K409R-E430G or crossblocking antibody IgG1-DR5-05-F405L-E430G to induce killing of HCT 116 colon cancer cells in comparison to the single antibodies. A crossblock ELISA for antibodies IgG1-chTRA8-F405L and IgG1-DR5-05-F405L was performed as described in Example 7 and confirmed by a sandwich binding assay on an Octet® HTX system (data not shown). The viability assay on HCT 116 cells was performed as described in Example 8 with a serial diluted antibody series ranging from 0.00005 to 20 µg/mL final concentrations in 5-fold dilutions. FIG. 8 shows that the efficacy of the single antibodies in killing of HCT116 cells was enhanced by combining the two non-crossblocking antibodies IgG1-chTRA8-F405L-E430G and IgG1-DR5-01-K409R-E430G (FIG. 8B) and not by combining the two crossblocking antibodies IgG1-chTRA8-F405L-E430G and IgG1-DR5-05-F405L-E430G (FIG. 8C).

Example 10: Capacity of the Combination of Non-Crossblocking Antibodies DR5-05+CONA and Bispecific Antibody DR5-05×CONA with Hexamerization-Enhancing Mutations to Induce Target Cell Killing A viability assay was performed to study the capacity of another combination of two non-crossblocking antibodies (IgG1-CONA-K409R-E430G+IgG1-DR5-05-F405L-E345K) and its bispecific derivative BsAb IgG1-CONA-K409R-E430G×DR5-05-F405L-E345K to induce killing of HCT 116 colon cancer cells in comparison to the combination of antibodies and the bispecific antibody without hexamerization-enhancing mutation, respectively. A crossblock ELISA for antibodies IgG1-CONA-K409R and IgG1-DR5-05-F405L was performed as described in Example 7 and confirmed by a sandwich binding assay on an Octet® HTX system (data not shown). The viability assay on HCT 116 cells was performed as described in Example 8 with a serial diluted antibody series ranging from 0.01 to 20,000 ng/mL final concentrations in 5-fold dilutions. FIG. 9 shows that the combination of non-crossblocking antibodies IgG1-CONA-K409R-E430G+IgG1-DR5-05-F405L-E345K and BsAb IgG1-CONA-K409R-E430G×DR5-05-F405L-E345K with hexamerization-enhancing mutations showed enhanced efficacy in killing of HCT116 cells compared to these antibodies without the hexamerization-enhancing mutations E430G or E345K.

Example 11: Capacity of the DR5-01+DR5-05 Antibody Combination with E430G Hexamerization-Enhancing Mutation to Induce Target Cell Killing in Different Cancer Cell Lines A viability assay was performed to study the capacity of the combination of human-mouse chimeric antibodies IgG1-DR5-01-K409R+IgG1-DR5-05-F405L with and without the hexamerization-enhancing mutation E430G to induce killing of COLO 205, HCT-15, HCT 116, HT-29 and SW480 colon cancer, BxPC-3, HPAF-II and PANC-1 pancreatic cancer, SNU-5 gastric cancer, A549 and SK-MES-1 lung cancer, and A375 skin cancer cells. Adherent cells were harvested by trypsinization and passed through a cell strainer. Cells were pelleted by centrifugation for 5 minutes at 1,200 rpm and resuspended in culture medium at a concentration of 0.5×10$^5$ cells/mL [COLO 205, HCT-15, SW480 and BxPC-3: RPMI 1640 with 25 mM Hepes and L-Glutamine (Lonza Cat nr BE12-115F)+10% DBSI (Life Technologies Cat nr 10371-029)+Pen/Strep (Lonza Cat nr DE17-603E); HCT116 and HT-29: McCoy's5A Medium with L-Glutamine and Hepes (Lonza, Cat nr BE12-168F)+ 10% DBSI+Pen/Strep; HPAF-II and SK-MES-1: Eagle's Minimum Essential Medium (EMEM, ATCC Cat nr 30-2003)+10% DBSI+Pen/Strep; PANC-1 and A375: DMEM 4.5 g/L Glucose without L-Gln with HEPES (Lonza Cat nr LO BE12-709F)+10% DBSI+1 mM L-Glutamine (Lonza Cat nr BE17-605E)+Pen/Strep; SNU-5: IMDM (Lonza Cat nr BE12-722F)+10% DBSI+Pen/Strep; A549: F-12K Medium (ATCC Cat nr 30-2004)+10% DBSI+1 mM L-Glutamine+Pen/Strep]. 100 µL of the single cell suspensions (5,000 cells per well) were seeded in polystyrene 96-well flat-bottom plates (Greiner Bio-One, Cat nr 655182) and incubated overnight at 37° C. Supernatant of the adherent cells was replaced by 150 µL antibody sample (final concentration 10 µg/mL) and incubated for 3 days at 37° C. As a positive control, cells were incubated with 5 µM staurosporine (Sigma Aldrich, Cat nr S6942). The viability of the cell cultures was determined in a CellTiter-Glo luminescent cell viability assay as described in Example 8. For all tested cell lines, the percentage viable cells was significant lower after incubation with 10 µg/mL of the antibody combination IgG1-DR5-01-K409R-E430G+IgG1-DR5-05-F405L-E430G than after incubation with the non-target binding negative control antibody IgG1-b12 (FIG. 10). In all but two of the tested cell lines, the efficacy of the antibody combination IgG1-DR5-01-K409R-E430G+IgG1-DR5-05-F405L-E430G was significant better than for the combination IgG1-DR5-01-K409R+IgG1-DR5-05-F405L without hexamerization-enhancing mutation. These data indicate that the combination of chimeric DR5 antibodies with hexamerization-enhancing mutations IgG1-DR5-01-K409R-E430G+IgG1-DR5-05-F405L-E430G was very effective in killing of cancer target cells of different origin, including colon, pancreatic, gastric, lung and skin cancer, without the requirement of a secondary cross-linking agent. There was no correlation between killing efficacy of IgG1-DR5-01-K409R-E430G+IgG1-DR5-05-F405L-E430G and DR5 target expression levels (described in Example 2).

Example 12: Capacity of the Humanized DR5-01+DR5-05 Antibody Combination with E430G Hexamerization-Enhancing Mutation to Induce Target Cell Killing A viability assay was performed to compare the potency of the combination of chimeric antibodies IgG1-DR5-01-K409R-E430G+IgG1-DR5-05-F405L-E430G with the potency of the combination of humanized antibodies IgG1-hDR5-01-K409R-E430G+IgG1-hDR5-05-F405L-E430G to induce killing of BxPC-3 and PANC-1 pancreatic cancer cells in vitro. Cells were harvested by trypsinization and passed through a cell strainer. Cells were pelleted by centrifugation for 5 minutes at 1,200 rpm and resuspended in culture medium at a concentration of 0.5×10$^5$ cells/mL. 100 µL of the single cell suspensions (5,000 cells per well) were seeded in polystyrene 96-well flat-bottom plates (Greiner Bio-One, Cat nr 655182) and incubated overnight at 37° C. Supernatant of the adherent cells was replaced by 150 µL antibody sample of a serial dilution antibody preparation series and incubated for 3 days at 37° C. As a positive control, cells were incubated with 5 µM staurosporine (Sigma Aldrich, Cat nr S6942). The viability of the cell cultures was determined in a CellTiter-Glo luminescent cell viability assay as described in Example 8. The combination of the humanized antibodies with hexamerization-enhancing mutation IgG1-hDR5-01-K409R-E430G+IgG1-hDR5-05-F405L-E430G showed similar dose-response curves as the combination of the corresponding chimeric antibodies IgG1-DR5-01-K409R-E430G+IgG1-DR5-05-F405L-E430G (FIG. 11).

Example 13: Optimization of Antibody IgG1-hDR5-01-E430G

Amino acid sequence N55-G56 was identified as a potential asparagine (Asn) deamidation motif in the CDR2 regions of the IgG1-hDR5-01 and IgG1-hDR5-05 heavy chains (SEQ ID NO:2). Deamidation at this position was mimicked by introduction of the N55D mutation in IgG1-hDR5-01-K409R and IgG1-hDR5-05-F405L to test the effect of deamidation on target binding. IgG1-hDR5-01-N55D-K409R and IgG1-hDR5-05-N55D-F405L were tested for binding to HCT 116 cells by FACS analysis as described in Example 3. FIG. 12A shows that mimicking deamidation by introduction of the N55D mutation resulted in strongly decreased binding of IgG1-hDR5-01-K409R on HCT 116 cells. In contrast, IgG1-hDR5-05-F405L and IgG1-hDR5-05-N55D-F405L showed comparable binding curves. To reduce the risk of Asn deamidation in the DR5-01 antibody, the G56T mutation was introduced in IgG1-hDR5-01-E430G and this antibody variant was tested for binding to HCT 116 cells by FACS analysis as described in Example 3. FIG. 12B shows that the mutation had no effect on the binding of IgG1-hDR5-01-E430G to HCT 116 cells.

A viability assay was performed to compare the capacity of the combination of humanized antibodies IgG1-hDR5-01-G56T-E430G+IgG1-hDR5-05-E430G with the capacity of the combination of humanized antibodies IgG1-hDR5-01-E430G+IgG1-hDR5-05-E430G to induce killing of BxPC-3 pancreatic cancer cells. Viability was assessed as described in Example 11 with 1,000 cells per well and antibody concentrations series ranging from 0.0001 to 10,000 ng/mL final concentrations in 4-fold dilutions in a total volume of 200 µL. FIG. 12C shows that introduction of the G56T mutation in IgG1-hDR5-01-E430G had no effect on the killing efficacy of the antibody in combination with IgG1-hDR5-05-E430G.

Example 14: Cell Death Induction by the Combination of Humanized Antibodies hDR5-01-G56T-E430G and hDR5-05-E430G Requires Fc:Fc Interactions to Form Hexamers To analyse the requirement of antibody hexamer formation by IgG1-hDR5-01-G56T-E430G and IgG1-hDR5-05-E430G to induce cell death, we made use of the self-repulsing mutations K439E and S440K (Diebolder et al., Science. 2014 Mar. 14; 343(6176):1260-3). The Fc repulsion between antibodies that is introduced by the presence of either K439E or S440K in one IgG1 antibody or in a combination of antibodies results in inhibition of hexamerization, even in the presence of a hexamerization enhancing mutation such as E345K or E430G (WO2013/0044842). The repulsion by the K439E and S440K mutations is neutralized by combining both mutations in a mixture of two antibodies each harboring one or the other mutation, resulting in restoration of the Fc:Fc interactions and hexamerization. For both IgG1-hDR5-01-G56T-E430G and IgG1-hDR5-05-E430G, variants with either the K439E or S440K mutation were generated and tested in all different combinations. A viability assay was performed with serial dilution antibody preparation series ranging from 0.3 to 20,000 ng/mL total concentrations in 4-fold dilutions on BxPC-3 pancreatic and HCT-15 colon cancer cells as described in Example 11.

FIG. 13 shows that the combination of IgG1-hDR5-01-G56T-E430G and IgG1-hDR5-05-E430G variants that both harbor the same repulsion mutation (K439E or S440K) showed strongly diminished killing efficacy in BxPC-3 (A) and HCT-15 cells (B). Killing efficacy was restored when repulsion was neutralized by combining two antibodies each having one of the complementary mutations K439E or S440K. These data indicate that hexamerization by Fc-Fc interactions is required for the induction of cell death by IgG1-hDR5-01-G56T-E430G and IgG1-hDR5-05-E430G.

Example 15: Antibody Fc-Fc Interactions are Involved in DR5 Clustering and Induction of Apoptosis by the Antibody Combination IgG1-hDR5-01-G56T-E430G+IgG1-hDR5-05-E430G with Hexamerization Enhancing Mutations To test the involvement of Fc-Fc-mediated antibody hexamerization in the induction of cell death by the antibody combination IgG1-hDR5-01-G56T-E430G+IgG1-hDR5-05-E430G, we made use of the 13-residue peptide DCAWHLGELVWCT (DeLano et al., Science 2000 Feb. 18; 287(5456):1279-83) that binds the Fc in a region containing the core amino acids in the hydrophobic patch that are involved in Fc-Fc interactions (Diebolder et al., Science. 2014 Mar. 14; 343(6176):1260-3). A viability assay on BxPC-3 cells was performed as described in Example 11 for the antibody combination IgG1-hDR5-01-G56T-E430G+IgG1-hDR5-05-E430G in presence or absence of the DCAWHLGELVWCT peptide. Briefly, after overnight incubation of the cells at 37° C., culture medium was removed and replaced by 100 µL culture medium containing a dilution series (range 0-100 µg/mL) of the Fc-binding DCAWHLGELVWCT peptide, a non-specific control peptide GWTVFQKRLDGSV, or no peptide. Next, 50 µL antibody samples (833 ng/mL final concentration) were added and incubated for 3 days at 37° C. The capacity of the antibody combination IgG1-hDR5-01-G56T-E430G+IgG1-hDR5-05-E430G to induce killing of BxPC-3 cells was strongly inhibited by 100 µg/mL Fc-binding DCAWHLGELVWCT peptide (FIG. 14). These data indicate the involvement of Fc:Fc interactions in the capacity of the antibody combination IgG1-hDR5-01-G56T-E430G+IgG1-hDR5-05-E430G with hexamerization-enhancing mutations to induce DR5 clustering on the cell surface of cancer cells and induction of apoptosis.

Example 16: Capacity of Chimeric Antibody Combination DR5-01 and DR5-05 Antibodies with E430G Hexamerization Enhancing Mutation to Induce Cancer Cell Killing, at Different Combination Ratios A viability assay was performed to study the capacity of the antibody combination IgG1-DR5-01-K409R-E430G+IgG1-DR5-05-F405L-E430G to induce killing of BxPC-3 pancreatic cancer cells, when combined at different ratios of IgG1-DR5-01-K409R-E430G and IgG1-DR5-05-F405L-E430G. Cells were harvested by trypsinization and passed through a cell strainer. Cells were pelleted by centrifugation for 5 minutes at 1,200 rpm and resuspended in culture medium at a concentration of $0.5 \times 10^5$ cells/mL. 100 µL of the single cell suspensions (5,000 cells per well) were seeded in polystyrene 96-well flat-bottom plates (Greiner Bio-One, Cat nr 655182) and incubated overnight at 37° C. 50 µL antibody sample with different ratios of IgG1-DR5-01-K409R-E430G and IgG1-DR5-05-F405L-E430G (indicated as Ratio DR5-01:DR5-05 of 100:0, 90:10, 80:20, 70:30, 60:40, 50:50, 40:60, 30:70, 20:80, 10:90 and 0:100 in serial dilution series ranging from 0.06 to 20 µg/mL final concentrations in 5-fold dilutions) was added and incubated for 3 days at 37° C. As a positive control, cells were incubated with 5 µM staurosporine (Sigma Aldrich, Cat nr S6942). The viability of the cell cultures was determined in a CellTiter-Glo luminescent cell viability assay as described in Example 8. At 20 µg/mL and 4 µg/mL total antibody concentrations, killing was equally effective at all tested antibody ratios containing both antibodies IgG1-DR5-01-K409R-E430G and IgG1-DR5-05-F405L-E430G. At 0.8 µg/mL and 0.16 µg/mL total antibody concentrations, all tested antibody ratios containing both antibodies IgG1-DR5-01-K409R-E430G and IgG1-DR5-05-F405L-E430G induced killing (FIG. 15).

Example 17: Capacity of the Combination of Humanized Antibodies DR5-01 and DR5-05 Antibodies with E430G Hexamerization Enhancing Mutation to Induce Cancer Cell Killing, at Different Combination Ratios A viability assay was performed to study the capacity of the antibody combination IgG1-hDR5-01-G56T-E430G+IgG1-hDR5-05-E430G to induce killing of BxPC-3 pancreatic and HCT-15 colon cancer cells, when combined at different antibody ratios. Generally, the experiments were performed as described in Example 16. Briefly, pre-attached cells (5,000 cells per well) were incubated for 3 days at 37° C. in 150 µL in polystyrene 96-well flat-bottom plates with different ratios of IgG1-hDR5-01-G56T-E430G and IgG1-hDR5-05-E430G (indicated in FIG. 16 as Ratio DR5-01:DR5-05 of 100:0, 98:2, 96:4, 94:6, 92:8, 90:10, 50:50, 10:90, 8:92, 6:94, 4:96, 2:98 and 0:100) at final antibody concentrations of 10 µg/mL for BxPC-3 and 20 µg/mL for HCT-15. The viability of the cell cultures was determined in a CellTiter-Glo luminescent cell viability assay as described in Example 8. Killing was equally effective at all tested antibody ratios containing both antibodies IgG1-hDR5-01-G56T-E430G and IgG1-hDR5-05-E430G (FIG. 16).

Example 18: The Combination of Humanized DR5-01+DR5-05 Antibodies with the E430G Hexamerization-Enhancing Mutation Induce Caspase-Dependent Cytotoxicity A viability assay was performed to compare the cytotoxicity of the combination of humanized antibodies IgG1-hDR5-01-E430G+IgG1-hDR5-05-E430G in the presence and absence of a caspase inhibitor. PANC-1 and BxPC3 pancreatic cancer cells were harvested by trypsinization and passed through a cell strainer. Cells were pelleted by centrifugation for 5 minutes at 1,200 rpm and resuspended in culture medium at a concentration of $0.5 \times 10^5$ cells/mL. 100 µL of the single cell suspensions (5,000 cells per well) were seeded in polystyrene 96-well flat-bottom plates (Greiner Bio-One, Cat nr 655182) and incubated overnight at 37° C. 25 µL pan-caspase inhibitor Z-Val-Ala-DL-Asp-fluoromethylketone (Z-VAD-FMK, 5 µM end concentration in 150 µL, Bachem, Cat nr 4026865.0005) was added to the cell cultures and incubated for one hour at 37° C. before adding 25 µL antibody sample of a serial dilution antibody preparation series (range 1 to 20 µg/mL final concentrations in 4-fold dilutions) and further incubation for 3 days at 37° C. As a positive control, cells were incubated with 5 µM staurosporine (Sigma Aldrich, Cat nr S6942). Recombinant human TRAIL/APO-2L (eBioscience, Cat nr BMS356) was used at 6 µg/mL final concentration. The viability of the cell cultures was determined in a CellTiter-Glo luminescent cell viability assay as described in Example 8. The combination of the humanized antibodies with hexamerization-enhancing mutation IgG1-hDR5-01-E430G+IgG1-hDR5-05-E430G was unable to reduce the viability of PANC-1 and BxPC3 pancreatic cancer cells in presence of the pan-caspase inhibitor Z-VAD-FMK, indicating that the combination of IgG1-hDR5-01-E430G+IgG1-hDR5-05-E430G induced caspase-dependent programmed cell death (FIG. 17). This was also shown for the natural DR5 ligand TRAIL.

Example 19: Cell Death Induction Upon Binding of the Combination of Chimeric DR5-01 and DR5-05 Antibodies on COLO 205 Colon Cancer Cells, as Assessed by Annexin V/Propidium Iodide and Active Caspase-3 Staining The kinetics of cell death induction was analyzed by Annexin V/Propidium Iodide (PI) double staining and active caspase-3 staining. Annexin-V binds phosphatidylserine that is exposed on the cell surface after initiation of programmed cell death, which is a reversible process. PI is a dye that intercalates into double-stranded DNA and RNA when it enters cells. Because PI cannot pass intact plasma and nuclear membranes, it will not stain living cells but only enter and stain dying cells that have decreased membrane integrity. Due to these characteristics, the Annexin V/PI double staining can be applied to discriminate between initiation (Annexin V-positive/PI-negative) and irreversible (Annexin V-positive/PI-positive) programmed cell death. Caspase-3 is activated by both the extrinsic death receptor-induced and intrinsic mitochondrial cell death pathways. Therefore, active caspase-3 is also a marker for initiation of the death cascade. The induction of cell death upon binding of the combination of IgG1-DR5-01-K409R-E430G+IgG1-DR5-05-F405L-E430G was analyzed in the DR5-positive COLO 205 colon cancer cells. Cells were harvested by pooling the culture supernatant containing non-adherent cells and trypsinized adherent cells. Cells were passed through a cell strainer, pelleted by centrifugation for 5 minutes at 1,200 rpm and resuspended in culture medium at a concentration of $0.2 \times 10^6$ cells/mL. 500 µL of the single cell suspensions (100,000 cells per well) were seeded in 24-wells flat-bottom culture plates (Greiner Bio-One, Cat nr 662160) and incubated for 16 hours at 37° C. 500 µL antibody sample was added (1 µg antibody final concentration) and incubated for 5 hours or 24 hours at 37° C. As a positive control, cells were incubated with 5 µM staurosporine (Sigma Aldrich, Cat nr S6942). Cells were washed once with 250 µL 1xPBS. Adherent cells were harvested by incubating with 100 µL 0.05% trypsin for 10 minutes at 37° C. 200 µL medium was added to the trypsinized cells and cells were transferred to a 96-wells round-bottom FACS plate (Greiner Bio-One, Cat nr 650101) and pooled with the non-adherent cells. Cells were pelleted by centrifugation for 5 minutes at 1,200 rpm, resuspended in 200 µL ice cold PBS and divided into two samples of 100 µL in 96-Wells round-bottom FACS plates for the Annexin V/PI and active caspase-3 staining, respectively.

Annexin V/PI double staining was performed using the FITC Annexin V Apoptosis Detection Kit I (BD Pharmingen, Cat nr 556547). Cells were washed once with ice cold PBS and incubated in 50 µL Annexin V/PI Staining Solution (Annexin V-FITC 1:00 and PI 1:25) for 15 minutes at 4° C. Cells were washed with 100 µL Binding Buffer, resuspended in 20 µL Binding Buffer and fluorescence was measured on an iQue Screener (IntelliCyt) within 1 hour. Data were analyzed and plotted using GraphPad Prism software.

Active caspase-3 staining was performed using the PE Active Caspase-3 Apoptosis Kit (BD Pharmingen, Cat nr 550914). Cells were washed once with ice cold PBS, resuspended in 100 µL Cytofix/Cytoperm Fixation and Permeabilization Solution and incubated for 20 minutes on ice. Cells were pelleted at room temperature, washed twice with 100 µL 1x Perm/Wash Buffer and resuspended in 100 µL PE Rabbit Anti-Active Caspase-3 (1:10) for an incubation of 30 minutes at room temperature. Cells were pelleted at room temperature, washed once with 100 µL 1x Perm/Wash Buffer and resuspended in 20 µL 1x Perm/Wash Buffer. Fluorescence was measured on an iQue Screener. Data were analyzed and plotted using GraphPad Prism software.

FIG. 18 shows that, after 5 hours of incubation, the combination of the chimeric antibodies IgG1-DR5-01-K409R-E430G+IgG1-DR5-05-F405L-E430G efficiently induced the early stages of cell death as indicated by an increase in the percentage of Annexin V-positive/PI-negative (A) and Active Caspase-3-positive cells (B), compared to the negative control antibody IgG1-b12. The percentage of Annexin V-positive/PI-negative and Active Caspase-3 positive cells was higher in cells treated with the combination of IgG1-DR5-01-K409R-E430G+IgG1-DR5-05-F405L-E430G compared to the combination of the DR5 antibodies without the E430G mutation (IgG1-DR5-01-K409R+IgG1-DR5-05-F405L) or any of the single antibodies. At the 5 hour time point, the percentage of AnnexinV/PI double-positive cells was comparable to background levels in all samples (C).

After 24 hours incubation, the percentage of Annexin V/PI double-positive cells (D) was enhanced in samples treated with IgG1-DR5-01-K409R-E430G+IgG1-DR5-05-F405L-E430G, indicating that the cells had entered the irreversible stages of cell death. Also at this stage, the effect of the combination of IgG1-DR5-01-K409R-E430G+IgG1-DR5-05-F405L-E430G was stronger (larger increase in the percentage of Annexin V/PI double-positive cells (E)) than in samples treated with a combination of DR5 antibodies without the E430G mutation (IgG1-DR5-01-K409R+IgG1-DR5-05-F405L) or any of the single antibodies. At the same time point, the percentage of Active Caspase 3 positive cells was highest in cells treated with IgG1-DR5-01-K409R-E430G+IgG1-DR5-05-F405L-E430G.

These data indicate that the combination of IgG1-DR5-01-K409R-E430G+IgG1-DR5-05-F405L-E430G induces both the early and late stages of cell death in COLO 205 colon cancer cells, and does so more effectively than the combination of the antibodies without the E430G hexamerization enhancing mutation.

Example 20: Caspase-3 and -7 Activation Upon Binding of the Combination of Chimeric DR5-01 and DR5-05 Antibodies with Hexamerization-Enhancing Mutation on COLO 205 Colon Cancer Cells In example 19 it was described that incubation with the combination of chimeric DR5 antibodies IgG1-DR5-01-

K409R-E430G+IgG1-DR5-05-F405L-E430G induced caspase-3 activation in COLO 205 colon cancer cells. The percentage of active caspase-3-positive cells was higher after 5 hours than after 24 hours of incubation with the antibody combination. In this example, Caspase-3/7 activation was measured in time using the Caspase-Glo 3/7 assay (Promega, Cat nr G8091), in which a substrate with the Caspase-3/7 recognition motif DEVD releases aminoluciferin, a substrate of luciferase, upon cleavage. Cells were harvested by pooling the culture supernatant containing non-adherent cells and trypsinized adherent COLO 205. Cells were passed through a cell strainer, pelleted by centrifugation for 5 minutes at 1,200 rpm and resuspended in culture medium at a concentration of $0.8 \times 10^5$ cells/mL. 25 µL of the single cell suspensions (2,000 cells per well) were seeded in 384-wells culture plates (Perkin Elmer, Cat nr 6007680) and incubated for 16 hours at 37° C. 25 µL antibody sample was added (1 µg antibody final concentration) and incubated for 1, 2, 5 and 24 hours at 37° C. Plates were removed from the incubator to let the temperature decrease till room temperature. Cells were pelleted by centrifugation for three minutes at 300 g. 25 µL supernatant was removed and replaced by 25 µL Caspase-Glo 3/7 Substrate. After mixing by shaking for one minute at 500 rpm, the plates were incubated for one hour at room temperature. Luminescence was measured on an EnVision Multilabel Reader (PerkinElmer).

FIG. 19 shows that in the time course of 1, 2 to 5 hours, caspase-3/7 activation was induced by the antibody combinations IgG1-DR5-01-K409R-E430G+IgG1-DR5-05-F405L-E430G and IgG1-DR5-01-K409R+IgG1-DR5-05-F405L, and for the bispecific DR5 antibody BsAb IgG1-DR5-01-K409R-E430G×DR5-05-F405L-E430G. After 24 hours, caspase-3/7 activation was almost reduced to baseline levels for all tested DR5 antibodies. After 1 hour, caspase-3/7 activation was already observed in cells that had been treated with the combination IgG1-DR5-01-K409R-E430G+IgG1-DR5-05-F405L-E430G, whereas no caspase-3/7 activation was observed in cells that had been treated with the combination of IgG1-DR5-01-K409R+IgG1-DR5-05-F405L without the hexamerization-enhancing mutation.

Similarly, at 2 and 5 hours, the caspase-3/7 activation induced by the combination IgG1-DR5-01-K409R-E430G+IgG1-DR5-05-F405L-E430G was stronger than for the combination of IgG1-DR5-01-K409R+IgG1-DR5-05-F405L. These data indicate that the combination of chimeric DR5 antibodies with the hexamerization enhancing mutation IgG1-DR5-01-K409R-E430G+IgG1-DR5-05-F405L-E430G induced more rapid and more potent Caspase-3/7 activation than the combination of antibodies without the hexamerization enhancing mutation.

Example 21: The Potency of the Antibody Combination of Chimeric DR5-01 and DR5-05 with the E430G Hexamerization-Enhancing Mutation is Independent of the Presence of a Secondary Fc Crosslinker A viability assay was performed to compare the capacity of the antibody combination IgG1-DR5-01-K409R-E430G+IgG1-DR5-05-F405L-E430G in the absence and presence of secondary antibody crosslinker to induce killing of COLO 205 colorectal and BxPC-3 and PANC-1 pancreatic cancer cells. For comparison, two DR5 antibodies that are known to show enhanced killing in the presence of a secondary antibody crosslinker, IgG1-CONA and IgG1-chTRA8-F405L, were tested in the same settings. Cells were harvested by trypsinization and passed through a cell strainer. Cells were pelleted by centrifugation for 5 minutes at 1,200 rpm and resuspended in culture medium at a concentration of $0.5 \times 10^5$ cells/mL. 100 µL of the single cell suspensions (5,000 cells per well) were seeded in polystyrene 96-well flat-bottom plates (Greiner Bio-One, Cat nr 655182) and incubated overnight at 37° C. Supernatant of the adherent cells was replaced by 150 µL antibody sample (final concentration 10 µg/mL) in the absence or presence of F(ab')$_2$ fragments of a goat-anti-human IgG antibody (1/150; Jackson ImmunoResearch; Cat nr 109-006-098) and incubated for 3 days at 37° C. As a positive control for cell killing, cells were incubated with 5 µM staurosporine (Sigma Aldrich, Cat nr S6942). The viability of the cell cultures was determined in a CellTiter-Glo luminescent cell viability assay as described in Example 8. The antibody combination IgG1-DR5-01-K409R-E430G+IgG1-DR5-05-F405L-E430G induced significant killing compared to the negative control of COLO 205, BxPC-3 and PANC-1 cancer cells, both in presence or absence of an Fc crosslinker (FIG. 20). In contrast, DR5 antibodies IgG1-DR5-CONA and IgG1-DR5-chTRA8-F405L did not induce target cell killing in the absence of an Fc crosslinker. Fc crosslinking induced killing by IgG1-DR5-CONA and IgG1-DR5-chTRA8-F405L in COLO 205 and BxPC-3 cells, although with significantly lower potency than the antibody combination IgG1-DR5-01-K409R-E430G+IgG1-DR5-05-F405L-E430G in presence or absence of crosslinker. These data indicate that killing of COLO 205, BxPC-3 and PANC-1 cancer cells by the antibody combination IgG1-DR5-01-K409R-E430G+IgG1-DR5-05-F405L-E430G is independent of the presence of a secondary Fc crosslinker and that this crosslinker-independent killing is more efficient than for Fc-crosslinked IgG1-DR5-CONA and IgG1-DR5-chTRA8-F405L.

Example 22: Introduction of the K409R Mutation in IgG1-hDR5-01-430G and the F4051 Mutation in IgG1-hDR5-05-E430G has No Effect on the Potency of the Combination of Humanized Antibodies IgG1-hDR5-01-E430G+IgG1-hDR5-05-E430G In many of the experiments described in this application, the anti-DR5 antibodies IgG1-01 and IgG1-05 contain in the IgG Fc domain the K409R and F405L (EU numbering index) mutation, respectively. These mutations enable the generation of DR5 bispecific antibodies by Fab-arm-exchange reaction between IgG1-01-K409R and IgG1-05-F405L under controlled reducing conditions as described in WO2011/131746. Without Fab-arm exchange, human IgG1 antibodies bearing the K409R and F405L mutations are thought to show the same functional characteristics as wild type human IgG1 (Labrijn et al., Proc Natl Acad Sci USA. 2013 Mar. 26; 110(13):5145-50). Here we show that the presence of the K409R or F405L mutations has no effect on the capacity of the combination of the parental IgG1-01 and IgG1-05 antibodies to induce cell death in DR5-positive tumor cells in vitro. A viability assay was performed to compare the capacity of the combination of humanized antibodies IgG1-hDR5-01-K409R-E430G+IgG1-hDR5-05-F405L-E430G with the capacity of the combination of humanized antibodies IgG1-hDR5-01-E430G+IgG1-hDR5-05-E430G to induce killing of BxPC-3 pancreatic cancer cells. The viability assay on The BxPC-3 was performed as described in Example 11 with a serial diluted antibody series ranging from 0.001 to 20,000 ng/mL final concentrations in 4-fold dilutions. The BxPC-3 pancreatic cancer cell line showed similar viability curves after incubation with the combination of the humanized antibodies IgG1-hDR5-01-K409R-E430G+IgG1-hDR5-05-F405L-E430G as with the combination of the humanized antibodies IgG1-hDR5-01-E430G+IgG1-hDR5-05-E430G (FIG. 21). These data indicate that the K409R and F405L mutations had no effect on the potency of the combination of the humanized DR5-01 and DR5-05 antibodies with E430G hexamerization enhancing mutation.

Example 23: Chimeric Bispecific Antibody IgG1-DR5-01-K409R-E430G×DR5-05-F405L-E430G Induces Killing of DR5-Positive Tumor Cells A bispecific antibody targeting two different DR5 epitopes was generated by Fab-arm exchange between the chimeric antibodies IgG1-DR5-01-K409R-E430G and IgG1-DR5-05-F405L-E430G as described in Example 1. A viability assay was performed as described in Example 11 to test the capacity of 10 µg/mL of the chimeric BsAb IgG1-DR5-01-K409R-E430G×DR5-05-F405L-E430G to induce killing of cancer cells of different tissue origin (COLO 205 colorectal cancer, A375 skin cancer, SK-MES-1 lung cancer, B×PC-3 pancreatic cancer and SNU-5 gastric cancer cell lines). For all tested cell lines, the percentage viable cells was significantly lower when incubated with 10 µg/mL of the chimeric BsAb IgG1-DR5-01-K409R-E430G×DR5-05-F405L-E430G antibody compared to the non-target binding negative control antibody IgG1-b12 (FIG. 22). These data indicate that the bispecific anti-DR5×DR5' antibody with hexamerization-enhancing mutation E430G induced killing of cancer cells of different origin, including colon, pancreatic, gastric, lung and skin cancer, without the requirement of a secondary crosslinker.

Example 24: The Potency of the Chimeric BsAb IgG1-DR5-01-K409R-E430G×DR5-05-F4051-E430G is Independent of the Presence of a Secondary Fc Crosslinker A viability assay was performed to compare the potency of the chimeric BsAb IgG1-DR5-01-K409R-E430G×IgG1-DR5-05-F405L-E430G in the absence and presence of a secondary antibody crosslinker to induce killing of B×PC-3 pancreatic and COLO 205 colon cancer cells as described in Example 21. For comparison, two DR5 antibodies that are known to show enhanced killing in the presence of a secondary antibody crosslinker, IgG1-CONA and IgG1-chTRA8-F405L, were tested in the same setting. The chimeric BsAb IgG1-DR5-01-K409R-E430G×DR5-05-F405L-E430G showed significant killing compared to the negative control of COLO 205 and B×PC-3 cancer cells, both in presence or absence of an Fc crosslinker (FIG. 23). In contrast, DR5 antibodies IgG1-DR5-CONA and IgG1-DR5-chTRA8-F405L only induced killing in the presence of Fc crosslinker

Example 25: Cell Death Induction Upon Binding of the BsAb IgG1-DR5-01-K409R-E430G×DR5-05-F405L-E430G on COLO 205 Colon Cancer Cells, as Assessed by Annexin V/Propidium Iodide and Active Caspase-3 Staining The kinetics of cell death induction by 1 µg/mL BsAb IgG1-DR5-01-K409R-E430G×DR5-05-F405L-E430G on COLO 205 cells was analyzed by Annexin V/Propidium Iodide (PI) double staining and active caspase-3 staining as described in Example 19.

FIG. 24 shows that, after 5 hours of incubation, BsAb IgG1-DR5-01-K409R-E430G×DR5-05-F405L-E430G efficiently induced the early stages of cell death as indicated by an increase in the percentage of Annexin V-positive/PI-negative (A) and Active Caspase-3-positive cells (B), compared to the negative control antibody IgG1-b12. The percentage of Annexin V-positive/PI-negative and Active Caspase-3 positive cells was higher in cells that had been treated with BsAb IgG1-DR5-01-K409R-E430G×DR5-05-F405L-E430G compared to the bispecific antibody without the E430G mutation (BsAb IgG1-DR5-01-K409R×DR5-05-F405L) or any of the monospecific antibodies. At the 5 hour time point, the percentage of AnnexinV/PI double positive cells was comparable to background levels in all samples (C). After 24 hours incubation, the percentage of Annexin V/PI double-positive cells (D) was enhanced in samples treated with BsAb IgG1-DR5-01-K409R-E430G×DR5-05-F405L-E430G, indicating that the cells had entered the irreversible stages of cell death. Also at this stage, the effect of BsAb IgG1-DR5-01-K409R-E430G×DR5-05-F405L-E430G was stronger (larger increase in the percentage of Annexin V/PI double-positive cells (E) than in samples treated with the bispecific antibody without the E430G mutation (BsAb IgG1-DR5-01-K409R×DR5-05-F405L) or any of the monospecific antibodies. At the same time point, the percentage of Active Caspase 3 positive cells was highest in cells treated with BsAB IgG1-DR5-01-K409R-E430G×DR5-05-F405L-E430G.

These data indicate that BsAB IgG1-DR5-01-K409R-E430G×DR5-05-F405L-E430G induces both the early and late stages of cell death in COLO 205 colon cancer cells, and does so more effectively than the bispecific antibody without the E430G hexamerization enhancing mutation.

Example 26: In Vivo Efficacy of DR5-01 and DR5-05 Antibody Variants With and Without a Hexamerization-Enhancing Mutation in a Subcutaneous COLO 205 Colon Cancer Xenograft Model The in vivo anti-tumor efficacy of different anti-DR5 antibodies and the combination of DR5-01+DR5-05 antibodies with hexamerization enhancing mutation was evaluated in a subcutaneous model with COLO 205 human colon cancer cells. At day 0, cells were harvested by pooling the culture supernatant containing non-adherent cells and trypsinized adherent cells. $3 \times 10^6$ cells were injected in a volume of 200 µL PBS into the flank of 6-11 weeks old female SCID mice (C.B-17/IcrHan® Hsd-Prkdc$^{scid}$; Harlan). All experiments and animal handlings were approved by the local authorities, and were conducted according to all applicable international, national and local laws and guidelines. Tumor development was monitored at least twice per week by caliper (PLEXX) measurement as 0.52×(length)×(width)$^2$. Tumors were measured until an endpoint tumor volume of 1,500 mm$^3$, until tumors showed ulcerations, until serious clinical signs were observed, or until tumor growth blocked movements of the mouse. At day 6, the average tumor volume was ~200 mm$^3$ and the mice were sorted into groups with equal tumor size variance (Table 2 below). Mice were treated by intraperitoneal (i.p.) injection of 100 µg antibody in 200 µL PBS on day 6 and 13 (5 mg/kg per dose). To check for correct antibody administration, blood samples were obtained for IgG serum determination three days after the first dose. Three individual mice had no detectable human IgG plasma level and were excluded from statistical analysis (see Table 2 below). For the other mice, human antibody plasma concentrations were according to the expectations when assuming a 2-compartment model with Vcen=50 mL/kg, Vs=100 mL/kg and an elimination half-life of 11.6 days (data not shown). Tumors were measured until 16 weeks after tumor inoculation.

These data show that introduction of the E430G hexamerization-enhancing mutation in IgG1-DR5-05-F405L resulted in enhanced tumor inhibition in the subcutaneous COLO 205 colon cancer tumor model compared to IgG1-DR5-05-F405L without the hexamerization-enhancing mutation. Both DR5-01 and DR5-05 antibodies with hexamerization enhancing mutation (IgG1-DR5-01-K409R-E430G and IgG1-DR5-05-F405L-E430G), the bispecific

TABLE 2

Treatment groups and dosing

| # mice | # analyzed | Antibody | Total antibody dose | Dosing day after tumor inoculation |
|---|---|---|---|---|
| 8 | 7 | IgG1-DR5-01-K409R-E430G (50 µg) IgG1-DR5-05-F405L-E430G (50 µg) | 100 µg (5 mg/kg) | 6, 13 |
| 7 | 7 | IgG1-DR5-05-F405L (100 µg) | 100 µg (5 mg/kg) | 6, 13 |
| 8 | 8 | IgG1-DR5-01-K409R-E430G (100 µg) | 100 µg (5 mg/kg) | 6, 13 |
| 8 | 8 | IgG1-DR5-05-F405L-E430G (100 µg) | 100 µg (5 mg/kg) | 6, 13 |
| 8 | 8 | IgG1-CONA (100 µg) | 100 µg (5 mg/kg) | 6, 13 |
| 8 | 7 | BsAb DR5-01-K409R × DR5-05-F405L (100 µg) | 100 µg (5 mg/kg) | 6, 13 |
| 8 | 8 | BsAb DR5-01-K409R-E430G × DR5-05-F405L-E430G (100 µg) | 100 µg (5 mg/kg) | 6, 13 |
| 8 | 7 | IgG1-b12 (100 µg) | 100 µg (5 mg/kg) | 6, 13 |

FIG. 25A shows mean tumor volumes per treatment group in time. FIG. 25B represents mean tumor volumes on day 23 after tumor inoculation, when all groups were still intact. All anti-DR5 antibody samples inhibited tumor growth significantly compared to the negative control antibody IgG1-b12 (non-parametric ANOVA analysis (Kruskal-Wallis) followed by Dunn's multiple comparison test on day 23: $p<0.0001$). Complete tumor abrogation was observed for the combination of DR5-01+DR5-05 antibodies with hexamerization-enhancing mutation (IgG1-DR5-01-K409R-E430G+IgG1-DR5-05-F405L-E430G), for the bispecific antibodies with and without hexamerization-enhancing mutation (BsAb DR5-01-K409R×DR5-05-F405L and BsAb DR5-01-K409R-E430G×DR5-05-F405L-E430G), and for the anti-DR5 antibodies with hexamerization-enhancing mutation (IgG1-DR5-01-K409R-E430G and IgG1-DR5-05-F405L-E430G). IgG1-CONA and IgG1-DR5-05-F405L without hexamerization-enhancing mutation strongly inhibited tumor growth compared to IgG1-b12, but did not result in complete tumor abrogation.

FIG. 25C shows a Kaplan-Meier plot of tumor progression, with a cutoff set at a tumor volume>750 mm$^3$. Compared to mice treated with negative control antibody IgG1-b12, tumor outgrowth was significantly delayed in all groups treated with anti-DR5 antibodies (Mantel-Cox analysis at tumor size cut-off 750 mm$^3$: $p<0.001$). At the end of the study (day 112), the group of mice treated with the combination of DR5-01+DR5-05 antibodies with hexamerization enhancing mutation (IgG1-DR5-01-K409R-E430G+IgG1-DR5-05-F405L-E430G) showed significant less mice with tumor outgrowth than the conatumumab group (Fisher's exact contingency test $p<0.01$).

antibodies with and without hexamerization enhancing mutation (BsAb DR5-01-K409R×DR5-05-F405L and BsAb DR5-01-K409R-E430G×DR5-05-F405L-E430G) and the combination of antibodies with hexamerization-enhancing mutation (IgG1-DR5-01-K409R-E430G+IgG1-DR5-05-F405L-E430G) showed better tumor inhibition as IgG1-CONA and IgG1-DR5-05-F405L without hexamerization-enhancing mutation.

Example 27: In Vivo Efficacy of Different Doses of the Antibody Combination IgG1-DR5-01-K409R-E430G+IgG1-DR5-05-F405L-E430G in a Subcutaneous COLO 205 Colon Cancer Xenograft Model The in vivo anti-tumor efficacy of different doses IgG1-DR5-01-K409R-E430G+IgG1-DR5-05-F405L-E430G was evaluated and compared to an equivalent dosing of IgG1-CONA in the subcutaneous COLO 205 human colon cancer xenograft model. Tumor cell inoculation, mice handling, tumor outgrowth measurements and endpoint determination were performed as described in Example 26. At day 10, the average tumor volume was ~400 mm$^3$ and the mice were sorted into groups with equal tumor size variance (Table 3 below). Mice were treated by intravenous (i.v.) injection of 40 µg (2 mg/kg), 10 µg (0.5 mg/kg) or 2 µg (0.1 mg/kg) antibody in 100 µL PBS on day 10. Mice in the control group were treated with 40 µg (2 mg/kg) IgG1-b12. Tumors were measured until 17 weeks after tumor inoculation.

TABLE 3

Treatment groups and dosing

| # mice | Antibody | Total antibody dose | Dosing day after tumor inoculation |
|---|---|---|---|
| 8 | IgG1-DR5-01-K409R-E430G (20 µg) IgG1-DR5-05-F405L-E430G (20 µg) | 40 µg (2 mg/kg) | 10 |
| 8 | IgG1-DR5-01-K409R-E430G (5 µg) IgG1-DR5-05-F405L-E430G (5 µg) | 10 µg (0.5 mg/kg) | 10 |

TABLE 3-continued

Treatment groups and dosing

| # mice | Antibody | Total antibody dose | Dosing day after tumor inoculation |
|---|---|---|---|
| 8 | IgG1-DR5-01-K409R-E430G (1 μg) IgG1-DR5-05-F405L-E430G (1 μg) | 2 μg (0.1 mg/kg) | 10 |
| 8 | IgG1-CONA (40 μg) | 40 μg (2 mg/kg) | 10 |
| 8 | IgG1-CONA (10 μg) | 10 μg (0.5 mg/kg) | 10 |
| 8 | IgG1-CONA (0.1 μg) | 2 μg (0.1 mg/kg) | 10 |
| 8 | IgG1-b12 (40 μg) | 40 μg (2 mg/kg) | 10 |

FIG. 26A shows mean tumor volumes per treatment group. Treatment with a single dose of 0.5 mg/kg or 2 mg/kg of the antibody combination IgG1-DR5-01-K409R-E430G+IgG1-DR5-05-F405L-E430G resulted in complete tumor regression until the study was stopped on day 126. Treatment with 0.5 mg/kg and 2 mg/kg IgG1-CONA also induced tumor regression, but the regression was incomplete with recurring tumor outgrowth in all mice or almost all (7/8) mice, respectively. At 0.1 mg/kg, neither IgG1-CONA nor the combination of IgG1-DR5-01-K409R-E430G+IgG1-DR5-05-F405L-E430G showed anti-tumor activity. FIG. 26B shows that on day 16 after tumor inoculation, tumor inhibition by 2 mg/kg and 0.5 mg/kg IgG1-DR5-01-K409R-E430G+IgG1-DR5-05-F405L-E430G was significantly better compared to an equivalent dose IgG1-CONA (unpaired t-test).

FIG. 26C shows a Kaplan-Meier plot of tumor progression, with a cutoff set at a tumor volume>500 mm$^3$. At a dose of 0.5 mg/kg and 2 mg/kg, the combination IgG1-DR5-01-K409R-E430G+IgG1-DR5-05-F405L-E430G and IgG1-CONA significantly inhibited tumor growth progression compared to the negative control antibody IgG1-b12 (p<0.001 Mantel-Cox analysis at tumor size cut-off 500 mm$^3$). At a dose of 0.5 mg/kg inhibition of tumor growth progression was significantly better for the combination IgG1-DR5-01-K409R-E430G+IgG1-DR5-05-F405L-E430G to an equivalent dose IgG1-CONA.

These data indicate that the combination IgG1-DR5-01-K409R-E430G+IgG1-DR5-05-F405L-E430G had stronger anti-tumor efficacy compared to IgG1-CONA, since dosed at 2 mg/kg the combination IgG1-DR5-01-K409R-E430G+IgG1-DR5-05-F405L-E430G significantly reduced tumor load at day 16 compared to IgG1-CONA, and at 0.5 mg/kg the IgG1-DR5-01-K409R-E430G+IgG1-DR5-05-F405L-E430G combination significantly reduced tumor load at day 16 and prolonged progression free survival time (tumor size cut-off 500 mm$^3$) compared to IgG1-CONA.

Example 28: In Vivo Efficacy of Different Doses of the Antibody Combination IgG1-DR5-01-K409R-E430G+IgG1-DR5-05-F405L-E430G in a Subcutaneous BxPC-3 Pancreatic Cancer Xenograft Model The in vivo anti-tumor efficacy of different doses IgG1-DR5-01-K409R-E430G+IgG1-DR5-05-F405L-E430G was evaluated and compared to an equivalent dosing of IgG1-CONA-F405L in the subcutaneous BxPC-3 human pancreatic cancer xenograft model. At day 0, adherent cells were harvested by trypsinization. 5×10$^6$ cells were injected in a volume of 100 μL PBS into the flank of 6-11 weeks old female SCID mice (C.B-17/IcrHan® Hsd-Prkdc$^{scid}$; Harlan). Mice handling, tumor outgrowth measurements and endpoint determination were performed as described in Example 26. At day 10, the average tumor volume was ~250 mm$^3$ and the mice were sorted into groups with equal tumor size variance (Table 4 below). Mice were treated by i.v. injection of 200 μg (10 mg/kg), 40 μg (2 mg/kg) or 10 μg (0.5 mg/kg) antibody in 200 μL PBS on day 20 and 28. Mice in the control group were treated with 200 μg (10 mg/kg) IgG1-b12. To check for correct antibody administration, blood samples were obtained for IgG serum determination one week after dosing. Tumors were measured until 10 weeks after tumor inoculation.

TABLE 4

Treatment groups and dosing

| # mice | Antibody | Total antibody per dose | Dosing day after tumor inoculation |
|---|---|---|---|
| 8 | IgG1-DR5-01-K409R-E430G (20 μg) IgG1-DR5-05-F405L-E430G (20 μg) | 200 μg (10 mg/kg) | 20, 28 |
| 8 | IgG1-DR5-01-K409R-E430G (5 μg) IgG1-DR5-05-F405L-E430G (5 μg) | 40 μg (2 mg/kg) | 20, 28 |
| 8 | IgG1-DR5-01-K409R-E430G (1 μg) IgG1-DR5-05-F405L-E430G (1 μg) | 10 μg (0.5 mg/kg) | 20, 28 |
| 8 | IgG1-CONA-F405L (40 μg) | 200 μg (10 mg/kg) | 20, 28 |
| 8 | IgG1-CONA-F405L (10 μg) | 40 μg (2 mg/kg) | 20, 28 |
| 8 | IgG1-CONA-F405L (0.1 μg) | 10 μg (0.5 mg/kg) | 20, 28 |
| 8 | IgG1-b12 (40 μg) | 200 μg (10 mg/kg) | 20, 28 |

FIG. 27A shows median tumor volumes per treatment group. All tested doses of the antibody combination IgG1-DR5-01-K409R-E430G+IgG1-DR5-05-F405L-E430G inhibited tumor growth compared to the negative control antibody IgG1-b12, whereas the IgG1-CONA-F405L treatment groups did not. FIG. 27B shows that on day 48 after tumor inoculation, tumor growth inhibition by the combination of IgG1-DR5-01-K409R-E430G+IgG1-DR5-05-F405L-E430G was significantly better than equivalent doses IgG1-CONA-F405L (unpaired t-test, p<0.05).

FIG. 27C shows a Kaplan-Meier plot of tumor progression, with a cutoff set at a tumor volume>500 mm$^3$. The combination IgG1-DR5-01-K409R-E430G+IgG1-DR5-05-F405L-E430G significantly inhibited tumor growth progression compared to the negative control antibody IgG1-b12 and compared to IgG1-CONA-F405L (Mantel-Cox analysis at tumor size cutoff 500 mm$^3$: p<0.001).

These data indicate that the combination IgG1-DR5-01-K409R-E430G+IgG1-DR5-05-F405L-E430G inhibited tumor growth at different doses (0.5 mg/kg, 2 mg/kg and 10 mg/kg) and that anti-tumor efficacy was significantly better than for equivalent doses of IgG1-CONA-F405L in an in vivo BxPC-3 human pancreatic cancer xenograft model.

Example 29: In Vivo Efficacy of Different Doses of the Antibody Combination IgG1-DR5-01-K409R-E430G+IgG1-DR5-05-F405L-E430G in a Subcutaneous A375 Skin Cancer Xenograft Model The in vivo anti-tumor efficacy of different doses IgG1-DR5-01-K409R-E430G+IgG1-DR5-05-F405L-E430G was evaluated and compared to an equivalent dosing of IgG1-CONA-F405L in the subcutaneous A375 human skin cancer xenograft model. At day 0, adherent cells were harvested by trypsinization. 5×10$^6$ cells were injected in a volume of 100 µL PBS into the flank of 6-11 weeks old female SCID mice (C.B-17/IcrHan® Hsd-Prkdc$^{scid}$; Harlan). Mice handling, tumor outgrowth measurements and endpoint determination were performed as described in Example 26. At day 19, the average tumor volume was ~250 mm$^3$ and the mice were sorted into groups with equal tumor size variance (Table 5 below). Mice were treated by i.v. injection of 200 µg (10 mg/kg), 40 µg (2 mg/kg) or 10 µg (0.5 mg/kg) antibody in 200 µL PBS on day 19 and 26. Mice in the control group were treated with 200 µg (10 mg/kg) IgG1-b12. To check for correct antibody administration, blood samples were obtained for IgG serum determination one week after dosing. Tumor volumes were analyzed until 7 weeks after tumor inoculation.

treated with IgG1-b12 (p<0.05 for all dose levels, One-Way ANOVA with Dunnet's correction for multiple comparisons), and that the combination of IgG1-DR5-01-K409R-E430G+IgG1-DR5-05-F405L-E430G was significantly more potent than IgG1-CONA-F405L (Mann Whitney test, p<0.05) at equivalent doses These data indicate that the combination IgG1-DR5-01-K409R-E430G+IgG1-DR5-05-F405L-E430G inhibited tumor growth at different doses (0.5 mg/kg, 2 mg/kg and 10 mg/kg) and that anti-tumor efficacy was significantly better than for equivalent doses of IgG1-CONA-F405L in an in vivo A375 human skin cancer xenograft model.

Example 30: In Vivo Efficacy of Different Doses of the Antibody Combination IgG1-DR5-01-K409R-E430G+IgG1-DR5-05-F405L-E430G in a Subcutaneous HCT-15 Colon Cancer Xenograft Model The in vivo anti-tumor efficacy of different doses IgG1-DR5-01-K409R-E430G+IgG1-DR5-05-F405L-E430G was evaluated and compared to an equivalent dosing of IgG1-CONA in the subcutaneous HCT-15 human colon cancer xenograft model at CrownBiosciences, Taicang, China. The cells were maintained in vitro as a monolayer culture in RPMI-1640 medium supplemented with 10% fetal bovine serum at 37° C. in an atmosphere of 5% CO2 in air. Adherent cells in an exponential growth phase were harvested by trypsin-EDTA treatment. 5×10$^6$ cells were injected in a volume of 100 µL PBS into the flank of 6-8 weeks old female BALB/c nude mice (Shanghai Laboratory Animal Center). The care and use of animals during the study were conducted in accordance with the regulations of the Association for Assessment and Accreditation of Laboratory Animal Care (AAALAC). Tumor volumes were measured twice weekly in two dimensions using a caliper, and the volume was expressed in mm$^3$ using the formula: V=0.5 a×b2 where a and b are the long and short diameters of the tumor, respectively. Eleven days after tumor inoculation, the

TABLE 5

Treatment groups and dosing

| # mice | Antibody | Total antibody dose | Dosing day after tumor inoculation |
|---|---|---|---|
| 8 | IgG1-DR5-01-K409R-E430G (20 µg) IgG1-DR5-05-F405L-E430G (20 µg) | 200 µg (10 mg/kg) | 19, 26 |
| 8 | IgG1-DR5-01-K409R-E430G (5 µg) IgG1-DR5-05-F405L-E430G (5 µg) | 40 µg (2 mg/kg) | 19, 26 |
| 8 | IgG1-DR5-01-K409R-E430G (1 µg) IgG1-DR5-05-F405L-E430G (1 µg) | 10 µg (0.5 mg/kg) | 19, 26 |
| 8 | IgG1-CONA-F405L (40 µg) | 200 µg (10 mg/kg) | 19, 26 |
| 8 | IgG1-CONA-F405L (10 µg) | 40 µg (2 mg/kg) | 19, 26 |
| 8 | IgG1-CONA-F405L (0.1 µg) | 10 µg (0.5 mg/kg) | 19, 26 |
| 8 | IgG1-b12 (40 µg) | 200 µg (10 mg/kg) | 19, 26 |

FIG. 28A shows median tumor volumes per treatment group. All tested doses of the antibody combination IgG1-DR5-01-K409R-E430G+IgG1-DR5-05-F405L-E430G inhibited tumor growth compared to the negative control antibody IgG1-b12, whereas the IgG1-CONA-F405L treatment groups did not. FIG. 28B shows that on day 29 after tumor inoculation, the average tumor size in mice treated with the combination of IgG1-DR5-01-K409R-E430G+IgG1-DR5-05-F405L-E430G was smaller than in mice mean tumor size reached 186 mm$^3$ and mice were assigned into groups using randomized block design and treatments were started. Mice were treated twice according to a Q7D regimen by i.v. injection of 200 µg (10 mg/kg), 40 µg (2 mg/kg) or 10 µg (0.5 mg/kg) antibody in 10 µL PBS per g body weight. Mice in the control group were treated in parallel with 200 µg (10 mg/kg) IgG1-b12. After tumor inoculation, welfare of the animals was checked daily and tumor volumes were measured twice weekly.

TABLE 6

Treatment groups and dosing, Example 30

| # mice | # analyzed | Antibody | Total antibody dose | Dosing day after tumor inoculation |
|---|---|---|---|---|
| 8 | 8 | IgG1-DR5-01-K409R-E430G (20 μg) IgG1-DR5-05-F405L-E430G (20 μg) | 200 μg (10 mg/kg) | 11, 18 |
| 8 | 8 | IgG1-DR5-01-K409R-E430G (5 μg) IgG1-DR5-05-F405L-E430G (5 μg) | 40 μg (2 mg/kg) | 11, 18 |
| 8 | 8 | IgG1-DR5-01-K409R-E430G (1 μg) IgG1-DR5-05-F405L-E430G (1 μg) | 10 μg (0.5 mg/kg) | 11, 18 |
| 8 | 8 | IgG1-CONA (40 μg) | 200 μg (10 mg/kg) | 11, 18 |
| 8 | 8 | IgG1-CONA (10 μg) | 40 μg (2 mg/kg) | 11, 18 |
| 8 | 8 | IgG1-CONA (0.1 μg) | 10 μg (0.5 mg/kg) | 11, 18 |
| 8 | 8 | IgG1-b12 (40 μg) | 200 μg (10 mg/kg) | 11, 18 |

FIG. 29A shows mean tumor volumes per treatment group. All tested doses of the antibody combination IgG1-DR5-01-K409R-E430G+IgG1-DR5-05-F405L-E430G inhibited tumor growth compared to the negative control antibody IgG1-b12, whereas IgG1-CONA did not. FIG. 29B shows that on day 17 after start of treatment, tumor growth inhibition by the combination of IgG1-DR5-01-K409R-E430G+IgG1-DR5-05-F405L-E430G was significantly better than equivalent doses IgG1-CONA (Unpaired t test, $p<0.05$).

FIG. 29C shows a Kaplan-Meier plot of tumor progression, with a cutoff set at a tumor volume >500 mm$^3$. The combination IgG1-DR5-01-K409R-E430G+IgG1-DR5-05-F405L-E430G significantly inhibited tumor growth progression compared to negative control antibody IgG1-b12 and compared to an equivalent dose IgG1-CONA (Mantel-Cox analysis at tumor size cutoff 500 mm$^3$: $p<0.001$).

These data indicate that the combination IgG1-DR5-01-K409R-E430G+IgG1-DR5-05-F405L-E430G inhibited tumor growth at different doses (0.5 mg/kg, 2 mg/kg and 10 mg/kg) and that anti-tumor efficacy was significantly better than for equivalent doses of IgG1-CONA in an in vivo xenograft model with HCT-15 human colon cancer cells.

Example 31: In Vivo Efficacy of Different Doses of the Antibody Combination IgG1-DR5-01-K409R-E430G+IgG1-DR5-05-F405L-E430G in a Subcutaneous SW480 Colon Cancer Xenograft Model The in vivo anti-tumor efficacy of different doses IgG1-DR5-01-K409R-E430G+IgG1-DR5-05-F405L-E430G was evaluated and compared to an equivalent dosing of IgG1-CONA in the subcutaneous SW480 human colon cancer xenograft model at CrownBiosciences, Taicang, China. The cells were maintained in vitro as a monolayer culture in L-15 medium supplemented with 10% fetal bovine serum at 37° C. in 100% air. Adherent cells in an exponential growth phase were harvested by trypsin-EDTA treatment. $1 \times 10^7$ cells were injected in a volume of 200 μL PBS with Matrigel (1:1) into the flank of 6-8 weeks old female NOD/SCID mice (Beijing HFK Bioscience). Mouse handling and tumor volume measurements were performed as described in Example 30. Ten days after tumor inoculation, the mean tumor size reached 175 mm$^3$ and mice were assigned into groups using randomized block design and treatments were started. Mice were treated twice according to a Q7D regimen by i.v. injection of 200 μg (10 mg/kg), 40 μg (2 mg/kg) or 10 μg (0.5 mg/kg) antibody in 10 μL PBS per g body weight. Mice in the control group were treated in parallel with 200 μg (10 mg/kg) IgG1-b12. After tumor inoculation, welfare of the animals was checked daily and tumor volumes were measured twice weekly.

TABLE 7

Treatment groups and dosing, Example 31

| # mice | # analyzed | Antibody | Total antibody per dose | Dosing day after tumor inoculation |
|---|---|---|---|---|
| 8 | 8 | IgG1-DR5-01-K409R-E430G (20 μg) IgG1-DR5-05-F405L-E430G (20 μg) | 200 μg (10 mg/kg) | 10, 17 |
| 8 | 8 | IgG1-DR5-01-K409R-E430G (5 μg) IgG1-DR5-05-F405L-E430G (5 μg) | 40 μg (2 mg/kg) | 10, 17 |
| 8 | 8 | IgG1-DR5-01-K409R-E430G (1 μg) IgG1-DR5-05-F405L-E430G (1 μg) | 10 μg (0.5 mg/kg) | 10, 17 |
| 8 | 8 | IgG1-CONA (40 μg) | 200 μg (10 mg/kg) | 10, 17 |
| 8 | 8 | IgG1-CONA (10 μg) | 40 μg (2 mg/kg) | 10, 17 |
| 8 | 8 | IgG1-CONA (0.1 μg) | 10 μg (0.5 mg/kg) | 10, 17 |
| 8 | 8 | IgG1-b12 (40 μg) | 200 μg (10 mg/kg) | 10, 17 |

FIG. 30A shows mean tumor volumes per treatment group. All tested doses of the antibody combination IgG1-DR5-01-K409R-E430G+IgG1-DR5-05-F405L-E430G inhibited tumor growth compared to the negative control antibody IgG1-b12 (10 mg/kg $p<0.0001$; 2 mg/kg $p<0.001$; 0.5 mg/kg $p<0.05$). The IgG1-CONA treatment groups were only better than IgG1-b12 at the highest doses (10 mg/kg and 2 mg/kg $p<0.01$), but not at 0.5 mg/kg. FIG. 30B shows that on day 28 after start treatment, tumor growth inhibition by the combination of IgG1-DR5-01-K409R-E430G+IgG1-DR5-05-F405L-E430G was significantly better than equivalent doses IgG1-CONA at 10 mg/kg and 0.5 mg/kg (Unpaired t test, $p<0.05$).

FIG. 30C shows a Kaplan-Meier plot of tumor progression, with a cutoff set at a tumor volume>500 mm$^3$. The combination IgG1-DR5-01-K409R-E430G+IgG1-DR5-05-F405L-E430G dosed at 10 mg/kg significantly inhibited tumor growth progression compared to negative control antibody IgG1-b12 and compared to an equivalent dose IgG1-CONA (Mantel-Cox analysis at tumor size cutoff 500 mm$^3$: p<0.001.

These data indicate that the combination IgG1-DR5-01-K409R-E430G+IgG1-DR5-05-F405L-E430G inhibited tumor growth at different doses (0.5 mg/kg, 2 mg/kg and 10 mg/kg) and that anti-tumor efficacy for doses of 10 mg/kg and 0.5 mg/kg was significantly better than for equivalent doses of IgG1-CONA in an in vivo SW480 human colon cancer xenograft model.

Example 32: In Vivo Efficacy of Different Doses of the Antibody Combination IgG1-DR5-01-K409R-E430G+IgG1-DR5-05-F405L-E430G in a Subcutaneous SNU-5 Gastric Cancer Xenograft Model The in vivo anti-tumor efficacy of different doses IgG1-DR5-01-K409R-E430G+IgG1-DR5-05-F405L-E430G were evaluated and compared to an equivalent dosing of IgG1-CONA in the subcutaneous SNU-5 human gastric cancer xenograft model at CrownBiosciences, Taicang, China. The cells were maintained in vitro as a suspension culture in IMDM medium supplemented with 20% fetal bovine serum at 37° C. in an atmosphere of 5% CO2 in air. Cells in an exponential growth phase were harvested and 1×10$^7$ cells were injected in a volume of 200 μL PBS with Matrigel (1:1) into the flank of 6-8 weeks old female CB17/SCIDmice (Beijing HFK Bioscience). Mouse handling and tumor volume measurements were performed as described in Example 30. Eight days after tumor inoculation, the mean tumor size reached 169 mm$^3$ and mice were assigned into groups using randomized block design and treatments were started. Mice were treated twice according to a Q7D regimen by i.v. injection of 200 μg (10 mg/kg), 40 μg (2 mg/kg) or 10 μg (0.5 mg/kg) antibody in 10 μL PBS per g body weight. Mice in the control group were treated in parallel with 200 μg (10 mg/kg) IgG1-b12. After tumor inoculation, welfare of the animals was checked daily and tumor volumes were measured twice weekly.

FIG. 31A shows mean tumor volumes per treatment group. All tested doses of the antibody combination IgG1-DR5-01-K409R-E430G+IgG1-DR5-05-F405L-E430G inhibited tumor growth compared to the negative control antibody IgG1-b12. At the 2 mg/kg and 10 mg/kg doses, the antibody combination IgG1-DR5-01-K409R-E430G+IgG1-DR5-05-F405L-E430G resulted in complete tumor regression that lasted over the complete study time (7 weeks after start treatment). FIG. 31B shows that on day 23 after start treatment, tumor growth inhibition by the combination of IgG1-DR5-01-K409R-E430G+IgG1-DR5-05-F405L-E430G was significant better than equivalent doses IgG1-CONA (Mann Whitney test, p<0.05).

FIG. 31C shows a Kaplan-Meier plot of tumor progression, with a cutoff set at a tumor volume>500 mm$^3$. The combination IgG1-DR5-01-K409R-E430G+IgG1-DR5-05-F405L-E430G significantly inhibited tumor growth progression compared to negative control antibody IgG1-b12 and compared to an equivalent dose IgG1-CONA (Mantel-Cox analysis at tumor size cutoff 500 mm$^3$: p<0.05).

These data indicate that the combination IgG1-DR5-01-K409R-E430G+IgG1-DR5-05-F405L-E430G inhibited tumor growth at different doses (0.5 mg/kg, 2 mg/kg and 10 mg/kg) and that anti-tumor efficacy was significantly better than for equivalent doses of IgG1-CONA in an in vivo SNU-5 human gastric cancer xenograft model.

Example 33: In Vivo Efficacy of Different Doses of the Antibody Combination IgG1-DR5-01-K409R-E430G+IgG1-DR5-05-F405L-E430G in a Subcutaneous SK-MES-1 Lung Cancer Xenograft Model The in vivo anti-tumor efficacy of different doses IgG1-DR5-01-K409R-E430G+IgG1-DR5-05-F405L-E430G was evaluated and compared to an equivalent dosing of IgG1-CONA in the subcutaneous SK-MES-1 human lung cancer xenograft model at CrownBiosciences, Taicang, China. The cells were maintained in vitro as a monolayer culture in MEM medium supplemented with 10% fetal bovine serum and 0.01 mM NEAA at 37° C. in an atmosphere of 5% CO2 in air. At day 0, adherent cells in an exponential growth phase were harvested by trypsin-EDTA treatment. 5×10$^6$ cells were injected in a volume of 100 μL PBS into the flank of 6-8 weeks old female BALB/c mice (Shanghai Laboratory Animal Center). Mouse handling and tumor volume measurements were performed as described in Example 30. Twenty-one days after tumor inoculation, the mean tumor size reached 161 mm$^3$ and mice were assigned into groups using randomized block design and treatments were started. Mice were treated twice according to a Q7D regimen by i.v. injection of 200 μg (10 mg/kg), 40 μg (2 mg/kg) or 10 μg (0.5 mg/kg) antibody in 10 μL PBS per g body weight. Mice in the control group were treated in parallel with 200 μg (10 mg/kg) IgG1-b12. After tumor inoculation, welfare of the animals was checked daily and tumor volumes were measured twice weekly.

TABLE 8

Treatment groups and dosing, Example 32

| # mice | # analyzed | Antibody | Total antibody per dose | Dosing day after tumor inoculation |
|---|---|---|---|---|
| 8 | 8 | IgG1-DR5-01-K409R-E430G (20 μg) IgG1-DR5-05-F405L-E430G (20 μg) | 200 μg (10 mg/kg) | 8, 15 |
| 8 | 8 | IgG1-DR5-01-K409R-E430G (5 μg) IgG1-DR5-05-F405L-E430G (5 μg) | 40 μg (2 mg/kg) | 8, 15 |
| 8 | 8 | IgG1-DR5-01-K409R-E430G (1 μg) IgG1-DR5-05-F405L-E430G (1 μg) | 10 μg (0.5 mg/kg) | 8, 15 |
| 8 | 8 | IgG1-CONA (40 μg) | 200 μg (10 mg/kg) | 8, 15 |
| 8 | 8 | IgG1-CONA (10 μg) | 40 μg (2 mg/kg) | 8, 15 |
| 8 | 8 | IgG1-CONA (0.1 μg) | 10 μg (0.5 mg/kg) | 8, 15 |
| 8 | 8 | IgG1-b12 (40 μg) | 200 μg (10 mg/kg) | 8, 15 |

TABLE 9

Treatment groups and dosing, Example 33

| # mice | Antibody | Total antibody per dose | Dosing day after tumor inoculation |
|---|---|---|---|
| 8 | IgG1-DR5-01-K409R-E430G (20 µg) IgG1-DR5-05-F405L-E430G (20 µg) | 200 µg (10 mg/kg) | 21, 28 |
| 8 | IgG1-DR5-01-K409R-E430G (5 µg) IgG1-DR5-05-F405L-E430G (5 µg) | 40 µg (2 mg/kg) | 21, 28 |
| 8 | IgG1-DR5-01-K409R-E430G (1 µg) IgG1-DR5-05-F405L-E430G (1 µg) | 10 µg (0.5 mg/kg) | 21, 28 |
| 8 | IgG1-CONA (40 µg) | 200 µg (10 mg/kg) | 21, 28 |
| 8 | IgG1-CONA (10 µg) | 40 µg (2 mg/kg) | 21, 28 |
| 8 | IgG1-CONA (0.1 µg) | 10 µg (0.5 mg/kg) | 21, 28 |
| 8 | IgG1-b12 (40 µg) | 200 µg (10 mg/kg) | 21, 28 |

FIG. 32A shows mean tumor volumes per treatment group. All tested doses of the antibody combination IgG1-DR5-01-K409R-E430G+IgG1-DR5-05-F405L-E430G inhibited tumor growth significantly compared to the negative control antibody IgG1-b12 (p<0.0001), whereas IgG1-CONA only had a significant effect compared to IgG1-b12 at 10 mg/kg (p<0.01) and 2 mg/kg (p<0.05) but not at 0.5 mg/kg (one-way ANOVA followed by Dunnett's multiple comparisons test). FIG. 32B shows that on day 14 after start treatment, tumor growth inhibition by the combination of IgG1-DR5-01-K409R-E430G+IgG1-DR5-05-F405L-E430G was significant better than equivalent doses IgG1-CONA at 2 mg/kg and 0.5 mg/kg (unpaired t-test test, p<0.05 and p<0.01, respectively).

FIG. 32C shows a Kaplan-Meier plot of tumor progression, with a cutoff set at a tumor volume>1.000 mm$^3$. The combination IgG1-DR5-01-K409R-E430G+IgG1-DR5-05-F405L-E430G significantly inhibited tumor growth progression compared to negative control antibody IgG1-b12 (Mantel-Cox analysis at tumor size cutoff 1.000 mm$^3$: p≤0.001) and compared to an equivalent dose IgG1-CONA at 2 mg/kg and 0.5 mg/kg (Mantel-Cox analysis at tumor size cutoff 1.000 mm$^3$: p<0.05).

These data indicate that the combination IgG1-DR5-01-K409R-E430G+IgG1-DR5-05-F405L-E430G inhibited tumor growth at different doses (0.5 mg/kg, 2 mg/kg and 10 mg/kg) and that anti-tumor efficacy was significantly better than for equivalent doses of IgG1-CONA at 0.5 mg/kg and 2 mg/kg in an in vivo SK-MES-1 human lung cancer xenograft model.

Example 34: DR5 Expression Levels on Different Human Cancer Cell Lines

DR5 density per cell was quantified for different human cancer cell lines by indirect immunofluorescence using QIFIKIT with mouse monoclonal antibody B-K29 as described in Example 2. The cell lines were categorized according to low DR5 expression (ABC<10,000) and moderate DR5 expression (ABC>10,000). The human cancer cell lines SK-MEL-5 (ATCC, HTB-070) malignant melanoma, Jurkat (ATCC, TIB-152) acute T cell leukemia and Daudi (ATCC, CCL-231) Burkitt's lymphoma were found to have low DR5 expression (QIFIKIT ABC range 3,500-6,500). The human colorectal carcinoma cell lines SNU-C2B (ATCC, CCL-250), LS411N (ATCC, CRL-2159) and DLD-1 (ATCC, CCL-221) were found to have moderate DR5 expression (QIFIKIT ABC range 12,000-44,500).

Example 35: Introduction of a Hexamerization-Enhancing Mutation Does Not Affect Binding of IgG1-hDR5-01-G56T and IgG1-hDR5-05 Antibodies to DR5-Positive Human Colon Cancer Cells Binding to human colon cancer cells HCT 116 was analyzed by flow cytometry for purified antibody variants of IgG1-hDR5-01-G56T and IgG1-hDR5-05 with and without the E430G mutation. Single cell suspensions were prepared and binding was analyzed for serial dilution antibody preparation series (range 0.0006 to 10 µg/mL final concentrations in 4-fold dilutions) as described in Example 3. After incubation with the secondary antibody, cells were washed twice, resuspended in 100 µL FACS buffer, and antibody binding was analyzed on a BD LRSFFortessa cell analyzer (BD Biosciences). Binding curves were analyzed using non-linear regression analysis (sigmoidal dose-response with variable slope) using GraphPad Prism software.

FIG. 33 shows that the antibodies IgG1-hDR5-01-G56T-E430G and IgG1-hDR5-05-E430G showed similar dose-dependent binding to HCT 116 cells as their corresponding antibodies without the E430G mutation. Introduction of the E430G mutation had no effect on the binding of the DR5 antibodies. The EC50 values were calculated from six repeat experiments as 74.4 (+/−58.4) ng/mL for IgG1-hDR5-01-G56T-E430G and 101.2 (+/−52.6) ng/mL for IgG1-hDR5-05-E430G.

Example 36: Binding of IgG1-hDR5-01-G56T-E430G and IgG1-hDR5-05-E430G as Single Antibodies and as a Combination to DR5-Positive Human Cancer Cells Antibody binding to HCT 116 human cancer cells with moderate DR5 expression was analyzed by flow cytometry for purified samples of Alexa 647-labeled IgG1-hDR5-01-G56T-E430G and Alexa 647-labeled IgG1-hDR5-05-E430G, both as single agents and as a combination of the two antibodies. 1 mg/mL IgG1-hDR5-01-G56T-E430G and IgG1-hDR5-05-E430G were labeled for 1 hour at room temperature with a 5 molar excess of Alexa Fluor® 647 carboxylic acid, succinimidyl ester (Molecular Probes; Cat #A-20006) in 0.1 M NaHCO$_3$ conjugation buffer to reach a degree of labeling of three. Free excess Alexa 647 was removed on a PD 10 Column (Amersham Bioscience, Cat #17-0851-01). Single cell suspensions were prepared and binding was analyzed for serial dilution antibody preparation series (range 0.0019 to 30 µg/mL final concentrations in 5-fold dilutions) as described in Example 3. After antibody incubation, cells were washed twice, resuspended in 100 µL FACS buffer, and antibody binding was analyzed on a BD LRSFFortessa cell analyzer (BD Biosciences). Binding curves were analyzed using non-linear regression analysis (sigmoidal dose-response with variable slope) using GraphPad Prism software.

FIG. 35 shows that the antibodies IgG1-hDR5-01-G56T-E430G and IgG1-hDR5-05-E430G showed dose-dependent binding to human and cynomolgus DR5 expressed on CHO cells. For both IgG1-hDR5-01-G56T-E430G and IgG1-hDR5-05-E430G, $EC_{50}$ values for binding to human DR5 and cynomolgus DR5 were in the same range based on four repeat experiments (Table 10).

TABLE 10

EC50 values for binding of IgG1-hDR5-01-G56T-E430G and IgG1-hDR5-05-E430G to human and cynomolgus DR5. Based on four experiments.

|  | Human DR5-transfected CHO | | Cynomolgus DR5-transfected CHO | |
| --- | --- | --- | --- | --- |
|  | $EC_{50}$ (µg/mL) | SD | $EC_{50}$ (µg/mL) | SD |
| IgG1-hDR5-01-G56T-E430G | 0.13 | 0.034 | 0.27 | 0.175 |
| IgG1-hDR5-05-E430G | 0.12 | 0.027 | 0.17 | 0.084 | curves were analyzed using non-linear regression analysis (sigmoidal dose-response with variable slope) using GraphPad Prism software.

FIG. 34 shows that both the single antibodies and the combination of the non-crossblocking antibodies IgG1-hDR5-01-G56T-E430G and IgG1-hDR5-05-E430G showed dose-dependent binding on HCT 116 human cancer cells.

Example 37: Binding of Antibodies IgG1-hDR5-01-G56T-E430G and IgG1-hDR5-05-E430G to Cynomolgus Monkey DR5

Binding of purified IgG1-hDR5-01-G56T-E430G and IgG1-hDR5-05-E430G to CHO cells expressing the isoform short of human DR5 or cynomolgus monkey DR5 was analyzed by flow cytometry. Codon-optimized constructs for expression of the isoform short human DR5 protein with death domain loss-of-function mutation K386N (SEQ ID NO 47 based on Uniprot number O14763-2) and cynomolgus monkey DR5 protein with deletion of amino acids 185-213 and death domain loss-of-function mutation K420N (SEQ ID NO 50; based on NCBI accession number XP_005562887.1) were generated as described in Example 1. Binding to DR5-transfected CHO cells was analyzed, generally as described in Example 5. Transfected cells were stored in liquid nitrogen and quickly thawed at 37° C. and suspended in 10 mL medium. Cells were washed with PBS and resuspended in FACS buffer at a concentration of $1.0 \times 10^6$ cells/mL. 100 µL cell suspension samples (100,000 cells per well) were seeded in 96-well plates and pelleted by centrifugation at 300×g for 3 minutes at 4° C. 25 µL of serial dilution antibody preparation series (final concentrations 0 to 20 µg/mL in 6-fold dilutions) was added and incubated for 30 minutes at 4° C. Next, cells were washed and incubated with 50 µL secondary antibody R-PE-conjugated goat-anti-human IgG F(ab')$_2$ (Jackson ImmunoResearch; Cat nr 109-116-098; 1/100) for 30 minutes at 4° C. protected from light. Cells were washed twice with 150 µL FACS buffer, resuspended in 50 µL FACS buffer, and antibody binding was analyzed on a BD LRSFFortessa cell analyzer (BD Biosciences) by recording 10,000 events. Binding curves were Example 38: Introduction of the E430G Mutation Improves the Efficacy of Cell Death Induction by the Combination of Non-Crossblocking Antibodies IgG1-hDR5-01-G56T+IgG1-hDR5-05

A viability assay was performed to study the effect the hexamerization-enhancing mutation E430G in IgG1-hDR5-01-G56T and IgG1-hDR5-05 on the capacity of the antibodies to kill human colon cancer cells COLO 205. The antibodies with and without the E430G mutation were tested as single agent and as combinations of the two non-crossblocking antibodies. COLO 205 cells were harvested as described in Example 8. 100 µL of the single cell suspensions (5,000 cells per well) were seeded in polystyrene 96-well flat-bottom plates (Greiner Bio-One, Cat nr 655182) and allowed to adhere overnight at 37° C. Subsequently, 50 µL samples of antibody concentration series (range 0.3-20,000 ng/mL final concentration in 4-fold dilutions) were added and incubated for 3 days at 37° C. As a positive control, cells were incubated with 5 µM staurosporine (Sigma Aldrich, Cat nr S6942). The viability of the cell cultures was determined in a CellTiter-Glo luminescent cell viability assay as described in Example 8.

FIG. 36 shows that the combination of IgG1-hDR5-01-G56T-E430G+IgG1-hDR5-05-E430G was more potent than either antibody alone and more potent than the combination of the antibodies without the E430G mutation. These data show that introduction of the hexamerization-enhancing mutation E430G resulted in enhanced induction of cell killing upon binding of the combination of the non-crossblocking antibodies IgG1-hDR5-01-G56T-E430G+IgG1-hDR5-05-E430G to adherent COLO 205 colon cancer cells. In contrast to the experimental setup where antibodies were directly added when cells were seeded (Example 8), the single antibodies IgG1-hDR5-01-G56T-E430G and IgG1-hDR5-05-E430G did not show efficacy on COLO 205 cells in this experiment where the cells were first allowed to adhere to the 96-wells flat-bottom plate before adding the samples.

Example 39: Introduction of Hexamerization-Enhancing Mutation S440Y Improves the Efficacy of Anti-DR5 Antibodies to Induce Cell Death on Human Colon Cancer Cells The effect of the hexamerization-enhancing mutation S440Y on the capacity of the single antibodies and the combination of IgG1-hDR5-01-G56T and IgG1-hDR5-05 to kill COLO 205 human colon cancer cells was studied in a viability assay. Cells were harvested and a CellTiter-Glo luminescent cell viability assay was performed as described in Example 8. Briefly, 100 μL single cell suspensions (5,000 cells per well) were seeded in 96-well plates and at the same time, 50 μL of serial dilution antibody preparation series (range 0.0003 to 20 μg/mL final concentrations in 4-fold dilutions) were added and incubated for 3 days at 37° C.

FIG. 37A shows that in the experimental setup where antibodies were directly added when cells were seeded, introduction of the hexamerization-enhancing mutation S440Y resulted in dose-dependent killing by the single antibodies IgG1-hDR5-01-G56T-S440Y and IgG1-hDR5-05-S440Y, whereas the parental wild type antibodies IgG1-hDR5-01-G56T and IgG1-hDR5-05 were not able to kill COLO 205 colon cancer cells. Also the efficacy of the combination of IgG1-hDR5-01-G56T+IgG1-hDR5-05 was improved by introduction of the S440Y mutation in both antibodies, represented by the decreased EC50 (FIG. 37B).

Example 40: Introduction of the Hexamerization-Enhancing Mutation E430G Improves the Efficacy of Cell Death Induction by the Combination of Anti-DR5 Antibodies IgG1-DR5-CONA+IgG1-DR5-chTRA8

A crossblock ELISA for antibodies IgG1-DR5-CONA-K409R and IgG1-DR5-chTRA8-F405L was performed as described in Example 7. The K409R and F405L mutations are not relevant here and were previously shown to have no effect on the potency of antibodies with an E430G mutation (Example 22). FIG. 38A shows binding competition expressed as percentage inhibition of DR5ECD-FcHisCtag binding to coated antibody in presence of competing antibody, relative to binding of DR5ECD-FcHisCtag in absence of competing antibody (% inhibition=100−[(binding in presence of competing antibody/binding in absence of competing antibody)]*100). Binding of DR5ECD-FcHisCtag to coated IgG1-DR5-CONA-K409R was not inhibited in the presence of soluble IgG1-DR5-chTRA8-F405L. Vice versa, binding of DR5ECD-FcHistag to coated IgG1-DR5-chTRA8-F405L was also not inhibited in the presence of soluble IgG1-DR5-CONA-K409R. These data indicate that IgG1-DR5-CONA-K409R and IgG1-DR5-chTRA8-F405L did not compete with each other for binding of DR5ECD-FcHisCtag.

Next, the effect of the hexamerization-enhancing mutation E430G on the capacity of the combination of the non-crossblocking anti-DR5 antibodies IgG1-DR5-CONA-C49W+IgG1-DR5-chTRA-8 to kill attached BxPC-3 human pancreatic cancer cells was studied in a viability assay as described in Example 11. FIG. 38B shows that the antibody combination IgG1-DR5-CONA-C49W-E430G+IgG1-DR5-chTRA8-E430G with hexamerization-enhancing mutations showed increased dose-dependent killing of BxPC-3 cells compared to the combination of the parental antibodies without the E430G hexamerization-enhancing mutation.

Example 41: Capacity of the Antibody Combination IgG1-hDR5-01-G56T-E430G and IgG1-hDR5-05-E430G to Induce Target Cell Killing in Different Cancer Cell Lines The efficacy of the combination of the non-crossblocking antibodies IgG1-hDR5-01-G56T-E430G+IgG1-hDR5-05-E430G to induce killing was analyzed on different human cancer cell lines and compared to the parental antibody combination without the E430G mutation and TRAIL. A viability assay on HCT-15, HCT 116, HT-29 and SW480 colon cancer, BxPC-3, HPAF-II and PANC-1 pancreatic cancer, SNU-5 gastric cancer, A549 and SK-MES-1 lung cancer, and A375 skin cancer cells was performed, essentially as described in Example 11. Briefly, 100 μL single cell suspensions (5,000 cells per well) were seeded in 96-well plates and incubated at 37° C. overnight. 50 μL of antibody sample (133 nM final concentration) or human recombinant TRAIL/APO-2L (eBioscience, Cat nr BMS356; 133 nM final concentration) was added and incubated for 3 days at 37° C.

Both TRAIL and the antibody combination IgG1-hDR5-01-G56T-E430G+IgG1-hDR5-05-E430G show killing of human cancer target cell lines originating from different indications (FIG. 39). Killing of the antibody combination IgG1-hDR5-01-G56T-E430G+IgG1-hDR5-05-E430G was significant compared to the control antibody IgG1-b12 in 6 of the 11 tested cell lines. For these responding cell lines the percentage viable cells was significantly lower after incubation with the antibody combination IgG1-hDR5-01-G56T-E430G+IgG1-hDR5-05-E430G than after incubation with the antibody combination without the E430G mutation. There was no correlation between killing efficacy of IgG1-hDR5-01-K409R-E430G+IgG1-hDR5-05-F405L-E430G and DR5 target expression levels (described in Example 2).

Example 42: Screening of a Human Cancer Cell Line Panel for Cytotoxic Efficacy of the Antibody Combination IgG1-hDR5-01-G56T-E430G+IgG1-hDR5-05-E430G The activity of the antibody combination IgG1-hDR5-01-G56T-E430G+IgG1-hDR5-05-E430G was tested and compared to the activity of TRAIL in a panel of 235 cell lines representing 14 tumor lineages: kidney, neural tissue, colorectal, gastric, breast cancer (predominantly triple-negative breast cancer (TNBC)), non-small cell lung cancer (NSCLC), bladder, pancreatic, ovarian, melanoma, liver, endometrial, head and neck and small cell lung cancer (SCLC). A 72 hour ATPlite assay (except for DLD-1 and HCT116 cell lines, for which a 120 hour assay was performed) with growth inhibition analysis was performed in two parts at Horizon Discovery Ltd, UK. Samples were tested as four replicates in 384-well assay plates. Serial dilution series of antibody, starting from 0.072 μM final concentration was used for all tested cell lines. For TRAIL (Invitrogen; Cat #PHC1634) serial dilution series starting from 0.01 μM final concentration for the cell lines tested in the first part and 0.17 μM final concentration for the cell lines tested in the second part of the screening was used.

Percentage inhibition was calculated using the formulas: If T≥V(0) than percentage inhibition=100*[1−(T−V(0))/(V−V(0))]; If T<V(0) than percentage inhibition=100%, with T=luminescence of the test sample, V(0)=luminescence of the medium control sample on day 0 and V=luminescence of the medium control sample on day 3. Responder and non-responder cell lines were grouped by a maximum response threshold value categorizing cell lines showing 70% inhibition as responders and cell lines showing 69% inhibition as non-responders (FIG. 40; Table 11). Responder cell lines for both antibody (IgG1-hDR5-01-G56T-E430G+IgG1-hDR5-05-E430G) and TRAIL monotherapy were found for all tested tumor indications, except small cell lung cancer (SCLC).

TABLE 11

Results for antibody (IgG1-hDR5-01-G56T-E430G + IgG1-hDR5-05-E430G) and TRAIL monotherapy as determined in a 3-days viability assay screening at Horizon Discovery Ltd, UK, for a panel of cell lines representing different human cancer indications: kidney (A), neural tissue (B), colorectal (C), gastric (D), triple-negative breast cancer (TNBC) (E), non-small cell lung cancer (NSCLC) (F), bladder (G), pancreatic (H), ovarian (I), melanoma (J), liver (K), endometrial (L), head and neck (M) and small cell lung cancer (SCLC) (N). Tabulated are IC50 values and percentage maximal inhibition.

| Cell Line | Screening # | IgG1-hDR5-01-G56T-E430G + IgG1-hDR5-05-E430G | | TRAIL | |
|---|---|---|---|---|---|
| | | IC50 (nM) | Max Inhibition (%) | IC50 (nM) | Max Inhibition (%) |
| A: Kidney cancer cell line screening results for antibody (IgG1-hDR5-01-G56T-E430G + IgG1-hDR5-05-E430G) and TRAIL therapy as determined in a 3-days viability assay screening at Horizon, UK. | | | | | |
| A704 | 1 | 0.475 | 99.7 | 3.443 | 77.1 |
| A498 | 2 | 1.223 | 98.9 | 0.079 | 96.1 |
| G-401 | 2 | 0.509 | 94.1 | 0.068 | 76.6 |
| CAL-54 | 1 | 1.533 | 91.7 | 0.268 | 71.6 |
| ACHN | 2 | 0.843 | 89.9 | 0.356 | 32.4 |
| CAKI-2 | 1 | 1.565 | 87.3 | | 5.7 |
| 769-P | 2 | 0.957 | 57.7 | 1.941 | 39.4 |
| G-402 | 2 | 0.605 | 50.4 | 0.173 | 15.0 |
| 786-0 | 2 | 0.005 | 7.7 | 287.593 | 2.6 |
| B: Neural tissue cancer cell line screening results for antibody (IgG1-hDR5-01-G56T-E430G + IgG1-hDR5-05-E430G) and TRAIL therapy as determined in a 3-days viability assay screening at Horizon, UK. | | | | | |
| A172 | 2 | 0.888 | 100.0 | 0.029 | 98.2 |
| SF295 | 2 | 0.764 | 99.2 | 0.023 | 87.5 |
| SF126 | 2 | 0.713 | 98.9 | 0.013 | 85.6 |
| H4 | 2 | 0.459 | 98.8 | 0.007 | 98.9 |
| YH-13 | 2 | 1.248 | 94.4 | 0.317 | 39.5 |
| U-87 MG | 2 | 1.784 | 87.8 | 0.053 | 8.0 |
| DBTRG-05MG | 2 | 0.971 | 46.8 | 0.087 | 36.0 |
| KNS-81 | 2 | 13.008 | 30.6 | 0.013 | -6.6 |
| SNB-75 | 2 | 3.225 | 14.2 | 105.178 | 9.6 |
| NMC-G1 | 2 | 0.005 | 13.8 | 17.591 | 15.2 |
| C: Colorectal cancer cell line screening results for antibody (IgG1-hDR5-01-G56T-E430G + IgG1-hDR5-05-E430G) and TRAIL therapy as determined in a 3-days viability assay screening at Horizon, UK. | | | | | |
| CL-11 | 1 | 0.620 | 100.0 | 1.318 | 85.9 |
| GP2D | 1 | 0.738 | 100.0 | 0.003 | 100.0 |
| HT-115 | 1 | 2.101 | 100.0 | 0.107 | 99.7 |
| SNU-1197 | 1 | 1.076 | 100.0 | 0.053 | 100.0 |
| COLO-205 | 1 | 0.360 | 99.9 | 2.269 | 83.5 |
| COLO-206F | 1 | 0.200 | 99.9 | 0.146 | 99.2 |
| CL-34 | 1 | 0.380 | 99.8 | 0.024 | 98.8 |
| HRT-186 | 1 | 0.433 | 99.3 | 9.240 | 52.5 |
| HCT-15 | 1 | 0.813 | 98.8 | 0.129 | 98.6 |
| SNU-407 | 1 | 0.836 | 98.5 | 0.098 | 96.1 |
| MDST8 | 1 | 1.035 | 93.6 | 1.190 | 58.3 |
| COLO-201 | 1 | 0.568 | 93.6 | 0.168 | 89.1 |
| HT55 | 1 | 1.025 | 91.0 | 0.110 | 76.4 |
| SNU-175 | 1 | 1.813 | 90.1 | 0.122 | 96.2 |
| HCT-116_ARID1A (Q456*/Q456*) | 1 | 0.235 | 86.2 | 10.502 | 50.2 |
| DLD-1 | 1 | 0.938 | 83.1 | 3.954 | 55.1 |
| SNU283 | 1 | 5.628 | 81.9 | | 40.3 |
| CL-40 | 1 | 1.555 | 79.9 | 1.975 | 57.3 |
| HCT-116_KRAS (+/−) | 1 | 0.855 | 77.7 | 0.253 | 88.7 |
| SW837 | 1 | 1.399 | 76.6 | 0.940 | 83.8 |
| LOVO | 1 | 4.512 | 75.7 | | 44.5 |
| LS-411N | 1 | 3.549 | 73.1 | | 26.9 |
| HT-29 | 1 | 2.966 | 65.5 | | 12.2 |
| SNU1033 | 1 | 4.446 | 60.9 | 10.057 | 51.7 |
| SW480 | 1 | 1.093 | 60.2 | 2.037 | 55.2 |
| COLO-678 | 1 | 3.670 | 58.6 | | 10.1 |
| DLD-1_BRCA2 (−/−) | 1 | 1.826 | 58.3 | 0.516 | 60.0 |
| HCT-116_PIK3A (+/−)KO mt H1047R | 1 | 0.756 | 57.8 | 1.251 | 59.8 |
| C2BBe1 | 1 | | 49.5 | | 8.8 |
| SNU-C2B | 1 | | 43.0 | 0.713 | 71.3 |
| SW1116 | 1 | | 42.4 | | 23.1 |
| HCT-116_PAR-007 | 1 | | 29.0 | | 14.2 |
| HCT-116_TP53 (−/−) | 1 | | 19.6 | | 17.2 |
| SW1417 | 1 | | 19.1 | | 12.2 |
| RKO | 1 | | 14.5 | | 10.5 |
| HCT-116_PTEN (−/−) | 1 | | 11.9 | | 38.0 |
| COLO320DM | 1 | | 10.1 | | 8.0 |
| COLO-320 | 1 | | 9.9 | | 3.9 |

TABLE 11-continued

Results for antibody (IgG1-hDR5-01-G56T-E430G + IgG1-hDR5-05-E430G) and TRAIL monotherapy as determined in a 3-days viability assay screening at Horizon Discovery Ltd, UK, for a panel of cell lines representing different human cancer indications: kidney (A), neural tissue (B), colorectal (C), gastric (D), triple-negative breast cancer (TNBC) (E), non-small cell lung cancer (NSCLC) (F), bladder (G), pancreatic (H), ovarian (I), melanoma (J), liver (K), endometrial (L), head and neck (M) and small cell lung cancer (SCLC) (N). Tabulated are IC50 values and percentage maximal inhibition.

| | | IgG1-hDR5-01-G56T-E430G + IgG1-hDR5-05-E430G | | TRAIL | |
|---|---|---|---|---|---|
| Cell Line | Screening # | IC50 (nM) | Max Inhibition (%) | IC50 (nM) | Max Inhibition (%) |
| D: Gastric cancer cell line screening results for antibody (IgG1-hDR5-01-G56T-E430G + IgG1-hDR5-05-E430G) and TRAIL therapy as determined in a 3-days viability assay screening at Horizon, UK. | | | | | |
| SNU-620 | 1 | 0.809 | 100.0 | 0.045 | 99.9 |
| SNU-668 | 1 | 0.370 | 99.9 | 0.041 | 99.6 |
| SNU-719 | 1 | 1.483 | 98.9 | 1.132 | 85.4 |
| SNU-601 | 1 | 0.520 | 98.6 | 0.284 | 85.2 |
| NUGC-3 | 1 | 0.671 | 96.7 | | 38.7 |
| GSU | 1 | 0.169 | 96.4 | 0.454 | 81.6 |
| SNU5 | 1 | 0.729 | 95.9 | 0.109 | 91.2 |
| SNU-216 | 1 | 5.484 | 84.0 | | 49.6 |
| NCC-StC-K140 | 1 | 1.059 | 77.8 | | 9.8 |
| KE-97 | 1 | 1.175 | 57.2 | | 23.4 |
| LMSU | 1 | 3.563 | 56.6 | | 9.0 |
| RERF-GC-1B | 1 | | 45.1 | | 14.0 |
| MKN1 | 1 | | 36.8 | | 10.5 |
| SH-10-TC | 1 | | 31.6 | | 34.9 |
| ECC12 | 1 | | 22.7 | | 27.4 |
| GSS | 1 | | 11.8 | | 15.4 |
| ECC10 | 1 | | 8.3 | | 14.0 |
| E: Breast cancer cell line screening results for antibody (IgG1-hDR5-01-G56T-E430G + IgG1-hDR5-05-E430G) and TRAIL therapy as determined in a 3-days viability assay screening at Horizon, UK. | | | | | |
| SUM159PT* | 2 | 0.569 | 99.2 | 0.033 | 98.6 |
| DU-4475* | 2 | 1.102 | 94.5 | 0.079 | 87.0 |
| HCC1806* | 2 | 2.678 | 92.5 | 0.050 | 97.8 |
| BT-549* | 2 | 1.021 | 83.3 | 0.285 | 44.0 |
| BT-20* | 2 | 2.843 | 82.8 | 0.089 | 48.9 |
| HCC1187* | 2 | 1.521 | 82.8 | 0.066 | 99.4 |
| MDA-MB-436* | 2 | 0.762 | 77.7 | 0.053 | 76.3 |
| HCC38* | 2 | 0.903 | 70.6 | 0.080 | 96.9 |
| HCC70* | 2 | 18.703 | 69.3 | 346.839 | 3.6 |
| HMC-1-8* | 2 | 0.714 | 67.7 | 0.232 | 70.0 |
| MDA-MB-231* | 1 | 1.409 | 60.2 | 0.110 | 53.3 |
| SK-BR-3 | 2 | 1.757 | 40.4 | 0.518 | 38.1 |
| MDA-MB-468* | 2 | 3.772 | 33.3 | 0.647 | 89.4 |
| HCC1937* | 2 | 8.548 | 28.0 | 0.647 | 28.5 |
| T47D | 2 | 2.557 | 17.1 | 346.732 | 8.4 |
| MDA-MB-453* | 2 | 0.723 | 13.0 | 34.643 | 20.7 |
| MCF7 | 2 | 19.492 | 10.2 | 0.055 | 21.7 |
| F: Non-small-cell lung cancer (NSCLC) cell line screening results for antibody (IgG1-hDR5-01-G56T-E430G + IgG1-hDR5-05-E430G) and TRAIL therapy as determined in a 3-days viability assay screening at Horizon, UK. | | | | | |
| DV-90 | 1 | 0.215 | 100.0 | 1.189 | 96.1 |
| NCI-H820 | 1 | 0.857 | 99.7 | 0.023 | 100.0 |
| LCLC-97TM1 | 1 | 1.202 | 96.6 | | 4.6 |
| COR-L23-CPR | 1 | 0.707 | 96.0 | 5.482 | 58.4 |
| LOU-NH91 | 1 | 0.529 | 94.8 | 5.382 | 63.0 |
| LCLC-103H | 1 | 0.548 | 92.2 | 8.018 | 54.2 |
| T3M-10 | 1 | 1.058 | 90.1 | 0.495 | 83.7 |
| LU-99 | 1 | 1.879 | 81.9 | | 6.3 |
| HOP-62 | 1 | 0.899 | 81.7 | | 55.6 |
| EPLC-272H | 1 | 1.233 | 79.7 | | 51.7 |
| LUDLU-1 | 1 | 2.196 | 77.9 | 0.475 | 91.1 |
| RERF-LC-KJ | 1 | 2.771 | 71.4 | 0.633 | 68.9 |
| LXF-289 | 1 | 3.582 | 62.7 | | 12.7 |
| COR-L105 | 1 | 2.990 | 57.5 | | 35.7 |
| LC-1sq | 1 | 7.710 | 56.6 | 0.781 | 70.1 |
| NCI-H460 | 1 | 15.034 | 53.3 | 0.853 | 86.1 |
| LC1F | 1 | | 50.3 | 0.451 | 74.3 |
| SW1573 | 1 | 46.1 | 13.9 | | |
| LU-65 | 1 | 38.9 | 32.4 | | |
| HLC-1 | 1 | 36.8 | 32.6 | | |
| VMRC-LCD | 1 | 21.6 | 19.2 | | |
| LK-2 | 1 | 19.0 | 5.6 | | |
| Calu-1 | 1 | 13.0 | 22.0 | | |
| CAL-12T | 1 | 10.4 | 11.9 | | |
| COLO-699 | 1 | 7.7 | 2.8 | | |
| BEN | 1 | 7.5 | 8.1 | | |

TABLE 11-continued

Results for antibody (IgG1-hDR5-01-G56T-E430G + IgG1-hDR5-05-E430G) and TRAIL monotherapy as determined in a 3-days viability assay screening at Horizon Discovery Ltd, UK, for a panel of cell lines representing different human cancer indications: kidney (A), neural tissue (B), colorectal (C), gastric (D), triple-negative breast cancer (TNBC) (E), non-small cell lung cancer (NSCLC) (F), bladder (G), pancreatic (H), ovarian (I), melanoma (J), liver (K), endometrial (L), head and neck (M) and small cell lung cancer (SCLC) (N). Tabulated are IC50 values and percentage maximal inhibition.

| | | IgG1-hDR5-01-G56T-E430G + IgG1-hDR5-05-E430G | | TRAIL | |
|---|---|---|---|---|---|
| Cell Line | Screening # | IC50 (nM) | Max Inhibition (%) | IC50 (nM) | Max Inhibition (%) |
| G: Bladder cancer cell line screening results for antibody (IgG1-hDR5-01-G56T-E430G + IgG1-hDR5-05-E430G) and TRAIL therapy as determined in a 3-days viability assay screening at Horizon, UK. | | | | | |
| 5637 | 2 | 0.828 | 99.3 | 0.060 | 99.1 |
| SW780 | 1 | 0.421 | 98.5 | 0.016 | 97.9 |
| RT-112 | 2 | 3.520 | 96.1 | 0.325 | 50.9 |
| RT4 | 2 | 4.638 | 95.5 | 0.244 | 91.5 |
| UM-UC-3 | 1 | 0.906 | 94.4 | 0.005 | 99.4 |
| TCCSUP | 2 | 1.367 | 69.6 | 0.048 | 51.5 |
| T-24 | 2 | 1.300 | 63.0 | 0.166 | 20.5 |
| HT-1197 | 2 | 0.782 | 40.9 | 0.167 | 31.8 |
| SCaBER | 1 | 3.768 | 29.6 | 0.082 | 25.8 |
| J82 | 1 | 68.272 | 15.9 | 33.567 | 11.5 |
| HT-1376 | 2 | 67.114 | 15.3 | 159.873 | 10.6 |
| H: Pancreatic cancer cell line screening results for antibody (IgG1-hDR5-01-G56T-E430G + IgG1-hDR5-05-E430G) and TRAIL therapy as determined in a 3-days viability assay screening at Horizon, UK. | | | | | |
| HuP-T3 | 1 | 0.728 | 91.8 | 0.223 | 88.4 |
| PSN1 | 1 | 0.655 | 91.6 | 0.205 | 86.9 |
| Panc 02.13 | 1 | 2.288 | 85.9 | 1.905 | 60.5 |
| BxPC-3 | 1 | 0.448 | 83.9 | | 46.5 |
| KP-4 | 1 | 1.853 | 80.0 | | 23.6 |
| CFPAC-1 | 1 | 13.635 | 57.2 | | 13.2 |
| HPAF-II | 1 | 9.896 | 56.9 | | 13.3 |
| KP-2 | 1 | 10.251 | 54.2 | | 3.9 |
| KLM-1 | 1 | | 41.0 | | 12.7 |
| KP-3 | 1 | | 37.3 | | 23.5 |
| CAPAN-2 | 1 | | 20.6 | | 4.8 |
| PK-1 | 1 | | 6.4 | 0.548 | 88.3 |
| I: Ovary cancer cell line screening results for antibody (IgG1-hDR5-01-G56T-E430G + IgG1-hDR5-05-E430G) and TRAIL therapy as determined in a 3-days viability assay screening at Horizon, UK. | | | | | |
| SNU119 | 1 | 0.681 | 99.3 | 0.082 | 83.7 |
| 59M | 1 | 0.846 | 98.6 | 0.049 | 98.5 |
| JHOM-2B | 1 | 8.294 | 82.0 | | 21.7 |
| COV434 | 1 | 1.093 | 80.4 | 0.395 | 73.1 |
| OVCAR-5 | 1 | 2.731 | 79.0 | 1.120 | 70.6 |
| OVK18 | 1 | 0.865 | 73.2 | 0.230 | 80.0 |
| JHOM-1 | 1 | 1.835 | 68.8 | 0.596 | 58.1 |
| COV644 | 1 | 3.375 | 68.2 | 0.271 | 74.9 |
| MCAS | 1 | 13.877 | 57.2 | 56.779 | 48.4 |
| JHOS-4 | 1 | 73.734 | 49.6 | | 12.5 |
| OV7 | 1 | | 48.3 | | 20.4 |
| COV504 | 1 | | 19.0 | | 11.7 |
| OVTOKO | 1 | | 18.9 | | 28.0 |
| OVISE | 1 | | 13.5 | | 4.0 |
| KURAMOCHI | 1 | | 10.1 | | 13.4 |
| JHOC-5 | 1 | | 8.5 | | 18.4 |
| J: Melanoma cell line screening results for antibody (IgG1-hDR5-01-G56T-E430G + IgG1-hDR5-05-E430G) and TRAIL therapy as determined in a 3-days viability assay screening at Horizon, UK. | | | | | |
| COLO-679 | 1 | 0.524 | 99.5 | | 24.9 |
| COLO-783 | 1 | 0.503 | 98.2 | 0.224 | 80.9 |
| COLO-800 | 1 | 0.365 | 95.7 | | 33.5 |
| Hs 294T | 1 | 0.595 | 94.1 | 0.019 | 91.1 |
| RVH-421 | 1 | 0.577 | 91.3 | | 22.5 |
| MEL-HO | 1 | 0.760 | 89.2 | | 16.7 |
| WM-266-4 | 1 | 1.257 | 80.3 | | 42.5 |
| COLO858 | 1 | 0.567 | 68.1 | | 12.6 |
| MEL-JUSO | 1 | 1.349 | 67.6 | | 7.6 |
| COLO-818 | 1 | 1.061 | 64.8 | | 7.8 |
| IGR-39 | 1 | 0.813 | 63.9 | | 20.1 |
| IGR-1 | 1 | 1.066 | 60.1 | | 23.3 |
| IGR-37 | 1 | 9.359 | 54.7 | | 18.0 |
| COLO-849 | 1 | | 51.9 | | 17.6 |
| A375 | 1 | | 51.2 | | 47.1 |
| Hs 936.T | 1 | | 41.0 | | 20.7 |
| SK-MEL-30 | 1 | | 12.5 | | 6.1 |
| IPC-298 | 1 | | 11.2 | | 5.7 |
| HMCB | 1 | | 7.0 | | 1.0 |

TABLE 11-continued

Results for antibody (IgG1-hDR5-01-G56T-E430G + IgG1-hDR5-05-E430G) and TRAIL monotherapy as determined in a 3-days viability assay screening at Horizon Discovery Ltd, UK, for a panel of cell lines representing different human cancer indications: kidney (A), neural tissue (B), colorectal (C), gastric (D), triple-negative breast cancer (TNBC) (E), non-small cell lung cancer (NSCLC) (F), bladder (G), pancreatic (H), ovarian (I), melanoma (J), liver (K), endometrial (L), head and neck (M) and small cell lung cancer (SCLC) (N). Tabulated are IC50 values and percentage maximal inhibition.

| | | IgG1-hDR5-01-G56T-E430G + IgG1-hDR5-05-E430G | | TRAIL | |
|---|---|---|---|---|---|
| Cell Line | Screening # | IC50 (nM) | Max Inhibition (%) | IC50 (nM) | Max Inhibition (%) |

K: Liver cancer cell line screening results for antibody (IgG1-hDR5-01-G56T-E430G + IgG1-hDR5-05-E430G) and TRAIL therapy as determined in a 3-days viability assay screening at Horizon, UK.

| Cell Line | Screening # | IC50 (nM) | Max Inhibition (%) | IC50 (nM) | Max Inhibition (%) |
|---|---|---|---|---|---|
| SNU-878 | 1 | 0.709 | 99.5 | | 36.2 |
| SNU-308 | 1 | 1.521 | 98.8 | 0.937 | 72.4 |
| HuH-28 | 1 | 0.903 | 96.7 | | 17.5 |
| SNU-478 | 1 | 2.097 | 82.2 | 0.516 | 83.3 |
| HLE | 1 | 0.315 | 81.9 | 8.360 | 56.0 |
| SNU-869 | 1 | 1.842 | 68.8 | 2.951 | 58.6 |
| Li-7 | 1 | 1.614 | 65.9 | | 20.4 |
| HuCCT1 | 1 | 8.034 | 55.6 | | 7.5 |
| SNU-1196 | 1 | | 44.8 | | 44.3 |
| HUH-6-clone5 | 1 | | 42.3 | | 20.2 |
| SNU-1079 | 1 | | 40.3 | | 24.9 |
| HuH-1 | 1 | | 30.7 | | 47.7 |
| RH-41 | 1 | | 10.1 | | 3.0 |
| SNU-761 | 1 | | 9.1 | | 7.1 |

L: Endometrial cancer cell line screening results for antibody (IgG1-hDR5-01-G56T-E430G + IgG1-hDR5-05-E430G) and TRAIL therapy as determined in a 3-days viability assay screening at Horizon, UK.

| Cell Line | Screening # | IC50 (nM) | Max Inhibition (%) | IC50 (nM) | Max Inhibition (%) |
|---|---|---|---|---|---|
| HEC-265 | 1 | 0.399 | 100.0 | 0.021 | 100.0 |
| MES-SA | 1 | 0.510 | 100.0 | 0.107 | 92.6 |
| JHUEM-2 | 1 | 0.613 | 89.6 | 0.165 | 66.4 |
| RL95-2 | 1 | 1.649 | 88.0 | 0.155 | 97.7 |
| SNG-II | 1 | 1.049 | 79.3 | 1.028 | 77.2 |
| JHUEM-3 | 1 | | 46.2 | | 18.4 |
| TEN | 1 | | 43.2 | 1.205 | 70.0 |
| HEC-1-A | 1 | | 39.6 | | 22.8 |
| HEC-108 | 1 | | 32.8 | 1.479 | 64.9 |
| MFE-296 | 1 | | 22.7 | | 8.7 |
| COLO-684 | 1 | | 14.3 | | 16.6 |
| SK-UT-1 | 1 | | 13.4 | | 10.9 |
| HEC-1 | 1 | | 13.2 | | 8.1 |
| MFE-280 | 1 | | 11.4 | | 11.0 |
| HEC-50B | 1 | | 5.5 | | 16.6 |

M: Head and neck cancer cell line screening results for antibody (IgG1-hDR5-01-G56T-E430G + IgG1-hDR5-05-E430G) and TRAIL therapy as determined in a 3-days viability assay screening at Horizon, UK.

| Cell Line | Screening # | IC50 (nM) | Max Inhibition (%) | IC50 (nM) | Max Inhibition (%) |
|---|---|---|---|---|---|
| YD-15 | 1 | 1.369 | 100.0 | 0.114 | 100.0 |
| TE-4 | 1 | 0.879 | 99.9 | 0.107 | 81.0 |
| KYM-1 | 1 | 0.438 | 99.4 | | 30.2 |
| FTC-238 | 1 | 0.426 | 93.8 | 3.922 | 86.7 |
| KYSE-70 | 1 | 1.346 | 79.2 | | 46.0 |
| TE-10 | 1 | 3.602 | 68.0 | | 24.4 |
| TE-6 | 1 | 7.502 | 61.9 | 3.923 | 55.3 |
| TE-9 | 1 | 1.139 | 60.3 | 0.300 | 73.6 |
| TE-1 | 1 | 3.051 | 58.3 | | 23.0 |
| BICR 31 | 1 | 4.670 | 52.6 | | 38.9 |
| KYSE-410 | 1 | | 51.0 | | 10.6 |
| CJM | 1 | | 48.8 | | 12.8 |
| BICR 22 | 1 | | 42.0 | | 13.6 |
| KYSE-30 | 1 | | 38.0 | | 8.0 |
| SCC-15 | 1 | | 34.8 | | 19.4 |
| TE-8 | 1 | | 33.4 | | 39.6 |
| PE-CA-PJ34-cl C12 | 1 | | 28.9 | | 4.7 |
| EC-GI-10 | 1 | | 25.0 | | 29.6 |
| TE-5 | 1 | | 23.0 | | 11.6 |
| HSC-4 | 1 | | 12.8 | | 0.5 |
| YD-8 | 1 | | 10.8 | | 3.4 |
| KYSE-270 | 1 | | 7.1 | | 5.4 |
| BICR 18 | 1 | | −0.1 | | 3.4 |

N: Small cell lung cancer (SCLC) cancer cell line screening results for antibody (IgG1-hDR5-01-G56T-E430G + IgG1-hDR5-05-E430G) and TRAIL therapy as determined in a 3-days viability assay screening at Horizon, UK.

| Cell Line | Screening # | IC50 (nM) | Max Inhibition (%) | IC50 (nM) | Max Inhibition (%) |
|---|---|---|---|---|---|
| LU-134-A | 1 | | 47.7 | | 28.0 |
| IST-SL2 | 1 | | 24.4 | | 21.0 |
| NCI-H69 | 1 | | 23.2 | | 14.5 |
| NCI-H345 | 1 | | 19.2 | | 16.4 |

TABLE 11-continued

Results for antibody (IgG1-hDR5-01-G56T-E430G + IgG1-hDR5-05-E430G) and TRAIL monotherapy as determined in a 3-days viability assay screening at Horizon Discovery Ltd, UK, for a panel of cell lines representing different human cancer indications: kidney (A), neural tissue (B), colorectal (C), gastric (D), triple-negative breast cancer (TNBC) (E), non-small cell lung cancer (NSCLC) (F), bladder (G), pancreatic (H), ovarian (I), melanoma (J), liver (K), endometrial (L), head and neck (M) and small cell lung cancer (SCLC) (N). Tabulated are IC50 values and percentage maximal inhibition.

| | | IgG1-hDR5-01-G56T-E430G + IgG1-hDR5-05-E430G | | TRAIL | |
|---|---|---|---|---|---|
| Cell Line | Screening # | IC50 (nM) | Max Inhibition (%) | IC50 (nM) | Max Inhibition (%) |
| LU-139 | 1 | | 18.7 | | 10.0 |
| SHP-77 | 1 | | 9.2 | | 9.1 |
| NCI-H446 | 1 | | 7.3 | | 11.7 |
| LU-135 | 1 | | 6.0 | | 9.7 |

*TNBC

Example 43: Capacity of Antibody Combination IgG1-hDR5-01-G56T-E430G+IgG1-hDR5-05-E430G to Induce Cancer Cell Killing at Different Combination Ratios A viability assay was performed to study the capacity of the antibody combination IgG1-hDR5-01-G56T-E430G+IgG1-hDR5-05-E430G to induce killing of BxPC-3 pancreatic cancer cells and HCT-15 colon cancer cells, when combined at different ratios of IgG1-hDR5-01-G56T-E430G and IgG1-hDR5-05-E430G. Antibody ratios of 1:0, 9:1, 3:1, 1:1, 1:3, 1:9 and 0:1 in serial dilution series (ranging from 0.006 to 20 µg/mL final concentrations in 5-fold dilutions) were tested in a CellTiter-Glo luminescent cell viability assay as described in Example 16.

At 20 µg/mL, 4 µg/mL and 0.8 µg/mL total antibody concentrations, killing of BxPC-3 (FIG. 41A) and HCT-15 (FIG. 41B) cells was equally effective at all tested antibody ratios containing both antibodies IgG1-hDR5-01-G56T-E430G and IgG1-hDR5-05-E430G. In contrast, the single antibodies (ratios 1:0 and 0:1) did not induce killing. At 0.16 µg/mL total antibody concentrations, the tested combinations of IgG1-hDR5-01-G56T-E430G+IgG1-hDR5-05-E430G induced killing, although to a lesser extent than the higher antibody concentrations and efficacy is impacted by the using different ratios.

Example 44: The Antibody Combination IgG1-hDR5-01-G56T-E430G+IgG1-hDR5-05-E430G Induce Caspase-Dependent Programmed Cell Death A viability assay was performed to compare the cytotoxicity of the combination of antibody variants of IgG1-hDR5-01-G56T and IgG1-hDR5-05 with and without the hexamerization-enhancing mutation E430G in the presence and absence of a caspase inhibitor. A CellTiter-Glo luminescent cell viability assay with serial dilution series of antibody or TRAIL samples (range 0.002 to 133 nM final concentrations in 4-fold dilutions) was performed as described in Example 18.

The killing of BxPC-3 cells was inhibited in the presence of pan-caspase inhibitor Z-VAD-FMK for TRAIL and the antibody combinations IgG1-hDR5-01-G56T+IgG1-hDR5-05 and IgG1-hDR5-01-G56T-E430G+IgG1-hDR5-05-E430G (FIG. 42). These data indicate that, like TRAIL, the antibody combinations IgG1-hDR5-01-G56T+IgG1-hDR5-05 and IgG1-hDR5-01-G56T-E430G+IgG1-hDR5-05-E430G induced caspase-dependent programmed cell death.

Example 45: Caspase-3 and -7 Activation Upon Binding of the Antibody Combination IgG1-hDR5-01-G56T-E430G+IgG1-hDR5-05-E430G on Human Cancer Cells Caspase-3/7 activation was measured in time using the Caspase-Glo 3/7 assay, essentially as described in Example 20. Briefly, cells were harvested by trypsinization, passed through a cell strainer, pelleted by centrifugation for 5 minutes at 1,200 rpm and resuspended in culture medium at a concentration of $1.6 \times 10^5$ cells/mL. 25 µL of the single cell suspensions (4,000 cells per well) were seeded in 384-wells culture plates (Perkin Elmer, Cat nr 6007680) and incubated overnight at 37° C. 25 µL sample was added (26.6 nM final concentrations) and incubated for 1, 2, 4 and 6 hours at 37° C. Plates were removed from the incubator to let the temperature decrease till room temperature. Cells were pelleted by centrifugation for three minutes at 300 g. 25 µL supernatant was removed and replaced by 25 µL Caspase-Glo 3/7 Substrate. After mixing by shaking for one minute at 500 rpm, the plates were incubated for one hour at room temperature. Luminescence was measured on an EnVision Multilabel Reader (PerkinElmer).

In the time course of 1, 2, 4 to 6 hours, both TRAIL and the antibody combination IgG1-hDR5-01-G56T-E430G+IgG1-hDR5-05-E430G induced more rapid and more potent caspase-3/7 activation on BxPC-3 cells compared to the WT antibody combination IgG1-hDR5-01-G56T+IgG1-hDR5-05 without the hexamerization enhancing mutation (FIG. 43).

Example 46: The In Vitro Potency of the Antibody Combination IgG1-hDR5-01-G56T-E430G+IgG1-hDR5-05-E430G Does Not Require the Presence of a Secondary Fc Crosslinker A viability assay was performed to compare the capacity of the antibody combination IgG1-hDR5-01-G56T-E430G+IgG1-hDR5-05-E430G to induce killing of human HCT-15 colon cancer cells and BxPC-3 pancreatic cancer cells in the absence and presence of a secondary antibody crosslinker. IgG1-DR5-CONA, which is known to show enhanced killing in the presence of a secondary antibody crosslinker, was tested in the same assay for comparison. A viability assay in absence and presence of secondary crosslinker was performed, essentially as described in Example 21. Briefly, 100 µL of the single cell suspensions (5,000 cells per well) were seeded in 96-well plates and incubated overnight at 37° C. 50 µL antibody sample (final concentration 4 µg/mL) in the absence or presence of F(ab')₂ fragments of a goat-anti-human IgG antibody and incubated for 3 days at 37° C. As a positive control for cell killing, cells were incubated with 5 μM staurosporine. The viability of the cell cultures was determined in a CellTiter-Glo luminescent cell viability assay as described Example 8.

The combination IgG1-hDR5-01-G56T-E430G+IgG1-hDR5-05-E430G induced potent killing in BxPC-3 and HCT15 cells, and cytotoxicity was not further enhanced in the presence of a secondary crosslinker (FIG. 44). In contrast, the efficacy of IgG1-DR5-CONA and the wild type antibody combination IgG1-hDR5-01-G56T+IgG1-hDR5-05 was enhanced by the presence of a secondary crosslinker in both BxPC-3 and HCT15. These data indicate that killing of BxPC-3 and HCT15 cancer cells by the antibody combination IgG1-hDR5-01-G56T-E430G+IgG1-hDR5-05-E430G is independent of the presence of a secondary Fc crosslinker.

Example 47: Complement Activation Upon Binding of IgG1-hDR5-01-G56T-E430G and IgG1-hDR5-05-E430G to CHO Cells Transiently Transfected with Either Human or Cynomolgus DR5

To analyze the capacity of the antibodies IgG1-hDR5-01-G56T-E430G and IgG1-hDR5-05-E430G to activate complement, an in vitro complement-dependent cytotoxicity (CDC) assay and deposition of complement component C3c was measured on CHO cells that were transiently transfected with the isoform short of either human or monkey DR5. The DR5 constructs harbored the K386N (human) or K420N (cynomolgus monkey) mutation in their death domain to prevent killing by the induction of apoptosis upon binding of the agonistic antibodies. Transient transfections of CHO cells with human or monkey (*Macaca fascicularis*) DR5 were performed as described in Example 1.

For the CDC assay, 0.1×10⁶ cells were pre-incubated in polystyrene round-bottom 96-well plates (Greiner bio-one Cat #650101) with concentration series of purified antibodies in a total volume of 80 μL for 15 min on a shaker at RT. Next, 20 μL normal human serum (NHS; Cat #M0008 Sanquin, Amsterdam, The Netherlands) was added as a source of complement and incubated in a 37° C. incubator for 45 min (20% final NHS concentration; 0.003-10.0 μg/mL final antibody concentrations in 3-fold dilutions). The reaction was stopped by putting the plates on ice before pelleting the cells by centrifugation and replacing the supernatant by 30 μL of 2 μg/mL propidium iodide solution (PI; Sigma Aldrich, Zwijnaarde, The Netherlands). The percentage of PI-positive cells was determined by flow cytometry on an Intellicyt iQue™ screener (Westburg). The data were analyzed using best-fit values of a non-linear dose-response fit using log-transformed concentrations in GraphPad PRISM 5.

For the analysis of C3b deposition, 0.1×10⁶ cells were pre-incubated in round-bottom 96-well plates with concentration series of purified antibodies (0.003-10.0 μg/mL final antibody concentrations in 3-fold dilutions) in a total volume of 80 μL for 15 min on a shaker at RT. Next, 20 μL C5-depleted serum (Quidel; Cat #A501) was added as a source of complement and incubated in a 37° C. incubator for 45 min (20% final NHS concentration). Cells were pelleted and subsequently incubated with 50 μL FITC-labeled polyclonal rabbit-anti-human C3c complement (Dako; Cat #F0201; 2 μg/mL) in FACS buffer for 30 minutes at 4° C. Cells were washed twice with FACS buffer and resuspended in 30 μL FACS buffer. The C3b-deposition on cells was determined by flow cytometry on an Intellicyt iQue™ screener (Westburg). The data were analyzed using best-fit values of a non-linear dose-response fit using log-transformed concentrations in GraphPad PRISM 5.

Both complement-dependent killing (FIG. 45A-B) and C3b deposition (FIG. 45C-D) on DR5-transfected CHO cells was observed for IgG1-hDR5-01-G56T-E430G and IgG1-hDR5-05-E430G with dose-response curves for both the single antibodies and for the combination. These data indicate that the intrinsic capacity of the IgG1 antibodies IgG1-hDR5-01-G56T-E430G and IgG1-hDR5-05-E430G to induce complement activation upon target binding on the cell surface was preserved for both the single antibodies IgG1-hDR5-01-G56T-E430G and IgG1-hDR5-05-E430G and the combination IgG1-hDR5-01-G56T-E430G+IgG1-hDR5-05-E430G.

Example 48: Drug Combination Screen Analysis for Efficacy Enhancement of the Antibody Combination IgG1-hDR5-01-G56T-E430G+IgG1-hDR5-05-E430G with a Panel of Compounds on Human Colon Cancer Cell Lines In order to identify clinically relevant compounds that display synergistic inhibitory effects in combination with the antibody combination IgG1-hDR5-01-G56T-E430G+IgG1-hDR5-05-E430G, 100 compounds representing different therapeutic classes were screened for potential synergy in colon cancer cell lines. A 72 hour (for LS-411N, SNU-C2B and SW480) or 120 hour (for DLD-1 and HCT 116) ATPlite assay with growth inhibition analysis was performed in a 6×6 optimized combination matrix in 384-well assay plates at Horizon Discovery Ltd, UK. All samples were tested in four replicates. Percentage growth inhibition was calculated using the formulas: If $T \geq V(0)$ than percentage growth inhibition=$100*[1-(T-V(0))/(V-V(0))]$; If $T<V(0)$ than percentage growth inhibition=$100*[1-(T-V(0))/V(0)]$, with T=luminescence of the test sample, V(0)=luminescence of the medium control sample on day 0 and V=luminescence of the medium control sample on day 3. In order to identify synergistic effects, mean self-cross activity was determined for each therapeutic class using representative compounds. To measure combination effects in excess of Loewe additivity, Horizon Discovery Ltd has devised a scalar measure to characterize the strength of synergistic interaction termed the Synergy Score. The Synergy Score equation integrates the experimentally-observed activity volume at each point in the matrix in excess of a model surface numerically derived from the activity of the component agents using the Loewe model for additivity. Additional terms in the Synergy Score equation are used to normalize for various dilution factors used for individual agents and to allow for comparison of synergy scores across an entire experiment. The inclusion of positive inhibition gating or an Idata multiplier removes noise near the zero effect level, and biases results for synergistic interactions that occur at high activity levels. The Synergy Score (S) was calculated using the formula: $S = \log f_X \log f_Y \Sigma \max(0, \text{Idata})(\text{Idata} - \text{ILoewe})$ with $f_{x,y}$=dilution factors used for each single agent. Synergy Scores greater than the mean self-cross plus 3σ were considered candidate synergies at the 99% confidence levels.

Figure 46A:
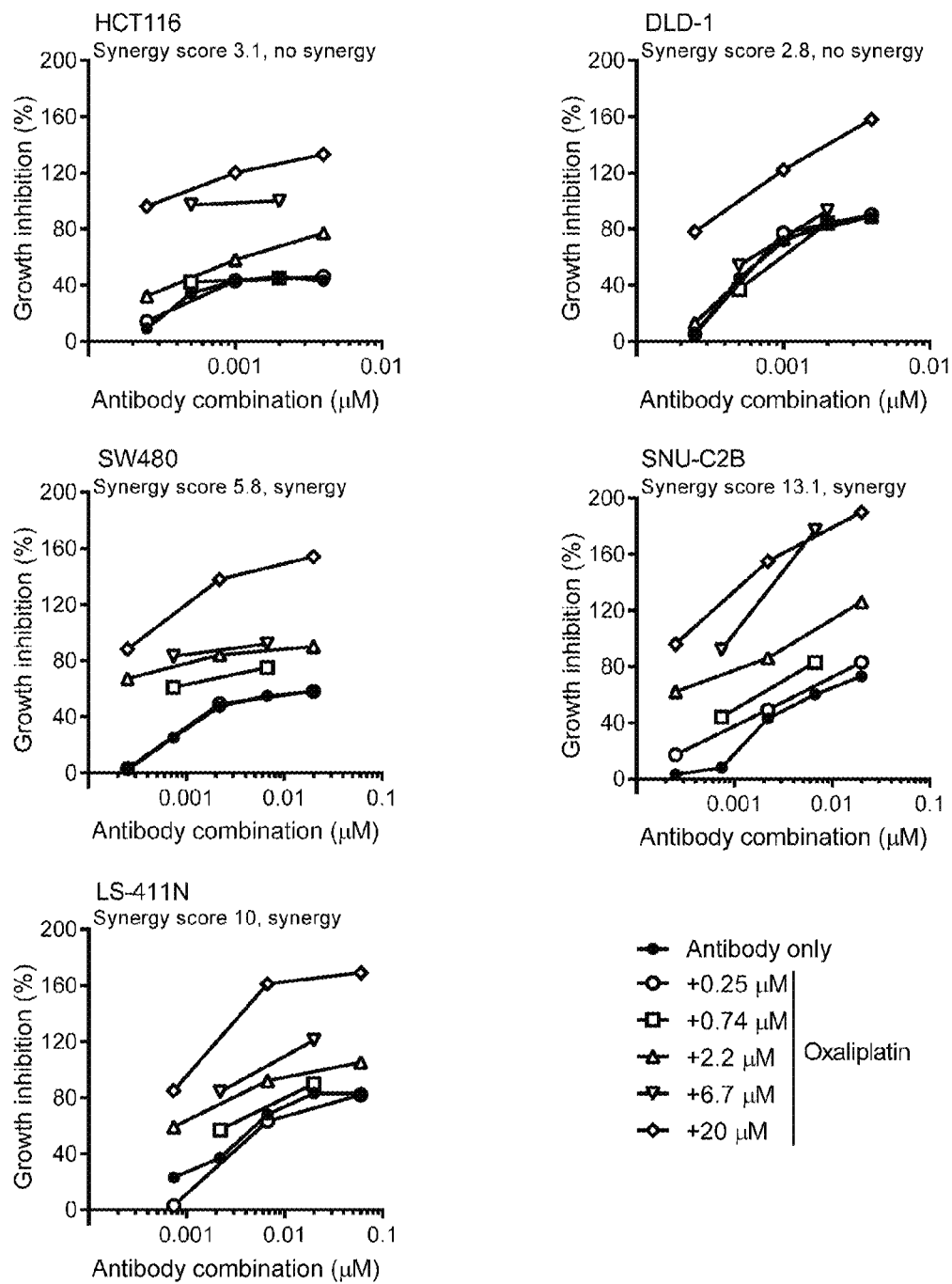
Figure 46C:
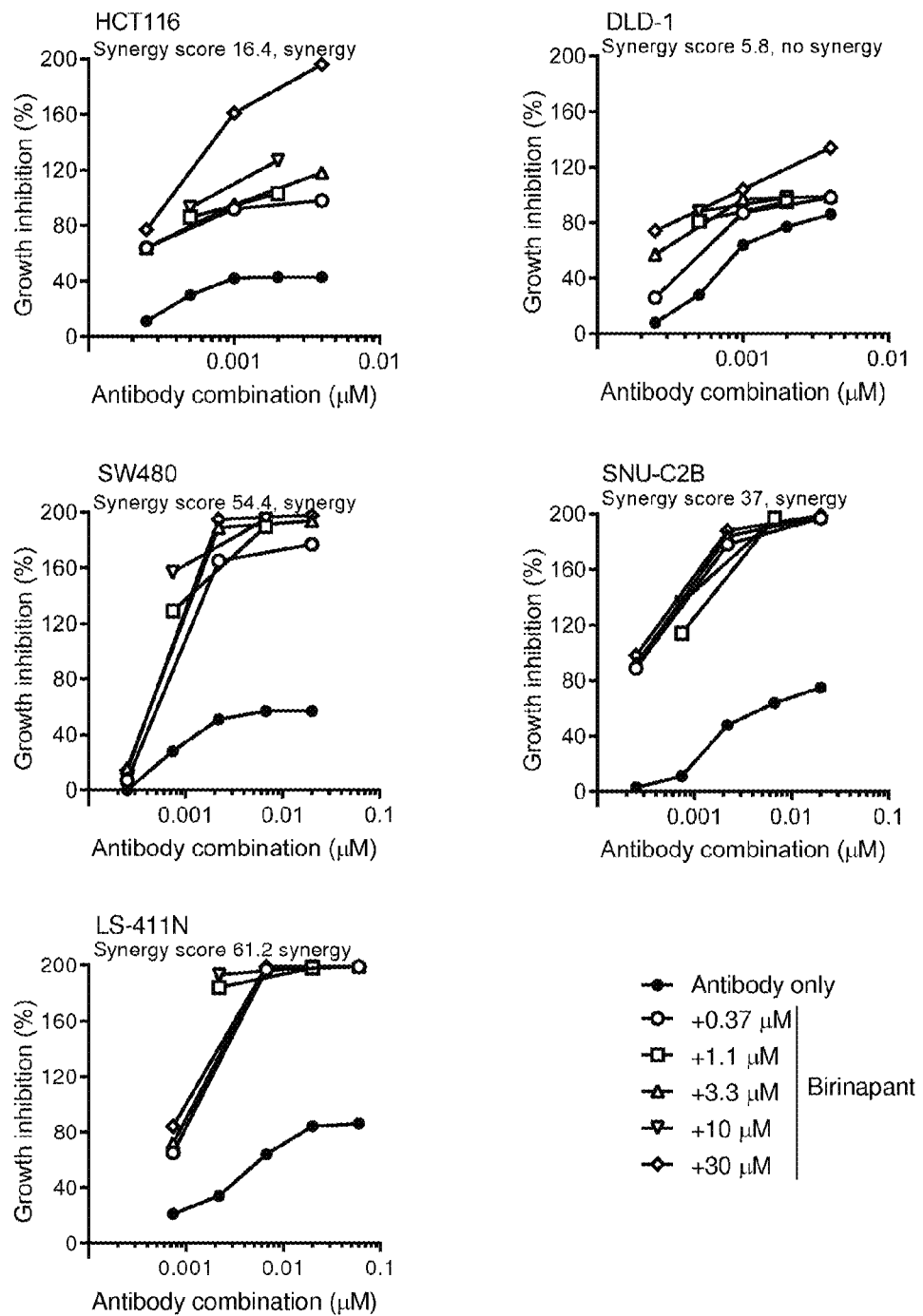
Figure 46D:
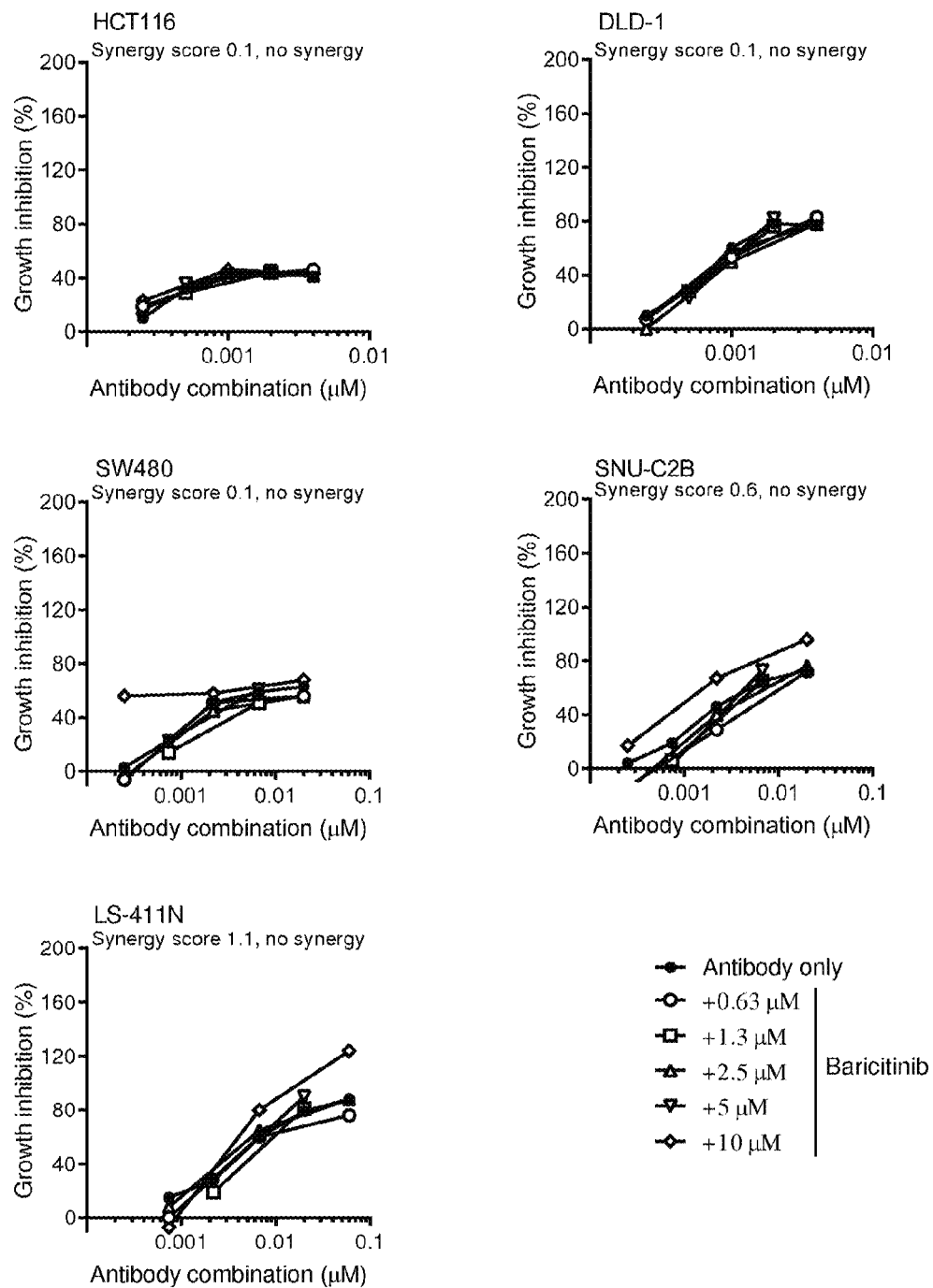

Table 12 shows the Synergy Scores for all 100 tested compounds. Synergy with the antibody combination IgG1-hDR5-01-G56T-E430G+IgG1-hDR5-05-E430G was observed for one or more cell lines with compounds from the different therapeutic classes, including chemotherapeutics (including cytoskeletal regulators and DNA/RNA damaging agents), kinase inhibitors, PI3K pathway inhibitors, RAS inhibitors, apoptosis-modulating agents, proteasome inhibitors, epigenetic modulators (including HDAC inhibitors) and others. FIG. 46 shows five examples of the growth inhibition effect of tested compounds in combination with the antibody combination IgG1-hDR5-01-G56T-E430G+ IgG1-hDR5-05-E430G. Birinapant (FIG. 46C), oxaliplatin (FIG. 46A), irinotecan (FIG. 46B) and paclitaxel (FIG. 46E) are examples that enhanced the effect of IgG1-hDR5-01-G56T-E430G+IgG1-hDR5-05-E430G, while baricitinib (FIG. 46D) is an example that showed no effect on the activity of IgG1-hDR5-01-G56T-E430G+IgG1-hDR5-05-E430G.

TABLE 12

Table 12: synergy scores for 100 compounds of different therapeutic classes that were tested in combination with IgG1-hDR5-01-G56T-E430G + IgG1-hDR5-05-E430G in viability assays on the colon cancer cell lines LS-411N, SNU-C2B, SW480, DLD-1 and HCT 116. Synergistic effects (Synergy Scores > mean self-cross + 3σ) are indicated in italics.

| Therapeutic class | Compound | Target | Synergy Scores in italics > mean self-cross + 3σ | | | | |
|---|---|---|---|---|---|---|---|
| | | | DLD-1 | HCT-116 | LS-411N | SNU-C2B | SW480 |
| Cytoskeletal regulator | vinblastine | TUBB2 | *17.7* | *14.6* | *36* | *12.6* | *16.8* |
| Cytoskeletal regulator | docetaxel | TUBB1 | *17.6* | 7.9 | *36.2* | *15.8* | *19.5* |
| Cytoskeletal regulator | paclitaxel | TUBB1 | *11.4* | *11.8* | *40.8* | *15.6* | *14.7* |
| Cytoskeletal regulator | vincristine | TUBB2 | *17.3* | *13.9* | *33* | *17.2* | *12.1* |
| Cytoskeletal regulator | vinorelbine | TUBB2 | 5.9 | *8.1* | *21.5* | 11 | 7.7 |
| DNA/RNA damaging agents | Gemcitabine | Antimetabolite | *20.3* | *12.2* | 5.7 | *18.5* | *31.1* |
| DNA/RNA damaging agents | Cytarabine | Antimetabolite | *20.8* | *10.7* | *11.4* | *24.6* | *19.6* |
| DNA/RNA damaging agents | Daunorubicin | DNA Intercalator | *13.8* | 5.5 | *10.4* | *17.5* | *16.7* |
| DNA/RNA damaging agents | Cisplatin | DNA Alkylating Agent | *8.8* | 6.7 | *15.4* | *12.9* | *18.9* |
| DNA/RNA damaging agents | Carboplatin | DNA Alkylating Agent | *11.3* | 5.8 | *12* | *11.6* | *19.5* |
| DNA/RNA damaging agents | Oxaliplatin | DNA Alkylating Agent | 2.8 | 3.1 | *10* | *13.1* | *5.8* |
| DNA/RNA damaging agents | Chlorambucil | DNA Alkylating Agent | 4.6 | 1 | 3.8 | *11.4* | 7.9 |
| DNA/RNA damaging agents | Melphalan | DNA Alkylating Agent | 6 | 1.1 | 3.4 | 9 | 7.6 |
| DNA/RNA damaging agents | Methotrexate | Antimetabolite | 0.1 | 0.5 | 6.6 | 1.7 | 2.5 |
| DNA/RNA damaging agents | Dacarbazine | DNA Alkylating Agent | 0.8 | 1.5 | 0.3 | 2 | 2.5 |
| DNA/RNA damaging agents | Fludarabine | Antimetabolite | 0.5 | 0.9 | 0.1 | 3.1 | 0.3 |
| DNA/RNA damaging agents | Fluorouracil | Antimetabolite | 1.2 | 1 | 1.1 | 0.4 | 0.8 |
| DNA/RNA damaging agents | Bendamustine | DNA Alkylating Agent | 0.1 | 0 | 0.3 | 3 | 0.6 |
| DNA/RNA damaging agents | Temozolomide | DNA Alkylating Agent | 0.1 | 0 | 0.1 | 0.6 | 0.8 |
| DNA/RNA damaging agents | Ifosfamide | DNA Alkylating Agent | 0.1 | 0 | 0.2 | 0.3 | 0.1 |
| Epigenetic Modulators | Belinostat | HDAC | *8.6* | 4.1 | *4.5* | *16.4* | *10.2* |
| Epigenetic Modulators | (+)-JQ1 | BET Bromodomain | *8.2* | 2.6 | *13.4* | *10.7* | *5.8* |
| Epigenetic Modulators | Decitabine | DNA Methyltransferase | 1.1 | 2.8 | 0 | *4.8* | 3.4 |
| PI3K Pathway Inhibitors | TIC10 | Akt, ERK | *15.5* | 2.2 | *23.3* | *13.1* | 3.4 |
| PI3K Pathway Inhibitors | GDC-0941 | PI3K | 4.9 | 2 | *12.4* | *7.1* | *12.9* |
| PI3K Pathway Inhibitors | AZD 8055 | mTOR | 3 | 1.7 | *10* | *12.2* | 3.9 |
| PI3K Pathway Inhibitors | PIK-93 | PI4K, PI3K | 1 | 1.2 | *5.2* | *5.1* | 4.1 |
| PI3K Pathway Inhibitors | BEZ235 | mTOR, PI3K | 2.4 | 1.4 | 1.1 | *5.4* | 3.2 |
| PI3K Pathway Inhibitors | Temsirolimus | mTOR | 0.7 | 0.6 | 0.6 | *4.5* | 1.6 |
| PI3K Pathway Inhibitors | Everolimus | mTOR | 0.4 | 0.4 | 0.3 | 3.2 | 1.6 |
| PI3K Pathway Inhibitors | GSK1059615 | mTOR, PI3K | 0.4 | 0.6 | 0.4 | 0.8 | 1.7 |
| PI3K Pathway Inhibitors | IPI-145 | PI3K | 0 | 0 | 0.2 | 1 | 0.1 |
| PI3K Pathway Inhibitors | IC-87114 | PI3K | 0 | 0.1 | 0.2 | 0.1 | 0 |
| Receptor Tyrosine Kinase Inhibitors | Crizotinib | c-Met, Alk | *13.4* | 7.7 | *16.1* | *5.4* | *8.9* |
| Receptor Tyrosine Kinase Inhibitors | RAF265 | RAF/VEGFR inhibitor | 5.6 | 2.5 | *10.5* | *13.7* | 4.5 |
| Receptor Tyrosine Kinase Inhibitors | Dasatinib | Abl and Src Family Kinases | *11.4* | 1.9 | *7.8* | 1 | *10.2* |
| Receptor Tyrosine Kinase Inhibitors | BMS-754807 | IGFR, InsR, c-Met, TrkB | *11.3* | 2.1 | *10.8* | 1.3 | *5.9* |
| Receptor Tyrosine Kinase Inhibitors | Sunitinib | VEGFR, PDGFR | 9.2 | 0.7 | 7.2 | 1.4 | 5.2 |
| Receptor Tyrosine Kinase Inhibitors | XL184 | VEGFR, c-Met, Ret, c-Kit, Flt, Tie, AXL | 4.1 | 1 | *5.8* | 1.5 | *6* |
| Receptor Tyrosine Kinase Inhibitors | Lapatinib | EGFR, HER2 | 1 | 0.4 | *7.3* | 2.6 | *6.4* |
| Receptor Tyrosine Kinase Inhibitors | AP24534 | Abl and Src Family Kinases | 4.3 | 1.4 | 2.6 | 1.8 | 3.7 |
| Receptor Tyrosine Kinase Inhibitors | GSK1904529A | IGF-1R | 1.4 | 0.2 | *6* | 2.7 | 2.2 |
| Receptor Tyrosine Kinase Inhibitors | Erlotinib | EGFR | 4.3 | 0.2 | 1.9 | 1.2 | 1 |
| Receptor Tyrosine Kinase Inhibitors | Gefitinib | EGFR | 4.9 | 0.2 | 1 | 1.1 | 1.3 |
| Receptor Tyrosine Kinase Inhibitors | OSI-906 | IGFR, InsR | 0.5 | 0.1 | 1.7 | 1 | 3.5 |
| Receptor Tyrosine Kinase Inhibitors | Masitinib | c-Kit, PDGFR | 0.6 | 0.3 | 1.4 | 1.7 | 1.9 |
| Receptor Tyrosine Kinase Inhibitors | BGJ398 | FGFR | 1 | 0.1 | 1.4 | 0.8 | 1.6 |

TABLE 12-continued

Table 12: synergy scores for 100 compounds of different therapeutic classes that were tested in combination with IgG1-hDR5-01-G56T-E430G + IgG1-hDR5-05-E430G in viability assays on the colon cancer cell lines LS-411N, SNU-C2B, SW480, DLD-1 and HCT 116. Synergistic effects (Synergy Scores > mean self-cross + 3σ) are indicated in italics.

| Therapeutic class | Compound | Target | DLD-1 | HCT-116 | LS-411N | SNU-C2B | SW480 |
|---|---|---|---|---|---|---|---|
| Receptor Tyrosine Kinase Inhibitors | MGCD-265 | c-Met, VEGFR | 0.2 | 0.1 | 0.7 | 3.1 | 0.5 |
| Receptor Tyrosine Kinase Inhibitors | AST-1306 | EGFR, HER2, HER4 | 0.3 | 0.1 | 1.8 | 0.7 | 0.9 |
| Receptor Tyrosine Kinase Inhibitors | Nilotinib | Abl and Src Family Kinases | 0.1 | 0 | 0.2 | 1.7 | 0.4 |
| Receptor Tyrosine Kinase Inhibitors | PCI-32765 | BTK | 0.5 | 0 | 0.3 | 0.6 | 0.4 |
| Receptor Tyrosine Kinase Inhibitors | Imatinib | Abl and Src Family Kinases | 0.2 | 0.1 | 0.3 | 0.3 | 0.3 |
| Receptor Tyrosine Kinase Inhibitors | INCB28060 | c-Met | 0.2 | 0.1 | 0 | 0.4 | 0 |
| Receptor Tyrosine Kinase Inhibitors | JNJ-38877605 | c-Met | 0.1 | 0 | 0.1 | 0.1 | 0 |
| Regulators of Apoptosis | Birinapant | XIAP, cIAP | 5.8 | *16.4* | *61.2* | *37* | *54.5* |
| Regulators of Apoptosis | TW-37 | Bcl family | *13.8* | 5.4 | *29.9* | *11.1* | *10.5* |
| Regulators of Apoptosis | Obatoclax | Bcl family | *6.1* | 1.6 | *22.8* | *4.7* | *11.8* |
| Regulators of Apoptosis | YM155 | Survivin | 5.2 | 0.5 | 9 | *11.5* | *12.1* |
| Regulators of Apoptosis | PAC 1 | Caspase | *10.6* | 4.2 | 2.9 | *6* | *3.9* |
| Regulators of Apoptosis | ABT-263 | Bcl family | 3.4 | 0 | *7.6* | 1 | *8* |
| Regulators of Apoptosis | ABT-737 | Bcl family | 1.5 | 0 | 4.2 | 1.1 | *7.5* |
| Regulators of Apoptosis | SB 415286 | GSK3 | 0.4 | 0.8 | 2.1 | 0.7 | *3.8* |
| Regulators of Apoptosis | SB-216763 | GSK3 | 0.5 | 0.1 | 1.1 | 0.3 | 1.4 |
| Regulators of Apoptosis | TNF-related apoptosis-inducing ligand | TRAIL | 0 | 0 | 0.1 | 0.2 | 0.9 |
| Regulators of Apoptosis | ABT-199 | Bcl family | 0 | 0 | 0.1 | 0 | 0 |
| Topoisomerase Inhibitors | Topotecan | Top1 | *20.3* | 5 | *29* | *21.2* | *30.5* |
| Topoisomerase Inhibitors | Teniposide | Top2 | 18.8 | 6.2 | *29.3* | *19.8* | *25.1* |
| Topoisomerase Inhibitors | 10-Hydroxycamptothecin | Top1 | *21.9* | 9.6 | *16.9* | *12.4* | *30.1* |
| Topoisomerase Inhibitors | Doxorubicin | Top2 | *16.2* | 4.6 | *9.4* | *18* | *20.5* |
| Topoisomerase Inhibitors | Irinotecan | Top1 | *15* | 4.4 | *6.8* | *13.4* | *24.7* |
| Topoisomerase Inhibitors | Etoposide | Top2 | *17* | 2 | *11.1* | *14.2* | *19.4* |
| Topoisomerase Inhibitors | Epirubicin | Top2 | *15.6* | 4.9 | 5.8 | *15.1* | *17.7* |
| | Tipifarnib | FTase | 3.1 | 3.3 | *24.3* | *7.2* | *5* |
| | Idasanutlin | MDM2 | *6.3* | 3.2 | *16.3* | *10.4* | *6.1* |
| | Suberoylanilide Hydroxamic Acid | | 4.4 | 2.5 | 4.4 | *11* | *7.3* |
| | Bortezomib | Proteasome | 3 | 2.6 | *7.2* | *7.5* | *8.9* |
| | GSK429286A | | 4.9 | 2.6 | *9.8* | *5.3* | 5.3 |
| | GF 109203X | | 4.3 | 3 | *5.3* | 1.6 | *6.2* |
| | AZD6244 | | 1.5 | 2.7 | 0.7 | 0.6 | *11.7* |
| | Trametinib | | 4.1 | 4 | 0.9 | 0.6 | *7.2* |
| | Sorafenib | | 2.6 | 0.5 | *6* | 2.9 | *3.9* |
| | Enzastaurin | | 0.9 | 0.6 | *5.6* | 0.5 | *6.3* |
| | Tamoxifen Citrate | | 0.3 | 0.3 | *8* | 0.7 | 2.9 |
| | Go 6976 | | 2.9 | 0.9 | 1.9 | 1.7 | *3.1* |
| | Olaparib | | 0.7 | 1.8 | 2.7 | 2.5 | 1 |
| | SP 600125 | | 3.3 | 0.6 | 0.5 | 2 | 0.9 |
| | Dabrafenib | | 2.2 | 0.7 | 0.5 | 0.5 | *3.1* |
| | GDC-0879 | | 0.1 | 0.2 | 0.4 | 0.7 | 1.6 |
| | PLX-4032 | | 0.6 | 0.1 | 0.6 | 0.5 | 1 |
| | Baricitinib | JAK inhibitors | 0.1 | 0.1 | 1.1 | 0.6 | 0.1 |
| | JNK-IN-8 | JNK inhibitor | 0.2 | 0 | 0.1 | 1.1 | 0.4 |
| | Dexamethasone | | 0.1 | 0 | 0.4 | 0.8 | 0 |
| | ABT-888 | | 0.2 | 0.2 | 0.7 | 0.1 | 0 |
| | Salirasib | | 0.1 | 0.1 | 0 | 0.4 | 0.4 |
| | CP-690550 | JAK inhibitors | 0.1 | 0 | 0.6 | 0.1 | 0 |
| | GDC-0449 | | 0.1 | 0 | 0.2 | 0.3 | 0.1 |
| | Methylprednisolone | | 0 | 0 | 0 | 0.6 | 0 |
| | Pomalidomide | | 0.1 | 0 | 0 | 0.5 | 0 |
| | Prednisone | | 0.1 | 0 | 0.1 | 0.2 | 0 |
| | Lenalidomide | | 0 | 0 | 0.1 | 0.2 | 0 |

Example 49: In Vivo Efficacy of the Anti-DR5 Antibodies IgG1-hDR5-01-G56T-E430G and IgG1-hDR5-05-E430G in a Subcutaneous COLO 205 Colon Cancer Xenograft Model The in vivo anti-tumor efficacy of antibodies IgG1-hDR5-01-G56T-E430G and IgG1-hDR5-05-E430G was evaluated for the single antibodies and the combination of both antibodies and compared to the parental antibodies without the E430G mutation in the subcutaneous COLO 205 human colon cancer xenograft model. Tumor cell inoculation, mice handling, tumor outgrowth measurements and endpoint determination were performed, essentially as described in Example 26. $3\times10^6$ cells were injected in a volume of 100 µL PBS into the flank of 5-8 weeks old female SCID mice (C.B-17/IcrHan® Hsd-Prkdc$^{scid}$; Harlan). At day 9, the average tumor volume was measured and the mice were sorted into groups with equal tumor size variance. Mice were treated by intravenous (i.v.) injection of 10 µg (0.5 mg/kg) antibody in 200 µL PBS on day 9. Mice in the control group were treated with 10 µg (0.5 mg/kg) IgG1-b12.

TABLE 13

Treatment groups and dosing

| # mice | # analyzed | Antibody | Total antibody dose | Dosing day after tumor inoculation |
|---|---|---|---|---|
| 8 | 8 | IgG1-hDR5-01-G56T-E430G | 0.5 mg/kg | 9 |
| 8 | 8 | IgG1-hDR5-05-E430G | 0.5 mg/kg | 9 |
| 8 | 8 | IgG1-hDR5-01-G56T-E430G IgG1-hDR5-05-E430G | 0.5 mg/kg | 9 |
| 8 | 8 | IgG1-hDR5-01-G56T | 0.5 mg/kg | 9 |
| 8 | 8 | IgG1-hDR5-05 | 0.5 mg/kg | 9 |
| 8 | 8 | IgG1-hDR5-01-G56T IgG1-hDR5-05 | 0.5 mg/kg | 9 |
| 8 | 8 | IgG1-b12 | 0.5 mg/kg | 9 |

FIG. 47A shows mean tumor volumes per treatment group in time. Introduction of the E430G mutation in the single antibodies IgG1-hDR5-01-G56T-E430G and IgG1-hDR5-05-E430G resulted in enhanced inhibition of tumor growth compared to the parental antibodies without the E430G mutation. Treatment with the antibody combinations induced complete tumor regression, both for IgG1-hDR5-01-G56T-E430G+IgG1-hDR5-05-E430G and for the combination of parental antibodies without the E430G mutation. At day 19 the average tumor size in all groups treated with DR5-antibodies was significantly smaller than in animals treated with the negative control antibody IgG1-b12 (Mann Whitney test (P<0.001))(data not shown). FIG. 47B shows a Kaplan-Meier plot of tumor progression, with a cutoff set at a tumor volume>500 mm$^3$. Compared to mice treated with negative control antibody IgG1-b12, tumor outgrowth was significantly delayed in all groups treated with anti-DR5 antibodies (Mantel-Cox analysis at tumor size cut-off 500 mm$^3$: p<0.0001). Mice treated with the single antibodies IgG1-hDR5-01-G56T and IgG1-hDR5-05 without the hexamerization-enhancing mutation E430G showed tumor outgrowth significantly earlier compared to the mice treated with the other tested anti-DR5 antibodies ((Mantel-Cox analysis at tumor size cut-off 500 mm$^3$: p<0.0001).

Example 50: Effect of a Hexamerization-Enhancing Mutation on the In Vivo Efficacy of the Combination of Anti-DR5 Antibodies IgG1-hDR5-01-G56T+IgG1-hDR5-05 in a Subcutaneous HCT15 Colon Cancer Xenograft Model The in vivo anti-tumor efficacy of the anti-DR5 antibody combination IgG1-hDR5-01-G56T-E430G+IgG1-hDR5-05-E430G was compared to that of IgG1-hDR5-01-G56T+IgG1-hDR5-05 without the E430G hexamerization-enhancing mutation in the subcutaneous HCT15 human colon cancer xenograft model at CrownBiosciences, Taicang, China. The cells were maintained in vitro as a monolayer culture in RPMI-1640 medium supplemented with 10% fetal bovine serum at 37° C. in an atmosphere of 5% CO2 in air. Adherent cells in an exponential growth phase were harvested by trypsin-EDTA treatment. $5\times10^6$ cells were injected in a volume of 100 µL PBS into the flank of 7-9 weeks old female BALB/c nude mice. The care and use of animals during the study were conducted in accordance with the regulations of the Association for Assessment and Accreditation of Laboratory Animal Care (AAALAC). Tumor volumes were measured twice weekly in two dimensions using a caliper, and the volume was expressed in mm$^3$ using the formula: V=0.5 a×b$^2$ where a and b are the long and short diameters of the tumor, respectively. Mice were assigned into groups using randomized block design and treatments were started when the mean tumor size reached 161 mm$^3$ (8 mice per group). Mice were treated three times according to a Q7D regimen by i.v. injection of 0.5 mg/kg antibody (0.25 mg/kg of each antibody in the combination). Mice in the control group were treated in parallel with 0.5 mg/kg IgG1-b12.

FIG. 48A shows mean tumor volumes per treatment group. The antibody combination IgG1-hDR5-01-G56T-E430G+IgG1-hDR5-05-E430G showed better tumor growth inhibition than IgG1-hDR5-01-G56T+IgG1-hDR5-05. At day 21 the average tumor size in mice treated with the combination IgG1-hDR5-01-G56T-E430G+IgG1-hDR5-05-E430G was significantly smaller than in mice treated with an equivalent dose IgG1-hDR5-01-G56T+IgG1-hDR5-05 (Mann Whitney test: P<0.0011) (FIG. 48B). FIG. 48C shows a Kaplan-Meier plot of tumor progression, with a cutoff set at a tumor volume>750 mm$^3$. Tumor outgrowth in mice treated with the combination IgG1-hDR5-01-G56T-E430G+IgG1-hDR5-05-E430G was significantly later than in mice treated with an equivalent dose IgG1-hDR5-01-G56T+IgG1-hDR5-05.

These data indicate that introduction of the E430G hexamerization-enhancing mutation in the anti-DR5 antibody combination IgG1-DR5-01-K409R-E430G+IgG1-DR5-05-F405L-E430G resulted in enhanced tumor growth inhibition in an in vivo xenograft model with HCT15 human colon cancer cells.

Example 51: In Vivo Efficacy of IgG1-hDR5-01-G56T-E430G+IgG1-hDR5-05-E430G in Combination with Paclitaxel in a Subcutaneous SK-MES-1 Human Lung Cancer Xenograft Model The in vivo anti-tumor efficacy of IgG1-hDR5-01-G56T-E430G+IgG1-hDR5-05-E430G was evaluated in combination with paclitaxel in the subcutaneous SK-MES-1 human lung cancer xenograft model at CrownBiosciences, Taicang, China. Cell culturing, tumor cell inoculation, mice handling, tumor outgrowth measurements and endpoint determination were performed as described in Example 33. 21 days after tumor inoculation, the mean tumor size reached 167 mm³ and mice were assigned into groups using randomized block design and treatments were started. Mice were treated twice according to a Q7D regimen by i.v. injections of 2 mg/kg antibody and 15 mg/kg paclitaxel both dosed in 10 μL PBS per g body weight as indicated in Table 14.

TABLE 14

Treatment groups and dosing, Example 53

| # mice | Compound | Total per dose | Dosing day after randomization |
|---|---|---|---|
| 8 | IgG1-hDR5-01-G56T-E430G IgG1-hDR5-05-E430G | 2 mg/kg | 0, 7 |
| 8 | Paclitaxel | 15 mg/kg | 0, 7 |
| 8 | IgG1-hDR5-01-G56T-E430G IgG1-hDR5-05-E430G Paclitaxel | 2 mg/kg antibody + 15 mg/kg paclitaxel | 0, 7 |
| 8 | IgG1-b12 | 2 mg/kg | 0, 7 |

FIG. 49A shows mean tumor volumes per treatment group. Antibody treatment alone (2 mg/kg IgG1-hDR5-01-G56T-E430G+IgG1-hDR5-05-E430G) or 2 mg/kg antibody treatment in combination with 15 mg/kg paclitaxel or 15 mg/kg paclitaxel alone all demonstrated anti-tumor efficacy compared to IgG1-b12. FIG. 49B shows tumor volume per treatment group at day 16. In all treatment groups, tumor load was significantly lower compared to IgG1-b12 (Mann-Whitney test, p<0.01). FIG. 49C shows a Kaplan-Meier plot of tumor progression, with a cutoff set at a tumor volume>500 mm³. The combination of 15 mg/kg paclitaxel with 2 mg/kg IgG1-hDR5-01-G56T-E430G+IgG1-hDR5-05-E430G antibody significantly prolonged progression-free survival compared to paclitaxel or antibody alone (Gehan-Breslow-Wilcoxon test, tumor size cut-off 500 mm³: p<0.05).

Example 52: Pharmacokinetic (PK) Analysis of IgG1-hDR5-01-G56T-E430G and IgG1-hDR5-05-E430G The clearance rate of IgG1-hDR5-01-G56T-E430G and IgG1-hDR5-05-E430G was studied in a PK experiment in SCID mice for the single compounds and for the combination of the two antibodies in comparison to the parental antibodies without the E430G mutation.

7-10 weeks old female SCID (C.B-17/IcrHan@Hsd-Prkdc<scid, Harlan) mice (3 mice per group) were injected intravenously with 20 μg antibody (1 mg/kg) in a 200 μL injection volume. 50-100 μL blood samples were collected from the saphenous vein at 10 minutes, 4 hours, 1 day, 2 days, 7 days, 14 days and 21 days after antibody administration. Blood was collected into heparin-containing vials and centrifuged for 5 minutes at 10,000 g. Plasma samples were diluted 1:20 for the four first time points (15 μL sample in 285 μL PBSA (PBS supplemented with 0.2% bovine serum albumin (BSA)) and 1:10 for the last two time points (30 μL sample in 270 μL PBSA) and stored at −20° C. until determination of antibody concentrations.

Total human IgG concentrations were determined using a sandwich ELISA. Mouse anti-human IgG-kappa mAb clone MH16 (CLB Sanquin, Cat ##M1268) was used as capturing antibody and coated in 100 μL overnight at 4° C. to 96-well Microlon ELISA plates (Greiner, Germany) at a concentration of 2 μg/mL in PBS. Plates were blocked by incubating on a plate shaker for 1 h at RT with PBSA. After washing, 100 μL of serial diluted plasma samples (range 0.037-1 μg/mL in 3-fold dilutions) were added and incubated on a plate shaker for 1 h at RT. Plates were washed three times with 300 μL PBST (PBS supplemented with 0.05% Tween 20) and subsequently incubated on a plate shaker for 1 h at RT with 100 μL peroxidase-labeled goat anti-human IgG immunoglobulin (#109-035-098, Jackson, West Grace, Pa.; 1:10.000 in PBST supplemented with 0.2% BSA). Plates were washed again three times with 300 μL PBST before incubation for 15 minutes at RT with 100 μL substrate 2,2'-azino-bis (3-ethylbenzthiazoline-6-sulfonic acid) [ABTS; Roche, Cat #11112 422001; 1 tablet in 50 mL ABTS buffer (Roche, Cat #11112 597001)] protected from light. The reaction was stopped by adding 100 μL 2% oxalic acid and incubation for 10 minutes at RT. Absorbance was measured in a microplate reader (Biotek, Winooski, Vt.) at 405 nm. Concentration was calculated by using the injected material as a reference curve. As a plate control, purified human IgG1 (The binding site, Cat #BP078) was included. Human IgG concentrations (in μg/mL) were plotted (FIG. 50A) and Area under the curve (AUC) was calculated using Graphpad prism 6.0. Clearance until the last day of blood sampling (day 21) was determined by the formula D*1.000/AUC, in which D is the dose of injection (1 mg/kg) (FIG. 50B).

No difference in the plasma clearance rate was observed between IgG1-hDR5-01-G56T-E430G or IgG1-hDR5-05-E430G and their parental antibodies without the E430G mutation, both when injected as single agents or as the combinations of those (FIG. 50).

Example 53: Anti-DR5 Antibody IgG1-DR5-CONA with a Hexamerization-Enhancing Mutation E430G is Able to Kill Human Colon Cancer Cells The present study illustrate the ability of the anti-DR5 antibody IgG1-DR5-CONA with the hexamerization-enhancing mutation E430G to kill attached human colon cancer cells COLO 205. COLO 205 cells were harvested as described in Example 8. 100 μL of the single cell suspensions (5,000 cells per well) were seeded in 96-well flat-bottom plates and incubated overnight at 37° C. 50 μL samples of antibody concentration series (range 0.04 to 10 μg/mL final concentrations in 4-fold dilutions) were added and incubated for 3 days at 37° C. As a positive control, cells were incubated with 5 μM staurosporine. The viability of the cell cultures was determined in a CellTiter-Glo luminescent cell viability assay as described in Example 8. Luminescence was measured on an EnVision Multilabel Reader (PerkinElmer). Data were analyzed and plotted using non-linear regression (sigmoidal dose-response with variable slope) using GraphPad Prism software. The percentage viable cells was calculated using the following formula: % viable cells=[(luminescence antibody sample−luminescence staurosporine sample)/(luminescence no antibody sample−luminescence staurosporine sample)]*100.

FIG. 51 shows that introduction of the hexamerization-enhancing mutation E430G resulted in dose-dependent killing by IgG1-DR5-CONA-E430G, whereas the parental wild type antibody IgG1-DR5-CONA was not able to kill attached COLO 205 colon cancer cells.

The invention claimed is:

1. An antibody which binds to human DR5 and comprises a variable heavy chain (VH) region and a variable light chain (VL) region, wherein the VH and VL regions comprise VHCDR1, VHCDR2, and VHCDR3 domains comprising the amino acid sequences set forth in SEQ ID NOs: 1, 8, and 3, respectively, and VLCDR1, VLCDR2 and VLCDR3 domains comprising the amino acid sequences set forth in SEQ ID NO: 5, the sequence FAS, and SEQ ID NO: 6, respectively, and a Fc region of a human immunoglobulin IgG, wherein in the Fc region, the amino acid at the position corresponding to E430 in human IgG1 is mutated to G, wherein the numbering is according to the EU Index.

2. The antibody of claim 1, wherein the antibody is an IgG1, IgG2, IgG3, IgG4, IgE, IgD or IgM isotype.

3. The antibody of claim 1, wherein the antibody is humanized or chimeric.

4. A composition comprising at least one antibody according to claim 1 and a carrier.

5. A nucleic acid construct comprising a nucleic acid encoding the heavy and light chain variable regions of the antibody according to claim 1.

6. An expression vector comprising one or more nucleic acid constructs according to claim 5.

7. A host cell comprising the expression vector of claim 6.

8. A kit comprising the antibody of claim 1, and instructions for use.

9. The composition of claim 4, which comprises
    (a) a first antibody that binds to human DR5 and comprises VH and VL regions, wherein the VH region comprises VHCDR1, VHCDR2, and VHCDR3 domains comprising the amino acid sequences set forth in SEQ ID NOs: 1, 8, and 3, respectively, and the VL region comprises VLCDR1, VLCDR2, and VLCDR3 domains comprising the amino acid sequences set forth in SEQ ID NO: 5, the sequence FAS, and SEQ ID NO: 6, respectively, and (b) a second antibody that binds to human DR5 and comprises VH and VL regions, wherein the VH region comprises VHCDR1, VHCDR2, and VHCDR3 domains comprising the amino acid sequences set forth in SEQ ID NOs: 10, 2, and 11, respectively, and the VL region comprises VLCDR1, VLCDR2, and VLCDR3 domains comprising the amino acid sequences set forth in SEQ ID NO: 13, the sequence RTS, and SEQ ID NO: 14, respectively, wherein both the first antibody and second antibody comprise a Fc region of a human immunoglobulin IgG, and wherein in the Fc region of both the first antibody and second antibody, the amino acid at the position corresponding to E430 in human IgG1 is mutated to G.

10. The antibody of claim 1, wherein the antibody comprises a VH region and a VL region comprising the amino acid sequences set forth in SEQ ID NOs: 9 and 7, respectively.

11. The antibody of claim 1, wherein the antibody comprises a heavy chain and a light chain comprising the amino acid sequences set forth in SEQ ID NOs: 38 and 39, respectively.

12. A composition comprising the antibody of claim 11 and a carrier.

13. The composition of claim 12, further comprising an antibody which comprises a heavy chain and a light chain comprising the amino acid sequences set forth in SEQ ID NOs: 42 and 43, respectively.

14. The composition of claim 9, wherein the second antibody comprises a VH region and a VL region comprising the amino acid sequences set forth in SEQ ID NOs: 12 and 15, respectively.

15. The composition of claim 9, wherein the second antibody comprises a heavy chain and a light chain comprising the amino acid sequences set forth in SEQ ID NOs: 42 and 43, respectively.

16. The composition of claim 9, wherein the first antibody comprises a VH region and a VL region comprising the amino acid sequences set forth in SEQ ID NOs: 9 and 7, respectively.

17. The composition of claim 16, wherein the second antibody comprises a VH region and a VL region comprising the amino acid sequences set forth in SEQ ID NOs: 12 and 15, respectively.

18. The composition of claim 16, wherein the second antibody comprises a heavy chain and a light chain comprising the amino acid sequences set forth in SEQ ID NOs: 42 and 43, respectively.

19. The composition of claim 9, wherein the first antibody comprises a heavy chain and a light chain comprising the amino acid sequences set forth in SEQ ID NOs: 38 and 39, respectively.

20. The composition of claim 19, wherein the second antibody comprises a VH region and a VL region comprising the amino acid sequences set forth in SEQ ID NOs: 12 and 15, respectively.

21. A composition comprising:
(a) a first antibody that binds to human DR5 and comprises a heavy chain variable (VH) region and a light chain variable (VL) region, wherein the VH region comprises VHCDR1, VHCDR2, and VHCDR3 domains comprising the amino acid sequences set forth in SEQ ID NOs: 1, 8, and 3, respectively, and the VL region comprises VLCDR1, VLCDR2, and VLCDR3 domains comprising the amino acid sequences set forth in SEQ ID NO: 5, the sequence FAS, and SEQ ID NO: 6, respectively, and
(b) a second antibody that binds to human DR5 and comprises VH and VL regions, wherein the VH region comprises VHCDR1, VHCDR2, and VHCDR3 domains comprising the amino acid sequences set forth in SEQ ID NOs: 10, 2, and 11, respectively, and the VL region comprises VLCDR1, VLCDR2, and VLCDR3 domains comprising the amino acid sequences set forth in SEQ ID NO: 13, the sequence RTS, and SEQ ID NO: 14, respectively,
wherein both the first antibody and second antibody comprise a Fc region of a human immunoglobulin IgG, and wherein in the Fc region of both the first antibody and second antibody, the amino acid at the position corresponding to E430 in human IgG1 is mutated to G.

22. A composition comprising:
(a) a first antibody that binds to human DR5 and comprises a heavy chain variable (VH) region and a light chain variable (VL) region comprising the amino acid sequences set forth in SEQ ID NOs: 9 and 7, respectively, and
(b) a second antibody that binds to human DR5 and comprises a VH region and a VL region comprising the amino acid sequences set forth in SEQ ID NOs: 12 and 15, respectively,
wherein both the first antibody and second antibody comprise a Fc region of a human immunoglobulin IgG, and wherein in the Fc region of both the first antibody and second antibody, the amino acid at the position corresponding to E430 in human IgG1 is mutated to G.

23. A composition comprising:
(a) a first antibody that binds to human DR5 and comprises a heavy chain and a light chain comprising the amino acid sequences set forth in SEQ ID NOs: 38 and 39, respectively, and
(b) a second antibody that binds to human DR5 and comprises a heavy chain and a light chain comprising the amino acid sequences set forth in SEQ ID NOs: 42 and 43, respectively.

* * * * *

UNITED STATES PATENT AND TRADEMARK OFFICE
CERTIFICATE OF CORRECTION

PATENT NO. : 10,882,913 B2
APPLICATION NO. : 16/451714
DATED : January 5, 2021
INVENTOR(S) : Marije Overdijk et al.

It is certified that error appears in the above-identified patent and that said Letters Patent is hereby corrected as shown below:

On the Title Page

At Column 1, item (30), Line 1 of the "Foreign Application Priority Data" section, delete "2015 00771" and insert --PA 2015 00771--.

At Column 1, item (30), Line 2 of the "Foreign Application Priority Data" section, delete "2015 00787" and insert --PA 2015 00787--.

At Column 1, item (30), Line 3 of the "Foreign Application Priority Data" section, delete "2015 00788" and insert --PA 2015 00788--.

At Column 1, item (30), Line 4 of the "Foreign Application Priority Data" section, delete "2016 00701" and insert --PA 2016 00701--.

At Column 1, item (30), Line 5 of the "Foreign Application Priority Data" section, delete "2016 00702" and insert --PA 2016 00702--.

Signed and Sealed this
Twenty-third Day of February, 2021

Drew Hirshfeld
*Performing the Functions and Duties of the
Under Secretary of Commerce for Intellectual Property and
Director of the United States Patent and Trademark Office*

```
                         SEQUENCE LISTING

<160> NUMBER OF SEQ ID NOS: 68

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Gly Phe Asn Ile Lys Asp Thr Phe
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Ile Asp Pro Ala Asn Gly Asn Thr
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetic

<400> SEQUENCE: 3

Val Arg Gly Leu Tyr Thr Tyr Tyr Phe Asp Tyr
1               5                   10

<210> SEQ ID NO 4
<211> LENGTH: 118
<212> TYPE: PRT
<213> ORGANISM: Artificial Sequence
<220> FEATURE:
<223> OTHER INFORMATION: Synthetic

<400> SEQUENCE: 4

Glu Val Gln Leu Gln Gln Ser Gly Ala Glu Val Val Lys Pro Gly Ala
1               5                   10                  15

Ser Val Lys Leu Ser Cys Lys Ala Ser Gly Phe Asn Ile Lys Asp Thr
            20                  25                  30

Phe Ile His Trp Val Lys Gln Ala Pro Gly Gln Gly Leu Glu Trp Ile
        35                  40                  45
```

-continued

Gly Arg Ile Asp Pro Ala Asn Gly Asn Thr Lys Tyr Asp Pro Lys Phe
        50                  55                  60

Gln Gly Lys Ala Thr Ile Thr Thr Asp Thr Ser Ser Asn Thr Ala Tyr
 65                  70                  75                  80

Met Glu Leu Ser Ser Leu Arg Ser Glu Asp Thr Ala Val Tyr Tyr Cys
                 85                  90                  95

Val Arg Gly Leu Tyr Thr Tyr Tyr Phe Asp Tyr Trp Gly Gln Gly Thr
                100                 105                 110

Leu Val Thr Val Ser Ser
            115

<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

Gln Ser Ile Ser Asn Asn
 1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Gln Gln Gly Asn Ser Trp Pro Tyr Thr
 1               5

<210> SEQ ID NO 7
<211> LENGTH: 107
<212> TYPE: PRT
<213> ORGANISM: Artificial Sequence
<220> FEATURE:
<223> OTHER INFORMATION: Synthetic

<400> SEQUENCE: 7

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Ile Ser Asn Asn
                 20                  25                  30

Leu His Trp Tyr Gln Gln Lys Pro Gly Gln Ala Pro Arg Leu Leu Ile
             35                  40                  45

Lys Phe Ala Ser Gln Ser Ile Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Gly Asn Ser Trp Pro Tyr
                 85                  90                  95

Thr Phe Gly Gln Gly Thr Lys Leu Glu Ile Lys
            100                 105

<210> SEQ ID NO 8
<211> LENGTH: 8
<212> TYPE: PRT
<213> ORGANISM: Artificial Sequence
<220> FEATURE:

```
<223> OTHER INFORMATION: Synthetic

<400> SEQUENCE: 8

Ile Asp Pro Ala Asn Thr Asn Thr
1               5

<210> SEQ ID NO 9
<211> LENGTH: 118
<212> TYPE: PRT
<213> ORGANISM: Artificial Sequence
<220> FEATURE:
<223> OTHER INFORMATION: Synthetic

<400> SEQUENCE: 9

Glu Val Gln Leu Gln Gln Ser Gly Ala Glu Val Val Lys Pro Gly Ala
1               5                   10                  15

Ser Val Lys Leu Ser Cys Lys Ala Ser Gly Phe Asn Ile Lys Asp Thr
                20                  25                  30

Phe Ile His Trp Val Lys Gln Ala Pro Gly Gln Gly Leu Glu Trp Ile
            35                  40                  45

Gly Arg Ile Asp Pro Ala Asn Thr Asn Thr Lys Tyr Asp Pro Lys Phe
        50                  55                  60

Gln Gly Lys Ala Thr Ile Thr Thr Asp Thr Ser Asn Thr Ala Tyr
65                  70                  75                  80

Met Glu Leu Ser Ser Leu Arg Ser Glu Asp Thr Ala Val Tyr Tyr Cys
                85                  90                  95

Val Arg Gly Leu Tyr Thr Tyr Tyr Phe Asp Tyr Trp Gly Gln Gly Thr
                100                 105                 110

Leu Val Thr Val Ser Ser
        115

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Gly Phe Asn Ile Lys Asp Thr His
1               5

<210> SEQ ID NO 11
<211> LENGTH: 11
<212> TYPE: PRT
<213> ORGANISM: Artificial Sequence
<220> FEATURE:
<223> OTHER INFORMATION: Synthetic

<400> SEQUENCE: 11

Ala Arg Trp Gly Thr Asn Val Tyr Phe Ala Tyr
1               5                   10

<210> SEQ ID NO 12
<211> LENGTH: 118
<212> TYPE: PRT
<213> ORGANISM: Artificial Sequence
<220> FEATURE:
<223> OTHER INFORMATION: Synthetic

<400> SEQUENCE: 12

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Phe Asn Ile Lys Asp Thr
            20                  25                  30

His Met His Trp Val Arg Gln Ala Pro Gly Gln Arg Leu Glu Trp Ile
        35                  40                  45

Gly Arg Ile Asp Pro Ala Asn Gly Asn Thr Glu Tyr Asp Gln Lys Phe
50                  55                  60

Gln Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Thr Asn Val Tyr Phe Ala Tyr Trp Gly Gln Gly Thr
            100                 105                 110

Leu Val Thr Val Ser Ser
        115
```

<210> SEQ ID NO 13
<211> LENGTH: 5
<212> TYPE: PRT
<213> ORGANISM: Artificial Sequence
<220> FEATURE:
<223> OTHER INFORMATION: Synthetic

<400> SEQUENCE: 13

```
Ser Ser Val Ser Tyr
1               5
```

<210> SEQ ID NO 14
<211> LENGTH: 9
<212> TYPE: PRT
<213> ORGANISM: Artificial Sequence
<220> FEATURE:
<223> OTHER INFORMATION: Synthetic

<400> SEQUENCE: 14

```
Gln Gln Tyr His Ser Tyr Pro Pro Thr
1               5
```

<210> SEQ ID NO 15
<211> LENGTH: 106
<212> TYPE: PRT
<213> ORGANISM: Artificial Sequence
<220> FEATURE:
<223> OTHER INFORMATION: Synthetic

<400> SEQUENCE: 15

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Tyr Trp Tyr Gln Gln Lys Pro Gly Lys Ala Pro Lys Pro Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Tyr His Ser Tyr Pro Pro Thr
                85                  90                  95

Phe Gly Gly Gly Thr Lys Val Glu Ile Lys
            100                 105
```

<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

```
Gly Gly Ser Ile Ser Ser Gly Asp Tyr Phe
1               5                   10
```

<210> SEQ ID NO 17
<211> LENGTH: 7
<212> TYPE: PRT
<213> ORGANISM: Artificial Sequence
<220> FEATURE:
<223> OTHER INFORMATION: Synthetic

<400> SEQUENCE: 17

```
Ile His Asn Ser Gly Thr Thr
1               5
```

<210> SEQ ID NO 18
<211> LENGTH: 14
<212> TYPE: PRT
<213> ORGANISM: Artificial Sequence
<220> FEATURE:
<223> OTHER INFORMATION: Synthetic

<400> SEQUENCE: 18

```
Ala Arg Asp Arg Gly Gly Asp Tyr Tyr Tyr Gly Met Asp Val
1               5                   10
```

<210> SEQ ID NO 19
<211> LENGTH: 122
<212> TYPE: PRT
<213> ORGANISM: Artificial Sequence
<220> FEATURE:
<223> OTHER INFORMATION: Synthetic

<400> SEQUENCE: 19

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Phe Trp Ser Trp Ile Arg Gln Leu Pro Gly Lys Gly Leu Glu
        35                  40                  45

Cys Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
                85                  90                  95

Cys Ala Arg Asp Arg Gly Gly Asp Tyr Tyr Tyr Gly Met Asp Val Trp
            100                 105                 110

Gly Gln Gly Thr Thr Val Thr Val Ser Ser
        115                 120
```

<210> SEQ ID NO 20
<211> LENGTH: 122
<212> TYPE: PRT
<213> ORGANISM: Artificial Sequence
<220> FEATURE:

<223> OTHER INFORMATION: Synthetic

<400> SEQUENCE: 20

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Phe Trp Ser Trp Ile Arg Gln Leu Pro Gly Lys Gly Leu Glu
        35                  40                  45

Trp Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
                85                  90                  95

Cys Ala Arg Asp Arg Gly Gly Asp Tyr Tyr Tyr Gly Met Asp Val Trp
            100                 105                 110

Gly Gln Gly Thr Thr Val Thr Val Ser Ser
        115                 120

<210> SEQ ID NO 21
<211> LENGTH: 7
<212> TYPE: PRT
<213> ORGANISM: Artificial Sequence
<220> FEATURE:
<223> OTHER INFORMATION: Synthetic

<400> SEQUENCE: 21

Gln Gly Ile Ser Arg Ser Tyr
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic

<400> SEQUENCE: 22

Gln Gln Phe Gly Ser Ser Pro Trp Thr
1               5

<210> SEQ ID NO 23
<211> LENGTH: 108
<212> TYPE: PRT
<213> ORGANISM: Artificial Sequence
<220> FEATURE:
<223> OTHER INFORMATION: Synthetic

<400> SEQUENCE: 23

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Ser Arg Ser
            20                  25                  30

Tyr Leu Ala Trp Tyr Gln Gln Lys Pro Gly Gln Ala Pro Ser Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

```
Pro Glu Asp Phe Ala Val Tyr Tyr Cys Gln Gln Phe Gly Ser Ser Pro
                85                  90                  95

Trp Thr Phe Gly Gln Gly Thr Lys Val Glu Ile Lys
            100                 105
```

<210> SEQ ID NO 24
<211> LENGTH: 439
<212> TYPE: PRT
<213> ORGANISM: Homo Sapiens

<400> SEQUENCE: 24

```
Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Pro
                20                  25                  30

Arg Val Pro Lys Thr Leu Val Leu Val Val Ala Ala Val Leu Leu Leu
                35                  40                  45

Val Ser Ala Glu Ser Ala Leu Ile Thr Gln Gln Asp Leu Ala Pro Gln
50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
                100                 105                 110

Cys Leu Arg Cys Thr Arg Cys Asp Ser Gly Glu Val Glu Leu Ser Pro
                115                 120                 125

Cys Thr Thr Thr Arg Asn Thr Val Cys Gln Cys Glu Glu Gly Thr Phe
                130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Val Pro
                180                 185                 190

Ala Val Glu Glu Thr Val Thr Ser Ser Pro Gly Thr Pro Ala Ser Pro
                195                 200                 205

Cys Ser Leu Ser Gly Ile Ile Ile Gly Val Thr Val Ala Ala Val Val
                210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Ser Gly Gly Gly Asp Pro Glu
                245                 250                 255

Arg Val Asp Arg Ser Ser Gln Arg Pro Gly Ala Glu Asp Asn Val Leu
                260                 265                 270

Asn Glu Ile Val Ser Ile Leu Gln Pro Thr Gln Val Pro Glu Gln Glu
                275                 280                 285

Met Glu Val Gln Glu Pro Ala Glu Pro Thr Gly Val Asn Met Leu Ser
                290                 295                 300

Pro Gly Glu Ser Glu His Leu Leu Glu Pro Ala Glu Ala Glu Arg Ser
305                 310                 315                 320

Gln Arg Arg Arg Leu Leu Val Pro Ala Asn Glu Gly Asp Pro Thr Glu
                325                 330                 335

Thr Leu Arg Gln Cys Phe Asp Asp Phe Ala Asp Leu Val Pro Phe Asp
                340                 345                 350
```

```
Ser Trp Glu Pro Leu Met Arg Lys Leu Gly Leu Met Asp Asn Glu Ile
        355                 360                 365

Lys Val Ala Lys Ala Glu Ala Ala Gly His Arg Asp Thr Leu Tyr Thr
370                 375                 380

Met Leu Ile Lys Trp Val Asn Lys Thr Gly Arg Asp Ala Ser Val His
385                 390                 395                 400

Thr Leu Leu Asp Ala Leu Glu Thr Leu Gly Glu Arg Leu Ala Lys Lys
                405                 410                 415

Ile Glu Asp His Leu Leu Ser Ser Gly Lys Phe Met Tyr Leu Glu Gly
            420                 425                 430

Asn Ala Asp Ser Ala Met Ser
            435

<210> SEQ ID NO 25
<211> LENGTH: 440
<212> TYPE: PRT
<213> ORGANISM: Macaca mulatta

<400> SEQUENCE: 25

Met Gly Gln Leu Arg Gln Ser Ala Pro Ala Ser Gly Ala Arg Lys
1               5                   10                  15

Gly Arg Gly Pro Gly Pro Arg Glu Ala Arg Gly Ala Arg Pro Gly Leu
                20                  25                  30

Arg Val Leu Lys Thr Leu Val Leu Val Ala Ala Ala Arg Val Leu
            35                  40                  45

Val Ser Ala Asp Cys Ala Pro Ile Thr Arg Gln Ser Leu Asp Pro Gln
50                  55                  60

Arg Arg Ala Ala Pro Gln Gln Lys Arg Ser Ser Pro Thr Glu Gly Leu
65                  70                  75                  80

Cys Pro Pro Gly His His Ile Ser Glu Asp Ser Arg Asp Cys Ile Ser
                85                  90                  95

Cys Lys Tyr Gly Gln Asp Tyr Ser Thr His Trp Asn Asp Phe Leu Phe
            100                 105                 110

Cys Leu Arg Cys Thr Lys Cys Asp Ser Gly Glu Val Glu Val Asn Ser
        115                 120                 125

Cys Thr Thr Thr Arg Asn Thr Val Cys Gln Cys Glu Glu Gly Thr Phe
130                 135                 140

Arg Glu Glu Asp Ser Pro Glu Ile Cys Arg Lys Cys Arg Thr Gly Cys
145                 150                 155                 160

Pro Arg Gly Met Val Lys Val Lys Asp Cys Thr Pro Trp Ser Asp Ile
                165                 170                 175

Glu Cys Val His Lys Glu Ser Gly Thr Lys His Thr Gly Glu Val Pro
            180                 185                 190

Ala Val Glu Lys Thr Val Thr Thr Ser Pro Gly Thr Pro Ala Ser Pro
        195                 200                 205

Cys Ser Leu Ser Gly Ile Ile Gly Val Ile Val Phe Val Val Ile
210                 215                 220

Val Val Val Ala Val Ile Val Trp Lys Thr Ser Leu Trp Lys Lys Val
225                 230                 235                 240

Leu Pro Tyr Leu Lys Gly Val Cys Ser Gly Asp Gly Asp Pro Glu
                245                 250                 255

Arg Val Asp Ser Ser Pro Gln Arg Pro Gly Ala Glu Asp Asn Ala Leu
            260                 265                 270

Asn Glu Ile Val Ser Ile Val Gln Pro Ser Gln Val Pro Glu Gln Glu
```

```
                275                 280                 285
Met Glu Val Gln Glu Pro Ala Glu Gln Thr Asp Val Asn Thr Leu Ser
290                 295                 300

Pro Gly Glu Ser Glu His Leu Leu Glu Pro Ala Lys Ala Glu Gly Pro
305                 310                 315                 320

Gln Arg Arg Gly Gln Leu Val Pro Val Asn Glu Asn Asp Pro Thr Glu
                325                 330                 335

Thr Leu Arg Gln Cys Phe Asp Asp Phe Ala Ala Ile Val Pro Phe Asp
                340                 345                 350

Ala Trp Glu Pro Leu Val Arg Gln Leu Gly Leu Thr Asn Asn Glu Ile
                355                 360                 365

Lys Val Ala Lys Ala Glu Ala Ala Ser Ser Arg Asp Thr Leu Tyr Val
                370                 375                 380

Met Leu Ile Lys Trp Val Asn Lys Thr Gly Arg Ala Ala Ser Val Asn
385                 390                 395                 400

Thr Leu Leu Asp Ala Leu Glu Thr Leu Glu Glu Arg Leu Ala Lys Gln
                405                 410                 415

Lys Ile Gln Asp Arg Leu Leu Ser Ser Gly Lys Phe Met Tyr Leu Glu
                420                 425                 430

Asp Asn Ala Asp Ser Ala Thr Ser
                435                 440

<210> SEQ ID NO 26
<211> LENGTH: 381
<212> TYPE: PRT
<213> ORGANISM: Mus Musculus

<400> SEQUENCE: 26

Met Glu Pro Pro Gly Pro Ser Thr Pro Thr Ala Ser Ala Ala Ala Arg
1               5                   10                  15

Ala Asp His Tyr Thr Pro Gly Leu Arg Pro Leu Pro Lys Arg Arg Leu
                20                  25                  30

Leu Tyr Ser Phe Ala Leu Leu Leu Ala Val Leu Gln Ala Val Phe Val
                35                  40                  45

Pro Val Thr Ala Asn Pro Ala His Asn Arg Pro Ala Gly Leu Gln Arg
                50                  55                  60

Pro Glu Glu Ser Pro Ser Arg Gly Pro Cys Leu Ala Gly Gln Tyr Leu
65                  70                  75                  80

Ser Glu Gly Asn Cys Lys Pro Cys Arg Glu Gly Ile Asp Tyr Thr Ser
                85                  90                  95

His Ser Asn His Ser Leu Asp Ser Cys Ile Leu Cys Thr Val Cys Lys
                100                 105                 110

Glu Asp Lys Val Val Glu Thr Arg Cys Asn Ile Thr Thr Asn Thr Val
                115                 120                 125

Cys Arg Cys Lys Pro Gly Thr Phe Glu Asp Lys Asp Ser Pro Glu Ile
                130                 135                 140

Cys Gln Ser Cys Ser Asn Cys Thr Asp Gly Glu Glu Leu Thr Ser
145                 150                 155                 160

Cys Thr Pro Arg Glu Asn Arg Lys Cys Val Ser Lys Thr Ala Trp Ala
                165                 170                 175

Ser Trp His Lys Leu Gly Leu Trp Ile Gly Leu Leu Val Pro Val Val
                180                 185                 190

Leu Leu Ile Gly Ala Leu Leu Val Trp Lys Thr Gly Ala Trp Arg Gln
                195                 200                 205
```

```
Trp Leu Leu Cys Ile Lys Arg Gly Cys Glu Arg Asp Pro Glu Ser Ala
            210                 215                 220

Asn Ser Val His Ser Ser Leu Leu Asp Arg Gln Thr Ser Ser Thr Thr
225                 230                 235                 240

Asn Asp Ser Asn His Asn Thr Glu Pro Gly Lys Thr Gln Lys Thr Gly
            245                 250                 255

Lys Lys Leu Leu Val Pro Val Asn Gly Asn Asp Ser Ala Asp Asp Leu
            260                 265                 270

Lys Phe Ile Phe Glu Tyr Cys Ser Asp Ile Val Pro Phe Asp Ser Trp
            275                 280                 285

Asn Arg Leu Met Arg Gln Leu Gly Leu Thr Asp Asn Gln Ile Gln Met
290                 295                 300

Val Lys Ala Glu Thr Leu Val Thr Arg Glu Ala Leu Tyr Gln Met Leu
305                 310                 315                 320

Leu Lys Trp Arg His Gln Thr Gly Arg Ser Ala Ser Ile Asn His Leu
            325                 330                 335

Leu Asp Ala Leu Glu Ala Val Glu Glu Arg Asp Ala Met Glu Lys Ile
            340                 345                 350

Glu Asp Tyr Ala Val Lys Ser Gly Arg Phe Thr Tyr Gln Asn Ala Ala
            355                 360                 365

Ala Gln Pro Glu Thr Gly Pro Gly Gly Ser Gln Cys Val
370                 375                 380

<210> SEQ ID NO 27
<211> LENGTH: 453
<212> TYPE: PRT
<213> ORGANISM: Artificial Sequence
<220> FEATURE:
<223> OTHER INFORMATION: Synthetic

<400> SEQUENCE: 27

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Leu
            20                  25                  30

Arg Val Pro Lys Thr Leu Val Leu Val Val Ala Ala Val Leu Leu Leu
            35                  40                  45

Val Ser Ala Glu Ser Ala Leu Ile Thr Gln Gln Asp Leu Ala Pro Gln
50                  55                  60

Gln Arg Val Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
            85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
            115                 120                 125

Cys Thr Thr Thr Arg Asn Thr Val Cys Gln Cys Glu Glu Gly Thr Phe
            130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
            165                 170                 175

Glu Cys Val His Lys Glu Ser Gly Thr Lys His Ser Gly Glu Ala Pro
            180                 185                 190
```

```
Ala Val Glu Glu Thr Val Thr Ser Ser Pro Gly Thr Pro Ala Ser Pro
            195                 200                 205

Cys Ser Pro Lys Ser Cys Asp Lys Thr His Thr Cys Pro Pro Cys Pro
        210                 215                 220

Ala Pro Glu Ala Glu Gly Ala Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Ala Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys His His His His His His
        435                 440                 445

His Glu Pro Glu Ala
    450

<210> SEQ ID NO 28
<211> LENGTH: 192
<212> TYPE: PRT
<213> ORGANISM: Artificial Sequence
<220> FEATURE:
<223> OTHER INFORMATION: Synthetic

<400> SEQUENCE: 28

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Pro
            20                  25                  30

Arg Val Pro Lys Thr Leu Val Leu Val Val Ala Ala Val Leu Leu Leu
        35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95
```

```
Cys Lys Tyr Gly Gln Asp Tyr Ser Thr His Trp Asn Asp Leu Leu Phe
                100                 105                 110

Cys Leu Arg Cys Thr Arg Cys Asp Ser Gly Glu Val Glu Leu Ser Pro
            115                 120                 125

Cys Thr Thr Thr Arg Asn Thr Val Cys Gln Cys Glu Glu Gly Thr Phe
        130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly His His His His His His
            180                 185                 190

<210> SEQ ID NO 29
<211> LENGTH: 329
<212> TYPE: PRT
<213> ORGANISM: Homo Sapiens

<400> SEQUENCE: 29

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Arg
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285
```

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
            325

<210> SEQ ID NO 30
<211> LENGTH: 329
<212> TYPE: PRT
<213> ORGANISM: Homo Sapiens

<400> SEQUENCE: 30

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
            325

```
<210> SEQ ID NO 31
<211> LENGTH: 329
<212> TYPE: PRT
<213> ORGANISM: Homo Sapiens

<400> SEQUENCE: 31

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Pro
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 32
<211> LENGTH: 329
<212> TYPE: PRT
<213> ORGANISM: Homo Sapiens
```

```
<400> SEQUENCE: 32

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Pro
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Gly Leu His Asn His Tyr Thr Gln
305                 310                 315                 320

Lys Ser Leu Ser Leu Ser Pro Gly Lys
                325

<210> SEQ ID NO 33
<211> LENGTH: 448
<212> TYPE: PRT
<213> ORGANISM: Artificial Sequence
<220> FEATURE:
<223> OTHER INFORMATION: Synthetic

<400> SEQUENCE: 33

Glu Val Gln Leu Gln Gln Ser Gly Ala Glu Val Val Lys Pro Gly Ala
1               5                   10                  15

Ser Val Lys Leu Ser Cys Lys Ala Ser Gly Phe Asn Ile Lys Asp Thr
```

```
            20                  25                  30
Phe Ile His Trp Val Lys Gln Ala Pro Gly Gln Gly Leu Glu Trp Ile
        35                  40                  45
Gly Arg Ile Asp Pro Ala Asn Gly Asn Thr Lys Tyr Asp Pro Lys Phe
 50                  55                  60
Gln Gly Lys Ala Thr Ile Thr Thr Asp Thr Ser Ser Asn Thr Ala Tyr
 65                  70                  75                  80
Met Glu Leu Ser Ser Leu Arg Ser Glu Asp Thr Ala Val Tyr Tyr Cys
                85                  90                  95
Val Arg Gly Leu Tyr Thr Tyr Tyr Phe Asp Tyr Trp Gly Gln Gly Thr
                100                 105                 110
Leu Val Thr Val Ser Ser Ala Ser Thr Lys Gly Pro Ser Val Phe Pro
                115                 120                 125
Leu Ala Pro Ser Ser Lys Ser Thr Ser Gly Gly Thr Ala Ala Leu Gly
                130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
                180                 185                 190
Ser Leu Gly Thr Gln Thr Tyr Ile Cys Asn Val Asn His Lys Pro Ser
                195                 200                 205
Asn Thr Lys Val Asp Lys Arg Val Glu Pro Lys Ser Cys Asp Lys Thr
                210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
                275                 280                 285
Lys Thr Lys Pro Arg Glu Glu Gln Tyr Asn Ser Thr Tyr Arg Val Val
                290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Glu Glu Met Thr Lys Asn Gln Val Ser Leu Thr Cys
                355                 360                 365
Leu Val Lys Gly Phe Tyr Pro Ser Asp Ile Ala Val Glu Trp Glu Ser
                370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
                435                 440                 445
```

<210> SEQ ID NO 34
<211> LENGTH: 448
<212> TYPE: PRT
<213> ORGANISM: Artificial Sequence
<220> FEATURE:
<223> OTHER INFORMATION: Synthetic

<400> SEQUENCE: 34

Glu Val Gln Leu Gln Gln Ser Gly Ala Glu Val Val Lys Pro Gly Ala
1               5                   10                  15

Ser Val Lys Leu Ser Cys Lys Ala Ser Gly Phe Asn Ile Lys Asp Thr
            20                  25                  30

Phe Ile His Trp Val Lys Gln Ala Pro Gly Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Thr Asp Thr Ser Ser Asn Thr Ala Tyr
65                  70                  75                  80

Met Glu Leu Ser Ser Leu Arg Ser Glu Asp Thr Ala Val Tyr Tyr Cys
                85                  90                  95

Val Arg Gly Leu Tyr Thr Tyr Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Lys Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 35
<211> LENGTH: 448
<212> TYPE: PRT
<213> ORGANISM: Artificial Sequence
<220> FEATURE:
<223> OTHER INFORMATION: Synthetic

<400> SEQUENCE: 35

Glu Val Gln Leu Gln Gln Ser Gly Ala Glu Val Val Lys Pro Gly Ala
1               5                   10                  15

Ser Val Lys Leu Ser Cys Lys Ala Ser Gly Phe Asn Ile Lys Asp Thr
            20                  25                  30

Phe Ile His Trp Val Lys Gln Ala Pro Gly Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Thr Asp Thr Ser Ser Asn Thr Ala Tyr
65                  70                  75                  80

Met Glu Leu Ser Ser Leu Arg Ser Glu Asp Thr Ala Val Tyr Tyr Cys
                85                  90                  95

Val Arg Gly Leu Tyr Thr Tyr Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

```
Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Gly Ala
            420                 425                 430

Leu His Asn His Tyr Thr Gln Lys Ser Leu Ser Leu Ser Pro Gly Lys
        435                 440                 445

<210> SEQ ID NO 36
<211> LENGTH: 448
<212> TYPE: PRT
<213> ORGANISM: Artificial Sequence
<220> FEATURE:
<223> OTHER INFORMATION: Synthetic

<400> SEQUENCE: 36

Glu Val Gln Leu Gln Gln Ser Gly Ala Glu Val Val Lys Pro Gly Ala
1               5                   10                  15

Ser Val Lys Leu Ser Cys Lys Ala Ser Gly Phe Asn Ile Lys Asp Thr
            20                  25                  30

Phe Ile His Trp Val Lys Gln Ala Pro Gly Gln Gly Leu Glu Trp Ile
        35                  40                  45

Gly Arg Ile Asp Pro Ala Asn Thr Asn Thr Lys Tyr Asp Pro Lys Phe
50                  55                  60

Gln Gly Lys Ala Thr Ile Thr Thr Asp Thr Ser Ser Asn Thr Ala Tyr
65                  70                  75                  80

Met Glu Leu Ser Ser Leu Arg Ser Glu Asp Thr Ala Val Tyr Tyr Cys
                85                  90                  95

Val Arg Gly Leu Tyr Thr Tyr Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

Asn Thr Lys Val Asp Lys Arg Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 37
<211> LENGTH: 448
<212> TYPE: PRT
<213> ORGANISM: Artificial Sequence
<220> FEATURE:
<223> OTHER INFORMATION: Synthetic

<400> SEQUENCE: 37

Glu Val Gln Leu Gln Gln Ser Gly Ala Glu Val Val Lys Pro Gly Ala
1               5                   10                  15

Ser Val Lys Leu Ser Cys Lys Ala Ser Gly Phe Asn Ile Lys Asp Thr
            20                  25                  30

Phe Ile His Trp Val Lys Gln Ala Pro Gly Gln Gly Leu Glu Trp Ile
        35                  40                  45

Gly Arg Ile Asp Pro Ala Asn Thr Asn Thr Lys Tyr Asp Pro Lys Phe
    50                  55                  60

Gln Gly Lys Ala Thr Ile Thr Thr Asp Thr Ser Ser Asn Thr Ala Tyr
65                  70                  75                  80

Met Glu Leu Ser Ser Leu Arg Ser Glu Asp Thr Ala Val Tyr Tyr Cys
                85                  90                  95

Val Arg Gly Leu Tyr Thr Tyr Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

-continued

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 38
<211> LENGTH: 448
<212> TYPE: PRT
<213> ORGANISM: Artificial Sequence
<220> FEATURE:
<223> OTHER INFORMATION: Synthetic

<400> SEQUENCE: 38

Glu Val Gln Leu Gln Gln Ser Gly Ala Glu Val Val Lys Pro Gly Ala
1               5                   10                  15

Ser Val Lys Leu Ser Cys Lys Ala Ser Gly Phe Asn Ile Lys Asp Thr
            20                  25                  30

Phe Ile His Trp Val Lys Gln Ala Pro Gly Gln Gly Leu Glu Trp Ile
        35                  40                  45

```
Gly Arg Ile Asp Pro Ala Asn Thr Asn Thr Lys Tyr Asp Pro Lys Phe
         50                  55                  60

Gln Gly Lys Ala Thr Ile Thr Thr Asp Thr Ser Ser Asn Thr Ala Tyr
 65                  70                  75                  80

Met Glu Leu Ser Ser Leu Arg Ser Glu Asp Thr Ala Val Tyr Tyr Cys
                 85                  90                  95

Val Arg Gly Leu Tyr Thr Tyr Tyr Phe Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Gly Ala
            420                 425                 430

Leu His Asn His Tyr Thr Gln Lys Ser Leu Ser Leu Ser Pro Gly Lys
        435                 440                 445
```

<210> SEQ ID NO 39
<211> LENGTH: 214

```
<212> TYPE: PRT
<213> ORGANISM: Artificial Sequence
<220> FEATURE:
<223> OTHER INFORMATION: Synthetic

<400> SEQUENCE: 39

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Phe Ala Ser Gln Ser Ile Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Gly Asn Ser Trp Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 40
<211> LENGTH: 448
<212> TYPE: PRT
<213> ORGANISM: Artificial Sequence
<220> FEATURE:
<223> OTHER INFORMATION: Synthetic

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

His Met His Trp Val Arg Gln Ala Pro Gly Gln Arg Leu Glu Trp Ile
        35                  40                  45

Gly Arg Ile Asp Pro Ala Asn Gly Asn Thr Glu Tyr Asp Gln Lys Phe
    50                  55                  60

Gln Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Thr Asn Val Tyr Phe Ala Tyr Trp Gly Gln Gly Thr
            100                 105                 110
```

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 41
<211> LENGTH: 448
<212> TYPE: PRT
<213> ORGANISM: Artificial Sequence
<220> FEATURE:
<223> OTHER INFORMATION: Synthetic

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

```
His Met His Trp Val Arg Gln Ala Pro Gly Gln Arg Leu Glu Trp Ile
        35                  40                  45

Gly Arg Ile Asp Pro Ala Asn Gly Asn Thr Glu Tyr Asp Gln Lys Phe
 50                  55                  60

Gln Gly Arg Val Thr Ile Thr Val Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp Gly Thr Asn Val Tyr Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

-continued

```
<210> SEQ ID NO 42
<211> LENGTH: 448
<212> TYPE: PRT
<213> ORGANISM: Artificial Sequence
<220> FEATURE:
<223> OTHER INFORMATION: Synthetic

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

His Met His Trp Val Arg Gln Ala Pro Gly Gln Arg Leu Glu Trp Ile
        35                  40                  45

Gly Arg Ile Asp Pro Ala Asn Gly Asn Thr Glu Tyr Asp Gln Lys Phe
    50                  55                  60

Gln Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Thr Asn Val Tyr Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365
```

```
Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Gly Ala
            420                 425                 430

Leu His Asn His Tyr Thr Gln Lys Ser Leu Ser Leu Ser Pro Gly Lys
        435                 440                 445
```

<210> SEQ ID NO 43
<211> LENGTH: 213
<212> TYPE: PRT
<213> ORGANISM: Artificial Sequence
<220> FEATURE:
<223> OTHER INFORMATION: Synthetic

<400> SEQUENCE: 43

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Tyr Trp Tyr Gln Gln Lys Pro Gly Lys Ala Pro Lys Pro Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Tyr His Ser Tyr Pro Pro Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 44
<211> LENGTH: 440
<212> TYPE: PRT
<213> ORGANISM: Homo Sapiens

<400> SEQUENCE: 44

```
Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Pro
```

```
            20                  25                  30
Arg Val Pro Lys Thr Leu Val Leu Val Val Ala Ala Val Leu Leu Leu
             35                  40                  45
Val Ser Ala Glu Ser Ala Leu Ile Thr Gln Gln Asp Leu Ala Pro Gln
 50                  55                  60
Gln Arg Ala Ala Pro Gln Gln Lys Arg Ser Ser Pro Ser Glu Gly Leu
 65                  70                  75                  80
Cys Pro Pro Gly His His Ile Ser Glu Asp Gly Arg Asp Cys Ile Ser
                 85                  90                  95
Cys Lys Tyr Gly Gln Asp Tyr Ser Thr His Trp Asn Asp Leu Leu Phe
                100                 105                 110
Cys Leu Arg Cys Thr Arg Cys Asp Ser Gly Glu Val Glu Leu Ser Pro
                115                 120                 125
Cys Thr Thr Thr Arg Asn Thr Val Cys Gln Cys Glu Glu Gly Thr Phe
                130                 135                 140
Arg Glu Glu Asp Ser Pro Glu Met Cys Arg Lys Cys Arg Thr Gly Cys
145                 150                 155                 160
Pro Arg Gly Met Val Lys Val Gly Asp Cys Thr Pro Trp Ser Asp Ile
                165                 170                 175
Glu Cys Val His Lys Glu Ser Gly Thr Lys His Ser Gly Glu Val Pro
                180                 185                 190
Ala Val Glu Glu Thr Val Thr Ser Ser Pro Gly Thr Pro Ala Ser Pro
                195                 200                 205
Cys Ser Leu Ser Gly Ile Ile Ile Gly Val Thr Val Ala Ala Val Val
                210                 215                 220
Leu Ile Val Ala Val Phe Val Cys Lys Ser Leu Leu Trp Lys Lys Val
225                 230                 235                 240
Leu Pro Tyr Leu Lys Gly Ile Cys Ser Gly Gly Gly Gly Asp Pro Glu
                245                 250                 255
Arg Val Asp Arg Ser Ser Gln Arg Pro Gly Ala Glu Asp Asn Val Leu
                260                 265                 270
Asn Glu Ile Val Ser Ile Leu Gln Pro Thr Gln Val Pro Glu Gln Glu
                275                 280                 285
Met Glu Val Gln Glu Pro Ala Glu Pro Thr Gly Val Asn Met Leu Ser
                290                 295                 300
Pro Gly Glu Ser Glu His Leu Leu Glu Pro Ala Glu Ala Glu Arg Ser
305                 310                 315                 320
Gln Arg Arg Arg Leu Leu Val Pro Ala Asn Glu Gly Asp Pro Thr Glu
                325                 330                 335
Thr Leu Arg Gln Cys Phe Asp Asp Phe Ala Asp Leu Val Pro Phe Asp
                340                 345                 350
Ser Trp Glu Pro Leu Met Arg Lys Leu Gly Leu Met Asp Asn Glu Ile
                355                 360                 365
Lys Val Ala Lys Ala Glu Ala Ala Gly His Arg Asp Thr Leu Tyr Thr
                370                 375                 380
Met Leu Ile Lys Trp Val Asn Lys Thr Gly Arg Asp Ala Ser Val His
385                 390                 395                 400
Thr Leu Leu Asp Ala Leu Glu Thr Leu Gly Glu Arg Leu Ala Asn Gln
                405                 410                 415
Lys Ile Glu Asp His Leu Leu Ser Ser Gly Lys Phe Met Tyr Leu Glu
                420                 425                 430
Gly Asn Ala Asp Ser Ala Met Ser
                435                 440
```

<210> SEQ ID NO 45
<211> LENGTH: 440
<212> TYPE: PRT
<213> ORGANISM: Homo Sapiens

<400> SEQUENCE: 45

```
Met Glu Gln Arg Gly Gln Asn Ala Pro Ala Ser Gly Ala Arg Lys
1               5                   10                  15

Arg His Gly Pro Gly Pro Arg Glu Ala Arg Gly Ala Arg Pro Gly Leu
                20                  25                  30

Arg Val Pro Lys Thr Leu Val Leu Val Val Ala Val Leu Leu Leu
            35                  40                  45

Val Ser Ala Glu Ser Ala Leu Ile Thr Gln Gln Asp Leu Ala Pro Gln
50                  55                  60

Gln Arg Val Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
            115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Ala Pro
            180                 185                 190

Ala Val Glu Glu Thr Val Thr Ser Ser Pro Gly Thr Pro Ala Ser Pro
            195                 200                 205

Cys Ser Leu Ser Gly Ile Ile Ile Gly Val Thr Val Ala Ala Val Val
    210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Ser Gly Gly Gly Gly Asp Pro Glu
                245                 250                 255

Arg Val Asp Arg Ser Ser Gln Arg Pro Gly Ala Glu Asp Asn Val Leu
            260                 265                 270

Asn Glu Ile Val Ser Ile Leu Gln Pro Thr Gln Val Pro Glu Gln Glu
            275                 280                 285

Met Glu Val Gln Glu Pro Ala Glu Pro Thr Gly Val Asn Met Leu Ser
    290                 295                 300

Pro Gly Glu Ser Glu His Leu Leu Glu Pro Ala Glu Ala Glu Arg Ser
305                 310                 315                 320

Gln Arg Arg Arg Leu Leu Val Pro Ala Asn Glu Gly Asp Pro Thr Glu
                325                 330                 335

Thr Leu Arg Gln Cys Phe Asp Asp Phe Ala Asp Leu Val Pro Phe Asp
            340                 345                 350

Ser Trp Glu Pro Leu Met Arg Lys Leu Gly Leu Met Asp Asn Glu Ile
            355                 360                 365

Lys Val Ala Lys Ala Glu Ala Ala Gly His Arg Asp Thr Leu Tyr Thr
```

```
                    370              375              380
Met Leu Ile Lys Trp Val Asn Lys Thr Gly Arg Asp Ala Ser Val His
385                 390              395                  400

Thr Leu Leu Asp Ala Leu Glu Thr Leu Gly Glu Arg Leu Ala Lys Gln
                405              410                  415

Lys Ile Glu Asp His Leu Leu Ser Ser Gly Lys Phe Met Tyr Leu Glu
                420              425              430

Gly Asn Ala Asp Ser Ala Met Ser
            435              440

<210> SEQ ID NO 46
<211> LENGTH: 440
<212> TYPE: PRT
<213> ORGANISM: Homo Sapiens

<400> SEQUENCE: 46

Met Glu Gln Arg Gly Gln Asn Ala Pro Ala Ser Gly Ala Arg Lys
1               5                  10                  15

Arg His Gly Pro Gly Pro Arg Glu Ala Arg Gly Ala Arg Pro Gly Pro
                20                  25                  30

Arg Val Pro Lys Thr Leu Val Leu Val Val Ala Ala Val Leu Leu Leu
            35                  40                  45

Val Ser Ala Glu Ser Ala Leu Ile Thr Gln Gln Asp Leu Ala Pro Gln
50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                    85                  90                  95

Cys Lys Tyr Gly Gln Asp Tyr Ser Thr His Trp Asn Asp Leu Leu Phe
                100                 105                 110

Cys Leu Arg Cys Thr Arg Cys Asp Ser Gly Glu Val Glu Leu Ser Pro
            115                 120                 125

Cys Thr Thr Thr Arg Asn Thr Val Cys Gln Cys Glu Glu Gly Thr Phe
130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Val Pro
            180                 185                 190

Ala Val Glu Glu Thr Val Thr Ser Ser Pro Gly Thr Pro Ala Ser Pro
            195                 200                 205

Cys Ser Leu Ser Gly Ile Ile Ile Gly Val Thr Val Ala Ala Val Val
210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Ser Gly Gly Gly Gly Asp Pro Glu
                245                 250                 255

Arg Val Asp Arg Ser Ser Gln Arg Pro Gly Ala Glu Asp Asn Val Leu
            260                 265                 270

Asn Glu Ile Val Ser Ile Leu Gln Pro Thr Gln Val Pro Glu Gln Glu
            275                 280                 285

Met Glu Val Gln Glu Pro Ala Glu Pro Thr Gly Val Asn Met Leu Ser
290                 295                 300
```

-continued

```
Pro Gly Glu Ser Glu His Leu Leu Glu Pro Ala Glu Ala Glu Arg Ser
305                 310                 315                 320

Gln Arg Arg Arg Leu Leu Val Pro Ala Asn Glu Gly Asp Pro Thr Glu
            325                 330                 335

Thr Leu Arg Gln Cys Phe Asp Asp Phe Ala Asp Leu Val Pro Phe Asp
            340                 345                 350

Ser Trp Glu Pro Leu Met Arg Lys Leu Gly Leu Met Asp Asn Glu Ile
            355                 360                 365

Lys Val Ala Lys Ala Glu Ala Ala Gly His Arg Asp Thr Leu Tyr Thr
            370                 375                 380

Met Leu Ile Lys Trp Val Asn Lys Thr Gly Arg Asp Ala Ser Val His
385                 390                 395                 400

Thr Leu Leu Asp Ala Leu Glu Thr Leu Gly Glu Arg Leu Ala Lys Gln
            405                 410                 415

Lys Ile Glu Asp His Leu Leu Ser Ser Gly Lys Phe Met Tyr Leu Glu
            420                 425                 430

Gly Asn Ala Asp Ser Ala Met Ser
            435                 440

<210> SEQ ID NO 47
<211> LENGTH: 411
<212> TYPE: PRT
<213> ORGANISM: Homo Sapiens

<400> SEQUENCE: 47

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Pro
            20                  25                  30

Arg Val Pro Lys Thr Leu Val Leu Val Val Ala Ala Val Leu Leu Leu
            35                  40                  45

Val Ser Ala Glu Ser Ala Leu Ile Thr Gln Gln Asp Leu Ala Pro Gln
50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
            85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
            115                 120                 125

Cys Thr Thr Thr Arg Asn Thr Val Cys Gln Cys Glu Glu Gly Thr Phe
            130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
            165                 170                 175

Glu Cys Val His Lys Glu Ser Gly Ile Ile Ile Gly Val Thr Val Ala
            180                 185                 190

Ala Val Val Leu Ile Val Ala Val Phe Val Cys Lys Ser Leu Leu Trp
            195                 200                 205

Lys Lys Val Leu Pro Tyr Leu Lys Gly Ile Cys Ser Gly Gly Gly Gly
            210                 215                 220

Asp Pro Glu Arg Val Asp Arg Ser Ser Gln Arg Pro Gly Ala Glu Asp
225                 230                 235                 240
```

```
Asn Val Leu Asn Glu Ile Val Ser Ile Leu Gln Pro Thr Gln Val Pro
                245                 250                 255

Glu Gln Glu Met Glu Val Gln Glu Pro Ala Glu Pro Thr Gly Val Asn
            260                 265                 270

Met Leu Ser Pro Gly Ser Glu His Leu Leu Glu Pro Ala Glu Ala
        275                 280                 285

Glu Arg Ser Gln Arg Arg Leu Leu Val Pro Ala Asn Glu Gly Asp
    290                 295                 300

Pro Thr Glu Thr Leu Arg Gln Cys Phe Asp Asp Phe Ala Asp Leu Val
305                 310                 315                 320

Pro Phe Asp Ser Trp Glu Pro Leu Met Arg Lys Leu Gly Leu Met Asp
                325                 330                 335

Asn Glu Ile Lys Val Ala Lys Ala Glu Ala Ala Gly His Arg Asp Thr
                340                 345                 350

Leu Tyr Thr Met Leu Ile Lys Trp Val Asn Lys Thr Gly Arg Asp Ala
            355                 360                 365

Ser Val His Thr Leu Leu Asp Ala Leu Glu Thr Leu Gly Glu Arg Leu
        370                 375                 380

Ala Asn Gln Lys Ile Glu Asp His Leu Leu Ser Ser Gly Lys Phe Met
385                 390                 395                 400

Tyr Leu Glu Gly Asn Ala Asp Ser Ala Met Ser
                405                 410

<210> SEQ ID NO 48
<211> LENGTH: 445
<212> TYPE: PRT
<213> ORGANISM: Macaca fascicularis

<400> SEQUENCE: 48

Met Gly Gln Leu Arg Gln Ser Ala Pro Ala Ser Gly Ala Arg Lys
1               5                   10                  15

Gly Arg Gly Pro Gly Pro Arg Glu Ala Arg Gly Ala Arg Pro Gly Leu
            20                  25                  30

Arg Val Leu Lys Thr Leu Val Leu Val Ala Ala Arg Val Leu
        35                  40                  45

Leu Ser Val Ser Ala Asp Cys Ala Pro Ile Thr Arg Gln Ser Leu Asp
    50                  55                  60

Pro Gln Arg Arg Ala Ala Pro Gln Gln Lys Arg Ser Ser Pro Thr Glu
65                  70                  75                  80

Gly Leu Cys Pro Pro Gly His His Ile Ser Glu Asp Ser Arg Glu Cys
                85                  90                  95

Ile Ser Cys Lys Tyr Gly Gln Asp Tyr Ser Thr His Trp Asn Asp Phe
                100                 105                 110

Leu Phe Cys Leu Arg Cys Thr Lys Cys Asp Ser Gly Glu Val Glu Val
            115                 120                 125

Asn Ser Cys Thr Thr Thr Arg Asn Thr Val Cys Gln Cys Glu Glu Gly
        130                 135                 140

Thr Phe Arg Glu Glu Asp Ser Pro Glu Ile Cys Arg Lys Cys Arg Thr
145                 150                 155                 160

Gly Cys Pro Arg Gly Met Val Lys Val Lys Asp Cys Thr Pro Trp Ser
                165                 170                 175

Asp Ile Glu Cys Val His Lys Glu Ser Gly Thr Lys His Thr Gly Glu
            180                 185                 190

Val Pro Ala Val Glu Lys Thr Val Thr Thr Ser Pro Gly Thr Pro Ala
```

```
            195                 200                 205
Ser Pro Cys Ser Leu Ser Gly Ile Ile Gly Val Ile Leu Val
    210                 215                 220

Val Ile Val Val Ala Val Ile Val Trp Lys Thr Ser Leu Trp Lys
225                 230                 235                 240

Lys Val Leu Pro Tyr Leu Lys Gly Val Cys Ser Gly Gly Gly Asp
                    245                 250                 255

Pro Glu Arg Val Asp Ser Ser His Ser Pro Gln Arg Pro Gly Ala
                260                 265                 270

Glu Asp Asn Ala Leu Asn Glu Ile Val Ser Ile Val Gln Pro Ser Gln
                275                 280                 285

Val Pro Glu Gln Glu Met Glu Val Gln Glu Pro Ala Glu Gln Thr Asp
290                 295                 300

Val Asn Thr Leu Ser Pro Gly Glu Ser Glu His Leu Leu Glu Pro Ala
305                 310                 315                 320

Lys Ala Glu Gly Pro Gln Arg Arg Gly Gln Leu Val Pro Val Asn Glu
                325                 330                 335

Asn Asp Pro Thr Glu Thr Leu Arg Gln Cys Phe Asp Asp Phe Ala Ala
                340                 345                 350

Ile Val Pro Phe Asp Ala Trp Glu Pro Leu Val Arg Gln Leu Gly Leu
                355                 360                 365

Thr Asn Asn Glu Ile Lys Val Ala Lys Ala Glu Ala Ala Ser Ser Arg
370                 375                 380

Asp Thr Leu Tyr Val Met Leu Ile Lys Trp Val Asn Lys Thr Gly Arg
385                 390                 395                 400

Ala Ala Ser Val Asn Thr Leu Leu Asp Ala Leu Glu Thr Leu Glu Glu
                405                 410                 415

Arg Leu Ala Lys Gln Lys Ile Gln Asp Arg Leu Leu Ser Ser Gly Lys
                420                 425                 430

Phe Met Tyr Leu Glu Asp Asn Ala Asp Ser Ala Thr Ser
                435                 440                 445

<210> SEQ ID NO 49
<211> LENGTH: 445
<212> TYPE: PRT
<213> ORGANISM: Macaca fascicularis

<400> SEQUENCE: 49

Met Gly Gln Leu Arg Gln Ser Ala Pro Ala Ser Gly Ala Arg Lys
1               5                   10                  15

Gly Arg Gly Pro Gly Pro Arg Glu Ala Arg Gly Ala Arg Pro Gly Leu
                20                  25                  30

Arg Val Leu Lys Thr Leu Val Leu Val Ala Ala Arg Val Leu
                35                  40                  45

Leu Ser Val Ser Ala Asp Cys Ala Pro Ile Thr Arg Gln Ser Leu Asp
    50                  55                  60

Pro Gln Arg Arg Ala Ala Pro Gln Gln Lys Arg Ser Ser Pro Thr Glu
65                  70                  75                  80

Gly Leu Cys Pro Pro Gly His His Ile Ser Glu Asp Ser Arg Glu Cys
                85                  90                  95

Ile Ser Cys Lys Tyr Gly Gln Asp Tyr Ser Thr His Trp Asn Asp Phe
                100                 105                 110

Leu Phe Cys Leu Arg Cys Thr Lys Cys Asp Ser Gly Glu Val Glu Val
                115                 120                 125
```

```
Asn Ser Cys Thr Thr Thr Arg Asn Thr Val Cys Gln Cys Glu Glu Gly
    130                 135                 140

Thr Phe Arg Glu Glu Asp Ser Pro Glu Ile Cys Arg Lys Cys Arg Thr
145                 150                 155                 160

Gly Cys Pro Arg Gly Met Val Lys Val Lys Asp Cys Thr Pro Trp Ser
                165                 170                 175

Asp Ile Glu Cys Val His Lys Glu Ser Gly Thr Lys His Thr Gly Glu
            180                 185                 190

Val Pro Ala Val Glu Lys Thr Val Thr Thr Ser Pro Gly Thr Pro Ala
        195                 200                 205

Ser Pro Cys Ser Leu Ser Gly Ile Ile Ile Gly Val Ile Val Leu Val
    210                 215                 220

Val Ile Val Val Ala Val Ile Val Trp Lys Thr Ser Leu Trp Lys
225                 230                 235                 240

Lys Val Leu Pro Tyr Leu Lys Gly Val Cys Ser Gly Gly Gly Gly Asp
                245                 250                 255

Pro Glu Arg Val Asp Ser Ser His Ser Pro Gln Arg Pro Gly Ala
                260                 265                 270

Glu Asp Asn Ala Leu Asn Glu Ile Val Ser Ile Val Gln Pro Ser Gln
    275                 280                 285

Val Pro Glu Gln Glu Met Glu Val Gln Glu Pro Ala Glu Gln Thr Asp
290                 295                 300

Val Asn Thr Leu Ser Pro Gly Glu Ser Glu His Leu Leu Glu Pro Ala
305                 310                 315                 320

Lys Ala Glu Gly Pro Gln Arg Arg Gly Gln Leu Val Pro Val Asn Glu
                325                 330                 335

Asn Asp Pro Thr Glu Thr Leu Arg Gln Cys Phe Asp Asp Phe Ala Ala
            340                 345                 350

Ile Val Pro Phe Asp Ala Trp Glu Pro Leu Val Arg Gln Leu Gly Leu
        355                 360                 365

Thr Asn Asn Glu Ile Lys Val Ala Lys Ala Glu Ala Ala Ser Ser Arg
    370                 375                 380

Asp Thr Leu Tyr Val Met Leu Ile Lys Trp Val Asn Lys Thr Gly Arg
385                 390                 395                 400

Ala Ala Ser Val Asn Thr Leu Leu Asp Ala Leu Glu Thr Leu Glu Glu
                405                 410                 415

Arg Leu Ala Asn Gln Lys Ile Gln Asp Arg Leu Leu Ser Ser Gly Lys
                420                 425                 430

Phe Met Tyr Leu Glu Asp Asn Ala Asp Ser Ala Thr Ser
            435                 440                 445

<210> SEQ ID NO 50
<211> LENGTH: 416
<212> TYPE: PRT
<213> ORGANISM: Macaca fascicularis

<400> SEQUENCE: 50

Met Gly Gln Leu Arg Gln Ser Ala Pro Ala Ser Gly Ala Arg Lys
1               5                   10                  15

Gly Arg Gly Pro Gly Pro Arg Glu Ala Arg Gly Ala Arg Pro Gly Leu
                20                  25                  30

Arg Val Leu Lys Thr Leu Val Leu Val Ala Ala Arg Val Leu
            35                  40                  45

Leu Ser Val Ser Ala Asp Cys Ala Pro Ile Thr Arg Gln Ser Leu Asp
        50                  55                  60
```

-continued

Pro Gln Arg Arg Ala Ala Pro Gln Gln Lys Arg Ser Ser Pro Thr Glu
 65                  70                  75                  80

Gly Leu Cys Pro Pro Gly His His Ile Ser Glu Asp Ser Arg Glu Cys
             85                  90                  95

Ile Ser Cys Lys Tyr Gly Gln Asp Tyr Ser Thr His Trp Asn Asp Phe
            100                 105                 110

Leu Phe Cys Leu Arg Cys Thr Lys Cys Asp Ser Gly Glu Val Glu Val
        115                 120                 125

Asn Ser Cys Thr Thr Thr Arg Asn Thr Val Cys Gln Cys Glu Glu Gly
130                 135                 140

Thr Phe Arg Glu Glu Asp Ser Pro Glu Ile Cys Arg Lys Cys Arg Thr
145                 150                 155                 160

Gly Cys Pro Arg Gly Met Val Lys Val Lys Asp Cys Thr Pro Trp Ser
                165                 170                 175

Asp Ile Glu Cys Val His Lys Glu Ser Gly Ile Ile Gly Val Ile
                180                 185                 190

Val Leu Val Val Ile Val Val Ala Val Ile Val Trp Lys Thr Ser
        195                 200                 205

Leu Trp Lys Lys Val Leu Pro Tyr Leu Lys Gly Val Cys Ser Gly Gly
210                 215                 220

Gly Gly Asp Pro Glu Arg Val Asp Ser Ser His Ser Pro Gln Arg
225                 230                 235                 240

Pro Gly Ala Glu Asp Asn Ala Leu Asn Glu Ile Val Ser Ile Val Gln
                245                 250                 255

Pro Ser Gln Val Pro Glu Gln Glu Met Glu Val Gln Glu Pro Ala Glu
                260                 265                 270

Gln Thr Asp Val Asn Thr Leu Ser Pro Gly Glu Ser Glu His Leu Leu
            275                 280                 285

Glu Pro Ala Lys Ala Glu Gly Pro Gln Arg Arg Gly Gln Leu Val Pro
290                 295                 300

Val Asn Glu Asn Asp Pro Thr Glu Thr Leu Arg Gln Cys Phe Asp Asp
305                 310                 315                 320

Phe Ala Ala Ile Val Pro Phe Asp Ala Trp Glu Pro Leu Val Arg Gln
                325                 330                 335

Leu Gly Leu Thr Asn Asn Glu Ile Lys Val Ala Lys Ala Glu Ala Ala
            340                 345                 350

Ser Ser Arg Asp Thr Leu Tyr Val Met Leu Ile Lys Trp Val Asn Lys
        355                 360                 365

Thr Gly Arg Ala Ala Ser Val Asn Thr Leu Leu Asp Ala Leu Glu Thr
    370                 375                 380

Leu Glu Glu Arg Leu Ala Asn Gln Lys Ile Gln Asp Arg Leu Leu Ser
385                 390                 395                 400

Ser Gly Lys Phe Met Tyr Leu Glu Asp Asn Ala Asp Ser Ala Thr Ser
                405                 410                 415

<210> SEQ ID NO 51
<211> LENGTH: 8
<212> TYPE: PRT
<213> ORGANISM: Artificial Sequence
<220> FEATURE:
<223> OTHER INFORMATION: Synthetic

<400> SEQUENCE: 51

Gly Phe Thr Phe Ser Ser Tyr Val
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Ile Ser Ser Gly Gly Ser Tyr Thr
1               5

<210> SEQ ID NO 53
<211> LENGTH: 12
<212> TYPE: PRT
<213> ORGANISM: Artificial Sequence
<220> FEATURE:
<223> OTHER INFORMATION: Synthetic

<400> SEQUENCE: 53

Ala Arg Arg Gly Asp Ser Met Ile Thr Thr Asp Tyr
1               5                   10

<210> SEQ ID NO 54
<211> LENGTH: 6
<212> TYPE: PRT
<213> ORGANISM: Artificial Sequence
<220> FEATURE:
<223> OTHER INFORMATION: Synthetic

<400> SEQUENCE: 54

Gln Asp Val Gly Thr Ala
1               5

<210> SEQ ID NO 55
<211> LENGTH: 8
<212> TYPE: PRT
<213> ORGANISM: Artificial Sequence
<220> FEATURE:
<223> OTHER INFORMATION: Synthetic

<400> SEQUENCE: 55

Gln Gln Tyr Ser Ser Tyr Arg Thr
1               5

<210> SEQ ID NO 56
<211> LENGTH: 449
<212> TYPE: PRT
<213> ORGANISM: Artificial Sequence
<220> FEATURE:
<223> OTHER INFORMATION: Synthetic

<400> SEQUENCE: 56

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Val Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys

```
                   85                  90                  95
Ala Arg Arg Gly Asp Ser Met Ile Thr Thr Asp Tyr Trp Gly Gln Gly
                100                 105                 110

Thr Thr Leu Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 57
<211> LENGTH: 213
<212> TYPE: PRT
<213> ORGANISM: Artificial Sequence
<220> FEATURE:
<223> OTHER INFORMATION: Synthetic

<400> SEQUENCE: 57
```

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Arg Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 58
<211> LENGTH: 329
<212> TYPE: PRT
<213> ORGANISM: Artificial Sequence
<220> FEATURE:
<223> OTHER INFORMATION: Synthetic

<400> SEQUENCE: 58

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Arg
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
            165                 170                 175

Gln Tyr Asn Ser Thr Tyr Arg Val Val Ser Val Leu Thr Val Leu His
        180                 185                 190

Gln Asp Trp Leu Asn Gly Lys Glu Tyr Lys Cys Lys Val Ser Asn Lys
            195                 200                 205

Ala Leu Pro Ala Pro Ile Glu Lys Thr Ile Ser Lys Ala Lys Gly Gln
210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
            290                 295                 300

Phe Ser Cys Ser Val Met His Gly Ala Leu His Asn His Tyr Thr Gln
305                 310                 315                 320

Lys Ser Leu Ser Leu Ser Pro Gly Lys
                325

<210> SEQ ID NO 59
<211> LENGTH: 329
<212> TYPE: PRT
<213> ORGANISM: Artificial Sequence
<220> FEATURE:
<223> OTHER INFORMATION: Synthetic

<400> SEQUENCE: 59

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Arg
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
            165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
            195                 200                 205

Ala Leu Pro Ala Pro Ile Glu Lys Thr Ile Ser Lys Ala Lys Gly Gln
210                 215                 220

Pro Arg Lys Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
            245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
            290                 295                 300

Phe Ser Cys Ser Val Met His Glu Ala Leu His Asn His Tyr Thr Gln
305                 310                 315                 320

Lys Ser Leu Ser Leu Ser Pro Gly Lys
            325

<210> SEQ ID NO 60
<211> LENGTH: 329
<212> TYPE: PRT
<213> ORGANISM: Artificial Sequence
<220> FEATURE:
<223> OTHER INFORMATION: Synthetic

<400> SEQUENCE: 60

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
            35                  40                  45

Val His Thr Phe Pro Ala Val Leu Gln Ser Ser Gly Leu Tyr Ser Leu
50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Arg
            85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
            115                 120                 125

Pro Lys Asp Thr Leu Met Ile Ser Arg Thr Pro Glu Val Thr Cys Val
            130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
            165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
            195                 200                 205

```
Ala Leu Pro Ala Pro Ile Glu Lys Thr Ile Ser Lys Ala Lys Gly Gln
        210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Tyr Leu Ser Leu Ser Pro Gly Lys
                325

<210> SEQ ID NO 61
<211> LENGTH: 329
<212> TYPE: PRT
<213> ORGANISM: Artificial Sequence
<220> FEATURE:
<223> OTHER INFORMATION: Synthetic

<400> SEQUENCE: 61

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Arg
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240
```

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Gly Ala Leu His Asn His Tyr Thr Gln
305                 310                 315                 320

Glu Ser Leu Ser Leu Ser Pro Gly Lys
                325

<210> SEQ ID NO 62
<211> LENGTH: 329
<212> TYPE: PRT
<213> ORGANISM: Artificial Sequence
<220> FEATURE:
<223> OTHER INFORMATION: Synthetic

<400> SEQUENCE: 62

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Arg
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
        290                 295                 300

Phe Ser Cys Ser Val Met His Gly Ala Leu His Asn His Tyr Thr Gln
305                 310                 315                 320

Lys Lys Leu Ser Leu Ser Pro Gly Lys
            325

<210> SEQ ID NO 63
<211> LENGTH: 329
<212> TYPE: PRT
<213> ORGANISM: Artificial Sequence
<220> FEATURE:
<223> OTHER INFORMATION: Synthetic

<400> SEQUENCE: 63

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Arg
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Arg Leu Thr Val Asp Lys Ser Arg Trp Gln Gln Gly Asn Val
    290                 295                 300

```
Phe Ser Cys Ser Val Met His Glu Ala Leu His Asn His Tyr Thr Gln
305                 310                 315                 320

Lys Ser Leu Ser Leu Ser Pro Gly Lys
            325
```

<210> SEQ ID NO 64
<211> LENGTH: 329
<212> TYPE: PRT
<213> ORGANISM: Artificial Sequence
<220> FEATURE:
<223> OTHER INFORMATION: Synthetic

<400> SEQUENCE: 64

```
Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Arg
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Lys Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Arg Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
            325
```

<210> SEQ ID NO 65
<211> LENGTH: 329
<212> TYPE: PRT
<213> ORGANISM: Artificial Sequence
<220> FEATURE:
<223> OTHER INFORMATION: Synthetic

<400> SEQUENCE: 65

```
Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Arg
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Arg Leu Thr Val Asp Lys Ser Arg Trp Gln Gln Gly Asn Val
    290                 295                 300

Phe Ser Cys Ser Val Met His Gly Ala Leu His Asn His Tyr Thr Gln
305                 310                 315                 320

Lys Ser Leu Ser Leu Ser Pro Gly Lys
                325
```

<210> SEQ ID NO 66
<211> LENGTH: 329
<212> TYPE: PRT
<213> ORGANISM: Artificial Sequence
<220> FEATURE:
<223> OTHER INFORMATION: Synthetic

<400> SEQUENCE: 66

```
Ser Thr Lys Gly Pro Ser Val Phe Pro Leu Ala Pro Ser Ser Lys Ser
1               5                   10                  15
Thr Ser Gly Gly Thr Ala Ala Leu Gly Cys Leu Val Lys Asp Tyr Phe
            20                  25                  30
Pro Glu Pro Val Thr Val Ser Trp Asn Ser Gly Ala Leu Thr Ser Gly
        35                  40                  45
Val His Thr Phe Pro Ala Val Leu Gln Ser Ser Gly Leu Tyr Ser Leu
    50                  55                  60
Ser Ser Val Val Thr Val Pro Ser Ser Ser Leu Gly Thr Gln Thr Tyr
65                  70                  75                  80
Ile Cys Asn Val Asn His Lys Pro Ser Asn Thr Lys Val Asp Lys Arg
                85                  90                  95
Val Glu Pro Lys Ser Cys Asp Lys Thr His Thr Cys Pro Pro Cys Pro
            100                 105                 110
Ala Pro Glu Leu Leu Gly Gly Pro Ser Val Phe Leu Phe Pro Pro Lys
        115                 120                 125
Pro Lys Asp Thr Leu Met Ile Ser Arg Thr Pro Glu Val Thr Cys Val
    130                 135                 140
Val Val Asp Val Ser His Glu Asp Pro Glu Val Lys Phe Asn Trp Tyr
145                 150                 155                 160
Val Asp Gly Val Glu Val His Asn Ala Lys Thr Lys Pro Arg Glu Glu
                165                 170                 175
Gln Tyr Asn Ser Thr Tyr Arg Val Val Ser Val Leu Thr Val Leu His
            180                 185                 190
Gln Asp Trp Leu Asn Gly Lys Glu Tyr Lys Cys Lys Val Ser Asn Lys
        195                 200                 205
Ala Leu Pro Ala Pro Ile Glu Lys Thr Ile Ser Lys Ala Lys Gly Gln
    210                 215                 220
Pro Arg Glu Pro Gln Val Tyr Thr Leu Pro Pro Ser Arg Glu Glu Met
225                 230                 235                 240
Thr Lys Asn Gln Val Ser Leu Thr Cys Leu Val Lys Gly Phe Tyr Pro
                245                 250                 255
Ser Asp Ile Ala Val Glu Trp Glu Ser Asn Gly Gln Pro Glu Asn Asn
            260                 265                 270
Tyr Lys Thr Thr Pro Pro Val Leu Asp Ser Asp Gly Ser Phe Leu Leu
        275                 280                 285
Tyr Ser Lys Leu Thr Val Asp Lys Ser Arg Trp Gln Gln Gly Asn Val
    290                 295                 300
Phe Ser Cys Ser Val Met His Glu Ala Leu His Asn His Tyr Thr Gln
305                 310                 315                 320
Lys Ser Leu Ser Leu Ser Pro Gly Lys
                325
```

<210> SEQ ID NO 67
<211> LENGTH: 329
<212> TYPE: PRT
<213> ORGANISM: Artificial Sequence
<220> FEATURE:
<223> OTHER INFORMATION: Synthetic

<400> SEQUENCE: 67

Ser Thr Lys Gly Pro Ser Val Phe Pro Leu Ala Pro Ser Ser Lys Ser

```
                1               5                   10                  15
            Thr Ser Gly Gly Thr Ala Ala Leu Gly Cys Leu Val Lys Asp Tyr Phe
                            20                  25                  30

Pro Glu Pro Val Thr Val Ser Trp Asn Ser Gly Ala Leu Thr Ser Gly
                            35                  40                  45

Val His Thr Phe Pro Ala Val Leu Gln Ser Ser Gly Leu Tyr Ser Leu
                50                  55                  60

Ser Ser Val Val Thr Val Pro Ser Ser Ser Leu Gly Thr Gln Thr Tyr
            65                  70                  75                  80

Ile Cys Asn Val Asn His Lys Pro Ser Asn Thr Lys Val Asp Lys Arg
                            85                  90                  95

Val Glu Pro Lys Ser Cys Asp Lys Thr His Thr Cys Pro Pro Cys Pro
                            100                 105                 110

Ala Pro Glu Leu Leu Gly Gly Pro Ser Val Phe Leu Phe Pro Pro Lys
                            115                 120                 125

Pro Lys Asp Thr Leu Met Ile Ser Arg Thr Pro Glu Val Thr Cys Val
                130                 135                 140

Val Val Asp Val Ser His Glu Asp Pro Glu Val Lys Phe Asn Trp Tyr
            145                 150                 155                 160

Val Asp Gly Val Glu Val His Asn Ala Lys Thr Lys Pro Arg Glu Glu
                            165                 170                 175

Gln Tyr Asn Ser Thr Tyr Arg Val Val Ser Val Leu Thr Val Leu His
                            180                 185                 190

Gln Asp Trp Leu Asn Gly Lys Glu Tyr Lys Cys Lys Val Ser Asn Lys
                            195                 200                 205

Ala Leu Pro Ala Pro Ile Glu Lys Thr Ile Ser Lys Ala Lys Gly Gln
                210                 215                 220

Pro Arg Lys Pro Gln Val Tyr Thr Leu Pro Pro Ser Arg Glu Glu Met
            225                 230                 235                 240

Thr Lys Asn Gln Val Ser Leu Thr Cys Leu Val Lys Gly Phe Tyr Pro
                            245                 250                 255

Ser Asp Ile Ala Val Glu Trp Glu Ser Asn Gly Gln Pro Glu Asn Asn
                            260                 265                 270

Tyr Lys Thr Thr Pro Pro Val Leu Asp Ser Asp Gly Ser Phe Leu Leu
                            275                 280                 285

Tyr Ser Lys Leu Thr Val Asp Lys Ser Arg Trp Gln Gln Gly Asn Val
                290                 295                 300

Phe Ser Cys Ser Val Met His Glu Ala Leu His Asn His Tyr Thr Gln
            305                 310                 315                 320

Lys Ser Leu Ser Leu Ser Pro Gly Lys
                            325

<210> SEQ ID NO 68
<211> LENGTH: 329
<212> TYPE: PRT
<213> ORGANISM: Artificial Sequence
<220> FEATURE:
<223> OTHER INFORMATION: Synthetic

<400> SEQUENCE: 68

Ser Thr Lys Gly Pro Ser Val Phe Pro Leu Ala Pro Ser Ser Lys Ser
            1               5                   10                  15

Thr Ser Gly Gly Thr Ala Ala Leu Gly Cys Leu Val Lys Asp Tyr Phe
                            20                  25                  30

Pro Glu Pro Val Thr Val Ser Trp Asn Ser Gly Ala Leu Thr Ser Gly
```

-continued

```
             35                  40                  45
Val His Thr Phe Pro Ala Val Leu Gln Ser Ser Gly Leu Tyr Ser Leu
     50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Arg
             85                  90                  95

Val Glu Pro Lys Ser Cys Asp Lys Thr His Thr Cys Pro Pro Cys Pro
             100                 105                 110

Ala Pro Glu Leu Leu Gly Gly Pro Ser Val Phe Leu Phe Pro Pro Lys
             115                 120                 125

Pro Lys Asp Thr Leu Met Ile Ser Arg Thr Pro Glu Val Thr Cys Val
             130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
             165                 170                 175

Gln Tyr Asn Ser Thr Tyr Arg Val Val Ser Val Leu Thr Val Leu His
             180                 185                 190

Gln Asp Trp Leu Asn Gly Lys Glu Tyr Lys Cys Lys Val Ser Asn Lys
             195                 200                 205

Ala Leu Pro Ala Pro Ile Glu Lys Thr Ile Ser Lys Ala Lys Gly Gln
             210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                 245                 250                 255

Ser Asp Ile Ala Val Glu Trp Glu Ser Asn Gly Gln Pro Glu Asn Asn
             260                 265                 270

Tyr Lys Thr Thr Pro Pro Val Leu Asp Ser Asp Gly Ser Phe Leu Leu
             275                 280                 285

Tyr Ser Lys Leu Thr Val Asp Lys Ser Arg Trp Gln Gln Gly Asn Val
     290                 295                 300

Phe Ser Cys Ser Val Met His Gly Ala Leu His Asn His Tyr Thr Gln
305                 310                 315                 320

Lys Ser Leu Ser Leu Ser Pro Gly Lys
                 325
```